United States Patent
Woods et al.

(10) Patent No.: US 11,744,243 B2
(45) Date of Patent: Sep. 5, 2023

(54) SYSTEMS AND METHODS FOR EXTRACTION AND CRYOPRESERVATION OF BONE MARROW

(71) Applicant: OSSIUM HEALTH, INC., San Francisco, CA (US)

(72) Inventors: Erik J. Woods, Carmel, IN (US); Brian H. Johnstone, Fishers, IN (US); Dongsheng Gu, Indianapolis, IN (US); Aubrey Marie Sherry, Carmel, IN (US); Kelsey Gwen Musall, Avon, IN (US)

(73) Assignee: OSSIUM HEALTH, INC., San Francisco, CA (US)

( * ) Notice: Subject to any disclaimer, the term of this patent is extended or adjusted under 35 U.S.C. 154(b) by 0 days.

(21) Appl. No.: 17/684,259

(22) Filed: Mar. 1, 2022

(65) Prior Publication Data

US 2022/0183275 A1 Jun. 16, 2022

Related U.S. Application Data

(63) Continuation of application No. PCT/US2021/055081, filed on Oct. 14, 2021.

(60) Provisional application No. 63/168,178, filed on Mar. 30, 2021, provisional application No. 63/130,255, filed on Dec. 23, 2020, provisional application No. 63/110,571, filed on Nov. 6, 2020, provisional application No. 63/091,890, filed on Oct. 14, 2020.

(51) Int. Cl.
*A01N 1/02* (2006.01)

(52) U.S. Cl.
CPC ......... *A01N 1/0284* (2013.01); *A01N 1/0221* (2013.01); *A01N 1/0252* (2013.01)

(58) Field of Classification Search
CPC ... A01N 1/0284; A01N 1/0221; A01N 1/0252
See application file for complete search history.

(56) References Cited

U.S. PATENT DOCUMENTS

| | | | |
|---|---|---|---|
| 4,674,184 | A | 6/1987 | Anderson |
| 4,710,472 | A | 12/1987 | Saur et al. |
| 5,474,687 | A | 12/1995 | Van Vlasselaer |
| 5,672,346 | A | 9/1997 | Srour et al. |
| 5,766,944 | A | 6/1998 | Ruiz |

(Continued)

FOREIGN PATENT DOCUMENTS

| | | |
|---|---|---|
| CN | 107012119 A | 8/2017 |
| EP | 3107995 B1 | 10/2019 |

(Continued)

OTHER PUBLICATIONS

AATB. Guidance Document, in Evaluation of Body Cooling at Standard D5.400. 2013. American Association of Tissue Banks: McLean, VA. p. 13.

(Continued)

*Primary Examiner* — Michael L Hobbs
(74) *Attorney, Agent, or Firm* — Wilson Sonsini Goodrich & Rosati

(57) ABSTRACT

Methods, systems, and compositions are provided for extracting bone marrow cells from bone obtained from deceased donors, for preparing the bone marrow for cryopreservation, and for obtaining desired cells from cryopreserved and fresh bone marrow.

20 Claims, 41 Drawing Sheets

(56) References Cited

U.S. PATENT DOCUMENTS

| | | | |
|---|---|---|---|
| 5,840,580 A | 11/1998 | Terstappen et al. | |
| 5,858,782 A | 1/1999 | Long et al. | |
| 6,739,112 B1 | 5/2004 | Marino | |
| 6,900,029 B1* | 5/2005 | Coulter | G01N 33/56972 435/173.9 |
| 7,470,538 B2 | 12/2008 | Laughlin et al. | |
| 7,547,210 B1 | 6/2009 | Valen | |
| 7,794,705 B2 | 9/2010 | Pecora et al. | |
| 7,915,043 B2 | 3/2011 | Caligiuri et al. | |
| 7,927,785 B2 | 4/2011 | Milhem et al. | |
| 8,048,618 B2 | 11/2011 | Luk et al. | |
| 8,088,370 B2 | 1/2012 | Pecora et al. | |
| 8,343,485 B2 | 1/2013 | Pecora et al. | |
| 8,425,899 B2 | 4/2013 | Pecora et al. | |
| 8,637,005 B2 | 1/2014 | Pecora et al. | |
| 8,709,403 B2 | 4/2014 | Pecora et al. | |
| 8,956,862 B2* | 2/2015 | Pal | A61P 9/00 435/325 |
| 9,034,316 B2 | 5/2015 | Pecora et al. | |
| 9,078,429 B2 | 7/2015 | McGann et al. | |
| 9,192,695 B2 | 11/2015 | Shi | |
| 9,241,959 B2 | 1/2016 | Tang | |
| 9,402,377 B2 | 8/2016 | Flavell et al. | |
| 9,409,906 B2 | 8/2016 | Sauvageau et al. | |
| 9,499,792 B2 | 11/2016 | Chretien et al. | |
| 9,504,717 B2 | 11/2016 | Strober et al. | |
| 9,533,010 B2 | 1/2017 | Pecora et al. | |
| 9,534,202 B2 | 1/2017 | Pecora et al. | |
| 9,561,253 B2 | 2/2017 | Strober et al. | |
| 9,675,643 B2 | 6/2017 | Weston et al. | |
| 9,675,644 B2 | 6/2017 | Weston et al. | |
| 9,687,511 B2 | 6/2017 | Weston et al. | |
| 9,808,558 B2 | 11/2017 | Shi | |
| 9,814,803 B2 | 11/2017 | Shi | |
| 9,828,586 B2 | 11/2017 | Tom et al. | |
| 9,945,854 B2 | 4/2018 | Altman et al. | |
| 9,963,678 B2 | 5/2018 | Tom et al. | |
| 9,974,807 B2 | 5/2018 | Strober et al. | |
| 10,047,344 B2 | 8/2018 | Poon et al. | |
| 10,076,113 B2 | 9/2018 | Chretien et al. | |
| 10,076,542 B2 | 9/2018 | Strober et al. | |
| 10,080,769 B2 | 9/2018 | Strober et al. | |
| 10,143,562 B2 | 12/2018 | Malinin | |
| 10,159,694 B2 | 12/2018 | Strober et al. | |
| 10,183,043 B2 | 1/2019 | Strober et al. | |
| 10,258,648 B2 | 4/2019 | Strober et al. | |
| 10,286,112 B2 | 5/2019 | Govil | |
| 10,400,218 B2 | 9/2019 | Itescu et al. | |
| 10,472,608 B2 | 11/2019 | Bader et al. | |
| 10,513,690 B2 | 12/2019 | Ganey et al. | |
| 10,550,369 B2 | 2/2020 | Tom et al. | |
| 10,603,340 B2 | 3/2020 | Strober et al. | |
| 10,645,921 B2 | 5/2020 | Temple et al. | |
| 10,660,329 B2 | 5/2020 | Ivanovic et al. | |
| 10,660,954 B2 | 5/2020 | Mitchell et al. | |
| 10,669,528 B2 | 6/2020 | Rossi et al. | |
| 10,995,318 B2 | 5/2021 | Woods et al. | |
| 11,085,024 B2 | 8/2021 | Woods et al. | |
| 11,104,882 B2 | 8/2021 | Woods et al. | |
| 2002/0039786 A1 | 4/2002 | Reid et al. | |
| 2002/0182186 A1 | 12/2002 | Loeb | |
| 2003/0082158 A1 | 5/2003 | Symonds et al. | |
| 2004/0072347 A1 | 4/2004 | Schuler et al. | |
| 2004/0258670 A1 | 12/2004 | Laughlin et al. | |
| 2005/0233299 A1 | 10/2005 | Sawa et al. | |
| 2007/0036734 A1 | 2/2007 | Tahara et al. | |
| 2007/0224587 A1 | 9/2007 | Forsell et al. | |
| 2010/0178279 A1 | 7/2010 | Cunningham-Rundles et al. | |
| 2010/0260721 A1 | 10/2010 | McGonagie et al. | |
| 2010/0310535 A1 | 12/2010 | Nakamura et al. | |
| 2010/0310536 A1 | 12/2010 | Nakamura et al. | |
| 2012/0052049 A1 | 3/2012 | Woods et al. | |
| 2012/0276581 A1 | 11/2012 | Arav et al. | |
| 2012/0276628 A1 | 11/2012 | Khan et al. | |
| 2013/0011376 A1 | 1/2013 | Peled et al. | |
| 2013/0216495 A1 | 8/2013 | Motlagh et al. | |
| 2013/0236433 A1 | 9/2013 | Webster | |
| 2013/0302293 A1 | 11/2013 | Webster | |
| 2015/0216911 A1 | 8/2015 | Vines et al. | |
| 2016/0000062 A1 | 1/2016 | Chen et al. | |
| 2016/0089401 A1 | 3/2016 | Woods et al. | |
| 2016/0101134 A1 | 4/2016 | Tang | |
| 2017/0035935 A1 | 2/2017 | Uveges et al. | |
| 2017/0151287 A1 | 6/2017 | Von Maltzahn et al. | |
| 2017/0198257 A1 | 7/2017 | Bader et al. | |
| 2017/0239390 A1 | 8/2017 | Ganey et al. | |
| 2017/0240862 A1 | 8/2017 | Ganey et al. | |
| 2017/0247659 A1 | 8/2017 | Ganey et al. | |
| 2018/0169301 A1 | 6/2018 | Temple et al. | |
| 2018/0221410 A1 | 8/2018 | Strober et al. | |
| 2018/0243337 A1 | 8/2018 | Strober et al. | |
| 2018/0282762 A1 | 10/2018 | Gori | |
| 2018/0326122 A1 | 11/2018 | Ganey et al. | |
| 2018/0334655 A1 | 11/2018 | Ganey et al. | |
| 2018/0353541 A1* | 12/2018 | Delaney | A61K 35/28 |
| 2019/0000877 A1 | 1/2019 | Strober et al. | |
| 2019/0083530 A1 | 3/2019 | Strober et al. | |
| 2019/0091262 A1 | 3/2019 | Strober et al. | |
| 2019/0151506 A1 | 5/2019 | Ganey et al. | |
| 2019/0191694 A1 | 6/2019 | Temple et al. | |
| 2019/0192561 A1 | 6/2019 | Strober et al. | |
| 2019/0192562 A1 | 6/2019 | Strober et al. | |
| 2019/0298762 A1 | 10/2019 | Strober et al. | |
| 2019/0336528 A1 | 11/2019 | Strober et al. | |
| 2019/0343112 A1 | 11/2019 | Woods et al. | |
| 2019/0345450 A1 | 11/2019 | Radtke et al. | |
| 2019/0358257 A1 | 11/2019 | Strober et al. | |
| 2020/0016198 A1 | 1/2020 | Jongen et al. | |
| 2020/0254015 A1 | 8/2020 | Strober et al. | |
| 2020/0325451 A1 | 10/2020 | Woods et al. | |
| 2020/0337648 A1 | 10/2020 | Saripalli et al. | |
| 2020/0399606 A1 | 12/2020 | Woods et al. | |
| 2020/0399607 A1 | 12/2020 | Woods et al. | |
| 2021/0214688 A1 | 7/2021 | Johnstone et al. | |

FOREIGN PATENT DOCUMENTS

| | | |
|---|---|---|
| WO | WO-9307824 A1 | 4/1993 |
| WO | WO-03024215 A1 | 3/2003 |
| WO | WO-2011069117 A1 | 6/2011 |
| WO | WO-2011151452 A1 | 12/2011 |
| WO | WO-2016210292 A1 | 12/2016 |
| WO | WO-2017127755 A1 | 7/2017 |
| WO | WO-2017216775 A3 | 2/2018 |
| WO | WO-2017218948 A3 | 2/2018 |
| WO | WO-2018022651 A1 | 2/2018 |
| WO | WO-2019006328 A1 | 1/2019 |
| WO | WO-2020047236 A1 | 3/2020 |
| WO | WO-2020058324 A1 | 3/2020 |
| WO | WO-2020061180 A1 | 3/2020 |
| WO | WO-2020214400 A1 | 10/2020 |
| WO | WO-2022020210 A1 | 1/2022 |
| WO | WO-2022081909 A1 | 4/2022 |

OTHER PUBLICATIONS

Ahrens et al.: Mesenchymal stem cell content of human vertebral bone marrow. Transplantation, 2004. 78(6): p. 925-929.

Al-Muhem et al.: University of Cincinnati. Cryopreservation and Hyopthermal Storage of Hematopoietic Stem Cells. (2013).

Banfi et al.: Replicative aging and gene expression in long-term cultures of human bone marrow stromal cells. Tissue Eng, 2002. 8(6): p. 901-10.

Bara et al.: Concise review: Bone marrow-derived mesenchymal stem cells change phenotype following in vitro culture: implications for basic research and the clinic. Stem Cells, 2014. 32(7): p. 1713-23.

Baumert et al.: Bone marrow of multiorgan donors underutilized: implications for improvement of accessibility of hematopoietic cells for transplantations. Transplantation 93(2): 165-171, 2012.

Baxter et al.: Study of telomere length reveals rapid aging of human marrow stromal cells following in vitro expansion. Stem Cells, 2004. 22(5): p. 675-82.

(56) References Cited

OTHER PUBLICATIONS

Bender et al.: Impact of freeze-thaw on isolation of viable CD34+ cells from human cadaveric bone marrow. The FASEB Journal. 34(S1) (2020) Abstract.
Bensidhoum et al.: Homing of in vitro expanded Stro-1- or Stro-1 + human mesenchymal stem cells into the NOD/SCID mouse and their role in supporting human CD34 cell engraftment. Blood, 2004. 103(9): p. 3313-9.
Berz et al.: Cryopreservation of hematopoietic stem cells. Am J Hematol 82(6):463-472 (2007).
Bieback et al.: Human Alternatives to Fetal Bovine Serum for the Expansion of Mesenchymal Stromal Cells from Bone Marrow. Stem Cells. 27(9):2331-2341 (2009).
Blashki et al.: Mesenchymal stem cells from cortical bone demonstrate increased clonal incidence, potency, and developmental capacity compared to their bone marrow-derived counterparts. J Tissue Eng, 2016. 7: p. 2041731416661196.
Blazar et al.: Successful donor cell engraftment in a recipient of bone marrow from a cadaveric donor. Blood 67(6):1655-1660 (1986).
Bork et al.: DNA methylation pattern changes upon long-term culture and aging of human mesenchymal stromal cells. Aging Cell, 2010. 9(1): p. 54-63.
Bruder et al.: Growth kinetics, self-renewal, and the osteogenic potential of purified human mesenchymal stem cells during extensive subcultivation and following cryopreservation. J Cell Biochem, 1997. 64(2): p. 278-94.
Busilacchi et al.: A novel method to evaluate prethawing viability of cryopreserved CD34+ hematopoietic stem cells for autologous transplantation. The Journal of AABB. Transfusion. 60(7):1529-1535 (2020).
Chilima et al.: Designing the optimal manufacturing strategy for an adherent allogeneic cell therapy. BioProcess International, 2016. 14(9): p. 24-32.
Chinnadurai et al.: Immune dysfunctionality of replicative senescent mesenchymal stromal cells is corrected by IFNgamma priming. Blood Adv, 2017. 1(11): p. 628-643.
Choi et al.: Dissecting Cellular Heterogeneity Using Single-Cell RNA Sequencing. Mol Cells, 2019. 42(3): p. 189-199.
ClinicalTrials.gov Identifier: NCT01459107 (2011).
Cox et al.: High abundance of CD271(+) multipotential stromal cells (MSCs) in intramedullary cavities of long bones. Bone, 2012. 50(2): p. 510-7.
CRYO2018: The 55th Annual Meeting of The Society for Cryobiology. CSIC (2018) p. 1-2.
CRYO2019: The 56th Annual Meeting of The Society for Cryobiology. CSIC (2019) p. 1-6.
Delloyd's Lab Tech. Standard sieves and Mesh sizes. Online publication. http://delloyd.50megs.com/moreinfo/mesh.html. pp. 2-3 (2018).
Dennis et al.: The STRO-1 + marrow cell population is multipotential. Cells Tissues Organs, 2002. 170(2-3): p. 73-82.
Digirolamo et al.: Propagation and senescence of human marrow stromal cells in culture: a simple colony forming assay identifies samples with the greatest potential to propagate and differentiate. Br J Haematol, 1999. 107(2): p. 275-81.
Dominici et al.: Minimal criteria for defining multipotent mesenchymal stromal cells. The International Society for Cellular Therapy position statement. Cytotherapy, 2006. 8(4): p. 315-7.
Donnenberg et al.: Clinical implementation of a procedure to prepare bone marrow cells from cadaveric vertebral bodies. Regen Med, 2011. 6(6): p. 701-6.
Donnenberg, Ph.D.: Working with Bone Marrow on a Grand Scale. McGowan Retreat. Mar. 2011.
Du et al.: Rational Design of a Fluorescent Hydrogen Peroxide Probe Based on the Umbelliferone Fluorophore. Tetrahedron Letters. 49(19):3045-3048 (2008).
Dykstra et al.: Concise Review: Fat and Furious: Harnessing the Full Potential of Adipose-Derived Stromal Vascular Fraction. Stem Cells Trans! Med, 2017. 6(4): p. 1096-1108.

Eagle et al.: Assessment of an improved bone washing protocol for deceased donor human bone. Cell Tissue Bank. 16:83-90 (2014) DOI:10.1007/s10561-014-9443-z.
Eckardt et al.: Comparison of engraftment and acute GVHD in patients undergoing cryopreserved or fresh allogeneic BMT. Bone Marrow Transplant, 1993. 11(2): p. 125-31.
Ferrari et al.: Beta regression for modeling rates and proportions. J. Applied Statistics, 2004. 31(7): p. 799-815.
Ferrebee et al.: The Collection, Storage and Preparation of Viable Cadaver Marrow for Intravenous Use. Blood. 14(2):140-147 (1959).
Flood et al.: Does practice make perfect? Part 1: The relations between hospital volume and outcomes for selected diagnostic categories. Medical Care, 1984. 22(2): p. 98-114.
Flood et al.: Does practice make perfect? Part II: The relation between vols. and other hospital characteristics. Medical Care, 1984. 22(2): p. 115-125.
Fresenius Kabi AG. 510(k) Summary. Bone Marrow Collection Stand. (2017) https://www.fda.gov/media/106490/download.
Galipeau et al.: International Society for Cellular Therapy perspective on immune functional assays for mesenchymal stromal cells as potency release criterion for advanced phase clinical trials. Cytotherapy, 2016. 18(2): p. 151-9.
Galipeau et al.: Mesenchymal Stromal Cells: Clinical Challenges and Therapeutic Opportunities. Cell Stem Cell, 2018. 22(6): p. 824-833.
GE Healthcare Life Sciences. Cell Separation Media Reference (2014).
Gorantla et al.: Development and validation of a procedure to isolate viable bone marrow cells from the vertebrae of cadaveric organ donors for composite organ grafting. Cytotherapy, 2012. 14(1): p. 104-13.
Gronthos et al.: Molecular and cellular characterisation of highly purified stromal stem cells derived from human bone marrow. J Cell Sci, 2003. 116(Pt 9): p. 1827-35.
Han et al.: Optimization of human umbilical cord mesenchymal stem cell isolation and culture methods. Cytotechnology. 65(5):819-827 (2013).
Harrel Jr.: Regression modeling strategies with applications to linear models, logistic regression, and survival analysis. 2nd ed. Springer Series in Statistics. 2001, NY: 582.
Harrison et al.: Cell therapy-processing economics: small-scale microfactories as a stepping stone toward large-scale macrofactories. Regen Med, 2018. 13(2): p. 159-173.
Heathman et al.: Characterization of human mesenchymal stem cells from multiple donors and the implications for large scale bioprocess development. Biochemical Engineering Journal, 2016. 108: p. 14-23.
Hemacare Corporation. Isolation of Peripheral Blood Mononuclear Cells (PBMCs) Using a Density Gradient Reagent. Technical Protocol. PROT-IPBMC-V1.1 1018 (2016).
Hibino et al.: Comparison of Human Bone Marrow Mononuclear Cells Isolation Methods for Creating Tissue-Engineered Vascular Grafts: Novel Filter System Versus Traditional Density Centrifugation Method. Tissue Engineering. Part C:17(10) (2011).
Hotta et al.: Long-term Nonhuman Primate Renal Allograft Survival Without Ongoing Immunosuppression in Recipients of Delayed Donor Bone Marrow Transplantation. Transplantation, 2018. 102(4): p. e128-e136.
Hunt. Cryopreservation of Human Stem Cells for Clinical Application: A Review. Transfus Med Hemother 38(2):107-123 (2011).
Hwang et al.: Single-cell RNA sequencing technologies and bioinformatics pipelines. Exp Mol Med, 2018. 50(8):p. 96.
Jonhstone: Edit Identification and Characterization of a Large Source of Primary Mesenchymal Stem Cells Tightly Adhered to Bone Surfaces of Human Vertebral Body Marrow Cavities. ISSCR Abstract (2020).
Johnstone et al.: Identification and characterization of a large source of primary mesenchymal stem cells tightly adhered to bone surfaces of human vertebral body marrow cavities. Cytotherapy. (2020) 1-12.
Johnstone et al.: Identification and characterization of a large source of primary mesenchymal stem cells tightly adhered to bone surfaces of human vertebral body marrow cavities. Reprint https://doi.org/10.1101/2020.05.04.076950 (2020) 40 pages.

(56) References Cited

OTHER PUBLICATIONS

Johnstone et al.: Identification and characterization of a large source of primary mesenchymal stem cells tightly adhered to bone surfaces of human vertebral body marrow cavities. ScienceDirect. Cytotherapy. 22:617-628 (2020).

Jones et al.: Large-scale extraction and characterization of CD271+ multipotential stromal cells from trabecular bone in health and osteoarthritis: implications for bone regeneration strategies based on uncultured or minimally cultured multipotential stromal cells. Arthritis Rheum, 2010. 62(7): p. 1944-54.

Jossen et al.: Manufacturing human mesenchymal stem cells at clinical scale: process and regulatory challenges. Appl Microbiol Biotechnol, 2018. 102(9): p. 3981-3994.

Kawai et al.: Long-term results in recipients of combined HLA-mismatched kidney and bone marrow transplantation without maintenance immunosuppression. Am J Transplant, 2014. 14(7): p. 1599-611.

Kenyon et al.: Effect of depletion of class II bright cells on the immunogenicity and stem cell content of human vertebral body bone marrow. Transplant Proc27(6):3419 (1995).

Knebel et al.: Allocation of scarce resources after a nuclear detonation: setting the context. Disaster Med Public Health Prep, 2011.5 Suppl 1: p. S20-31.

Lechanteur et al.: Large-scale clinical expansion of mesenchymal stem cells in the GMP-compliant, closed automated Quantum(R) cell expansion system: Comparison with expansion in traditional T-flasks. Stem Cell Research & Therapy, 2014. 4(8): p. 1-11.

Li et al.: Therapeutic Delivery Specifications Identified Through Compartmental Analysis of a Mesenchymal Stromal Cell-Immune Reaction. Sci Rep, 2018. 8(1): p. 6816.

Linch et al.: Bone marrow processing and cryppreservation. Journal of Clinical Pathology. 35(2):186-190 (1982).

Lioznov et al.: Transportation and cryopreservation may impair haematopoietic stem cell function and engraftment of allogeneic PBSCs, but not BM. Bone Marrow Transplant, 2008. 42(2): p. 121-8.

Lipsitz et al.: A roadmap for cost-of-goods planning to guide economic production of cell therapy products. Cytotherapy, 2017. 19(12): p. 1383-1391.

Lockhart et al.: Use of Freshly Isolated Human Adipose Stromal Cells for Clinical Applications. Aesthet Surg J, 2017. 37(suppl_3): p. S4-S8.

Long et al.: Accumulation of CD11b+ Gr-1+ cells in the lung, blood and bone marrow of mice infected with highly pathogenic H5N1 and H1N1 influenza viruses. Archives of Virology. 158(6):1305-1322 (2013).

Mendicino et al.: MSC-based product characterization for clinical trials: an FDA perspective. Cell Stem Cell, 2014. 14(2): p. 141-5.

Michalova et al.: Hematopoietic Stem Cells Survive Circulation Arrest and Reconstitute Hematopoiesis in Myeloablated Mice. Biology of Blood and Bone Marrow Transplantation. 17(9):1273-1281 (2011).

Miller et al.: Phenotypic and Functional Equivalency of Digested Bone Marrow Mesenchymal Stem Cells to Aspirated Bone Marrow Mesenchymal Stem Cells. FASEB 33(S1) (2019).

Miltenyi Biotec: Isolation of Mononuclear Cells from human bone marrow aspirates by density gradient centrifugation. (2008).

Mizukami et al.: Technologies for large-scale umbilical cord-derived MSC expansion: Experimental performance and cost of g000ds analysis. Biochemical Engineering Journal, 2018. 135: p. 36-48.

Moravcikova et al.: Proteomic Profiling of Native Unpassaged and Culture-Expanded Mesenchymal Stromal Cells (MSC). Cytometry A, 2018. 93(9): p. 894-904.

Morgenstern et al.: Post-thaw viability of cryopreserved peripheral blood stem cells (PBSC) does not guarantee functional activity: important implications for quality assurance of stem cell transplant programmes. Br J Haematol 174(6):942-951 (2016).

Muraglia et al.: Clonal mesenchymal progenitors from human bone marrow differentiate in vitro according to a hierarchical model. J Cell Sci, 2000. 113 ( Pt 7): p. 1161-6.

Oetjen et al.: Human bone marrow assessment by single-cell RNA sequencing, mass cytometry, and flow cytometry. JCI Insight. 3(23):7 e124928 (2018).

Olsen et al.: Peak MSC—Are We There Yet? Front Med (Lausanne), 2018. 5: p. 178.

Oseni et al.: Optimization of chondrocyte isolation and characterization for large-scale cartilage tissue engineering. Journal of Surgical Research. 181:41-48 (2013).

PCT/US2020/025778 International Preliminary Report on Patentability dated Oct. 28, 2021.

PCT/US2020/025778 ISR and Written Opinion dated Sep. 16, 2020.

PCT/US2021/055081 International Search Report and Written Opinion dated Jan. 20, 2021.

Pennington et al.: Evaluation of a Sterling Cycle Controlled Rate Freezing Device for Simultaneous Cryopreservation of Multiple Units. Cryobiology. 91:146-197 (2019) Abstract.

Pereira et al.: Impact of allogeneic stem cell manufacturing decisions on cost of goods, process robustness and reimbursement. Biochemical Engineering J, 2018. 137: p. 132-151.

Picard et al.: Cook, Cross-validation of regression models. J . Am. Stat. Assoc, 1984. 79(428):9 pages.

Pittenger et al.: Multilineage potential of adult human mesenchymal stem cells. Science, 1999. 284(5411): p. 143-7.

Quah et al.: Monitoring lymphocyte proliferation in vitro and in vivo with the intracellular fluorescent dye carboxyfluorescein diacetate succinimidyl ester. Nat Protoc, 2007. 2(9): p. 2049-56.

Redaelli From cytogenomicto epigenomic profiles: monitoring the biologic behavior of in vitro cultured human bone marrow mesenchymal stem cells. Stem Cell Res Ther, 2012. 3(6): p. 47.

Rybka et al.: Hematopoietic progenitor cell content of vertebral body marrow used for combined solid organ and bone marrow transplantation. Transplantation, 1995. 59(6): p. 871-4.

Schneeberger et al.: Upper-extremity transplantation using a cell-based protocol to minimize immunosuppression. Ann Surg, 2013. 257(2): p. 345-51.

Schwartz et al.: Explanatory and pragmatic attitudes in therapeutical trials. J Chronic Dis, 1967. 20(8): p. 637-48.

Sherry et al.: The Influence of Warm Ischemic Time on the Viability of Deceased Organ Donor Derived Bone Marrow. The FASEB Journal. 32(S1) Abstract (2018).

Shu et al.: Development of a reliable low-cost controlled cooling rate instrument for the cryopreservation of hematopoietic stem cells. Cytotherapy 12(2):161-169 (2010).

Siclari et al.: Mesenchymal proenitors residing close to the bone surface are functionally distinct from those in the central bone marrow. Bone, 2013. 53(2): p. 575-86.

Simaria et al.: Allogeneic cell therapy bioprocess economics and optimization: single-use cell expansion technologies. Biotechnol Bioeng, 2014. 111(1): p. 69-83.

Simmons et al.: Identification of stromal cell precursors in human bone marrow by a novel monoclonal antibody, STRO-1. Blood, 1991. 78(1): p. 55-62.

Soderdahl et al.: Cadaveric bone marrow and spleen cells for transplantation. Bone Marrow Transplant, 1998. 21(1): p. 79-84.

Spitzer et al.: Twenty Year Follow Up of Histocompatibility Leukocyte Antigen-Matched Kidney and Bone Marrow Co-Transplantation for Multiple Myeloma with End Stage Renal Disease: Lessons Learned. Transplantation, 103(11): 2366-2372 (2019).

Squillaro et al.: Clinical Trials With Mesenchymal Stem Cells: An Update. Cell Transplant, 2016. 25(5): p. 829-48.

Stenn et al.: Dispase, a Neutral Protease From Bacillus Polymyxa, Is a Powerful Fibronectinase and Type IV Collagenase. J Invest Dermatol. 93(2):287-290 (1989).

Stockschlader et al.: Long-term follow-up of leukaemia patients after related cryopreserved allogeneic bone marrow transplantation. Br J of Hematology. 96:382-386 (1997).

Stockschlader et al.: Use of cryopreserved bone marrow in allogeneic bone marrow transplantation. Bone Marrow Transplant, 1995. 15(4): p. 569-72.

(56) References Cited

OTHER PUBLICATIONS

Stockschlader et al.: Use of cryopreserved bone marrow in unrelated allogeneic transplantation. Bone Marrow Transplant, 1996. 17(2): p. 197-9 (Abstract).
Suire et al.: Isolation of the stromal-vascular fraction of mouse bone marrow markedly enhances the yield of clonogenic stromal progenitors. Blood. 119(11):e86-e95 (2012).
Sutherland The guidelines for CD34+ cell determination by flow cytometry. International Society of Hematotherapy and Graft Engineering. J Hematother 1996. 5(3):213-26.
Thomas et al.: Intravenous infusion of bone marrow in patients receiving radiation and chemotherapy. N Engl J Med 257(11):491-496 (1957).
Thompson et al.: Time and Temperature Dependent Ficoll Separation of Aged Whole Blood Neutrophils. The FASEB Journal. 33(S1) Abstract (2019).
Thompson: Preparing Skeletons for Research and Teaching from Preserved Human Specimens. Thesis, pp. 1-162 (2015).
U.S. Appl. No. 17/013,379 Office Action dated Feb. 18, 2021.
U.S. Appl. No. 17/013,379 Restriction Requirement dated Dec. 14, 2020.
U.S. Appl. No. 17/013,389 Final Office Action dated Feb. 19, 2021.
U.S. Appl. No. 17/013,389 First Action Interview dated Dec. 11, 2020.
U.S. Appl. No. 17/013,389 Non-Final Office Action dated Apr. 7, 2021.
U.S. Appl. No. 17/013,395 Final Office Action dated Mar. 12, 2021.
U.S. Appl. No. 17/013,395 Final Office Action dated Sep. 27, 2021.
U.S. Appl. No. 17/013,395 First Action Interview dated Dec. 1, 2020.
U.S. Appl. No. 17/013,395 Non-Final Office Action dated Apr. 13, 2021.
U.S. Appl. No. 17/013,400 Final Office Action dated Sep. 2, 2021.
U.S. Appl. No. 17/013,400 First Action Interview dated Dec. 28, 2020.
U.S. Appl. No. 17/013,400 Non-Final Office Action dated Apr. 13, 2021.
U.S. Appl. No. 17/013,407 Office Action dated Dec. 18, 2020.
U.S. Appl. No. 17/013,407 Restriction Requirement dated Nov. 10, 2020.

Walter et al.: Molecular and Functional Phenotypes of Human Bone Marrow-Derived Mesenchymal Stromal Cells Depend on Harvesting Techniques. International Journal of Molecular Sciences. 23.4382:1-12 (2020).
Warwick et al.: Collagenase Clostridium histolyticum: emerging practice patterns and treatment advances. Journal of Plastic Surgery and Hand Surgery. 50(5):251-326 (2016).
Weinstock et al.: Radiologic and nuclear events: contingency planning for hematologists/oncologists. Blood, 2008. 111(12): p. 5440-5.
Woods et al.: Ischemia considerations for the development of an organ and tissue donor derived bone marrow bank. Journal of Translational Medicine. 18:300 (2020) 11 pages.
Woods et al.: Off the shelf cellular therapeutics: Factors to consider during cryopreservation and storage of human cells for clinical use. Cytotherapy, 2016. 18(6): p. 697-711.
Woods et al.: Packaging considerations for biopreservation. Transfusion Medicine and Hemotherapy 38(2):149-156 (2011).
Woods et al.: The learning curve and the cost of heart transplantation. Health Sery Res, 1992. 27(2): p. 219-38.
Wright, T., Factors affecting the cost of airplanes. J Aeronautical Sci 1936. 3(2): p. 122-128.
Wuchter et al.: Standardization of Good Manufacturing Practice-compliant production of bone marrow-derived human mesenchymal stromal cells for immunotherapeutic applications. Cytotherapy, 2014. 17(2): p. 128-39.
Yamada et al.: Overcoming memory T-cell responses for induction of delayed tolerance in nonhuman primates. Am J Transplant, 2012. 12(2): p. 330-40.
Yescom. All Steel PEX Pipe Tube Cpvc Tubing Cutter up to 1-5/8" Hose Ratchet Style New. Publication [online], https:\\www.amazon.com/Steel-Tubing-Cutter-Ratchet-Style/dp/BOOLSEHSSE. p. 1 (2014).
Yusop et al.: Isolation and Characterisation of Mesenchymal Stem Cells from Rat Bone Marrow and the Endosteal Niche: A Comparative Study. Stem Cells Int, 2018. 2018: p. 6869128.
Chiang et al.: Allogeneic Mesenchymal Stem Cells in Combination with Hyaluronic Acid for the Treatment of Osteoarthritis in Rabbits. Plos One. 11(2):e0149835 pp. 1-15 (2016).
Gorantla et al.: 2007-05-R11A Procedure for preparation of bone marrow cells from cadaveric vertebral bodies. University of Pittsburgh Medical Center, pp. 1-11 (2007).
U.S. Appl. No. 16/734,713 Final Office Action dated Jan. 17, 2023.
U.S. Appl. No. 17/013,395 Non-Final Office Action dated Jan. 13, 2023.
U.S. Appl. No. 17/199,376 Office Action dated Nov. 17, 2022.

* cited by examiner

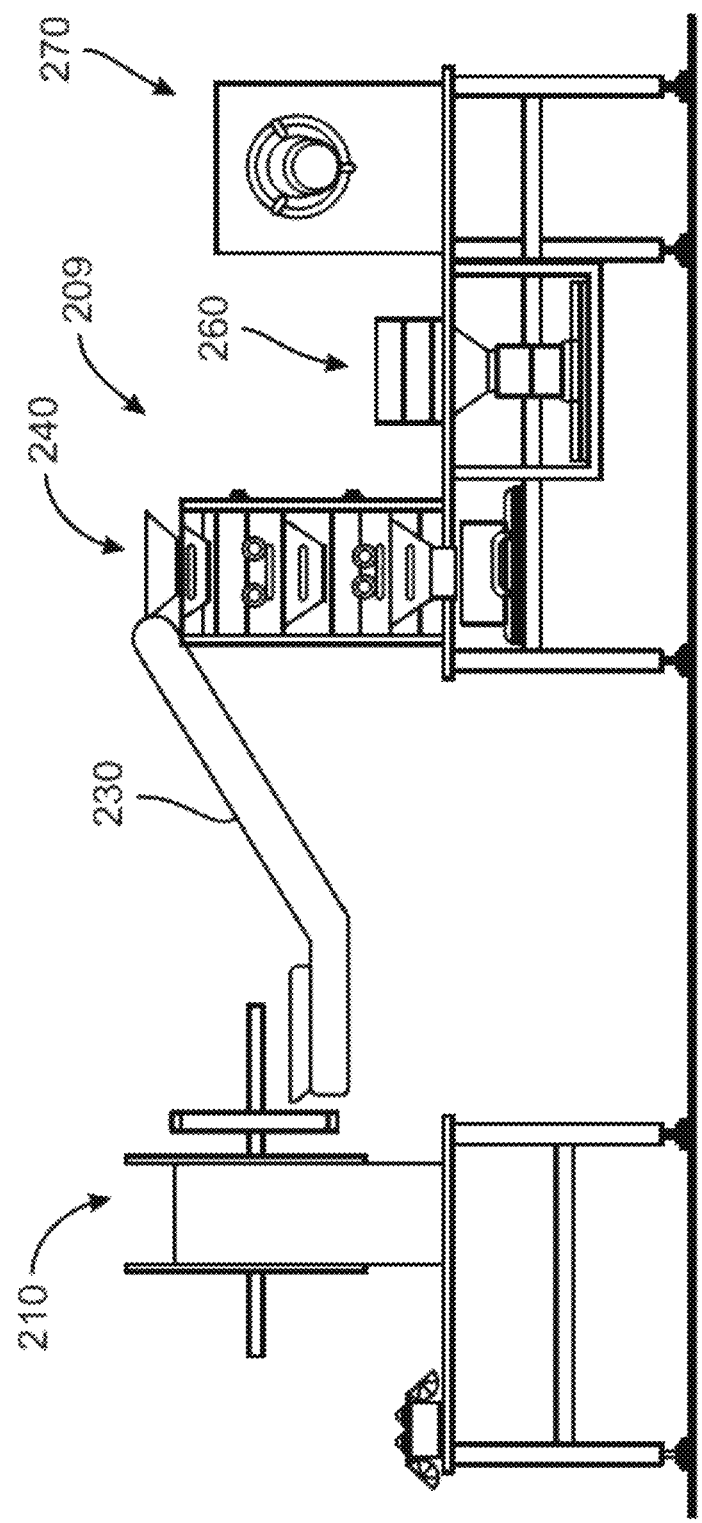

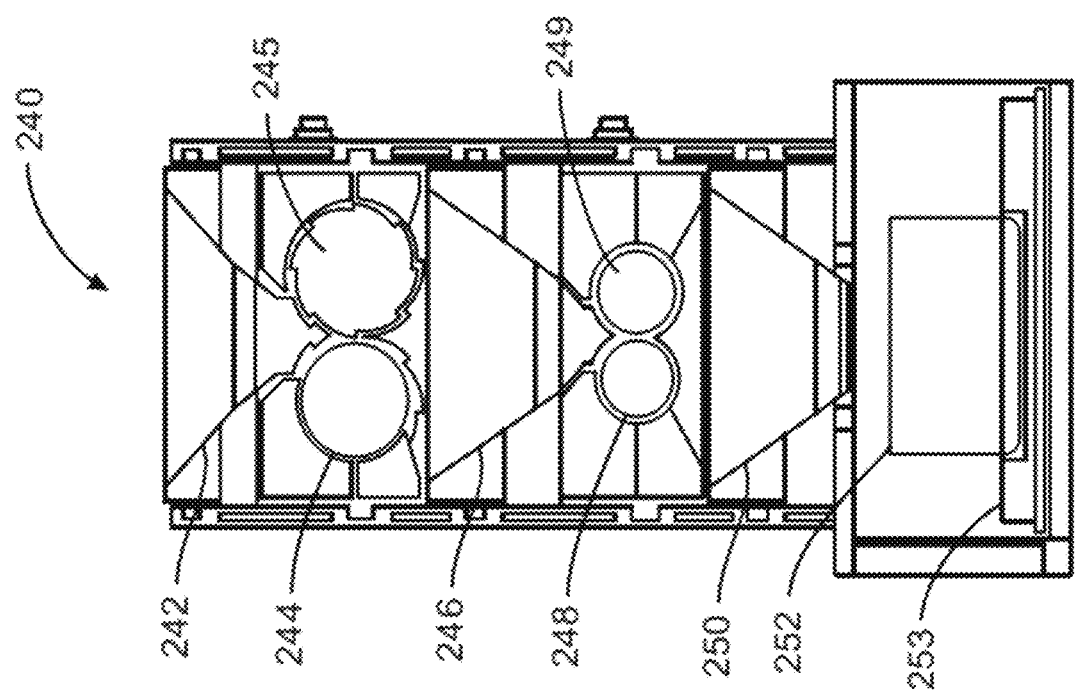

With Body Cooling: WIT is constant at its minimum = 0.05 hours, BCT and CIT vary from their observed minimum to maximum values.

| CIT | BCT=1.07 %Viable CD34 | BCT=1.07 Total Ischemia | BCT=1.62 %Viable CD34 | BCT=1.62 Total Ischemia | BCT=2.20 %Viable CD34 | BCT=2.20 Total Ischemia | BCT=3.39 %Viable CD34 | BCT=3.39 Total Ischemia | BCT=6.00 %Viable CD34 | BCT=6.00 Total Ischemia |
|---|---|---|---|---|---|---|---|---|---|---|
| 7.40 | 93.74% | 8.52 | 93.11% | 9.07 | 92.43% | 9.65 | 90.98% | 10.84 | 87.80% | 13.45 |
| 8.90 | 92.80% | 10.02 | 92.10% | 10.57 | 91.34% | 11.15 | 89.73% | 12.34 | 86.22% | 14.95 |
| 10.40 | 91.82% | 11.52 | 91.04% | 12.07 | 90.20% | 12.65 | 88.42% | 13.84 | 84.57% | 16.45 |
| 11.90 | 90.78% | 13.02 | 89.93% | 13.57 | 89.01% | 14.15 | 87.07% | 15.34 | 82.89% | 17.95 |
| 13.40 | 89.72% | 14.52 | 88.79% | 15.07 | 87.78% | 15.65 | 85.68% | 16.84 | 81.17% | 19.45 |
| 13.55 | 89.61% | 14.67 | 88.67% | 15.22 | 87.66% | 15.80 | 85.53% | 16.99 | 81.00% | 19.60 |
| 14.90 | 88.63% | 16.02 | 87.62% | 16.57 | 86.53% | 17.15 | 84.27% | 18.34 | 79.45% | 20.95 |
| 16.40 | 87.52% | 17.52 | 86.44% | 18.07 | 85.28% | 18.65 | 82.85% | 19.84 | 77.74% | 22.45 |
| 17.90 | 86.42% | 19.02 | 85.27% | 19.57 | 84.03% | 20.15 | 81.45% | 21.34 | 76.07% | 23.95 |
| 19.40 | 85.34% | 19.62 | 84.11% | 20.17 | 82.80% | 20.75 | 80.08% | 21.94 | 74.44% | 24.55 |
| 20.90 | 84.28% | 20.52 | 82.99% | 21.07 | 81.60% | 21.65 | 78.76% | 22.84 | 72.89% | 25.45 |
| 22.40 | 83.26% | 20.63 | 81.91% | 21.18 | 80.46% | 21.76 | 77.50% | 22.95 | 71.42% | 25.56 |
| 23.90 | 82.29% | 22.02 | 80.89% | 22.57 | 79.39% | 23.15 | 76.31% | 24.34 | 70.04% | 26.95 |
| 25.40 | 81.39% | 23.52 | 79.94% | 24.07 | 78.38% | 24.65 | 75.22% | 25.84 | 68.78% | 28.45 |
| 26.90 | 80.57% | 25.02 | 79.07% | 25.57 | 77.47% | 26.15 | 74.22% | 27.34 | 67.65% | 29.95 |
| 28.40 | 79.83% | 25.84 | 78.29% | 26.39 | 76.66% | 26.97 | 73.33% | 28.16 | 66.64% | 30.77 |
| 29.90 | 79.19% | 26.52 | 77.62% | 27.07 | 75.95% | 27.65 | 72.56% | 28.84 | 65.77% | 31.45 |
| 31.40 | 78.65% | 28.02 | 77.05% | 28.57 | 75.35% | 29.15 | 71.92% | 30.34 | 65.05% | 32.95 |
| 32.90 | 78.22% | 29.52 | 76.60% | 30.07 | 74.88% | 30.65 | 71.41% | 31.84 | 64.48% | 34.45 |
| 34.40 | 77.91% | 31.02 | 76.27% | 31.57 | 74.53% | 32.15 | 71.03% | 33.34 | 64.06% | 35.95 |
| 35.90 | 77.71% | 32.52 | 76.06% | 33.07 | 74.31% | 33.65 | 70.79% | 34.84 | 63.79% | 37.45 |
| 37.40 | 77.63% | 32.73 | 75.97% | 33.28 | 74.22% | 33.86 | 70.70% | 35.05 | 63.69% | 37.66 |
| 38.90 | 77.66% | 34.02 | 76.01% | 34.57 | 74.27% | 35.15 | 70.74% | 36.34 | 63.74% | 38.95 |
| 40.40 | 77.82% | 35.52 | 76.18% | 36.07 | 74.44% | 36.65 | 70.93% | 37.84 | 63.94% | 40.45 |
| 41.90 | 78.09% | 37.02 | 76.47% | 37.57 | 74.74% | 38.15 | 71.25% | 39.34 | 64.31% | 41.95 |

Without Body Cooling. BCT = 0 hours. WIT and CIT are varied from their observed minimum to maximum values.

| WIT | CIT=1.70 CPU-TOTAL | Total Ischemia | CIT=23.75 CPU-TOTAL | Total Ischemia | CIT=27.41 CPU-TOTAL | Total Ischemia | CIT=39.75 CPU-TOTAL | Total Ischemia | CIT=67.75 CPU-TOTAL | Total Ischemia |
|---|---|---|---|---|---|---|---|---|---|---|
| 1.08 | 693,630 | 12.78 | 639,001 | 24.83 | 622,416 | 28.49 | 566,466 | 40.83 | 439,527 | 68.83 |
| 1.83 | 686,798 | 13.53 | 632,170 | 25.58 | 615,585 | 29.24 | 559,634 | 41.58 | 432,696 | 69.58 |
| 2.58 | 679,967 | 14.28 | 625,339 | 26.33 | 608,754 | 29.99 | 552,803 | 42.33 | 425,865 | 70.33 |
| 3.33 | 673,136 | 15.03 | 618,507 | 27.08 | 601,922 | 30.74 | 545,972 | 43.08 | | |
| 4.08 | 666,305 | 15.78 | 611,676 | 27.83 | 595,091 | 31.49 | 539,140 | 43.83 | | |
| 4.83 | 659,474 | 16.53 | 604,845 | 28.58 | 588,260 | 32.24 | 532,309 | 44.58 | | |
| 5.58 | 652,642 | 17.28 | 598,014 | 29.33 | 581,429 | 32.99 | 525,478 | 45.33 | | |
| 6.33 | 645,811 | 18.03 | 591,183 | 30.08 | 574,598 | 33.74 | 518,647 | 46.08 | | |
| 7.08 | 638,980 | 18.78 | 584,351 | 30.83 | 567,766 | 34.49 | 511,816 | 46.83 | | |
| 7.83 | 632,149 | 19.53 | 577,520 | 31.58 | 560,935 | 35.24 | 504,984 | 47.58 | | |
| 8.58 | 625,318 | 20.28 | 570,689 | 32.33 | 554,104 | 35.99 | 498,153 | 48.33 | | |
| 9.33 | 618,486 | 21.03 | 563,858 | 33.08 | 547,273 | 36.74 | 491,322 | 49.13 | | |
| 10.08 | 611,655 | 21.78 | 557,027 | 33.83 | 540,442 | 37.49 | | | | |
| 10.83 | 604,824 | 22.53 | 550,195 | 34.58 | 533,610 | 38.24 | | | | |
| 11.58 | 597,993 | 23.28 | 543,364 | 35.33 | 526,779 | 38.99 | | | | |
| 12.33 | 591,162 | 24.03 | 536,533 | 36.08 | 519,948 | 39.74 | | | | |
| 13.40 | 581,416 | 25.10 | 526,787 | 37.15 | 510,202 | 40.81 | | | | |

FIG. 12B

With Body Cooling: WIT is constant at its minimum (0.05 hours), while BCT and CIT are varied from their observed minimum to maximum values.

| CIT | BCT=1.07 CFU-TOTAL | Total Ischemia | BCT=6.54 CFU-TOTAL | Total Ischemia | BCT=9.78 CFU-TOTAL | Total Ischemia | BCT=15.00 CFU-TOTAL | Total Ischemia | BCT=22.50 CFU-TOTAL | Total Ischemia |
|---|---|---|---|---|---|---|---|---|---|---|
| 7.40 | 624,773 | 8.52 | 248,787 | 13.99 | 123,613 | 17.23 | 74,566 | 22.45 | 335,801 | 29.95 |
| 8.90 | 617,973 | 10.02 | 241,987 | 15.49 | 116,813 | 18.73 | | | 327,001 | 31.45 |
| 10.40 | 611,173 | 11.52 | 235,187 | 16.99 | 110,012 | 20.23 | | | 320,201 | 32.95 |
| 11.90 | 604,372 | 13.02 | 228,386 | 18.49 | 103,212 | 21.73 | | | 313,400 | 34.45 |
| 13.40 | 597,572 | 14.52 | 221,586 | 19.99 | 96,412 | 23.23 | | | 306,600 | 35.95 |
| 14.90 | 590,772 | 16.02 | 214,786 | 21.49 | | | | | 299,800 | 37.45 |
| 16.40 | 583,972 | 17.52 | 207,986 | 22.99 | | | | | 293,000 | 38.95 |
| 17.90 | 577,171 | 19.02 | 201,185 | 24.49 | | | | | 286,199 | 40.45 |
| 19.40 | 570,371 | 20.52 | 194,385 | 25.99 | | | | | 279,399 | 41.95 |
| 20.90 | 563,571 | 22.02 | 187,585 | 27.49 | | | | | | |
| 22.40 | 556,771 | 23.52 | 180,785 | 28.99 | | | | | | |
| 23.90 | 549,970 | 25.02 | 173,984 | 30.49 | | | | | | |
| 25.40 | 543,170 | 26.52 | 167,184 | 31.99 | | | | | | |
| 26.90 | 536,370 | 28.02 | | | | | | | | |
| 28.40 | 529,570 | 29.52 | | | | | | | | |
| 29.90 | 522,769 | 31.02 | | | | | | | | |
| 31.40 | 515,969 | 32.52 | | | | | | | | |
| 32.90 | 509,169 | 34.02 | | | | | | | | |
| 34.40 | | | | | | | | | | |
| 35.90 | | | | | | | | | | |
| 37.40 | | | | | | | | | | |
| 38.90 | | | | | | | | | | |
| 41.03 | | | | | | | | | | |

FIG. 12C

With Body Cooling: CIT is constant at its minimum value = 7.4 hours. BCT and WIT are varied from their observed minimum to observed maximum values.

| BCT | WIT=0.05 CFU-TOTAL | Total Ischemia | WIT=1.96 CFU-TOTAL | Total Ischemia | WIT=2.48 CFU-TOTAL | Total Ischemia | WIT=3.42 CFU-TOTAL | Total Ischemia | WIT=8.95 CFU-TOTAL | Total Ischemia |
|---|---|---|---|---|---|---|---|---|---|---|
| 1.07 | 624.77 | 8.52 | 607.36 | 10.43 | 602.64 | 10.95 | 394.08 | 11.89 | 543.71 | 17.42 |
| 2.07 | 540.59 | 9.52 | 523.19 | 11.43 | 518.46 | 11.95 | | | 459.53 | 18.42 |
| 3.07 | 463.32 | 10.52 | 445.92 | 12.43 | 441.18 | 12.95 | | | 382.25 | 19.42 |
| 4.07 | 392.96 | 11.52 | 375.56 | 13.43 | 370.82 | 13.95 | | | 311.89 | 20.42 |
| 5.07 | 329.61 | 12.52 | 312.11 | 14.43 | 307.37 | 14.95 | | | 248.44 | 21.42 |
| 6.07 | 272.97 | 13.52 | 255.57 | 15.43 | 250.84 | 15.95 | | | 191.91 | 22.42 |
| 7.07 | 223.35 | 14.52 | 205.95 | 16.43 | 201.21 | 16.95 | | | | |
| 8.07 | 180.64 | 15.52 | 163.24 | 17.43 | 158.50 | 17.95 | | | | |
| 9.07 | 144.83 | 16.52 | 127.44 | 18.43 | 122.70 | 18.95 | | | | |
| 10.07 | 115.95 | 17.52 | | | | | | | | |
| 11.07 | 93.97 | 18.52 | | | | | | | | |
| 12.07 | 78.91 | 19.52 | | | | | | | | |
| 13.07 | 70.76 | 20.52 | | | | | | | | |
| 14.07 | 69.52 | 21.52 | | | | | | | | |
| 15.07 | 75.19 | 22.52 | | | | | | | | |
| 16.07 | 87.77 | 23.52 | | | | | | | | |
| 17.07 | 107.27 | 24.52 | | | | | | | | |
| 18.07 | 133.68 | 25.52 | | | | | | | | |
| 19.07 | 167.00 | 26.52 | | | | | | | | |
| 20.07 | 207.23 | 27.52 | | | | | | | | |
| 21.07 | 254.37 | 28.52 | | | | | | | | |
| 22.50 | 333.80 | 29.95 | | | | | | | | |

FIG. 13A

Without Body Cooling; BCT is constant = 0 hours. WIT and CIT are varied from their observed minimum to observed maximum values.

| WIT | CIT=11.70 CFU-GEM | Total Ischemia | CIT=23.75 CFU-GEM | Total Ischemia | CIT=27.00 CFU-GEM | Total Ischemia | CIT=40.50 CFU-GM | Total Ischemia | CIT=67.75 CFU-GM | Total Ischemia |
|---|---|---|---|---|---|---|---|---|---|---|
| 1.08 | 96,457 | 12.78 | 97,503 | 24.58 | 97,814 | 28.08 | 99,012 | 41.58 | 101,429 | 68.83 |
| 1.68 | 91,589 | 13.38 | 92,636 | 25.18 | 92,946 | 28.68 | 94,144 | 42.18 | 96,561 | 69.43 |
| 2.28 | 86,721 | 13.98 | 87,768 | 25.78 | 88,078 | 29.28 | 89,276 | 42.78 | 91,694 | 70.03 |
| 2.88 | 81,853 | 14.58 | 82,900 | 26.38 | 83,211 | 29.88 | 84,408 | 43.38 | 86,826 | 70.63 |
| 3.48 | 76,985 | 15.18 | 78,032 | 26.98 | 78,343 | 30.48 | 79,541 | 43.98 | 81,958 | 71.23 |
| 4.08 | 72,118 | 15.78 | 73,165 | 27.58 | 73,475 | 31.08 | 74,673 | 44.58 | 77,090 | 71.83 |
| 4.68 | 67,250 | 16.38 | 68,297 | 28.18 | 68,607 | 31.68 | 69,805 | 45.18 | | |
| 5.28 | 62,382 | 16.98 | 63,429 | 28.78 | 63,740 | 32.28 | 64,937 | 45.78 | | |
| 5.88 | 57,514 | 17.58 | 58,561 | 29.38 | 58,872 | 32.88 | 60,069 | 46.38 | | |
| 6.48 | 52,647 | 18.18 | 53,693 | 29.98 | 54,004 | 33.48 | 55,202 | 46.98 | | |
| 7.08 | 47,779 | 18.78 | 48,826 | 30.58 | 49,136 | 34.08 | 50,334 | 47.58 | | |
| 7.68 | 42,911 | 19.38 | 43,958 | 31.18 | 44,268 | 34.68 | 45,466 | 48.18 | | |
| 8.28 | 38,043 | 19.98 | 39,090 | 31.78 | 39,401 | 35.28 | 40,598 | 48.78 | | |
| 8.88 | 33,175 | 20.58 | 34,222 | 32.38 | 34,533 | 35.88 | 35,731 | 49.38 | | |
| 9.48 | 28,308 | 21.18 | 29,355 | 32.98 | 29,665 | 36.48 | 30,863 | 49.98 | | |
| 10.08 | 23,440 | 21.78 | 24,487 | 33.58 | 24,797 | 37.08 | 25,995 | 50.58 | | |
| 10.68 | 18,572 | 22.38 | 19,619 | 34.18 | 19,930 | 37.68 | 21,127 | 51.18 | | |
| 11.28 | 13,704 | 22.98 | 14,751 | 34.78 | 15,062 | 38.28 | 16,260 | 51.78 | | |
| 11.88 | 8,837 | 23.58 | 9,884 | 35.38 | 10,194 | 38.88 | 11,392 | 52.38 | | |
| 12.48 | 3,969 | 24.18 | 5,016 | 35.98 | 5,326 | 39.48 | 6,524 | 52.98 | | |
| 13.04 | 0.000 | 24.74 | 0.473 | 36.54 | 0.783 | 40.04 | 1,981 | 53.54 | | |

FIG. 13B

With Body Cooling: WIT is constant at its minimum value = 0.05 hours, BCT and CIT are varied from their observed minimum to observed maximum values.

| CIT | BCT=1.07 CFU-TOTAL | Total Ischemia | BCT=6.04 CFU-TOTAL | Total Ischemia | BCT=9.78 CFU-TOTAL | Total Ischemia | BCT=13.90 CFU-TOTAL | Total Ischemia | BCT=22.50 CFU-TOTAL | Total Ischemia |
|---|---|---|---|---|---|---|---|---|---|---|
| 7.40 | 98,515 | 8.52 | 71,035 | 13.49 | 50,355 | 17.23 | 27,575 | 21.35 | 0.00 | 29.95 |
| 8.40 | 98,604 | 9.52 | 71,123 | 14.49 | 50,444 | 18.23 | 27,663 | 22.35 | 0.00 | 30.95 |
| 9.40 | 98,692 | 10.52 | 71,212 | 15.49 | 50,533 | 19.23 | 27,752 | 23.35 | 0.00 | 31.95 |
| 10.40 | 98,781 | 11.52 | 71,301 | 16.49 | 50,621 | 20.23 | 27,841 | 24.35 | 0.00 | 32.95 |
| 11.40 | 98,870 | 12.52 | 71,389 | 17.49 | 50,710 | 21.23 | 27,929 | 25.35 | 0.00 | 33.95 |
| 12.40 | 98,959 | 13.52 | 71,478 | 18.49 | 50,799 | 22.23 | 28,018 | 26.35 | 0.00 | 34.95 |
| 13.40 | 99,047 | 14.52 | 71,567 | 19.49 | 50,887 | 23.23 | 28,107 | 27.35 | 0.00 | 35.95 |
| 14.40 | 99,136 | 15.52 | 71,656 | 20.49 | 50,976 | 24.23 | 28,196 | 28.35 | 0.00 | 36.95 |
| 15.40 | 99,225 | 16.52 | 71,744 | 21.49 | 51,065 | 25.23 | 28,284 | 29.35 | | |
| 16.40 | 99,314 | 17.52 | 71,833 | 22.49 | 51,154 | 26.23 | 28,373 | 30.35 | | |
| 17.40 | 99,402 | 18.52 | 71,922 | 23.49 | 51,242 | 27.23 | 28,462 | 31.35 | | |
| 18.40 | 99,491 | 19.52 | 72,010 | 24.49 | 51,331 | 28.23 | 28,550 | 32.35 | | |
| 19.40 | 99,580 | 20.52 | 72,099 | 25.49 | 51,420 | 29.23 | 28,639 | 33.35 | | |
| 20.40 | 99,668 | 21.52 | 72,188 | 26.49 | 51,508 | 30.23 | 28,728 | 34.35 | | |
| 21.40 | 99,757 | 22.52 | 72,277 | 27.49 | 51,597 | 31.23 | 28,817 | 35.35 | | |

FIG. 13C

With Body Cooling: CIT is constant at its minimum value = 7.4 hours. BCT and WIT are varied from their observed minimum to observed maximum values.

| BCT | WIT=0.05 CFU-TOTAL | Total Ischemia | WIT=0.10 CFU-TOTAL | Total Ischemia | WIT=1.54 CFU-TOTAL | Total Ischemia | WIT=1.92 CFU-TOTAL | Total Ischemia | WIT=2.49 CFU-TOTAL | Total Ischemia |
|---|---|---|---|---|---|---|---|---|---|---|
| 1.07 | 98.52 | 8.52 | 98.11 | 8.57 | 86.43 | 10.01 | 83.34 | 10.39 | 78.72 | 10.96 |
| 2.07 | 92.99 | 9.52 | 92.58 | 9.57 | 80.90 | 11.01 | 77.81 | 11.39 | 73.19 | 11.96 |
| 3.07 | 87.46 | 10.52 | 87.05 | 10.57 | 75.37 | 12.01 | 72.29 | 12.39 | 67.66 | 12.96 |
| 4.07 | 81.93 | 11.52 | 81.52 | 11.57 | 69.84 | 13.01 | 66.76 | 13.39 | 62.13 | 13.96 |
| 5.07 | 76.40 | 12.52 | 75.99 | 12.57 | 64.31 | 14.01 | 61.23 | 14.39 | 56.60 | 14.96 |
| 6.07 | 70.87 | 13.52 | 70.46 | 13.57 | 58.78 | 15.01 | 55.70 | 15.39 | 51.07 | 15.96 |
| 7.07 | 65.34 | 14.52 | 64.93 | 14.57 | 53.25 | 16.01 | 50.17 | 16.39 | 45.54 | 16.96 |
| 8.07 | 59.81 | 15.52 | 59.40 | 15.57 | 47.72 | 17.01 | 44.64 | 17.39 | 40.01 | 17.96 |
| 9.07 | 54.28 | 16.52 | 53.88 | 16.57 | 42.19 | 18.01 | 39.11 | 18.39 | 34.49 | 18.96 |
| 10.07 | 48.75 | 17.52 | 48.35 | 17.57 | 36.66 | 19.01 | 33.58 | 19.39 | 28.96 | 19.96 |
| 11.07 | 43.22 | 18.52 | 42.82 | 18.57 | 31.13 | 20.01 | 28.05 | 20.39 | | |
| 12.07 | 37.69 | 19.52 | 37.29 | 19.57 | 25.60 | 21.01 | 22.52 | 21.39 | | |
| 13.07 | 32.16 | 20.52 | 31.76 | 20.57 | 20.08 | 22.01 | 16.99 | 22.39 | | |
| 14.07 | 26.63 | 21.52 | 26.23 | 21.57 | 14.55 | 23.01 | 11.46 | 23.39 | | |
| 15.07 | 21.11 | 22.52 | 20.70 | 22.57 | 9.02 | 24.01 | 5.93 | 24.39 | | |
| 16.07 | 15.58 | 23.52 | 15.17 | 23.57 | 3.49 | 25.01 | 0.40 | 25.39 | | |
| 17.07 | 10.05 | 24.52 | 9.64 | 24.57 | 0.00 | 26.01 | 0.00 | 26.39 | | |
| 18.07 | 4.52 | 25.52 | 4.11 | 25.57 | 0.00 | 27.01 | 0.00 | 27.39 | | |
| 19.07 | 0.00 | 26.52 | 0.00 | 26.57 | 0.00 | 28.01 | 0.00 | 28.39 | | |
| 20.07 | 0.00 | 27.52 | 0.00 | 27.57 | 0.00 | 29.01 | 0.00 | 29.39 | | |
| 21.07 | 0.00 | 28.52 | 0.00 | 28.57 | 0.00 | 30.01 | | | | |
| 22.50 | 0.00 | 29.52 | 0.00 | 30.00 | 0.00 | 31.44 | | | | |

SYSTEMS AND METHODS FOR EXTRACTION AND CRYOPRESERVATION OF BONE MARROW

CROSS-REFERENCE TO RELATED APPLICATIONS

This application is a continuation application of PCT Application No. PCT/US2021/055081, filed Oct. 14, 2021, which claims the benefit of U.S. Provisional Application No. 63/091,890, filed Oct. 14, 2020; U.S. Provisional Application No. 63/110,571, filed Nov. 6, 2020; U.S. Provisional Application No. 63/130,255, filed Dec. 23, 2020; and U.S. Provisional Application No. 63/168,178, filed Mar. 30, 2021, which are incorporated herein by reference in their entirety.

STATEMENT AS TO FEDERALLY SPONSORED RESEARCH

This invention was made with government support under AI129444 awarded by the National Institutes of Health. The government has certain rights in the invention.

BACKGROUND

Bone marrow for clinical purposes is currently harvested from HLA matched siblings or optimally matched unrelated donors. Other graft sources are also now utilized including mismatched haploidentical related or unrelated donors and umbilical cord blood (CB). When transplanted into patients with certain diseases, the hematopoietic stem cells (HSCs) in the donor bone marrow engraft in the patient and reconstitute immune and hematopoietic systems. Bone marrow is also a good source for mesenchymal stromal/stem cells (MSCs) which are self-renewing, multipotent progenitor cells with multilineage potential to differentiate into cell types of mesodermal origin, such as adipocytes, osteocytes, and chondrocytes.

Currently bone marrow is typically collected through a hole created in the cortical bone with a trocar needle and then using a bone marrow aspiration needle and a syringe to draw the marrow into the syringe. Multiple syringes are usually necessary to extract sufficient marrow from the bone. The syringes are then removed from the sterile field and each syringe is connected to a collection bag containing anticoagulants and the marrow is pushed into the bag. This step is repeated many times, typically in both pelvic bones, and can result in contamination of the aspirate.

It was recognized that whole bone marrow (BM) can be obtained from deceased donors. However, multiple barriers have prevented mainstream use of cadaveric bone marrow. One significant barrier has been in finding a streamlined process for controlled extraction and preservation of deceased donor bone marrow and the cell yields from that bone marrow. Another concern regarding the use of cadaveric bone relates to the cryopreservation and recovery of the bone. In particular, the concern relates to the quality of viable cells, such as HSCs, which can be obtained from cryopreserved donor bone.

SUMMARY

An aspect of the present disclosure comprises a method for processing a biological sample comprising cells or a derivative thereof, the method comprising: generating a first volume of the biological sample comprising cells or a derivative thereof, wherein the first volume comprises a first concentration of cells or a derivative thereof; generating a second volume of the biological sample comprising cells or a derivative thereof, wherein the second volume is less than the first volume and comprises a second concentration of the cells wherein the second concentration of the cells is no more than 30% different than the first concentration of the cells; and cooling the first volume at a first cooling rate and cooling the second volume at a second cooling rate, wherein the first cooling rate is about the same as the second cooling rate; wherein a post-thaw cell proliferation rate of the cells in the first volume is no more than 30% different than a post-thaw proliferation rate of the cells in the second volume. In some embodiments, the first volume is contained in a first container, wherein the second volume is contained in a second container, and wherein the first container and the second container are exposed to a common temperature. In some embodiments the second volume is less than 50% of the first volume. In some embodiments the second volume is less than 40% of the first volume. In some embodiments the second volume is less than 37.5% of the first volume. In some embodiments the second volume is less than 35% of the first volume. In some embodiments the second volume is less than 30% of the first volume. In some embodiments the second volume is less than 20% of the first volume. In some embodiments the second volume is less than 15% of the first volume. In some embodiments the second volume is less than 10% of the first volume. In some embodiments the second volume is less than 5% of the first volume. In some embodiments the second volume is less than 1% of the first volume. In some embodiments a post-thaw viability rate of the cells in the first volume is no more than 30% different than a post-thaw viability rate of the cells in the second volume. In some embodiments a post-thaw viability rate of the cells in the first volume is no more than 25% different than a post-thaw viability rate of the cells in the second volume. In some embodiments a post-thaw viability rate of the cells in the first volume is no more than 20% different than a post-thaw viability rate of the cells in the second volume. In some embodiments a post-thaw viability rate of the cells in the first volume is no more than 15% different than a post-thaw viability rate of the cells in the second volume. In some embodiments a post-thaw viability rate of the cells in the first volume is no more than 13.6% different than a post-thaw viability rate of the cells in the second volume. In some embodiments a post-thaw viability rate of the cells in the first volume is no more than 10% different than a post-thaw viability rate of the cells in the second volume. In some embodiments a post-thaw viability rate of the cells in the first volume is no more than 5% different than a post-thaw viability rate of the cells in the second volume. In some embodiments a post-thaw cell proliferation rate of the cells in the first volume is no more than 25% different than a post-thaw proliferation rate of the cells in the second volume. In some embodiments a post-thaw cell proliferation rate of the cells in the first volume is no more than 20% different than a post-thaw proliferation rate of the cells in the second volume. In some embodiments a post-thaw cell proliferation rate of the cells in the first volume is no more than 15% different than a post-thaw proliferation rate of the cells in the second volume. In some embodiments a post-thaw cell proliferation rate of the cells in the first volume is no more than 13.6% different than a post-thaw proliferation rate of the cells in the second volume. In some embodiments a post-thaw cell proliferation rate of the cells in the first volume is no more than 10% different than a post-thaw proliferation rate of the cells in the second volume. In some embodiments a post-thaw cell proliferation rate of the cells in the first volume is no more than 5% different than a post-thaw proliferation rate of the cells in the second volume. In some embodiments the post-thaw viability rate of the cells is at least 50%. In some embodiments the post-thaw proliferation rate of the cells is at least 1 CFU-GM/$10^5$ cells. In some embodiments the first cooling rate and the second cooling rate comprise a supra-freeze rate from about −0.1° C./min to about −5° C./min at least until ice has nucleated in a freezing medium. In some embodiments the first cooling rate and the second cooling rate comprise a supra-freeze rate from about −2.5° C./min to about −4° C./min at least until ice has nucleated in a freezing medium. In some embodiments the first cooling rate and the second cooling rate comprise a supra-freeze rate from about −2.5° C./min to about −3.5° C./min at least until ice has nucleated in a freezing medium. In some embodiments the first cooling rate and the second cooling rate comprise a sub-freeze rate from about −1° C./min to about −2° C./min. In some embodiments the post-thaw viability rate of the cells is at least 60%. In some embodiments the post-thaw viability rate of the cells is at least 70%. In some embodiments the post-thaw viability rate of the cells is at least 80%. In some embodiments the post-thaw viability rate of the cells is at least 90%. In some embodiments (c) occurs in one or more freezers. In some embodiments the first container and the second container are disposed in a first freezer of the one or more freezers. In some embodiments the first container is contained in a first freezer of the one or more freezers and the second container is contained in a second freezer of the one or more freezers. In some embodiments the one or more freezers comprise a static freezer. In some embodiments the first freezer, the second freezer, or both is a static freezer. method of any one of the preceding claims, wherein the one or more freezers comprise a controlled-rate freezer. In some embodiments the first freezer, the second freezer, or both is a controlled-rate freezer. In some embodiments the one or more freezers are set at about −70° C. to −90° C. In some embodiments the one or more freezers are set at less than −80° C. In some embodiments the one or more freezers are set at −86° C. In some embodiments the second volume is placed directly in an insulating container, such that each vial is in close proximity to the insulating material of the insulating container. In some embodiments the method further comprises arranging the first volume inside the static freezer such that the first volume does not contact a wall of the one or more freezers. In some embodiments the biological sample comprising cells or a derivative thereof, in the first volume and the biological sample comprising cells or a derivative thereof, in the second volume experience a same cooling rate. In some embodiments the cells are stem cells or immune cells. In some embodiments the stem cells comprise hematopoietic stem cells (HSC), mesenchymal stem cells (MSC), or both. In some embodiments the biological sample comprises one or more organs, blood, or both. In some embodiments the immune cells comprise T cells. In some embodiments the blood is cord blood or peripheral blood. In some embodiments the HSCs comprise CD34+ cells. In various embodiments, the method further comprises a step of transferring the first volume and the second volume to a long-term storage container, e.g., a long-term storage container is colder than −86° C.

Another aspect of the present disclosure comprises a method for processing bone marrow or a derivative thereof, the method comprising: generating a first volume of the bone marrow or a derivative thereof, wherein the first volume comprises a first concentration of the bone marrow or a derivative thereof; generating a second volume of the bone marrow or a derivative thereof, wherein the second volume is less than the first volume and comprises a second concentration wherein the second concentration is no more than 30% different than the first concentration; and cooling the first volume at a first cooling rate and cooling the second volume at a second cooling rate, wherein the first cooling rate is about the same as the second cooling rate; wherein a post-thaw cell proliferation rate of a population of bone marrow derived cells in the first volume is no more than 30% different than a post-thaw proliferation rate of a population of bone marrow derived cells in the second volume. In some embodiments the first volume is contained in a first container, wherein the second volume is contained in a second container, and wherein the first container and the second container are exposed to a single/same temperature. In some embodiments the second volume is less than 50% of the first volume. In some embodiments the second volume is less than 40% of the first volume. In some embodiments the second volume is less than 37.5% of the first volume. In some embodiments the second volume is less than 35% of the first volume. In some embodiments the second volume is less than 30% of the first volume. In some embodiments the second volume is less than 20% of the first volume. In some embodiments the second volume is less than 15% of the first volume. In some embodiments the second volume is less than 10% of the first volume. In some embodiments the second volume is less than 5% of the first volume. In some embodiments the second volume is less than 1% of the first volume. In some embodiments a post-thaw viability rate of a population of bone marrow derived cells in the first volume is no more than 30% different than a post-thaw viability rate of a population of bone marrow derived cells in the second volume. In some embodiments a post-thaw viability rate of the population of bone marrow derived cells in the first volume is no more than 25% different than a post-thaw viability rate of the population of bone marrow derived cells in the second volume. In some embodiments a post-thaw viability rate of the population of bone marrow derived cells in the first volume is no more than 20% different than a post-thaw viability rate of the population of bone marrow derived cells in the second volume. In some embodiments a post-thaw viability rate of the population of bone marrow derived cells in the first volume is no more than 15% different than a post-thaw viability rate of the population of bone marrow derived cells in the second volume. In some embodiments a post-thaw viability rate of the population of bone marrow derived cells in the first volume is no more than 13.6% different than a post-thaw viability rate of the population of bone marrow derived cells in the second volume. In some embodiments a post-thaw viability rate of the population of bone marrow derived cells in the first volume is no more than 10% different than a post-thaw viability rate of the population of bone marrow derived cells in the second volume. In some embodiments a post-thaw viability rate of the population of bone marrow derived cells in the first volume is no more than 5% different than a post-thaw viability rate of the population of bone marrow derived cells in the second volume. In some embodiments a post-thaw cell proliferation rate of the population of bone marrow derived cells in the first volume is no more than 25% different than a post-thaw proliferation rate of the population of bone marrow derived cells in the second volume. In some embodiments a post-thaw cell proliferation rate of the population of bone marrow derived cells in the first volume is no more than 20% different than a post-thaw proliferation rate of the population of bone marrow derived cells in the second volume. In some embodiments a post-thaw cell proliferation rate of the population of bone marrow derived cells in the first volume is no more than 15% different than a post-thaw proliferation rate of the population of bone marrow derived cells in the second volume. In some embodiments a post-thaw cell proliferation rate of the population of bone marrow derived cells in the first volume is no more than 13.6% different than a post-thaw proliferation rate of the population of bone marrow derived cells in the second volume. In some embodiments a post-thaw cell proliferation rate of the population of bone marrow derived cells in the first volume is no more than 10% different than a post-thaw proliferation rate of the population of bone marrow derived cells in the second volume. In some embodiments a post-thaw cell proliferation rate of the population of bone marrow derived cells in the first volume is no more than 5% different than a post-thaw proliferation rate of the population of bone marrow derived cells in the second volume. In some embodiments the post-thaw viability rate of a population of bone marrow derived cells is at least 50%. In some embodiments the post-thaw proliferation rate of a population of bone marrow derived cells is at least 1 CFU-GM/$10^5$ cells. In some embodiments the first cooling rate and the second cooling rate comprise a supra-freeze rate from about −0.1° C./min to about −5° C./min at least until ice has nucleated in a freezing medium. In some embodiments the first cooling rate and the second cooling rate comprise a supra-freeze rate from about −2.5° C./min to about −4° C./min at least until ice has nucleated in a freezing medium. In some embodiments the first cooling rate and the second cooling rate comprise a supra-freeze rate from about −2.5° C./min to about −3.5° C./min at least until ice has nucleated in a freezing medium. In some embodiments the first cooling rate and the second cooling rate comprise a sub-freeze rate from about −1° C./min to about −2° C./min. In some embodiments the post-thaw viability rate of a population of bone marrow derived cells is at least 60%. In some embodiments the post-thaw viability rate of a population of bone marrow derived cells is at least 70%. In some embodiments the post-thaw viability rate of a population of bone marrow derived cells is at least 80%. In some embodiments the post-thaw viability rate of a population of bone marrow derived cells is at least 90%. In some embodiments (c) occurs in one or more freezers. In some embodiments the first container and the second container are disposed in a first freezer of the one or more freezers. In some embodiments the first container is contained in a first freezer of the one or more freezers and the second container is contained in a second freezer of the one or more freezers. In some embodiments the one or more freezers comprise a static freezer. In some embodiments the first freezer, the second freezer, or both is a static freezer. method of any one of the preceding claims, wherein the one or more freezers comprise a controlled-rate freezer. In some embodiments the first freezer, the second freezer, or both is a controlled-rate freezer. In some embodiments the one or more freezers are set at about −70° C. to −90° C. In some embodiments the one or more freezers are set at less than −80° C. In some embodiments the one or more freezers are set at −86° C. In some embodiments the second volume is placed directly in an insulating container, such that each vial is in close proximity to the insulating material of the insulating container. In some embodiments the method further comprises arranging the first volume inside the static freezer such that the first volume does not contact a wall of the one or more freezers. In some embodiments the bone marrow or a derivative thereof, in the first volume and the bone marrow or a derivative thereof, in the second volume experience a same cooling rate. In some embodiments the bone marrow derived cells are stem cells or immune cells. In some embodiments the stem cells comprise hematopoietic stem cells (HSC), mesenchymal stem cells (MSC), or both. In some embodiments the HSCs comprise CD34+ cells. In various embodiments, the method further comprises a step of transferring the first volume and the second volume to a long-term storage container, e.g., a long-term storage container is colder than −86° C.

Another aspect of the present disclosure comprises a method for processing MSCs, the method comprising: generating a first volume of the MSCs, wherein the first volume comprises a first concentration of the bone marrow or a derivative thereof; generating a second volume of the MSCs, wherein the second volume is less than the first volume and comprises a second concentration wherein the second concentration is no more than 30% different than the first concentration; and cooling the first volume at a first cooling rate and cooling the second volume at a second cooling rate, wherein the first cooling rate is about the same as the second cooling rate; wherein a post-thaw cell proliferation rate of the MSCs in the first volume is no more than 30% different than a post-thaw proliferation rate of the MSCs in the second volume. In some embodiments the first volume is contained in a first container, wherein the second volume is contained in a second container, and wherein the first container and the second container are exposed to a single/same temperature. In some embodiments the second volume is less than 50% of the first volume. In some embodiments the second volume is less than 40% of the first volume. In some embodiments the second volume is less than 37.5% of the first volume. In some embodiments the second volume is less than 35% of the first volume. In some embodiments the second volume is less than 30% of the first volume. In some embodiments the second volume is less than 20% of the first volume. In some embodiments the second volume is less than 15% of the first volume. In some embodiments the second volume is less than 10% of the first volume. In some embodiments the second volume is less than 5% of the first volume. In some embodiments the second volume is less than 1% of the first volume. In some embodiments a post-thaw viability rate of the MSCs in the first volume is no more than 30% different than a post-thaw viability rate of the MSCs in the second volume. In some embodiments a post-thaw viability rate of the MSCs in the first volume is no more than 25% different than a post-thaw viability rate of the MSCs in the second volume. In some embodiments a post-thaw viability rate of the MSCs in the first volume is no more than 20% different than a post-thaw viability rate of the MSCs in the second volume. In some embodiments a post-thaw viability rate of the MSCs in the first volume is no more than 15% different than a post-thaw viability rate of the MSCs in the second volume. In some embodiments a post-thaw viability rate of the MSCs in the first volume is no more than 13.6% different than a post-thaw viability rate of the MSCs in the second volume. In some embodiments a post-thaw viability rate of the MSCs in the first volume is no more than 10% different than a post-thaw viability rate of the MSCs in the second volume. In some embodiments a post-thaw viability rate of the MSCs in the first volume is no more than 5% different than a post-thaw viability rate of the MSCs in the second volume. In some embodiments a post-thaw cell proliferation rate of the MSCs in the first volume is no more than 25% different than a post-thaw proliferation rate of the MSCs in the second volume. In some embodiments a post-thaw cell proliferation rate of the MSCs in the first volume is no more than 20% different than a post-thaw proliferation rate of the MSCs in the second volume. In some embodiments a post-thaw cell proliferation rate of the MSCs in the first volume is no more than 15% different than a post-thaw proliferation rate of the MSCs in the second volume. In some embodiments a post-thaw cell proliferation rate of the MSCs in the first volume is no more than 13.6% different than a post-thaw proliferation rate of the MSCs in the second volume. In some embodiments a post-thaw cell proliferation rate of the MSCs in the first volume is no more than 10% different than a post-thaw proliferation rate of the MSCs in the second volume. In some embodiments a post-thaw cell proliferation rate of the MSCs in the first volume is no more than 5% different than a post-thaw proliferation rate of the MSCs in the second volume. In some embodiments the post-thaw viability rate of the MSCs is at least 50%. In some embodiments the post-thaw proliferation rate of the MSCs is at least 1 CFU-GM/$10^5$ MSCs. In some embodiments the first cooling rate and the second cooling rate comprise a supra-freeze rate from about −0.1° C./min to about −5° C./min at least until ice has nucleated in a freezing medium. In some embodiments the first cooling rate and the second cooling rate comprise a supra-freeze rate from about −2.5° C./min to about −4° C./min at least until ice has nucleated in a freezing medium. In some embodiments the first cooling rate and the second cooling rate comprise a supra-freeze rate from about −2.5° C./min to about −3.5° C./min at least until ice has nucleated in a freezing medium. In some embodiments the first cooling rate and the second cooling rate comprise a sub-freeze rate from about −1° C./min to about −2° C./min. In some embodiments the post-thaw viability rate of the MSCs is at least 60%. In some embodiments the post-thaw viability rate of the MSCs is at least 70%. In some embodiments the post-thaw viability rate of the MSCs is at least 80%. In some embodiments the post-thaw viability rate of the MSCs is at least 90%. In some embodiments (c) occurs in one or more freezers. In some embodiments the first container and the second container are disposed in a first freezer of the one or more freezers. In some embodiments the first container is contained in a first freezer of the one or more freezers and the second container is contained in a second freezer of the one or more freezers. In some embodiments the one or more freezers comprise a static freezer. In some embodiments the first freezer, the second freezer, or both is a static freezer. In some embodiments the one or more freezers comprise a controlled-rate freezer. In some embodiments the first freezer, the second freezer, or both is a controlled-rate freezer. In some embodiments the one or more freezers are set at about −70° C. to −90° C. In some embodiments the one or more freezers are set at less than −80° C. In some embodiments the one or more freezers are set at −86° C. In some embodiments the second volume is placed directly in an insulating container, such that each vial is in close proximity to the insulating material of the insulating container. In some embodiments the method further comprises arranging the first volume inside the static freezer such that the first volume does not contact a wall of the one or more freezers. In some embodiments the MSCs in the first volume and the MSCs in the second volume experience a same cooling rate. In some embodiments the MSCs are bone marrow derived MSCs (BM-MSC) or vertebral bone adherent MSCs (vBA-MSC).

Another aspect of the present disclosure comprises a method for processing a biological sample comprising cells or a derivative thereof, the method comprising: generating a first volume of the biological sample comprising cells or a derivative thereof, wherein the first volume comprises a first concentration of cells or a derivative thereof; generating a second volume of the biological sample comprising cells or a derivative thereof, wherein the second volume is less than the first volume and comprises a second concentration of the cells wherein the second concentration of the cells is no more than 30% different than the first concentration of the cells; generating a freezing curve specific for the cells; cooling the first volume at a first cooling rate, wherein the first cooling rate is generated from the freezing curve; and cooling the second volume at a second cooling rate, wherein the first cooling rate is generated from the freezing curve; wherein the first cooling rate is about the same as than the second cooling rate and wherein a post-thaw cell proliferation rate of the cells in the first volume is no more than 30% different than a post-thaw proliferation rate of the cells in the second volume. The method of claim 1, wherein the first volume is contained in a first container, wherein the second volume is contained in a second container, and wherein the first container and the second container are exposed to a single/same temperature. In some embodiments the second volume is less than 50% of the first volume. In some embodiments the second volume is less than 40% of the first volume. In some embodiments the second volume is less than 37.5% of the first volume. In some embodiments the second volume is less than 35% of the first volume. In some embodiments the second volume is less than 30% of the first volume. In some embodiments the second volume is less than 20% of the first volume. In some embodiments the second volume is less than 15% of the first volume. In some embodiments the second volume is less than 10% of the first volume. In some embodiments the second volume is less than 5% of the first volume. In some embodiments the second volume is less than 1% of the first volume. In some embodiments a post-thaw viability rate of the cells in the first volume is no more than 30% different than a post-thaw viability rate of the cells in the second volume. In some embodiments a post-thaw viability rate of the cells in the first volume is no more than 25% different than a post-thaw viability rate of the cells in the second volume. In some embodiments a post-thaw viability rate of the cells in the first volume is no more than 20% different than a post-thaw viability rate of the cells in the second volume. In some embodiments a post-thaw viability rate of the cells in the first volume is no more than 15% different than a post-thaw viability rate of the cells in the second volume. In some embodiments a post-thaw viability rate of the cells in the first volume is no more than 13.6% different than a post-thaw viability rate of the cells in the second volume. In some embodiments a post-thaw viability rate of the cells in the first volume is no more than 10% different than a post-thaw viability rate of the cells in the second volume. In some embodiments a post-thaw viability rate of the cells in the first volume is no more than 5% different than a post-thaw viability rate of the cells in the second volume. In some embodiments a post-thaw cell proliferation rate of the cells in the first volume is no more than 25% different than a post-thaw proliferation rate of the cells in the second volume. In some embodiments a post-thaw cell proliferation rate of the cells in the first volume is no more than 20% different than a post-thaw proliferation rate of the cells in the second volume. In some embodiments a post-thaw cell proliferation rate of the cells in the first volume is no more than 15% different than a post-thaw proliferation rate of the cells in the second volume. In some embodiments a post-thaw cell proliferation rate of the cells in the first volume is no more than 13.6% different than a post-thaw proliferation rate of the cells in the second volume. In some embodiments a post-thaw cell proliferation rate of the cells in the first volume is no more than 10% different than a post-thaw proliferation rate of the cells in the second volume. In some embodiments a post-thaw cell proliferation rate of the cells in the first volume is no more than 5% different than a post-thaw proliferation rate of the cells in the second volume. In some embodiments the post-thaw viability rate of the cells is at least 50%. In some embodiments the post-thaw proliferation rate of the cells is at least 1 CFU-GM/$10^5$ cells. In some embodiments the post-thaw viability rate of the cells is at least 60%. In some embodiments the post-thaw viability rate of the cells is at least 70%. In some embodiments the post-thaw viability rate of the cells is at least 80%. In some embodiments the post-thaw viability rate of the cells is at least 90%. In some embodiments (c) occurs in one or more freezers. In some embodiments the first container and the second container are disposed in a first freezer of the one or more freezers. In some embodiments the first container is contained in a first freezer of the one or more freezers and the second container is contained in a second freezer of the one or more freezers. In some embodiments the one or more freezers comprise a static freezer. In some embodiments the first freezer, the second freezer, or both is a static freezer. method of any one of the preceding claims, wherein the one or more freezers comprise a controlled-rate freezer. In some embodiments the first freezer, the second freezer, or both is a controlled-rate freezer. In some embodiments the one or more freezers are set at about −70° C. to −90° C. In some embodiments the one or more freezers are set at less than −80° C. In some embodiments the one or more freezers are set at −86° C. In some embodiments the second volume is placed directly in an insulating container, such that each vial is in close proximity to the insulating material of the insulating container. In some embodiments the method further comprises arranging the first volume inside the static freezer such that the first volume does not contact a wall of the one or more freezers. In some embodiments the biological sample comprising cells or a derivative thereof, in the first volume and the biological sample comprising cells or a derivative thereof, in the second volume experience a same cooling rate. In some embodiments the cells are stem cells or immune cells. In some embodiments the stem cells comprise hematopoietic stem cells (HSC), mesenchymal stem cells (MSC), or both. In some embodiments the biological sample comprises one or more organs, blood, or both. In some embodiments the immune cells comprise T cells. In some embodiments the blood is cord blood or peripheral blood. In some embodiments the HSCs comprise CD34+ cells. In various embodiments, the method further comprises a step of transferring the first volume and the second volume to a long-term storage container, e.g., a long-term storage container is colder than −86° C.

Another aspect of the present disclosure comprises a method for processing bone marrow or a derivative thereof, wherein the bone marrow or the derivative thereof is derived from a deceased donor, the method comprising: obtaining a bone or bone fragment from a deceased donor, optionally, processing the bone into bone fragments; extracting the bone marrow or the derivative thereof from the bone or bone fragment; and cryopreserving the bone marrow or the derivative thereof, wherein the cryopreserving comprises decreasing temperature of the bone marrow or the derivative thereof at a freeze rate of more than about −1° C./min in a static temperature freezer. In some embodiments, the cryopreserving comprises cooling the bone marrow or the derivative thereof at a supra-freeze rate from about −2.5° C./min to about −5° C./min at least until ice has nucleated in a freezing medium. In some embodiments, the cryopreserving comprises cooling the bone marrow or the derivative thereof at a supra-freeze rate from about −2.5° C./min to about −4° C./min at least until ice has nucleated in a freezing medium. In some embodiments, the cryopreserving comprises cooling the bone marrow or the derivative thereof at a supra-freeze rate from about −2.5° C./min to about −3.5° C./min at least until ice has nucleated in a freezing medium. In some embodiments, the cryopreserving comprises cooling the bone marrow or the derivative thereof at a sub-freeze rate from about −1° C./min to about −2° C./min. In some embodiments, the supra-freeze rate and the sub-freeze rate are maintained without the use of a passive cool box. In some embodiments, the cryopreserving comprises arranging one or more aliquots of the bone marrow or the derivative thereof inside the static freezer such that no aliquot contacts a wall of the static freezer. In various embodiments, within the static freezer, no aliquot of the bone marrow or the derivative thereof is stored directly on top of another aliquot of the bone marrow or the derivative thereof. In some embodiments, the bone marrow or the derivative thereof comprises a population of CD34+ cells. In some embodiments, the population of CD34+ cells comprises at least 70% viable CD34+ cells after the bone marrow or the derivative thereof is thawed. In some embodiments, the population of CD34+ cells comprises at least 80% viable CD34+ cells after the bone marrow or the derivative thereof is thawed. In some embodiments, the static freezer is set at about −70° C. to −90° C. In some embodiments, the static freezer is set at −86° C. In some embodiments, the static freezer is set at less than −80° C.

An aspect of the present disclosure comprises a method for processing bone marrow or a derivative thereof, wherein the bone marrow or the derivative thereof is derived from a deceased donor, the method comprising: obtaining a bone from a deceased donor; contacting the bone with a bleach solution for at least about 10 minutes to at least about 25 minutes, wherein the bone is submerged in the bleach solution; extracting the bone marrow or the derivative thereof from the bone, wherein at least 90% of CD34+ cells comprised in the bone marrow or the derivative thereof are viable. In some embodiments, the bone marrow or derivative thereof is contacted with the bleach solution for at least about 25 minutes. In some embodiments, the bleach solution comprises 10% bleach. In some embodiments, the bone is a vertebral body. In some embodiments, the hydrogen peroxide is a 3% hydrogen peroxide solution. In some embodiments, the method further comprises transferring the bleached bone product from a container comprising the bleach solution to a container containing the hydrogen peroxide solution. In some embodiments, the method further comprises agitating the bleached bone product within the hydrogen peroxide solution. In some embodiments, c) of submerging the bleached bone product in a solution comprising hydrogen peroxide comprises: submerging the bleached bone product in a container containing the hydrogen peroxide solution; detecting foam or froth associated with the bleached bone product; and repeating i and/or ii until no foam or froth is detected. In some embodiments, the method further comprises manually removing soft tissue from a bleached bone product that is associated with foam or froth in ii. In some embodiments, an inert contrast dye is added to the solution comprising hydrogen peroxide to enhance visibility of any foam or froth associated with the bleached bone product.

Yet another aspect of the present disclosure is a method for processing bone marrow or a derivative thereof, wherein the bone marrow or the derivative thereof is derived from a deceased donor, the method comprising: obtaining a bone or bone fragment from a deceased donor, optionally, processing the bone into bone fragments; mechanically grinding the bone or bone fragment in the presence of a grinding solution to generate a plurality of bone grindings; placing the plurality of bone grindings on a shaker at about 100 to about 200 rotations per minute ("RPM") for about 1 to about 20 minutes; and removing the solution from the shaker, wherein the solution comprises the bone marrow or the derivative thereof and wherein the bone marrow or the derivative thereof comprises at least about 1,000 CD34+ cells/ml, 1,500 CD34+ cells/ml, 3,000 CD34+ cells/ml, 5,000 CD34+ cells/ml, 10,000 CD34+ cells/ml, 15,000 CD34+ cells/ml, 30,000 CD34+ cells/ml, 50,000 CD34+ cells/ml, 100,000 CD34+ cells/ml, 150,000 CD34+ cells/ml, 200,000 CD34+ cells/ml, 250,000 CD34+ cells/ml, 300,000 CD34+ cells/ml, 350,000 CD34+ cells/ml, 400,000 CD34+ cells/ml, 450,000 CD34+ cells/ml, 500,000 CD34+ cells/ml, 550,000 CD34+ cells/ml, 600,000 CD34+ cells/ml, 650,000 CD34+ cells/ml, 700,000 CD34+ cells/ml, 750,000 CD34+ cells/ml, 800,000 CD34+ cells/ml, 850,000 CD34+ cells/ml, 900,000 CD34+ cells/ml, 950,000 CD34+ cells/ml, 1,000,000 CD34+ cells/ml, 1,050,000 CD34+ cells/ml, 1,100,000 CD34+ cells/ml, 1,150,000 CD34+ cells/ml, 1,200,000 CD34+ cells/ml, 1,250,000 CD34+ cells/ml, 1,300,000 CD34+ cells/ml, 1,350,000 CD34+ cells/ml, 1,400,000 CD34+ cells/ml, 1,450,000 CD34+ cells/ml, 1,500,000 CD34+ cells/ml, 1,550,000 CD34+ cells/ml, 1,600,000 CD34+ cells/ml, 1,650,000 CD34+ cells/ml, 1,700,000 CD34+ cells/ml, 1,750,000 CD34+ cells/ml, 1,800,000 CD34+ cells/ml, 1,850,000 CD34+ cells/ml, 1,900,000 CD34+ cells/ml, 1950,000 CD34+ cells/ml, 2,000,000 CD34+ cells/ml, 2,000,000 CD34+ cells/ml, 3,000,000 CD34+ cells/ml, 5,000,000 CD34+ cells/ml, or 10,000,000 CD34+ cells/ml or more, of the bone marrow or the derivative thereof.

In some embodiments, the method further comprises, contacting the solution with a rinse media and repeating c. and then removing the solution from the shaker. In some embodiments, the method further comprises repeating step c. and then removing the solution from the shaker one or more times. In some embodiments, the at least about 1,500,000 CD34+ cells/ml of the bone marrow or the derivative thereof comprises at least 85% viable CD34+ cells. In some embodiments, the at least about 1,500,000 CD34+ cells/ml of the bone marrow or the derivative thereof comprises at least 90% viable CD34+ cells.

Another aspect of the present disclosure comprises a method for processing a population of CD34+ cells obtained from bone marrow or a derivative thereof, wherein the bone marrow or the derivative thereof is derived from a deceased donor, the method comprising: obtaining a bone or bone fragment from a deceased donor, optionally, processing the bone into bone fragments; extracting the bone marrow or derivative thereof from the bone or bone fragment; and contacting the bone marrow or derivative thereof with a stabilization buffer, wherein the stabilization buffer comprises more than about 3 U/ml of a nuclease; performing a CD34+ cell isolation assay to generate a cellular composition comprising the population of CD34+ cells, wherein the composition comprising the population of CD34+ cells comprises at least about 80,000 CD34+ cells/750 µl of the bone marrow or the derivative thereof contacted with the stabilization buffer. In some embodiments, the at least about 80,000 CD34+ cells/750 µl of the bone marrow or the derivative thereof contacted with the stabilization buffer comprise at least 70% viable CD34+ cells. In some embodiments, the at least about 80,000 CD34+ cells/750 µl of the bone marrow or the derivative thereof contacted with the stabilization buffer comprise at least 80% viable CD34+ cells. In some embodiments, the at least about 80,000 CD34+ cells/750 µl of the bone marrow or the derivative thereof contacted with the stabilization buffer comprise at least 90% viable CD34+ cells. In some embodiments, the stabilization buffer comprises more than about 5 U/ml of a nuclease. In some embodiments, the stabilization buffer comprises more than about 10 U/ml of a nuclease. In some embodiments, the stabilization buffer comprises more than about 15 U/ml of a nuclease. In some embodiments, the stabilization buffer comprises about 20 U/ml of a nuclease. In some embodiments, the stabilization buffer comprises more than about 20 U/ml of a nuclease. In some embodiments, the nucleases is Benzonase® or Denarase®. In some embodiments, the stabilization buffer further comprises more than about 5 U/ml of an anticoagulant. In some embodiments, the stabilization buffer further comprises more than about 10 U/ml of an anticoagulant. In some embodiments, the stabilization buffer further comprises about 10 U/ml of an anticoagulant. In some embodiments, the anticoagulant is heparin. In some embodiments, the stabilization buffer further comprises human serum albumin (HSA). In some embodiments, the stabilization buffer comprises 0.5% HSA.

Another aspect of the present disclosure comprises a stabilization buffer comprising: at least 5 U/ml of an anticoagulant; and more than 3 U/ml of a nuclease. In some embodiments, the stabilization buffer comprises more than about 5 U/ml of a nuclease. In some embodiments, the stabilization buffer comprises more than about 10 U/ml of a nuclease. In some embodiments, the stabilization buffer comprises more than about 15 U/ml of a nuclease. In some embodiments, the stabilization buffer comprises more than about 20 U/ml of a nuclease. In some embodiments, the stabilization buffer comprises about 20 U/ml of a nuclease. In some embodiments, the nuclease is Benzonase® or Denarase®. In some embodiments, the stabilization buffer further comprises more than about 10 U/ml of an anticoagulant. In some embodiments, the stabilization buffer further comprises about 10 U/ml of an anticoagulant. In some embodiments, the anticoagulant is heparin. In some embodiments, the stabilization buffer further comprises human serum albumin (HSA). In some embodiments, the stabilization buffer comprises 0.5% HSA.

Any aspect or embodiment described herein can be combined with any other aspect or embodiment as disclosed herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIGS. 7A and 7B are side and perspective views of an automated bone processing system according to one aspect of the present disclosure.

FIGS. 9A and 9B are perspective and front views of a bone grinding station of the system shown in FIG. 7A and FIG. 7B.

FIGS. 11A-11C are tables of CD34+ cell viability as a function of warm and cold ischemia times, without and without body cooling.

FIGS. 12A-12C are tables of CFU-Total as a function of warm and cold ischemia times, with and without body cooling.

FIGS. 13A-13C are tables of CFU-Total as a function of warm and cold ischemia times, with and without body cooling.

FIG. 17A shows the bone marrow cells slurry after antibody labeling. The numerical numbering corresponds to the buffer used. Bone marrow cell sample processed with the stabilization buffer (4) exhibited absence of aggregates. FIG. 17B shows lack of aggregate being trapped after filtration in the bone marrow cell sample processed with the stabilization buffer. FIG. 17C and FIG. 17D illustrates the formation of aggregates of bone marrow cells processed with CliniMACS buffer (FIG. 17C) or absence of aggregates of bone marrow cells processed with the stabilization buffer (FIG. 17D).

FIG. 17E shows that the bone marrow cells processed with the stabilization buffer exhibited increased yield of viability and CD34 expression of bone marrow cells. Purity was greater than 60%, and above 60% CD34 cells were recovered. The ratio between CD3 count and CD34 count was 0.5% (e.g. 5 cells expressing CD3 per 100 cells expressing CD34).

Figure 1:
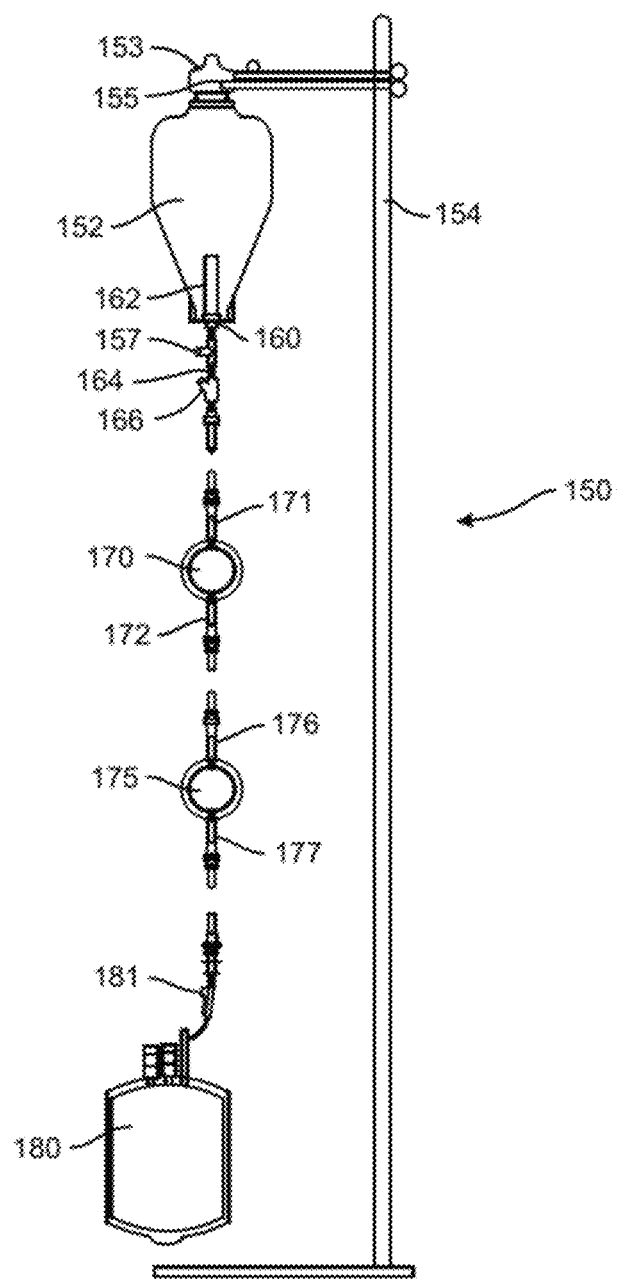
FIG. 1 is a view of a filtration system according to one feature of the present disclosure.

The novel features of the disclosure are set forth with particularity in the appended claims. A better understanding of the features and advantages of the present disclosure will be obtained by reference to the following detailed description that sets forth illustrative embodiments.

DETAILED DESCRIPTION

Introduction

The compositions, systems, and methods disclosed herein provide a needed complement to existing bone marrow and stem cell sources. Specifically, the compositions, systems, and methods disclosed herein provide techniques for the isolation, processing, and use of bone marrow and hematopoietic stem cells ("HSCs") from human cadavers. Features that are unique to the compositions, systems, and methods described herein result in improvements to the current state of the art. These features result in significantly improved yield of functional bone marrow and HSCs, lessening the overall burden on resources typically required for bone marrow and HSC isolation, processing, and use.

The compositions, systems, and methods disclosed herein provide a departure from the isolation and processing techniques of bone marrow and HSCs known in the art, particularly those techniques utilized for processing bone marrow and HSCs from living donors. The present disclosure describes various embodiments the processing techniques utilized to generate the bone marrow and HSC compositions described herein.

As described below, various bones are removed from deceased donors and prepared for mechanic and enzymatic processing. The bones are then mechanically processed where bone marrow and/or bone marrow derived cells (e.g. HSCs) filtered to produce viable bone marrow (and HSCs contained in or adjacent to the bone marrow) compositions. The bone and cellular compositions are further mechanically/enzymatically processed to produce optimal yields of viable cells. These processing steps provide deviations from the current state of the art that result in improved cellular compositions and methods of processing.

The bone marrow is then further processed for either immediate use or preservation. In some embodiments, the bone marrow is further processed to generate cellular compositions comprising specific HSC populations (e.g. CD34+ cells). Optimized compositions, systems, and methods are described herein, providing for improved bone marrow and HSC processing techniques and compositions.

These optimized compositions, systems, and methods described herein present unique solutions to the current problems realized by medical practitioners (e.g. immunology, regenerative medicine). Utilizing the optimized compositions, systems, and methods described herein can result in bone marrow "banks" or depots that will have more viable cells than current depots, and the bone marrow depots generated using the compositions, systems, and methods described herein will also have more diverse (e.g. different HLA phenotypes) bone marrow/HSC compositions, resulting in a larger population of potential subjects that can benefit from the bone marrow depots generated using the compositions, systems, and methods described herein.

Aspects of the present disclosure provide a cryopreserved cell product that is divided into two volumes, with a first volume (e.g., cryopreservation bag) for containing the cell product for transplant into a subject in need thereof and a second volume that acts as a surrogate for the first volume. As used herein, a surrogate vial is typically a smaller volume of the cell product and the surrogate can be thawed and assayed as needed, e.g., for cell viability (and especially "function viability" as determined by post-thaw proliferation). The assay results for the surrogate vial represent the expected assay results for the first (larger) volume; however, by using the surrogate it is unnecessary to thaw the first volume for assaying and, instead, it is thawed when needing to be used, e.g., for transplanting into a subject in need.

Without wishing to be bound by theory, for a given cell type, a specific, optimum cooling rate is required for that cell type or cell product to survive cryopreservation. This optimum cooling rate balances damage from intracellular ice formation (IIF) with damage from high solute concentration resulting from extracellular ice formation. If cells are cooled too fast, damaging IIF is likely; if cells are cooled too slowly, damaging solute effects are likely. For the surrogate vial to accurately represent the first volume, the cells in both volumes should be frozen at about the same rate, i.e., the optimized rate; this common rate results in equivalent survival and viability for cells in the two volumes. Importantly, the second volume may be stored in the same long-term storage system as the first volume, and will therefore be exposed to the same conditions over long-term storage durations; thus, promoting the ability of the surrogate vial to accurate represent the cryopreservation bag that contains cell for transplant. These ultimately allows the second volume to be tested to determine, at least, if storage of the cryopreservation bag was maintained appropriately and without having to manipulate and test the cells of the first volume. More specifically, by assaying the surrogate vial, the cryopreservation bag does not need to be warmed and/or handled prior to its immediate use. This feature is especially helpful to a subject's outcome and welfare in two ways. First, the cells for transplanting are thawed only when ready to be administered to the subject (and preferably at the site of administration) rather than being thawed two weeks or so before use so that assays can be performed to ensure that the cell product is suitable for use; this two week delay during which the cells are kept at room temperature, on ice, or at 37° C.—or worse refrozen and returned to cold storage—could adversely affect their viability and utility once transplanted. Second, since a subject likely undergoes myeloablative conditioning prior to transplant, the patient can forestall myeloablative conditioning until a cell product has been assayed and determined to be suitable for use, which usually takes about two weeks; by having an surrogate vial, a subject begins myeloablative conditioning once a suitable product has been identified, thereby shortening the length of time that the subject remains immune compromised.

The present disclosure provides methods for ensuring that the two volumes cool at the same rate. Based, at least, on laws of physics, a smaller volume of a cell product will cool at a faster rate than a larger volume of the cell product. And, the smaller volume, with a faster cooling rate should have increased IIF relative to the larger volume, which has a slower cooling rate. Methods of the present disclosure promote an equivalent rate of cell cooling between the first (larger) volume and the second (smaller) volume such that each volume will have similar amounts of IFF and, as such, the surrogate vial (smaller volume) will accurately represent the larger first volume. Without wishing to be bound by theory, methods of the present disclosure slow the rate of cooling for the second (smaller) volume to the rate experienced by the first (larger) volume based, in part, on use of different types of containers that directly holds or indirectly holds either a first volume or the second volume and/or positioning of containers within the same freezer, e.g., a static temperature freezer. As a result, cells in the smaller volume (i.e., the second volume/surrogate vial) and cells in the larger volume (i.e., the first volume/cryopreservation bag) experience similar rates of cooling (e.g., about −1° C./minute) when placed in the same static freezer, e.g., a −86° C. static freezer. Importantly, to slow the cooling rate of the smaller second volume, a surrogate vial is placed directly into an insulated vial container, e.g., CoolCell® freezing storage system, which when placed in a static freezer that is colder than −80° C., e.g., a −86° C. static freezer, the cells in the surrogate vial experience rate of freezing at the rate of about −1° C./minute; without use of the insulated vial container, the cells in the surrogate vial would experience rate of freezing at the rate of about −10° C./minute, which would likely cause damage from IIF On the other hand, the larger first volume, cryopreservation bag, does not need to be directly placed in an insulated container and instead, when the bags are placed in cassettes—which are not insulated (to avoid slowing the cooling rate of the bag)—and moved to −86° C. static freezer, the cells in the cryopreservation bag preferably experience freezing rate of about −1° C./minute. By "directly placed" means that each vial is in close proximity to the insulating material of the insulating container. These manipulation cause cells of the first and the second volumes to have roughly equivalent osmosis of intracellular water into the extracellular space for cells; this osmosis increases the solute concentration intracellularly, and helps avoid formation of (harmful) intracellular ice crystals and promotes extracellular ice formation (which is less harmful to the cell). Once the first step of freezing (in the −86° C. static freezer), the cryopreservation bag and the surrogate vial are placed in the same long-term storage device (e.g., a liquid nitrogen storage tank) and in a roughly similar position within the long-term storage device.

Accordingly, methods of the present disclosure allow production of a surrogate sample of the cell product that is expected to accurately represent the portion of the cell product that is to be administered to a subject in need thereof and provides a cell product that is, not only therapeutically beneficial to the subject, but promotes subject's outcome and welfare in ways that are not achievable when a cryopreserved cell product in merely contained in a single bag and without a surrogate vial.

Preparing the Donor Bone

The vertebral body and the ilium represent the largest consistent reservoirs of high-quality red marrow. Utilizing one or both sources has optimized the recovery of bone marrow, particularly with the implementation of an industrialized, scalable, GMP process disclosed herein. In some embodiments, completion of the process disclosed herein results in cryopreservation of a final product of storing a 60-70 ml volume at a target of 100-150 million total nucleated cells/ml in standard blood bags. In some cases, the methods of manufacturing provide a system in which skilled tissue processing technicians can process sets of donor bones within a six-hour window to yield meaningful quantities of viable marrow.

In some embodiments, the donor bone is vertebral bodies. However, it is understood that the methods described herein can be used on the ilium, a combination of the vertebral bodies and ilium, or other bones suitable for extraction of bone marrow and cells from the marrow, even donor bones with lower expected yields.

It is understood that the donor bones can be procured according to fixed protocols for clinical recovery. Bones can be recovered by surgeons or by personnel at a trained organ procurement organization (OPO) using an osteotome and mallet from consented organ and tissue donors. Vertebral segments must be carefully recovered, preferably from the thoracic and lumbar vertebrae. The segments are incised and removed using an osteotome and mallet. As much of the spinal cord as possible is removed. A licensed surgeon may have oversight of these steps to assure effective recovery of VBs and prevention of disease transmission and translocation of bacteria.

Once recovered, the vertebral segments are swabbed for microbial culture testing and placed in a sterile, labeled bag with saline-soaked sterile pads, sponges, or towels to ensure moisture retention during hypothermic shipment. These are then positioned between wet ice packs in a cooler for shipment. Recovery of VBs must occur with a minimal warm ischemia time (≤8 hours). Shipment and initiation of processing must be completed within a minimal cold ischemia time (≤40 hours). The package is finally shipped to a processing facility.

VB logs are wrapped and double bagged. Bags are placed in an insulated shipper with bagged wet ice surrounding them. Shippers are sealed and sent to Ossium via medical courier. Upon arrival, packaging is checked for compliance with protocols and vertebral body temperature is measured to ensure compliance with shipping requirements.

The process for preparing the donor bone can occur soon after the bone is obtained from the deceased donor or can occur after the donor bone has been shipped in a hypothermic environment to a processing facility. Since the donor bone can experience prolonged periods of ischemia during recovery and shipment to the processing facility, care must be taken to track the length and type of ischemia—e.g., warm ischemia and cold ischemia. As described in more detail herein, bone subject to predetermined periods of warm ischemia and/or cold ischemia are suitable for obtaining meaningful quantities of viable bone marrow cells.

During the processing of the donor bone, the bone is debrided in an ISO-5 (class 100) environment (biosafety cabinet) with an ISO-7 (class 10,000) background (clean room), with special care taken to sterilize the bag containing the donor bone, such as by spraying with 70% isopropanol. In one embodiment, the debridement is conducted manually using scalpels, osteotomes and gouges. In processing vertebrae, typically a spinal segment including multiple vertebral levels will be provided. In a typical case, the spine segment runs from T8 to L5, for ten vertebral bodies. During initial debridement of the spinal segment, when enough soft tissue has been removed to visualize the pedicles, the pedicles are removed using either a tissue processing band saw or a bone saw, such as the Stryker System 6 Saw (Stryker, Kalamazoo, Mich.), or with the hand tool shown in FIG. 1A to FIG. 1D. Special care is taken to avoid breaching the cortical bone which would expose the cancellous bone, to ensure that the hypoxic cancellous bone marrow remains protected throughout the entire debriding process. The anterior element of the vertebral bodies, which contain the cancellous bone material, remain, while the pedicles and posterior elements are discarded.

Using a boning knife or tissue processing band saw, the vertebral bodies (VB) are separated at the intervertebral discs. The intervertebral disc and soft tissue remaining on each vertebral body is removed with a scalpel, scissors and/or osteotomes, leaving clean, separated VBs. In the case of donor ilium, the soft tissue can be removed with gouges and a scalpel, with special care again taken to ensure that the cortical bone is not breached. Any anatomical pathologies or injuries of the bone are noted and recorded as part of the batch record for the marrow ultimately obtained from the bones. Bones damaged during the recovery process are discarded.

In some cases, cadaver bones undergo a "pre-processing" to reduce contaminants carried by the cadaver bone and which risk transferring the contamination to the facility that the bone is processed. In these cases, two technicians perform different aspects of the pre-processing. A first technician opens a package containing harvested cadaver bones, preferably contained in a sealed, inner bag. The second technician, wearing sterile gloves, removes the cadaver bone from the package and places the tissue in a first (rinse) basin. The second technician scrubs all surfaces of cadaver bone vigorously with an about 4% chlorhexidine gluconate solution for about 3 minutes while in or above the rinse basin. The first technician, wearing sterile gloves, pours sterile saline onto the scrubbed cadaver bone, with the runoff being captured in the rinse basin. A sufficient amount of saline is poured onto the cadaver bone to rinse all of its surfaces. The rinsed cadaver bone is then placed on a sterile cloth adjacent to the rinse basin. The saline rinse may be repeated as necessary. Alcohol, e.g., 70% isopropyl alcohol, is poured over the cadaver bone. A sufficient amount of alcohol is poured onto the cadaver bone to contact all of its surfaces. The alcohol runoff is captured in the rinse basin. The cadaver bone is placed in an open container which is sprayed with alcohol and, then the open container and bone is transferred to a hood, where further processing of the bone can take place.

An aspect of the present disclosure comprises a method for processing bone marrow or a derivative thereof, wherein the bone marrow or the derivative thereof is derived from a deceased donor, the method comprising: obtaining a bone from a deceased donor; contacting the bone with a bleach solution for at least about 10 minutes to at least about 25 minutes, wherein the bone is submerged in the bleach solution; extracting the bone marrow or the derivative thereof from the bone, wherein at least 90% of CD34+ cells comprised in the bone marrow or the derivative thereof are viable. In some embodiments, the bone marrow or derivative thereof is contacted with the bleach solution for at least about 25 minutes. In some embodiments, the bleach solution comprises 10% bleach. In some embodiments, the bone is a vertebral body. In some embodiments, the hydrogen peroxide is a 3% hydrogen peroxide solution. In some embodiments, the method further comprises transferring the bleached bone product from a container comprising the bleach solution to a container containing the hydrogen peroxide solution. In some embodiments, the method further comprises a step of agitating the bleached bone product within the hydrogen peroxide solution. In some embodiments, the submerging the bleached bone product in a solution comprising hydrogen peroxide comprises: submerging the bleached bone product in a container containing the hydrogen peroxide solution; detecting foam or froth associated with the bleached bone product; and repeating the submerging until no foam or froth is detected. In some embodiments, the method further comprises manually removing soft tissue from a bleached bone product that is associated with foam or froth. In some embodiments, an inert contrast dye is added to the solution comprising hydrogen peroxide to enhance visibility of any foam or froth associated with the bleached bone product.

In some embodiments, the bone in the bleach solution are agitated (e.g., shaken).

The VBs, either pre-processed or not, are placed into a sterile bag and submerged in an about 10% bleach solution (0.5% sodium hypochlorite in sterile water), yielding a concentration of 5,000 ppm free chlorine, for a predetermined period, typically from about 5 minutes to about 25 minutes, e.g., 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes or more and any length of time therebetween. Bleach has a broad spectrum of anti-microbial activity, does not leave a toxic residue, is unaffected by water hardness and is fast acting.

Bone marrow from each group of VBs processed at different duration of bleach treatment can be tested by flow cytometry to assess the viability of the cells isolated from the bone marrow. As exemplified in Table 4, soaking the VBs for more than 10 minutes yields no significant difference in cell viability compared to when the VBs are soaked for up to 25 minutes. However, without wishing to be bound by theory, an increase in bleaching time improves the ultimate product. For example, increasing the soaking of the VBs in bleach for longer period of time allows the bleach to fill the cavity or crevice of the VBs to further decontaminate or sterilize the VBs.

The bleach solution may be from about 5% bleach to about 15% bleach, e.g., about 5%, 6%, 7%, 8%, 9%, 10%, 11%, 12%, 13%, 14%, or about 15% bleach. In some embodiments, the bleach treatment comprises using 1%, 2%, 3%, 4%, 5%, 6%, 7%, 8%, 9%, 10%, 11%, 12%, 13%, 14%, 15%, 20%, 25%, 30%, 35%, 40%, 45%, 50%, or higher percentage of bleach. In some embodiments, the bleach treatment comprises contacting the VBs with bleach for at least 1 minute, 2 minutes, 3 minutes, 4 minutes, 5 minutes, 6 minutes, 7 minutes, 8 minutes, 9 minutes, 10 minutes, 11, minutes, 12 minutes, 13 minutes, 14 minutes, 15 minutes, 20 minutes, 25 minutes, 30 minutes, 35 minutes, 40 minutes, 45 minutes, 50 minutes, or longer duration. In some embodiments, the VBs are submerged in the bleach solution for at least about 10 minutes to at least about 25 minutes, e.g., about 10 to about 12 minutes, about 11 to about 14 minutes, about 13 to about 16 minutes, about 15 to about 18 minutes, about 17 to 20 minutes, about 19 to 22 minutes, or about 21 to 25 minutes and any interval therebetween. In some embodiments, the viability of the bone marrow cells isolated from the VBs treated with the bleach treatment is not decreased at any duration of bleach treatment described herein compared to bone marrow cells isolated from the VBs without the bleach treatment. In some embodiments, the viability of the bone marrow cells isolated from the VBs treated with 11 minutes, 12 minutes, 13 minutes, 14 minutes, 15 minutes, 20 minutes, 25 minutes, 30 minutes, 35 minutes, 40 minutes, 45 minutes, 50 minutes, or longer duration of the bleach treatment is not decreased or is decreased by less than 3% compared to the viability of the bone marrow cells isolated from the VBs treated with the 10 minutes bleach treatment. In some embodiments, the viability of the bone marrow cells isolated from the VBs treated with more than 10 minutes decreased by less than 2% compared to the viability of the bone marrow cells isolated from the VBs treated with the 10 minutes bleach treatment. In some embodiments, the viability of the bone marrow cells isolated from the VBs treated with more than 10 minutes decreased by less than 1% compared to the viability of the bone marrow cells isolated from the VBs treated with the 10 minutes bleach treatment.

Interestingly, bleach treatment provides surface sterilization of the bone, but does not penetrate the BM-containing compartment. Therefore, the bleach treatments disclosed herein do not substantially reduce the yield of viable cells obtained from BM.

In some embodiments, the percentage of viable CD34+ cells comprised in the bone marrow or derivative thereof extracted from the bone submerged in bleach is at least about 80% to about 95%. In some embodiments, the percentage of viable CD34+ cells comprised in the bone marrow or derivative thereof extracted from the bone submerged in bleach is at least about 80% to about 85%, about 80% to about 90%, about 80% to about 95%, about 85% to about 90%, about 85% to about 95%, or about 90% to about 95%. In some embodiments, the percentage of viable CD34+ cells comprised in the bone marrow or derivative thereof extracted from the bone submerged in bleach is at least about 80%, about 85%, about 90%, or about 95%. In some embodiments, the percentage of viable CD34+ cells comprised in the bone marrow or derivative thereof extracted from the bone submerged in bleach is at least at least about 80%, about 85%, or about 90%. In some embodiments, the percentage of viable CD34+ cells comprised in the bone marrow or derivative thereof extracted from the bone submerged in bleach is at least at most about 85%, about 90%, or about 95%.

At the end of the bleaching period, the bones are transferred to another sterile bag and submerged in a 3% hydrogen peroxide ($H_2O_2$) solution. In some cases, the $H_2O_2$ solution comprises PLASMA-LYTE™ (a multiple electrolyte injection that is a sterile, nonpyrogenic isotonic solution that is a base source of water and electrolyte-balanced crystalloids for the cells, obtained from Baxter Healthcare, Ltd.). In some cases, the $H_2O_2$ solution comprises PLASMA-LYTE™ and Human Serum Albumin (HSA) which is a stabilizing reagent and storage agent (it may be diluted in the $H_2O_2$ solution to achieve 2.5% HSA). The bag is closed and shaken briefly to ensure that the entire surface of the bone is in contact with the solution. Most living cells include catalase, which is an enzyme that catalyzes the breakdown of $H_2O_2$ into $H_2O$ and $O_2$. This breakdown manifests as foam or froth when the $H_2O_2$ solution contacts soft tissue but not bone. The foam level can be observed as an indication of the amount of soft tissue remaining on the bone. This observation can be performed manually by a human processor or, in another embodiment, by an automated processor. The automated processor incorporates a visualization device, such as a camera, and object recognition software that can determine foam levels within the bag. The addition of an inert contrast dye can help the human or automated processor detect the foam level. If any foam or froth is observed, the bone is returned for further processing to remove all of the remaining soft tissue from the bone. Once the VBs or ilium has been cleaned of all soft tissue, the bones are transferred to a new sterile bag. The bag is filled with 1 L of PLASMA-LYTE™, or other suitable sterile, nonpyrogenic isotonic solution. The bag is closed and shaken briefly to ensure that the entire bone is contacted with the PLASMA-LYTE™.

In some embodiments, the method further comprises a step of agitating the bleached bone product within the hydrogen peroxide solution. In some embodiments, the submerging the bleached bone product in a solution comprising hydrogen peroxide comprises: submerging the bleached bone product in a container containing the hydrogen peroxide solution; detecting foam or froth associated with the bleached bone product; and repeating the submerging until no foam or froth is detected. In some embodiments, the method further comprises manually removing soft tissue from a bleached bone product that is associated with foam or froth. In some embodiments, an inert contrast dye is added to the solution comprising hydrogen peroxide to enhance visibility of any foam or froth associated with the bleached bone product.

The bleaching step and the hydrogen peroxide steps may be repeated multiple times.

Without wishing to be bound by theory, it is believed that the $H_2O_2$ solution not only helps surface sterilize the bone, it helps break down any residual bleach into salt, oxygen, and water.

After the surface sterilization, the cadaver bone may be rinsed with water, a saline, or with a cryoprotectant solution. Then the surface sterilized cadaver bone may be placed in a closed container comprising a cryoprotectant solution and the pressure is reduced.

Cryoprotectant Infiltration into Cadaver Bone

Cadaver bone can be contacted with a cryoprotectant solution for a length of time and under conditions sufficient to allow infiltration of a cryoprotectant solution into the cadaver bone. Methods for cryopreserving bone is described below and elsewhere. In some cases, the conditions sufficient to allow infiltration of a cryoprotectant solution involve use of vacuum-assisted infiltration of a cryoprotectant into a cadaver bone as disclosed in PCT/US2021/042064, the contents of which are incorporated by reference in its entirety. In other cases, cadaver bone is submerged in a cryoprotectant solution and without use of a vacuum.

An aspect of the present disclosure is a method for cryopreserving a cadaver bone using vacuum to assist infiltration of a cryoprotectant into the cadaver bone. The method comprises steps of: (a) placing a cadaver bone in a closed container comprising a cryoprotectant solution; (b) reducing the pressure in the closed container, and optionally, holding the closed container at reduced pressure, to remove at least a portion of the water present in the cadaver bone; (c) raising the pressure in the closed container and holding the closed container at a raised pressure to allow infiltration of the cryoprotectant solution into the cadaver bone; (d) removing the cadaver bone from the closed container; and (e) chilling the cadaver bone to a temperature at least below 0° C., thereby cryopreserving the cadaver bone.

Surprisingly, by immersing a cadaver bone in a closed container of cryoprotectant and applying an intermittent vacuum to the closed container, the cryoprotectant infiltrates the cadaver bone significantly more rapidly that would occur by passive diffusion. With respect to PCT/US2021/042064, compare FIG. 2 with FIG. 4A and FIG. 4B and FIG. 3 with FIG. 5. Such effective infiltration of cryoprotectant contributes to reduced ice crystal formation during freezing of the cadaver bone and, ultimately, extraction of viable bone marrow cells that have replicative potential.

Steps (b) and (c) may occur only once or steps (b) and (c) may be repeated at least once, at least twice, at least four times, at least five times, or at least six times. In some embodiments, repeating the reduced pressure and the raised pressure may increase infiltration of a cryoprotectant into a cadaver bone. See, e.g., FIG. 5 of PCT/US2021/042064. In other embodiments, there is sufficient infiltration of cryoprotectant into a cadaver bone after a single cycle of reduced pressure and raised pressure.

In various embodiments, a cadaver bone (e.g., vertebral body) is bisected, cut into quarters, or more extensively divided prior to vacuum-assisted infiltration of the cryoprotectant.

The reduced pressure in the closed container may any pressure value from about −400 mmHg to about −800 mmHg. The pressure requirement should be sufficient to remove at least a portion of the water present in the cadaver bone. The reduced pressure in the closed container may have a value of about −400 mmHg, −425 mmHg, −450 mmHg, −475 mmHg, −500 mmHg, −525 mmHg, −550 mmHg, −575 mmHg, −600 mmHg, −625 mmHg, −650 mmHg, −675 mmHg, −700 mmHg, −725 mmHg, −750 mmHg, −775 mmHg, or −800 mmHg. In some embodiments, the reduced pressure in the closed container is from about −400 mmHg to about −500 mmHg.

In some embodiments, it takes from about one minute to about 10 minutes for the closed container to reach a desired reduced pressure once the pressure in the closed container begins reducing. As examples, the closed container is may take less than 1 minute, about 1 minute, 2 minutes, 3 minutes, 4 minutes, 5 minutes, 6 minutes, 7 minutes, 8 minutes, 9 minutes, or about 10 minutes and any length of time in between (e.g., a fraction of a minute, e.g., about 5 seconds, 10 seconds, 20 seconds, 30 seconds, 40 seconds, about 50 seconds, and any number of seconds therebetween) to reach the desired reduced pressure. In some embodiments, the cadaver bone reaches the desired reduced pressure rapidly, e.g., from about one second to about one minute.

In some embodiments, the cadaver bone is held at the reduced pressure once the reduced pressure has been reached. The cadaver bone may be held for from less than one minute to about 50 minutes. As examples, the closed container is held at reduced pressure for less than one minute, about 1 minute, 2 minutes, 3 minutes, 4 minutes, 5 minutes, 6 minutes, 7 minutes, 8 minutes, 9 minutes, 10 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, or about 50 minutes and any length of time in between (e.g., a fraction of a minute, e.g., about 5 seconds, 10 seconds, 20 seconds, 30 seconds, 40 seconds, about 50 seconds, and any number of seconds therebetween). In some embodiments, the cadaver bone is not held at reduced pressure for any measurable time and instead, the method progresses to step (c) of raising the pressure in the closed container.

In step (c), the pressure of the closed container is raised until the pressure is from about 0 mmHg to about 760 mmHg. In other words, the pressure is raised to up to standard atmospheric temperature. The exact raised pressure may be any amount within the specified range, e.g., 0 mmHg, 50 mmHg, 100 mmHg, 150 mmHg, 200 mmHg, 250 mmHg, 300 mmHg, 350 mmHg, 400 mmHg, 450 mmHg, 500 mmHg, 550 mmHg, 600 mmHg, 650 mmHg, 700 mmHg, or 750 mmHg. However, the raised pressure must be high enough to allow infiltration of the cryoprotectant solution into the cadaver bone.

The closed container may be held at the raised pressure for less than about two hours. As examples, for less than one hour, less than one-half hour, about one-half hour, or less time. In some embodiments, the closed container is held at the raised pressure for ten minutes. The duration that the closed container is held at the raised pressure must be long enough to allow infiltration of the cryoprotectant solution into the cadaver bone. As examples, the closed container is held at the raised pressure for about, 1 minute, 2 minutes, 3 minutes, 4 minutes, 5 minutes, 6 minutes, 7 minutes, 8 minutes, 9 minutes, 10 minutes, 21 minutes, 22 minutes, 23 minutes, 24 minutes, 25 minutes, 26 minutes, 27 minutes, 28 minutes, 29 minutes, or about 30 minutes, and any length of time in between (e.g., a fraction of a minute, e.g., about 5 seconds, 10 seconds, 20 seconds, 30 seconds, 40 seconds, about 50 seconds, and any number of seconds therebetween).

The closed container and the cryoprotectant contained therein may be at room temperature. Alternately, the closed container and the cryoprotectant contained therein may be below room temperature, e.g., as low as 4° C. The closed container and the cryoprotectant contained therein may be above room temperature, e.g., as high as 37° C.

Any suitable cryoprotectant may be used in a cryoprotectant solution. Examples of cryoprotectant include dimethyl sulfoxide (also known as DMSO, $C_2H_6OS$, and ME2SO); 1, 2 propane diol (also known as propylene glycol); ethylene glycol; glycerol; foramamide; ethanediol, butane 2, 3 diol; hydroxyethyl starch (HES); dextran; sucrose; trehalose; lactose; raffinose; ribotol; mannitol; and polyvinylpyrrolidone (PVP). In some embodiments, the cryoprotectant is DMSO. The cryoprotectant solution may comprise from about 5% DMSO to about 100% DMSO, e.g., about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% DMSO. The cryoprotectant solution may comprise about 10% DMSO. The cryoprotectant solution may comprise about 20% DMSO. In some embodiments, the cryoprotectant solution may comprise about 40% DMSO or 60% DMSO. In some embodiments, a higher percentage of cryoprotectant is preferred, e.g., percentages that are two times higher than equivalent cell suspension values to help drive osmotic penetration.

The cryoprotectant solution may have water or a saline as base. In some embodiments, the saline is isotonic to human tissues. In embodiments the saline is a 0.9% saline solution. Any commercially available saline solution may be used: sodium chloride solution, PBS, HEPES, Ringers or Lactate. The saline may be 0.9% sodium chloride.

The cryoprotectant solution may further comprise a protein. As examples, the protein may be a human albumin (e.g., HSA) or a constituent of a human platelet lysate. An example of a commercially available human platelet lysate product is Stemulate™ (from Cook® Regentec).

In some embodiments, the cryoprotectant solutions comprises about 10% protein, e.g., 10% human platelet lysate or 10% albumin.

In one example, the cryoprotectant solution comprises about 20% DMSO and about 10% human platelet lysate in 0.9% NaCl.

In another example, the cryoprotectant solution comprises about 40% DMSO and about 10% human platelet lysate in 0.9% NaCl.

In yet another example, the cryoprotectant solution comprises about 60% DMSO and about 10% human platelet lysate in 0.9% NaCl.

In a further example, the cryoprotectant solution comprises about 80% DMSO and about 10% human platelet lysate in 0.9% NaCl.

In an additional example, the cryoprotectant solution comprises about 100% DMSO in 0.9% NaCl.

In any of the above aspects, the method may comprise a step of increasing the pressure in the closed container comprising a cryoprotectant to above 760 mmHg by introducing a compressed gas (e.g., nitrogen, xenon, $CO_2$, argon, $H_2S$, or helium), a gas released by sublimination (e.g., $CO_2$ via dry ice), or a gas provided by evaporation (e.g., nitrogen via liquid nitrogen), thereby permeating gas into the cadaver bone. In embodiments, the gas is $CO_2$, e.g., compressed $CO_2$. In some embodiments, the gas is nitrogen, e.g., compressed nitrogen. The time required for gas infiltration into a vertebral body is less when the gas is compressed versus a gas obtained by sublimination.

Alternately, in any of the above-mentioned aspects, rather than placing a cadaver bone in closed container comprising a cryoprotectant solution, the cadaver bone is placed in a closed container that lacks a cryoprotectant solution. In these alternate aspects, the method comprises a step of increasing the pressure in the closed container (which lacks a cryoprotectant solution) to above 760 mmHg by introducing a compressed gas (e.g., nitrogen, xenon, $CO_2$, argon, $H_2S$, or helium), a gas released by sublimination (e.g., $CO_2$ via dry ice), or a gas provided by evaporation (e.g., nitrogen via liquid nitrogen), thereby permeating gas into the cadaver bone. Any method disclosed herein may be adapted by comprising initial steps of placing a cadaver bone in closed container that lacks a cryoprotectant solution and increasing the pressure in the closed container to above 760 mmHg by introducing a compressed gas, a gas released by sublimination, or a gas provided by evaporation; in a later step, a cryoprotectant solution is added to the closed container. In embodiments, the gas is $CO_2$, e.g., compressed $CO_2$. In some embodiments, the gas is nitrogen, e.g., compressed nitrogen.

Without wishing to be bound by theory, increasing the pressure in a closed container by introducing a compressed gas (e.g., nitrogen, xenon, $CO_2$, argon, $H_2S$, or helium), a gas released by sublimination (e.g., $CO_2$ via dry ice), or a gas provided by evaporation (e.g., nitrogen via liquid nitrogen), promotes infiltration of the cryoprotectant solution into the cadaver bone.

In some cases, the closed container comprises solid materials, e.g., metal, plastic, or other polymers. In some cases, the closed container comprises a foam material, e.g., Styrofoam.

In alternate aspects, a cadaver bone is infiltrated with a cryoprotectant without use of a vacuum. Here, an intact vertebral body, a vertebral body that has been bisected, cut into quarters, or more extensively divided is submerged into a cryoprotectant solution for a length of time and under conditions sufficient to allow infiltration of the cryoprotectant solution into the cadaver bone.

The bone or bone fragment is placed, e.g., submerged, in a cryoprotectant solution and incubated for 1 hour at about 4° C. In some embodiments, the incubation period is about 1 hour to about 3 hours. In some embodiments, the incubation period is about 1 hour to about 1.5 hours, about 1 hour to about 2 hours, about 1 hour to about 2.5 hours, about 1 hour to about 3 hours, about 1.5 hours to about 2 hours, about 1.5 hours to about 2.5 hours, about 1.5 hours to about 3 hours, about 2 hours to about 2.5 hours, about 2 hours to about 3 hours, or about 2.5 hours to about 3 hours. In some embodiments, the incubation period is about 1 hour, about 1.5 hours, about 2 hours, about 2.5 hours, or about 3 hours. In some embodiments, the incubation period is at least about 1 hour, about 1.5 hours, about 2 hours, or about 2.5 hours. In some embodiments, the incubation period is at most about 1.5 hours, about 2 hours, about 2.5 hours, or about 3 hours.

Any suitable cryoprotectant may be used in a cryoprotectant solution. Examples of cryoprotectant include dimethyl sulfoxide (also known as DMSO, $C_2H_6OS$, and ME2SO); 1, 2 propane diol (also known as propylene glycol); ethylene glycol; glycerol; foramamide; ethanediol; butane 2, 3 diol; hydroxyethyl starch (HES); dextran; sucrose; trehalose; lactose; raffinose; ribotol; mannitol; and polyvinylpyrrolidone (PVP). In some embodiments, the cryoprotectant is DMSO. The cryoprotectant solution may comprise from about 5% DMSO to about 100% DMSO, e.g., about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% DMSO. The cryoprotectant solution may comprise about 20% DMSO. In some embodiments, the cryoprotectant solution may comprise about 40% DMSO or 60% DMSO. In some embodiments, a higher percentage of cryoprotectant is preferred, e.g., percentages that are two times higher than equivalent cell suspension values to help drive osmotic penetration.

The cryoprotectant solution may have water or a saline as base. In some embodiments, the saline is isotonic to human tissues. In embodiments the saline is a 0.9% saline solution. Any commercially available saline solution may be used: sodium chloride solution, PBS, HEPES, Ringers or Lactate. The saline may be 0.9% sodium chloride.

The cryoprotectant solution may further comprise a protein. As examples, the protein may be a human albumin (e.g., HSA) or a constituent of a human platelet lysate. An example of a commercially available human platelet lysate product is Stemulate™ (from Cook® Regentec).

In some embodiments, the cryoprotectant solutions comprises about 10% protein, e.g., 10% human platelet lysate or 10% albumin.

In one example, the cryoprotectant solution comprises about 20% DMSO and about 10% human platelet lysate in 0.9% NaCl.

In another example, the cryoprotectant solution comprises about 40% DMSO and about 10% human platelet lysate in 0.9% NaCl.

In yet another example, the cryoprotectant solution comprises about 60% DMSO and about 10% human platelet lysate in 0.9% NaCl.

In a further example, the cryoprotectant solution comprises about 80% DMSO and about 10% human platelet lysate in 0.9% NaCl.

In an additional example, the cryoprotectant solution comprises about 100% DMSO in 0.9% NaCl.

Two-Step Chilling of Cadaver Bone

Figure 6:
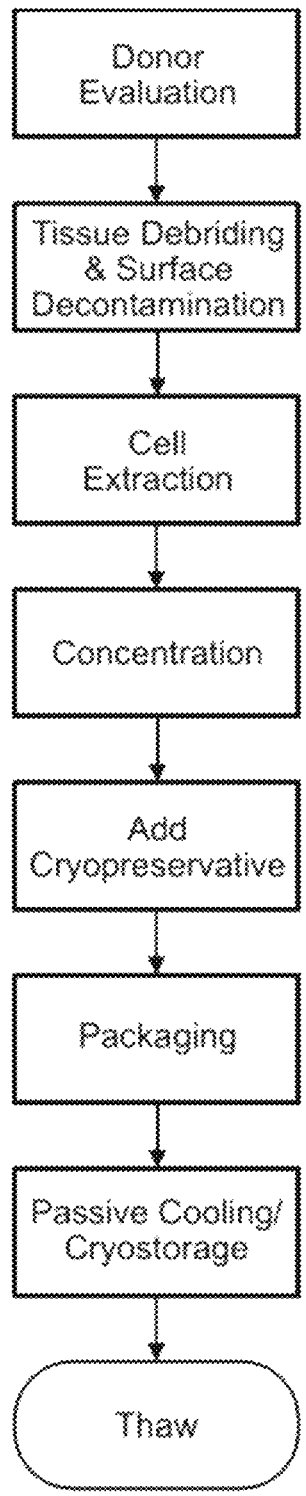
FIG. 6 is a flowchart of one method according to the present disclosure.

Once a cadaver bone is infiltrated with cryoprotectant (either with or without use of a vacuum), the cadaver bone then undergoes an initial chilling period. For this, the cadaver bone is placed in a static minus 80 freezer set at a temperature of colder than about −60° C., e.g., from about −70° C. to about −80° C., or colder than about −100° C. There, the cadaver bone undergoes an initial chilling period. In some embodiments, the cadaver bone is initially chilled in a static minus 80 freezer set at a temperature of about −86° C. Data showing the dynamics of the initial chilling period is shown in PCT/US2021/042064 at FIG. 6A.

In some cases, the static freezer is set at a range of temperature from about −60° C., about −65° C., about −70° C., about −75° C., about −80° C., about −82° C., about −84° C., about −86° C., about −88° C., about −90° C., about −95° C., or about −100° C. In some cases, the freezer can be set at a range of temperature from at least about −60° C., about −65° C., about −70° C., about −75° C., about −80° C., about −82° C., about −84° C., about −86° C., about −88° C., about −90° C., or about −95° C. In some cases, the freezer can be set at a range of temperature from at most about −65° C., about −70° C., about −75° C., about −80° C., about −82° C., about −84° C., about −86° C., about −88° C., about −90° C., about −95° C., or about −100° C.

The cadaver bone may be initially chilled at a rate of from about −0.3° C./min to about −5° C./min. In some embodiments, the cadaver bone is initially chilled at a rate of from about −0.4° C./min to about −0.9° C./min. As examples, the initial chilling rate may be about −0.3° C./min, −0.4° C./min, −0.5° C./min, −0.6° C./min, −0.7° C./min, −0.8° C./min, −0.9° C./min, to about −1° C./min. In other examples, the initial chilling rate may be about −1° C./min, −2° C./min, −3° C./min, −4° C./min, or about −5° C./min. In these rates, the minus sign ("−") means that the temperature is dropping by the stated amount.

The duration of the initial chilling period may vary from a few hours to overnight. The time should be sufficient for the cadaver bone to reach a temperature of colder than about −50° C., e.g., at −60° C. to −80° C. In some embodiments, the bone reaches the desired temperature in about 1 hour, 2 hours, 3 hours, 4 hours, 5 hours, 6 hours, 7 hours, 8 hours, 9 hours, 10 hours, 11 hours, or about 12 hours. Is some embodiments, the cadaver bone is initially chilled in the minus 80 freezer for at least 12 hours or at least overnight.

Without wishing to be bound by theory, it appears that the period of initial chilling in the presence of extracellular ice increases intracellular solute concentrations to an amount that allows intracellular vitrification in the subsequent chilling.

The cadaver bone may temporarily acquire a temperature of from about −5° C. to about −15° C., but this occurs as the temperature of the cadaver bone is continuously dropping towards the desired temperature, e.g., colder than about −50° C. Even though during the period of initial chilling, the cadaver bone is not held in a static freezer having its temperature set to from about −5° C. to about −15° C. and for a period of time from about 1 to about 30 minutes, the cadaver bone achieves a temperature of from about −5° C. to about −15° C. (as the bone continues to chill to the desired temperature.

Once the cadaver bone has reached the desired temperature, the cadaver bone undergoes a subsequent chilling period. For this, the cadaver bone is placed in liquid nitrogen or in liquid nitrogen vapor, e.g., at a temperature of about −200° C. Data showing the dynamics of the subsequent chilling period is shown in PCT/US2021/042064 at FIG. 6B. In some embodiments, the subsequent chilling period may occur in a suitable static freezer that is capable of maintaining temperatures equivalent to liquid nitrogen yet without use of liquid nitrogen, e.g., a cryogenic freezer.

During the subsequently chilling period, the cadaver bone is cooled at a rate of from about −2° C./min to about −6° C./min. In some embodiments, the cadaver bone is initially chilled at a rate of about −2° C./min, −2.2° C./min, −2.4° C./min, −2.6° C./min, −2.8° C./min, −3° C./min, −3.2° C./min, −3.4° C./min, −3.6° C./min, −3.8° C./min, −4° C./min, −4.2° C./min, −4.4° C./min, −4.6° C./min, −4.8° C./min, −5° C./min, −5.2° C./min, −5.4° C./min, −5.6° C./min, −5.8° C./min, or about −6° C./min. In these rates, the minus sign ("−") means that the temperature is dropping by the stated amount.

The cryopreserved cadaver bone may be held in liquid nitrogen, in liquid nitrogen vapor, or in a suitable static freezer indefinitely. As examples, the cryopreserved cadaver bone may be held for at least a day, at least a week, at least a month, at least a year, at least five years, or at least 20 years. The cryopreserved cadaver bone may be held in liquid nitrogen, in liquid nitrogen vapor, or suitable static freezer for hundreds or thousands of years.

Without wishing to be bound by theory, the two-step chilling of cadaver bone method, as disclosed herein, improves the viability of the extracted bone marrow cells (hematopoietic stem cells (HSCs; CD34+ cells) and/or mesenchymal stromal/stem cells (MSCs)) relative to methods that do not use the two-step chilling method. Therefore, using the methods of the present disclosure, a greater number of viable cells (HSCs and/or MSCs) are obtained relative to standard methods.

In some cases, the methods of the present disclosure provide from about 1% more viable cells to about 100% more viable cells, e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% more viable cells than from methods that do not use two-step chilling, as disclosed herein.

In some cases, the methods of the present disclosure provide from about 101% more viable cells to about 200% more viable cells, e.g., about 101%, 102%, 103%, 104%, 105%, 106%, 107%, 108%, 109%, 10%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, or about 200% more viable cells than from methods that do not use two-step chilling, as disclosed herein.

In some cases, the methods of the present disclosure provide from about 2-fold more viable cells to about 10-fold more viable cells, e.g., about 2-fold, 3-fold, 4-fold, 5-fold, 6-fold, 7-fold, 8-fold, 9-fold, about 10-fold, or any fold therebetween more viable cells than from methods that do not use two-step chilling, as disclosed herein. As examples, the methods of the present disclosure provide 2-fold to 3-fold, 3-fold to 4-fold, 4-fold to 5-fold, 5-fold to 6-fold, 6-fold to 7-fold, 7-fold to 8-fold, 8-fold to 9-fold, or 9-fold to 10-fold more viable cells than from methods that do not use two-step chilling, as disclosed herein.

In some cases, the methods of the present disclosure provide from about 10-fold more viable cells to about 100-fold more viable cells, e.g., about 10-fold, 20-fold, 30-fold, 40-fold, 50-fold, 60-fold, 70-fold, 80-fold, 90-fold, about 100-fold or any fold therebetween more viable cells than from methods that do not use two-step chilling, as disclosed herein. As examples, the methods of the present disclosure provide 10-fold to 20-fold, 20-fold to 30-fold, 30-fold to 40-fold, 40-fold to 50-fold, 50-fold to 60-fold, 60-fold to 70-fold, 70-fold to 80-fold, 80-fold to 90-fold, or 90-fold to 100-fold more viable cells than from methods that do not use two-step chilling, as disclosed herein.

In some cases, the methods of the present disclosure provide from about 100-fold more viable cells to about 1000-fold more viable cells, e.g., about 100-fold, 200-fold, 300-fold, 400-fold, 500-fold, 600-fold, 700-fold, 800-fold, 900-fold, about 1000-fold or any fold therebetween more viable cells than from methods that do not use two-step chilling, as disclosed herein. As examples, the methods of the present disclosure provide 100-fold to 200 fold, 200-fold to 300-fold, 300-fold to 400-fold, 400-fold to 500-fold, 500-fold to 600-fold, 600-fold to 700-fold, 700-fold to 800-fold, 800-fold to 900-fold, or 900-fold to 1000-fold more viable cells than from methods that do not use two-step chilling, as disclosed herein.

In some cases, the methods of the present disclosure provide from about 1000-fold more viable cells to about 10000-fold more viable cells, e.g., about 1000-fold, 2000-fold, 3000-fold, 4000-fold, 5000-fold, 6000-fold, 7000-fold, 8000-fold, 9000-fold, about 10000-fold or any fold therebetween more viable cells than from methods that do not use two-step chilling, as disclosed herein. As examples, the methods of the present disclosure provide 1000-fold to 200 fold, 2000-fold to 3000-fold, 3000-fold to 4000-fold, 4000-fold to 5000-fold, 5000-fold to 6000-fold, 6000-fold to 7000-fold, 7000-fold to 8000-fold, 8000-fold to 9000-fold, or 9000-fold to 10000-fold more viable cells than from methods that do not use two-step chilling, as disclosed herein.

Methods for Rapidly Warming a Cryopreserved Cadaver Bone

In some cases, the present disclosure provides a method for rapidly warming cadaver bone for providing bone marrow or a derivative thereof. PCT/US2021/042064 discloses methods for rapidly warming cryopreserved bone; the contents of which are incorporated by reference in its entirety. These disclosed methods may be useful in the methods of the present disclosure.

In some cases, the method for rapidly warming cadaver bone comprises steps of: obtaining a cryopreserved cadaver bone; dividing the cryopreserved cadaver bone to obtain fragments of the cryopreserved bone; transferring the fragments of the cryopreserved bone into a grinding medium having a temperature of from about 35° C. to about 45° C. for a time sufficient to warm the cadaver bone fragments to a surface temperature of about 20° C.

In some embodiments, a cryopreserved cadaver bone transferred into a grinding medium (as disclosed herein) without having been divided into fragments. Preferably, the cryopreserved cadaver bone has a temperature of at least below 0° C. when transferred into a grinding medium.

In alternate embodiments, the method comprises dividing the cryopreserved cadaver bone to obtain fragments of the cryopreserved bone. Preferably, the cryopreserved cadaver bone has a temperature of below 0° C. when dividing into fragments.

In order to simplify the process and for increased safety to the processing personnel, a custom bone cutting tool as described in US 2019/0343112, which is hereby incorporated by reference in its entirety, is used to divide the cryopreserved cadaver bone into smaller pieces. Another bone cutting tool may be used in combination, or in lieu of the custom bone cutting tool as described in US 2019/0343112.

The elements of the bone cutting tool are formed of medical grade stainless steel. The steel is preferably hardened steel capable of withstanding the forces required to cut through frozen bone. In the cleaning process, the tool is subjected to steam sterilization, which can be deleterious to the steel. Thus, in one feature of the present disclosure, the surfaces of the stainless-steel elements are passivated to prevent oxidation of the steel elements during sterilization.

The manual bone-cutting device for dividing the cryopreserved cadaver bone is capable of generating up to 1000 lbf when less than 50 lbf is applied. Such a manual bone-cutting device comprises: a force transmission mechanism, wherein the force transmission mechanism comprises an elongated force transducing member pivotally coupled to a gear mechanism; and a manually operable handle coupled to an end of the elongated force transducing member, wherein the end is opposite of the gear mechanism. The manual bone-cutting device comprises an upper cutting element and/or a lower cutting element. Its upper cutting element and/or lower cutting element each comprises one or more cutting blades that radiate outwards from a central portion of the upper cutting element and/or the lower cutting element. When the one or more cutting blades divide the cryopreserved cadaver bone into fragments that are generally sector shaped.

The manual bone-cutting device divides the cryopreserved cadaver bone into fragments of the cryopreserved bone. The fragments of the cryopreserved bone are transferred into a grinding medium having a temperature of from about 35° C. to 45° C. for a time sufficient to warm the cadaver bone fragments to a surface temperature of about 20° C. Alternately, whole cryopreserved bone, which has not been divided, is transferred into a grinding medium having a temperature of from about 35° C. and 45° C. for a time sufficient to warm the cadaver bone fragments to a surface temperature of about 20° C. In some embodiments, the surface temperature of the cadaver bone fragments is higher than 20° C., e.g., 25° C. or higher.

A suitable volume of grinding medium is warmed and held at a temperature of from about 35° C. to about 45° C., for example, by placing a container holding the grinding medium on a hot plate or in a water bath. In some examples, 300 ml, 500 ml or one liter of grinding medium is used to warm the cadaver bone. Preferably, the grinding medium has a temperature of about 37° C. to about 40° C. when the fragments of the cryopreserved bone are transferred to the grinding medium.

The cadaver bone fragments are warmed to a surface temperature of about 20° C. at a rate of from about 100° C./min to about 500° C./min. Is some embodiments, the warming rate is greater than about 300° C./min, e.g., about 300° C./min, 310° C./min, 320° C./min, 330° C./min, 340° C./min, 350° C./min, 360° C./min, 370° C./min, 380° C./min, 390° C./min, 400° C./min, 410° C./min, 420° C./min, 430° C./min, 440° C./min, 450° C./min, 460° C./min, 470° C./min, 480° C./min, 490° C./min, and about 500° C./min. In some embodiments, the warming rate is from about 400° C./min to about 500° C./min. In some instances, the cadaver bone fragments are warmed to a surface temperature of about 20° C. in less than one minute. In some cases, the cadaver bone fragments are warmed to a surface temperature of about 20° C. in about one minute or more, e.g., about 1 minute, 2 minutes, 3 minutes, 4 minutes, 5 minutes, 6 minutes, 7 minutes, 8 minutes, 9 minutes, or about 10 minutes. Data showing the dynamics of the fast warming is shown in PCT/US21/42064 at FIG. 15.

When whole cadaver bone is warmed in the grinding medium, the warming rate will be slower than when bone fragments are warmed. As examples, the cadaver bone is warmed to a surface temperature of about 20° C. at a rate of from about 100° C./min to about 250° C./min.

Without wishing to be bound by theory, the fast warming rate of the present disclosed methods prevents ice recrystallization during thawing of the bone fragments (or whole cadaver bone).

Without wishing to be bound by theory, the rapid warming of cadaver bone method, as disclosed herein, improves the viability of the extracted bone marrow cells (hematopoietic stem cells (HSCs; CD34+ cells) and/or mesenchymal stromal/stem cells (MSCs)) relative to methods that do not use the rapid warming method. Therefore, using the methods of the present disclosure, a greater number of viable cells (HSCs and/or MSCs) are obtained relative to standard methods.

In some cases, the methods of the present disclosure provide from about 1% more viable cells to about 100% more viable cells, e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% more viable cells than from methods that do not use the rapid warming method, as disclosed herein.

In some cases, the methods of the present disclosure provide from about 101% more viable cells to about 200% more viable cells, e.g., about 101%, 102%, 103%, 104%, 105%, 106%, 107%, 108%, 109%, 10%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, or about 200% more viable cells than from methods that do not use the rapid warming method, as disclosed herein.

In some cases, the methods of the present disclosure provide from about 2-fold more viable cells to about 10-fold more viable cells, e.g., about 2-fold, 3-fold, 4-fold, 5-fold, 6-fold, 7-fold, 8-fold, 9-fold, about 10-fold, or any fold therebetween more viable cells than from methods that do not use rapid warming, as disclosed herein. As examples, the methods of the present disclosure provide 2-fold to 3-fold, 3-fold to 4-fold, 4-fold to 5-fold, 5-fold to 6-fold, 6-fold to 7-fold, 7-fold to 8-fold, 8-fold to 9-fold, or 9-fold to 10-fold more viable cells than from methods that do not use rapid warming, as disclosed herein.

In some cases, the methods of the present disclosure provide from about 10-fold more viable cells to about 100-fold more viable cells, e.g., about 10-fold, 20-fold, 30-fold, 40-fold, 50-fold, 60-fold, 70-fold, 80-fold, 90-fold, about 100-fold or any fold therebetween more viable cells than from methods that do not use rapid warming, as disclosed herein. As examples, the methods of the present disclosure provide 10-fold to 20-fold, 20-fold to 30-fold, 30-fold to 40-fold, 40-fold to 50-fold, 50-fold to 60-fold, 60-fold to 70-fold, 70-fold to 80-fold, 80-fold to 90-fold, or 90-fold to 100-fold more viable cells than from methods that do not use rapid warming, as disclosed herein.

In some cases, the methods of the present disclosure provide from about 100-fold more viable cells to about 1000-fold more viable cells, e.g., about 100-fold, 200-fold, 300-fold, 400-fold, 500-fold, 600-fold, 700-fold, 800-fold, 900-fold, about 1000-fold or any fold therebetween more viable cells than from methods that do not use rapid warming, as disclosed herein. As examples, the methods of the present disclosure provide 100-fold to 200 fold, 200-fold to 300-fold, 300-fold to 400-fold, 400-fold to 500-fold, 500-fold to 600-fold, 600-fold to 700-fold, 700-fold to 800-fold, 800-fold to 900-fold, or 900-fold to 1000-fold more viable cells than from methods that do not use rapid warming, as disclosed herein.

In some cases, the methods of the present disclosure provide from about 1000-fold more viable cells to about 10000-fold more viable cells, e.g., about 1000-fold, 2000-fold, 3000-fold, 4000-fold, 5000-fold, 6000-fold, 7000-fold, 8000-fold, 9000-fold, about 10000-fold or any fold therebetween more viable cells than from methods that do not use rapid warming, as disclosed herein. As examples, the methods of the present disclosure provide 1000-fold to 200 fold, 2000-fold to 3000-fold, 3000-fold to 4000-fold, 4000-fold to 5000-fold, 5000-fold to 6000-fold, 6000-fold to 7000-fold, 7000-fold to 8000-fold, 8000-fold to 9000-fold, or 9000-fold to 10000-fold more viable cells than from methods that do not use rapid warming, as disclosed herein.

Extracting the Bone Marrow

The bone is removed from the bag and from the PLASMA-LYTE™, and a sterile gauze or sponge is used to absorb any liquid remaining on the VBs. In one approach, a saw and/or anvil shears are used to cut the VBs are cut into smaller pieces, such as 1.5 cm² pieces, that are small enough for fragmenting with a bone grinder. In order to simplify the process and for increased safety to the processing personnel, a custom bone cutting tool as described in US 2019/0343112, which is hereby incorporated by reference in its entirety, is provided is used to cut the VBs into the smaller pieces. Another custom bone cutting tool can be used in combination, or in lieu of the custom bone cutting tool as described in US 2019/0343112. The additional bone cutting tool is described in US 2020/0325451, which is hereby incorporated by reference in its entirety.

In some embodiments, the bone is freshly obtained from a cadaver. Alternately, the bone has previously been frozen and/or cryopreserved.

The elements of the bone cutting tool are formed of medical grade stainless steel. The steel is preferably hardened steel capable of withstanding the forces required to cut through bone. In the cleaning process, the tool is subjected to steam sterilization, which can be deleterious to the steel. Thus, in one feature of the present disclosure, the surfaces of the stainless-steel elements are passivated to prevent oxidation of the steel elements during sterilization.

The pieces produced by the bone cutting tool are immediately placed into a sterile pitcher and submerged in 300-500 ml of a grind media. In one aspect of the present system and method, the grind media uses PLASMA-LYTE™-A as a base with heparin, human serum albumin (HSA), and a nuclease (Merck KGAA Corporation). Heparin is used as an anticoagulant. Other anticoagulants at various quantities can also be used. HSA provides a protein source to prevent cell adherence and adsorption to surfaces, as well as reactive oxygen scavenging. It is noted that conventional grind media utilizes DNase, but for the present disclosure Benzonase® or Denarase® reagent is substituted for DNase™ reagent (Qiagen Sciences LLC). Whereas DNase works only on DNA, modern pharmaceutical biotechnology processing relies on enzymes that can cleave all forms of DNA and RNA, and can reduce the viscosity of the solution in which the cells are suspended. It is noted that IMDM (Iscove's Modified Dulbecco's Media) can substitute for the PLASMA-LYTE™-A, since IMDM is suitable for rapidly proliferating high-density cell cultures and ideal for supporting T- and B-lymphocytes. It is further noted that Denarase reagent (C-Lecta GmbH) is equivalent to Benzonase reagent in the same quantity in the present process.

In some embodiments, the amount of heparin in the grind media is about 5 U/ml to about 15 U/ml. In some embodiments, the amount of heparin in the grind media is about 5 U/ml, about 6 U/ml, about 7 U/ml, about 8 U/ml, about 9 U/ml, about 10 U/ml, about 11 U/ml, about 12 U/ml, about 13 U/ml, about 14 U/ml, or about 15 U/ml. In some embodiments, the amount of heparin in the grind media is about 5 U/ml to about 6 U/ml, about 5 U/ml to about 7 U/ml, about 5 U/ml to about 8 U/ml, about 5 U/ml to about 9 U/ml, about 5 U/ml to about 10 U/ml, about 5 U/ml to about 11 U/ml, about 5 U/ml to about 12 U/ml, about 5 U/ml to about 13 U/ml, about 5 U/ml to about 14 U/ml, about 5 U/ml to about 15 U/ml, about 6 U/ml to about 7 U/ml, about 6 U/ml to about 8 U/ml, about 6 U/ml to about 9 U/ml, about 6 U/ml to about 10 U/ml, about 6 U/ml to about 11 U/ml, about 6 U/ml to about 12 U/ml, about 6 U/ml to about 13 U/ml, about 6 U/ml to about 14 U/ml, about 6 U/ml to about 15 U/ml, about 7 U/ml to about 8 U/ml, about 7 U/ml to about 9 U/ml, about 7 U/ml to about 10 U/ml, about 7 U/ml to about 11 U/ml, about 7 U/ml to about 12 U/ml, about 7 U/ml to about 13 U/ml, about 7 U/ml to about 14 U/ml, about 7 U/ml to about 15 U/ml, about 8 U/ml to about 9 U/ml, about 8 U/ml to about 10 U/ml, about 8 U/ml to about 11 U/ml, about 8 U/ml to about 12 U/ml, about 8 U/ml to about 13 U/ml, about 8 U/ml to about 14 U/ml, about 8 U/ml to about 15 U/ml, about 9 U/ml to about 10 U/ml, about 9 U/ml to about 11 U/ml, about 9 U/ml to about 12 U/ml, about 9 U/ml to about 13 U/ml, about 9 U/ml to about 14 U/ml, about 9 U/ml to about 15 U/ml, about 10 U/ml to about 11 U/ml, about 10 U/ml to about 12 U/ml, about 10 U/ml to about 13 U/ml, about 10 U/ml to about 14 U/ml, about 10 U/ml to about 15 U/ml, about 11 U/ml to about 12 U/ml, about 11 U/ml to about 13 U/ml, about 11 U/ml to about 14 U/ml, about 11 U/ml to about 15 U/ml, about 12 U/ml to about 13 U/ml, about 12 U/ml to about 14 U/ml, about 12 U/ml to about 15 U/ml, about 13 U/ml to about 14 U/ml, about 13 U/ml to about 15 U/ml, or about 14 U/ml to about 15 U/ml. In some embodiments, the amount of heparin in the grind media is at least about 5 U/ml, about 6 U/ml, about 7 U/ml, about 8 U/ml, about 9 U/ml, about 10 U/ml, about 11 U/ml, about 12 U/ml, about 13 U/ml, or about 14 U/ml. In some embodiments, the amount of heparin in the grind media is at most about 6 U/ml, about 7 U/ml, about 8 U/ml, about 9 U/ml, about 10 U/ml, about 11 U/ml, about 12 U/ml, about 13 U/ml, about 14 U/ml, or about 15 U/ml.

In various embodiments, heparin is omitted from a grind medium.

In some embodiments, the amount of Benzonase® in the grind media is about 1 U/ml to about 10 U/ml. In some embodiments, the amount of Benzonase in the grind media is about 1 U/ml, about 2 U/ml, about 3 U/ml, about 4 U/ml, about 5 U/ml, about 6 U/ml, about 7 U/ml, about 8 U/ml, about 9 U/ml, or about 10 U/ml. In some embodiments, the amount of Benzonase in the grind media is about 1 U/ml to about 2 U/ml, about 1 U/ml to about 3 U/ml, about 1 U/ml to about 4 U/ml, about 1 U/ml to about 5 U/ml, about 1 U/ml to about 6 U/ml, about 1 U/ml to about 7 U/ml, about 1 U/ml to about 8 U/ml, about 1 U/ml to about 9 U/ml, about 1 U/ml to about 10 U/ml, about 2 U/ml to about 3 U/ml, about 2 U/ml to about 4 U/ml, about 2 U/ml to about 5 U/ml, about 2 U/ml to about 6 U/ml, about 2 U/ml to about 7 U/ml, about 2 U/ml to about 8 U/ml, about 2 Um' to about 9 U/ml, about 2 U/ml to about 10 U/ml, about 3 U/ml to about 4 U/ml, about 3 U/ml to about 5 U/ml, about 3 U/ml to about 6 U/ml, about 3 U/ml to about 7 U/ml, about 3 U/ml to about 8 U/ml, about 3 U/ml to about 9 U/ml, about 3 U/ml to about 10 U/ml, about 4 U/ml to about 5 U/ml, about 4 U/ml to about 6 U/ml, about 4 U/ml to about 7 U/ml, about 4 U/ml to about 8 U/ml, about 4 U/ml to about 9 U/ml, about 4 U/ml to about 10 U/ml, about 5 U/ml to about 6 U/ml, about 5 U/ml to about 7 U/ml, about 5 U/ml to about 8 U/ml, about 5 U/ml to about 9 U/ml, about 5 Um' to about 10 U/ml, about 6 U/ml to about 7 U/ml, about 6 U/ml to about 8 U/ml, about 6 U/ml to about 9 U/ml, about 6 U/ml to about 10 U/ml, about 7 U/ml to about 8 U/ml, about 7 U/ml to about 9 U/ml, about 7 U/ml to about 10 U/ml, about 8 U/ml to about 9 U/ml, about 8 U/ml to about 10 U/ml, or about 9 U/ml to about 10 U/ml. In some embodiments, the amount of Benzonase in the grind media is at least about 1 U/ml, about 2 U/ml, about 3 U/ml, about 4 U/ml, about 5 U/ml, about 6 U/ml, about 7 U/ml, about 8 U/ml, or about 9 U/ml. In some embodiments, the amount of Benzonase in the grind media is at most about 2 U/ml, about 3 U/ml, about 4 U/ml, about 5 U/ml, about 6 U/ml, about 7 U/ml, about 8 U/ml, about 9 U/ml, or about 10 U/ml.

In some cases, the amount of Benzonase® in a grind medium is about 3 U/ml and the amount of heparin in the grind medium is about 10 U/ml.

In some embodiments, the amount of Benzonase® or Denarase® in the grind media is about 11 U/ml to about 55 U/ml. In some embodiments, the amount of Benzonase in the grind media is about 11 U/ml, about 15 U/ml, about 20 U/ml, about 25 U/ml, about 30 U/ml, about 35 U/ml, about 40 U/ml, about 45 U/ml, about 50 U/ml, or about 55 U/ml. In some embodiments, the amount of Benzonase in the grind media is at least about 11 U/ml, about 15 U/ml, about 20 U/ml, about 25 U/ml, about 30 U/ml, about 35 U/ml, about 40 U/ml, about 45 U/ml, or about 50 U/ml. In some embodiments, the amount of Benzonase in the grind media is about 11 U/ml to about 15 U/ml, about 11 U/ml to about 20 U/ml, about 11 U/ml to about 25 U/ml, about 11 U/ml to about 30 U/ml, about 11 U/ml to about 35 U/ml, about 11 U/ml to about 40 U/ml, about 11 U/ml to about 45 U/ml, about 11 U/ml to about 50 U/ml, about 11 U/ml to about 55 U/ml, about 15 U/ml to about 20 U/ml, about 15 U/ml to about 25 U/ml, about 15 U/ml to about 30 U/ml, about 15 U/ml to about 35 U/ml, about 15 U/ml to about 40 U/ml, about 15 U/ml to about 45 U/ml, about 15 U/ml to about 50 U/ml, about 15 U/ml to about 55 U/ml, about 20 U/ml to about 25 U/ml, about 20 U/ml to about 30 U/ml, about 20 U/ml to about 35 U/ml, about 20 U/ml to about 40 U/ml, about 20 U/ml to about 45 U/ml, about 20 U/ml to about 50 U/ml, about 20 U/ml to about 55 U/ml, about 25 U/ml to about 30 U/ml, about 25 U/ml to about 35 U/ml, about 25 U/ml to about 40 U/ml, about 25 U/ml to about 45 U/ml, about 25 U/ml to about 50 U/ml, about 25 U/ml to about 55 U/ml, about 30 U/ml to about 35 U/ml, about 30 U/ml to about 40 U/ml, about 30 U/ml to about 45 U/ml, about 30 U/ml to about 50 U/ml, about 30 U/ml to about 55 U/ml, about 35 U/ml to about 40 U/ml, about 35 U/ml to about 45 U/ml, about 35 U/ml to about 50 U/ml, about 35 U/ml to about 55 U/ml, about 40 U/ml to about 45 U/ml, about 40 U/ml to about 50 U/ml, about 40 U/ml to about 55 U/ml, about 45 U/ml to about 50 U/ml, about 45 U/ml to about 55 U/ml, or about 50 U/ml to about 55 U/ml. In some embodiments, the amount of Benzonase in the grind media is at most about 15 U/ml, about 20 U/ml, about 25 U/ml, about 30 U/ml, about 35 U/ml, about 40 U/ml, about 45 U/ml, about 50 U/ml, or about 55 U/ml.

It is noted that Denarase® reagent (C-Lecta GmbH) is equivalent to Benzonase® reagent in the same quantity in the present process.

Notably, it has been discovered that a relationship exists between the amount of Benzonase® in a grinding medium and the amount of heparin, such that progressively lower amounts of Benzonase can be used as the amounts of heparin is reduced. Without wishing to be bound by theory, it is likely that heparin, through calcium chelation, helps prevent clumping of cells; however, more importantly, heparin chelates magnesium. Magnesium is an important co-factor for Benzonase. Therefore, in the presence of heparin, the presence and/or relative amounts of magnesium in a solution is reduced and this reduction in magnesium amounts reduces Benzonase activity. Thus, in some embodiments, the amount of heparin is lowered and in some embodiments, heparin is omitted.

In some embodiments, HSA is present in the grind media at about 0.5% to about 5%. In some embodiments, HSA is present in the grind media at about 0.5% to about 1%, about 0.5% to about 1.5%, about 0.5% to about 2%, about 0.5% to about 2.5%, about 0.5% to about 3%, about 0.5% to about 3.5%, about 0.5% to about 4%, about 0.5% to about 4.5%, about 0.5% to about 5%, about 1% to about 1.5%, about 1% to about 2%, about 1% to about 2.5%, about 1% to about 3%, about 1% to about 3.5%, about 1% to about 4%, about 1% to about 4.5%, about 1% to about 5%, about 1.5% to about 2%, about 1.5% to about 2.5%, about 1.5% to about 3%, about 1.5% to about 3.5%, about 1.5% to about 4%, about 1.5% to about 4.5%, about 1.5% to about 5%, about 2% to about 2.5%, about 2% to about 3%, about 2% to about 3.5%, about 2% to about 4%, about 2% to about 4.5%, about 2% to about 5%, about 2.5% to about 3%, about 2.5% to about 3.5%, about 2.5% to about 4%, about 2.5% to about 4.5%, about 2.5% to about 5%, about 3% to about 3.5%, about 3% to about 4%, about 3% to about 4.5%, about 3% to about 5%, about 3.5% to about 4%, about 3.5% to about 4.5%, about 3.5% to about 5%, about 4% to about 4.5%, about 4% to about 5%, or about 4.5% to about 5%. In some embodiments, HSA is present in the grind media at about 0.5%, about 1%, about 1.5%, about 2%, about 2.5%, about 3%, about 3.5%, about 4%, about 4.5%, or about 5%. In some embodiments, HSA is present in the grind media at least about 0.5%, about 1%, about 1.5%, about 2%, about 2.5%, about 3%, about 3.5%, about 4%, or about 4.5%. In some embodiments, HSA is present in the grind media at most about 1%, about 1.5%, about 2%, about 2.5%, about 3%, about 3.5%, about 4%, about 4.5%, or about 5%.

Another pitcher of 300-500 ml of grind media is retained for collecting the bone fragments after grinding, and another supply of about 100 ml of the grind media is retained for rinsing through the grinder during the grinding process to prevent bone fragments from sticking to the surface of the pitcher of the grinding components. In some embodiments, the additional grind media may have different quantities of heparin, HSA, and Benzonase as compared to the initial grind media.

An electric bone grinder or a purpose-built bone grinder, such as the grinder of Biorep Technologies Inc, (Miami, Fla.) can be used in an ISO-5 environment within an ISO-7 clean room. Bone types are kept separate if both VB and ilium from the same donor are being processed. The bone is kept submerged in grind media at all times during and after the grinding process. Once all of the donor bone pieces are ground, the chamber of the bone grinder is thoroughly rinsed with fresh processing media. The bone fragments are discharged from the grinder into the pitcher containing grind media.

In some cases, bone marrow and bone grindings from are shaken for 10 minutes at 150 RPM.

The contents of the pitcher are transferred to sterile bags. Next, the contents of the sterile bags are filtered to extract the solid components. In one embodiment, the contents of each bag are passed through a series of stainless-steel sieves. In this embodiment, a 425 µm or 500 µm sieve is stacked on top of a 177 µm or 200 µm sieve, which is seated over a catch-pan to receive the liquid filter contents. The sterile bags containing the output from the grinder is swirled and then poured evenly over the sieve stack or filtration sets. The filtering process is observed to ensure that excessive clumping is not occurring, which can signal the presence of soft tissue or other contaminants. Bone fragments retained on the surface of the sieves are distributed evenly on the sieves and rinsed with 250 ml of fresh processing medium. In one embodiment, the processing medium used for rinsing is the grind media described above or PLASMA-LYTE™ with 2.5% HSA. The sieved bone marrow product, which can be approximately 1000 ml in a well-performed process, is transferred to sterile packs for subsequent processing and analysis. The contents of each bag are visually inspected to confirm that the contents do not include any visible bone fragments or soft tissue.

In some embodiments, the rinse media can contain the various amounts of HSA as described for the grind media. In some embodiments, the rinse media can contain, additionally, heparin and/or Benzonase.

In some cases, the amount of Benzonase® in a rinse medium is about 3 U/ml and the amount of heparin in the rinse medium is about 10 U/ml.

In another embodiment, the contents of each bag are passed through bone marrow filtration units, as depicted in FIG. 1. In this embodiment, the system 150 includes a stand 154 configured to support a sterile collection bag 152 which contains the bone fragments and media from the grinding operation described above. The stand includes a container hanger 155 configured to engage the cap 153 of the sterile bag to suspend the container. The bottom of the bag includes a discharge assembly 160 that includes a pre-filter 162 projecting into the body of the collection bag. In one specific embodiment the pre-filter 162 is an 850 µm filter. In some embodiments, the bone marrow passes first through an 800 µm pre-filter. The filter 162 is connected to an output tube 164 that is connected by a container claim 166 to the input line 171 of a first in-line filter 170. In the specific embodiment, the first in-line filter is a 200 µm or a 500 µm filter. The output line 172 of the first in-line filter is connected to the input line 176 of a second in-line filter 175. The second in-line filter is a 200 µm or a 500 µm filter. The two in-line filters are initially both 500 µm for a first pass through the filter system 150. A second rinse is then performed on the grindings with the two in-line filters being 200 µm. This double-pass filtration results in a cleaner suspension and enhances removal of fat from the suspension. The second in-line filter 175 has an output line 177 that can be engaged to a sterile bag, such as bag 152 for the second filtration pass. On the second pass through the system, the output line 177 of the second in-line filter 175 can be engaged to a container clamp 181 of a transfer pack container 180. The transfer pack container can be a 600-2000 ml bag to accommodate the filtered bone marrow product, which can be approximately 1000 ml in a well-performed process.

The Total Nucleated Count (TNC) from a filtered bone marrow product can be calculated:

$$TNC(\times 10^3 \text{ cells/L}) = \text{Cell Count}(\times 10^3 \text{ cells/L}) \times \text{Total Mass of Bone Marrow Extract (g)} \times 1000)$$

Agitation of Bone Grindings and/or Bone Grinding Filtrate

Described herein, in some embodiments, is a method for processing bone marrow or derivative thereof, the method comprises mechanically agitating the bone grindings and/or bone grinding filtrate during the grinding and filtration portion of the processing of the bone marrow. In some instances, the bone marrow can be obtained from a deceased donor. In some cases, the bone marrow can be obtained from a sample (e.g. bone or VB) that was previously chilled. In some cases, the bone marrow can be obtained from a sample (e.g. bone or VB) that was previously chilled but not frozen.

In some cases, the bone marrow can be obtained from a sample (e.g. bone or VB) that is thawed. In some cases, the bone marrow can be processed for obtaining bone marrow cells. In some embodiments, the bone marrow cells can be hematopoietic stem cells (HSCs). In some embodiments, the bone marrow cells can be mesenchymal stem cells (MSCs).

Aspect disclosed in the present disclosure comprises a method for processing bone marrow or a derivative thereof, wherein the bone marrow or the derivative thereof is derived from a deceased donor, the method comprising: obtaining a bone or bone fragment from a deceased donor, optionally, processing the bone into bone fragments; mechanically grinding the bone or bone fragment in the presence of a grinding solution to generate a plurality of bone grindings; placing the plurality of bone grindings on a shaker at about 100 to about 200 rounds per minute ("RPM") for about 1 to about 20 minutes; and removing the solution from the shaker, wherein the solution comprises the bone marrow or the derivative thereof and wherein the bone marrow or the derivative thereof comprises at least about 1,500,000 CD34+ cells/ml of the bone marrow or the derivative thereof. In some embodiments, the method further comprises contacting the solution with a rinse media and repeating the placing of the bone grindings on the shaker and then removing the solution from the shaker. In some embodiments, the method further comprises repeating step placing the bone grinding on the shaker and then removing the solution from the shaker one or more times. In some embodiments, the at least about 1,500,000 CD34+ cells/ml of the bone marrow or the derivative thereof comprises at least 85% viable CD34+ cells. In some embodiments, the method further comprises the at least about 1,500,000 CD34+ cells/ml of the bone marrow or the derivative thereof comprises at least 90% viable CD34+ cells.

The mechanical agitation can comprise agitating the bone grindings in a linear fashion. In some embodiments, the mechanical agitation can comprise agitating the bone grindings in a three-dimensional fashion. In some cases, the mechanical agitation of the bone grindings can comprise orbital shaking (via an orbital shaker) such as placing the bone grinding on a shaker. In some cases, the bone grindings can be mechanically agitated by the shaker at a rate at least about 10 rounds per minute (RPM), 20 RPM, 30 RPM, 40 RPM, 50 RPM, 60 RPM, 70 RPM, 80 RPM, 90 RPM, 100 RPM, 110 RPM, 120 RPM, 130 RPM, 140 RPM, 150 RPM, 160 RPM, 170 RPM, 180 RPM, 190 RPM, 200 RPM, 210 RPM, 220 RPM, 230 RPM, 240 RPM, 250 RPM, or more. In some cases, the bone grindings can be mechanically agitated by centrifugation (e.g. spinning). In some embodiments, the bone grindings can be spun at least 10 RPM, 20 RPM, 30 RPM, 40 RPM, 50 RPM, 60 RPM, 70 RPM, 80 RPM, 90 RPM, 100 RPM, 110 RPM, 120 RPM, 130 RPM, 140 RPM, 150 RPM, 160 RPM, 170 RPM, 180 RPM, 190 RPM, 200 RPM, 210 RPM, 220 RPM, 230 RPM, 240 RPM, 250 RPM, or more. In some embodiments, the bone grindings can be spun at least 300 RPM, 400 RPM, 500 RPM, 600 RPM, or more. In some embodiments, the bone grindings can be mechanically agitated by both shaking and spinning. In some embodiments, the mechanical agitation of the bone grindings can be for at least 1 minute, 2 minutes, 3 minutes, 4 minutes, 5 minutes, 10 minutes, 15 minutes, 20 minutes, 25 minutes, 30 minutes, or longer.

In some embodiments, the mechanical agitation of the bone grindings increases the yield of the bone marrow cells obtained. In some instances, the yield of the bone marrow cells obtained by mechanical agitation of the bone grindings is increased by at least about 10%, 20%, 30%, 40%, 50%, 60%, 70%, 80%. 90%, 100%, 2 fold, 3 fold, 4 fold, 5 fold, 10 fold, 20 fold, 50 fold, or more compared to yield of bone marrow cells obtained without the mechanical agitation.

In some embodiments, the mechanical agitation of the bone grindings increases the viability of the bone marrow cells obtained. In some instances, the viability of the bone marrow cells obtained by mechanical agitation of the bone grindings is increased by at least about 10%, 20%, 30%, 40%, 50%, 60%, 70%, 80%. 90%, 100%, 2 fold, 3 fold, 4 fold, 5 fold, 10 fold, 20 fold, 50 fold, or more compared to the viability of bone marrow cells obtained without the mechanical agitation.

In some embodiments, the mechanical agitation of the bone grindings increases the number of CD34 expressing bone marrow cells obtained. In some instances, the number of CD34 expressing bone marrow cells obtained by mechanical agitation of the bone grindings is increased by at least about 10%, 20%, 30%, 40%, 50%, 60%, 70%, 80%. 90%, 100%, 2 fold, 3 fold, 4 fold, 5 fold, 10 fold, 20 fold, 50 fold, or more compared to the number of CD34 expressing bone marrow cells obtained without the mechanical agitation.

In some embodiments, the mechanical agitation of the bone grindings increases the number of CD45 expressing bone marrow cells obtained by the methods described herein. In some instances, the number of CD45 expressing bone marrow cells obtained by mechanical agitation of the bone grindings is increased by at least about 10%, 20%, 30%, 40%, 50%, 60%, 70%, 80%. 90%, 100%, 2 fold, 3 fold, 4 fold, 5 fold, 10 fold, 20 fold, 50 fold, or more compared to the number of CD45 expressing bone marrow cells obtained without the mechanical agitation.

The above mentioned agitation can occur before the filtration steps described previously.

In certain embodiments, the amount of CD34+ cells/ml of the bone marrow or the derivative thereof obtained is at least about 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 1,050,000, 1,100,000, 1,150,000, 1,200,000, 1,250,000, 1,300,000, 1,350,000, 1,400,000, 1,450,000, 1,500,000, 1,550,000, 1,600,000, 1,650,000, 1,700,000, 1,750,000, 1,800,000, 1,850,000, 1,900,000, 1,950,000, 2,000,000, or more than 2,000,000 CD34+ cells/ml. In some embodiments, the amount of CD34+ cells/ml of the bone marrow or the derivative thereof obtained is at least about 1,500,000 CD34+ cells/ml to about 2,000,000 CD34+ cells/ml. In some embodiments, the amount of CD34+ cells/ml of the bone marrow or the derivative thereof obtained is at least about 1,500,000 CD34+ cells/ml to about 1,750,000 CD34+ cells/ml, about 1,500,000 CD34+ cells/ml to about 2,000,000 CD34+ cells/ml, or about 1,750,000 CD34+ cells/ml to about 2,000,000 CD34+ cells/ml. In some embodiments, the amount of CD34+ cells/ml of the bone marrow or the derivative thereof obtained is at least about 1,500,000 CD34+ cells/ml, about 1,750,000 CD34+ cells/ml, or about 2,000,000 CD34+ cells/ml. In some embodiments, the amount of CD34+ cells/ml of the bone marrow or the derivative thereof obtained is at least at least about 1,500,000 CD34+ cells/ml, or about 1,750,000 CD34+ cells/ml. In some embodiments, the amount of CD34+ cells/ml of the bone marrow or the derivative thereof obtained is at least at most about 1,750,000 CD34+ cells/ml, or about 2,000,000 CD34+ cells/ml.

In some embodiments, the viability of the CD34+ cells is at least about 70% to about 95%. In some embodiments, the viability of the CD34+ cells is at least about 70% to about 75%, about 70% to about 80%, about 70% to about 85%, about 70% to about 90%, about 70% to about 95%, about 75% to about 80%, about 75% to about 85%, about 75% to about 90%, about 75% to about 95%, about 80% to about 85%, about 80% to about 90%, about 80% to about 95%, about 85% to about 90%, about 85% to about 95%, or about 90% to about 95%. In some embodiments, the viability of the CD34+ cells is at least about 70%, about 75%, about 80%, about 85%, about 90%, or about 95%. In some embodiments, the viability of the CD34+ cells is at least at least about 70%, about 75%, about 80%, about 85%, or about 90%. In some embodiments, the viability of the CD34+ cells is at least at most about 75%, about 80%, about 85%, about 90%, or about 95%.

For quality control, a small quantity of bone marrow, such as 0.3 mL, is extracted from the sterile pack 152 using a syringe at an injection site 157 and conducting inversion mixing before pulling the sample. The sample can be tested by a hematology analyzer, such as a Sysmex Hematology Analyzer, to determine the total nucleated cell (TNC) content of the sample, as an indicator of the TNC content of the bone marrow being subsequently processed.

Fat Removal and Concentration

Figure 2:
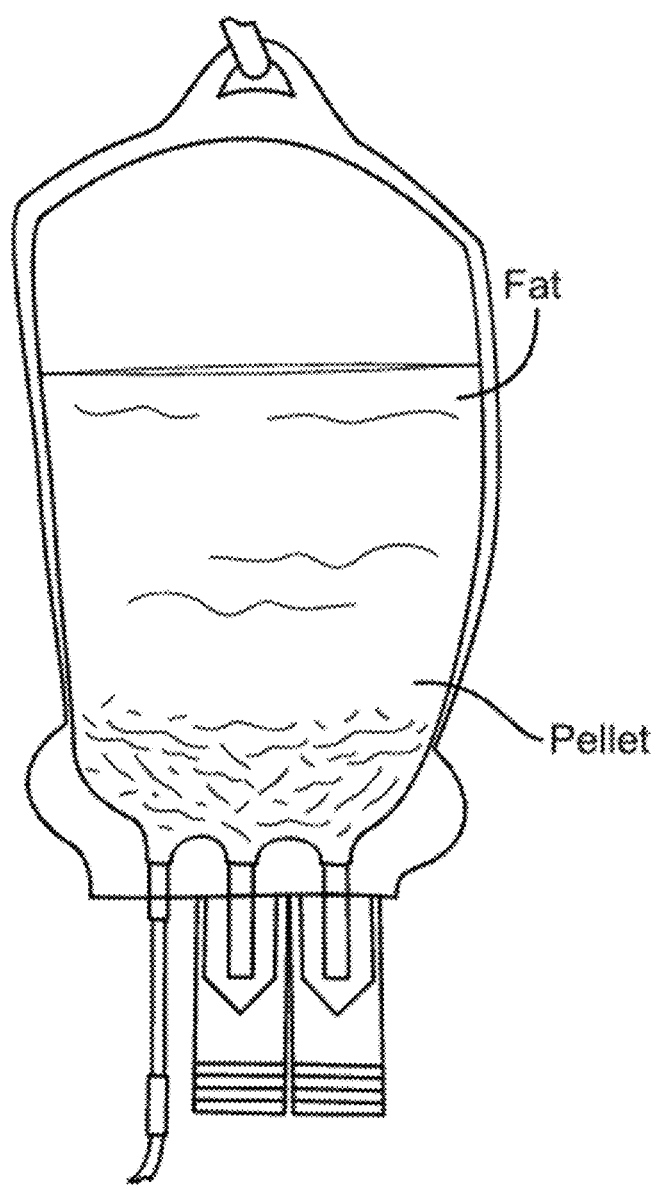
FIG. 2 is a view of a sterile bag containing a bone marrow pellet processed according to the methods of the present disclosure.
Figure 3:
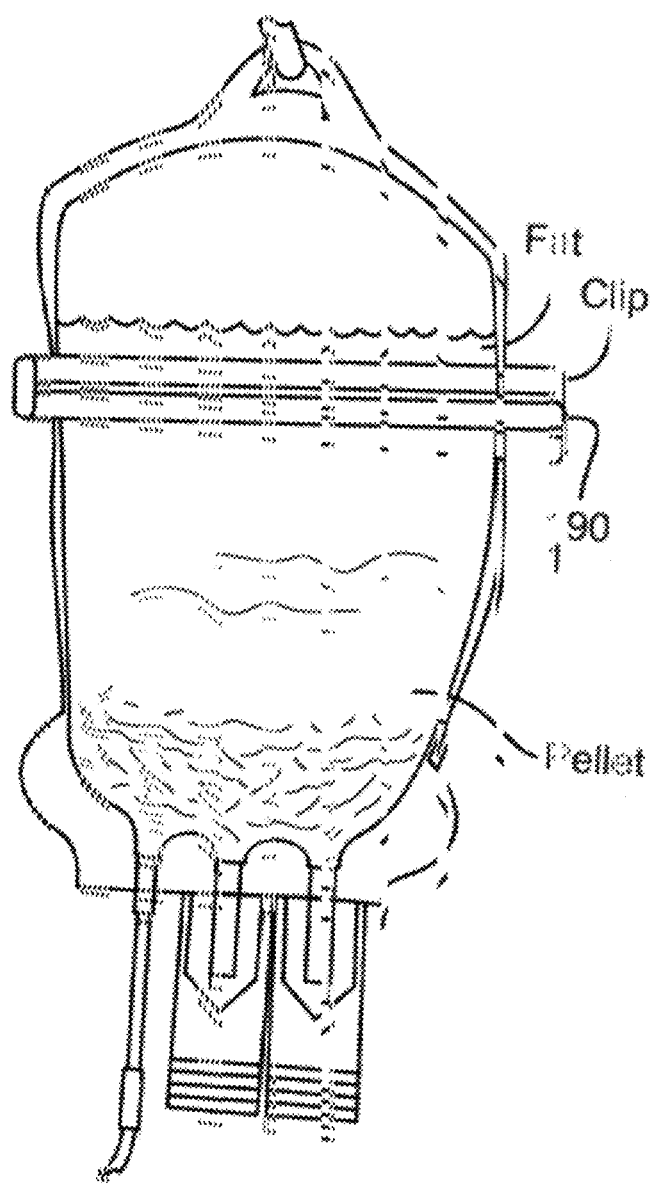
FIG. 3 is a view of the sterile bag of FIG. 2 with a clip engaging the bag to separate the fat from the bone marrow pellet.

The bone marrow product collected from the filtering is essentially a fatty emulsion. The fat content of the suspension obtained from the sieve filtering approach disclosed above is greater than the fat content of the suspension obtained from the double-pass filtration system 150. However, in both cases, there is a need to remove the fat content from the suspension. The suspension obtained from the filtering is recovered into 250 ml bags which are hermetically sealed with tube welders. Pairs of sterile bags and taring sticks are mounted within a centrifuge with bag ports facing down, and balanced. Volume compensating plates are used to prevent creasing of the bags during centrifugation. In one embodiment, the bags are centrifuged at 500×g for 15 minutes at room temperature to concentrate the cells, preferably to $2-3\times10^8$/ml. After centrifugation is complete, each bag is individually hung on a ring stand. The distinct layers within the bag are visible, with the fat layer clearly delineated on top of the supernatant with the bone marrow pellet at the bottom, as shown in FIG. 2. A new sterile bag is welded to the bag removed from the centrifuge. A bag clamp or clip 190 is placed on the bag just below the fat layer, as shown in FIG. 3, to clamp off or squeeze the bag closed beneath the fat layer. The pellet is then drained from the centrifuge bag into the new sterile bag, with the bag clip preventing passage of the fat layer. The pellet is agitated as it is drained to resuspend all of the pellet. After about half of the pellet has drained into the new bag, the tubing is closed with a hemostat or tube sealer. The second centrifuge bag is then welded to the new bag containing the pellet, and the contents of this second centrifuge bag are drained into the new bag.

Figure 4:
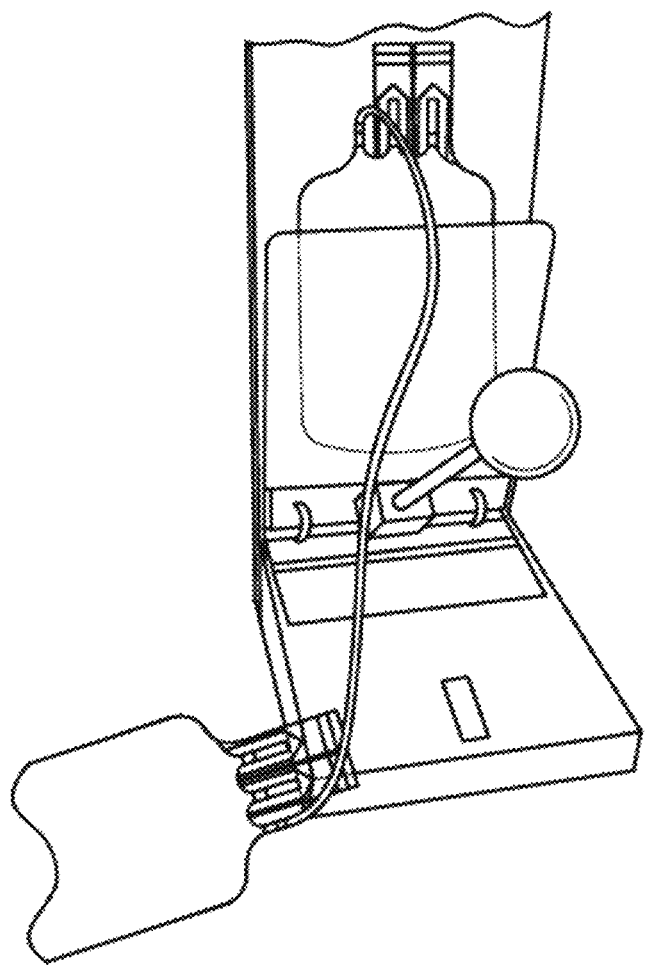
FIG. 4 shows the set-up for isolation of the bone marrow pellet.
Figure 5:
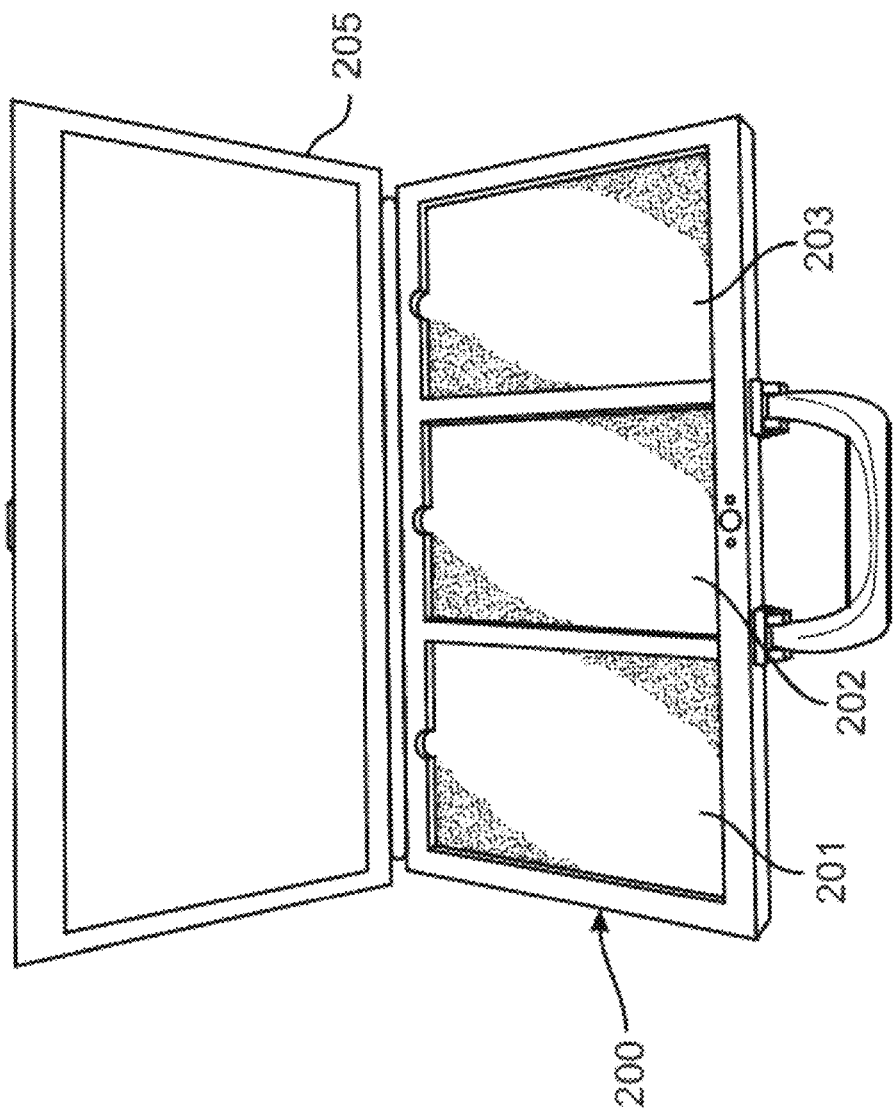
FIG. 5 is a perspective view of a cooling box according to one aspect of the present disclosure.

The result is new sterile bags containing the bone marrow centrifuged to remove the fat. These bags of de-fatted bone marrow are then centrifuged at 500×g for 15 minutes at room temperature, with volume compensating plates to prevent creasing of the bags. Each bag is removed and suspended on a ring stand and a waste bag is welded to the bag, and a plasma extractor is used to remove the supernatant into the waste bag, as shown in FIG. 4. The tubing is clamped with a hemostat when the pellet rises or breaks. The tubing is then sealed and severed to remove the pellet-containing bag from the waste bag, which is discarded. A Luer connection is welded to the pellet-containing bag. The pellets from each bag are combined into a bulk bag using a large syringe. The pellet-containing bags are rinsed into the bulk bag using a rinse media. The bulk bag is inverted several times to ensure that all of the pellet is resuspended. A small quantity of the processed BM, such as 0.5 mL, can be removed for quality control testing for density and cell count. The test sample can also be evaluated for human leukocyte antigens, CCR5delta 32 mutation and apolipoprotein (APOE), among other things.

In some embodiments, the centrifuge settings at one or more steps can be increased. In some embodiments, the centrifuge is spun at about 400 g to about 650 g. In some embodiments, the centrifuge is spun at about 400 g to about 450 g, about 400 g to about 500 g, about 400 g to about 550 g, about 400 g to about 600 g, about 400 g to about 650 g, about 450 g to about 500 g, about 450 g to about 550 g, about 450 g to about 600 g, about 450 g to about 650 g, about 500 g to about 550 g, about 500 g to about 600 g, about 500 g to about 650 g, about 550 g to about 600 g, about 550 g to about 650 g, or about 600 g to about 650 g. In some embodiments, the centrifuge is spun at about 400 g, about 450 g, about 500 g, about 550 g, about 600 g, or about 650 g. In some embodiments, the centrifuge is spun at least about 400 g, about 450 g, about 500 g, about 550 g, or about 600 g. In some embodiments, the centrifuge is spun at most about 450 g, about 500 g, about 550 g, about 600 g, or about 650 g. In some embodiments, the centrifuge is spun for about 10 minutes to about 40 minutes. In some embodiments, the centrifuge is spun for about 10 minutes to about 15 minutes, about 10 minutes to about 20 minutes, about 10 minutes to about 25 minutes, about 10 minutes to about 30 minutes, about 10 minutes to about 35 minutes, about 10 minutes to about 40 minutes, about 15 minutes to about 20 minutes, about 15 minutes to about 25 minutes, about 15 minutes to about 30 minutes, about 15 minutes to about 35 minutes, about 15 minutes to about 40 minutes, about 20 minutes to about 25 minutes, about 20 minutes to about 30 minutes, about 20 minutes to about 35 minutes, about 20 minutes to about 40 minutes, about 25 minutes to about 30 minutes, about 25 minutes to about 35 minutes, about 25 minutes to about 40 minutes, about 30 minutes to about 35 minutes, about 30 minutes to about 40 minutes, or about 35 minutes to about 40 minutes. In some embodiments, the centrifuge is spun for about 10 minutes, about 15 minutes, about 20 minutes, about 25 minutes, about 30 minutes, about 35 minutes, or about 40 minutes. In some embodiments, the centrifuge is spun for at least about 10 minutes, about 15 minutes, about 20 minutes, about 25 minutes, about 30 minutes, or about 35 minutes. In some embodiments, the centrifuge is spun for at most about 15 minutes, about 20 minutes, about 25 minutes, about 30 minutes, about 35 minutes, or about 40 minutes. In some cases, a bag comprising extracted bone marrow can be concentrated by centrifuging at 600×g (~2315 rpm) for 30 minutes. The supernatant is removed from the bone marrow pellets using a plasma extractor and into a waste bag. Waste is discarded using standard biohazard protocol. The pellets are then combined into a pre-weighed bulk bag and resuspended using rinse media. In some embodiments, the centrifuge is stopped without the use of a brake. In some embodiments, the centrifuge is stopped with a brake. In some embodiments, the centrifuge brake is set at about 25% to about 100%. In some embodiments, the centrifuge brake is set at about 25% to about 50%, about 25% to about 75%, about 25% to about 100%, about 50% to about 75%, about 50% to about 100%, or about 75% to about 100%. In some embodiments, the centrifuge brake is set at about 25%, about 50%, about 75%, or about 100%. In some embodiments, the centrifuge brake is set at least about 25%, about 50%, or about 75%. In some embodiments, the centrifuge brake is set at most about 50%, about 75%, or about 100%.

In some cases, fat removal can be occur using a commercial cell processing device (e.g., COBE® 2991 cell processor, TerumoBCT). See the World Wide Web (at) terumobct.com/2991. Such commercial cell processing devices may also concentrate cell products.

The cell product is aliquoted into one or more second volumes, i.e., segregate vials.

Cryopreservation of the Bone Marrow

The present method provides a system for extracting and banking bone marrow for future clinical use according to the processing methods described above, as summarized in the flowchart of FIG. 6. This method can eliminate the failures of the current methods of matching bone marrow donors to groups that are tough to match, such as certain minorities. Once the bone marrow is cryopreserved and banked there is no uncertainty as to the source of the bone marrow, there is no wait for a future recipient and the bone marrow is available in large, repeatable volumes.

Methods of the present disclosure further provide distinct containers for a given bone marrow product with a first (larger) volume that contains cells to be provided to a subject in need and a second (smaller) volume that acts as a surrogate for the first volume, with cells of the second volume, i.e., the surrogate, being used for assays to determine suitability of the first volume for administration to a subject in need.

It is contemplated that each bone donor can yield three or more bags of bone marrow through the process described above, based on ten vertebrae and/or the ilium obtained from the donor. If at the end of the process for a given donor three bags of bone marrow are not obtained, the donor can be flagged as potentially not passing overall quality control. A predetermined volume of bone marrow in each bag is contemplated, such as 70 ml contained in 250 ml bags. This predetermined volume is used to calculate the volume of freeze media components necessary for efficient cryopreservation of the bone marrow pellet. The freeze media is a solution of a rinse media and a cryopreservation composition. The cryoprotectant can be a cell-permeable media, such as dimethyl sulfoxide (DMSO); 1, 2 propane diol (also known as propylene glycol); ethylene glycol; glycerol; foramamide; ethanediol or butane 2, 3 diol; and/or a non-permeable media, such as hydroxyethyl starch (HES), dextran, sucrose, trehalose, lactose, raffinose, ribotol, Mannitol or polyvinylpyrrolidone (PVP). Each bone donor can also provide at least three surrogate vials, e.g., 3, 4, 5, 6, 7, 8, 9, 10, 11, 12 or more surrogate vial. The greater number of cryopreservation bags obtained from a donor, the greater number of surrogate vials that can be prepared, so that each cryopreservation bag has at least one vial, preferably, two, three, four, or more vials per cryopreservation bag.

HSA also provides cryoprotection through oncotic pressure, cell surface protein stabilization and reactive oxygen scavenging. In a preferred embodiment, the cryoprotectant is DMSO. The rinse media can be an electrolyte medium, such as PlasmaLyte, Isolyte, IMDM or other electrolyte solutions suitable for infusion. The freeze media can also include concentrations of oxyrase to reduce oxygen content to less than atmospheric, such as to less than 3% of atmospheric concentrations. The addition of oxyrase produces a hypobaric composition that can facilitate cryopreservation.

In some embodiments, for a method provided herein, a bone marrow product is cryopreserved in a freeze media, wherein said freeze media comprises an electrolyte formulation, human serum albumin (HSA), dimethyl sulfoxide (DMSO), or any combination thereof.

In some embodiments, said freeze media and/or rinse media comprises about 1% to about 10%, about 1% to about 9%, about 1% to about 8%, about 1% to about 7%, about 1% to about 6%, about 1% to about 5%, about 1% to about 4%, about 1% to about 3%, about 1% to about 2%, about 2% to about 10%, about 2% to about 9%, about 2% to about 8%, about 2% to about 7%, about 2% to about 6%, about 2% to about 5%, about 2% to about 4%, about 2% to about 3%, about 3% to about 10%, about 3% to about 9%, about 3% to about 8%, about 3% to about 7%, about 3% to about 6%, about 3% to about 5%, about 3% to about 4%, about 4% to about 10%, about 4% to about 9%, about 4% to about 8%, about 4% to about 7%, about 4% to about 6%, about 4% to about 5%, about 5% to about 10%, about 5% to about 9%, about 5% to about 8%, about 5% to about 7%, about 5% to about 6%, about 6% to about 10%, about 6% to about 9%, about 6% to about 8%, about 6% to about 7%, about 7% to about 10%, about 7% to about 9%, about 7% to about 8%, about 8% to about 10%, about 8% to about 9%, or about 9% to about 10% HSA. In some embodiments, said freeze media and/or rinse media comprises about 1% to about 5% HSA. In some embodiments, said freeze media and/or rinse media comprises about 2.5% HSA.

In some embodiments, said freeze media comprises about 1% to about 10%, about 1% to about 9%, about 1% to about 8%, about 1% to about 7%, about 1% to about 6%, about 1% to about 5%, about 1% to about 4%, about 1% to about 3%, about 1% to about 2%, about 2% to about 10%, about 2% to about 9%, about 2% to about 8%, about 2% to about 7%, about 2% to about 6%, about 2% to about 5%, about 2% to about 4%, about 2% to about 3%, about 3% to about 10%, about 3% to about 9%, about 3% to about 8%, about 3% to about 7%, about 3% to about 6%, about 3% to about 5%, about 3% to about 4%, about 4% to about 10%, about 4% to about 9%, about 4% to about 8%, about 4% to about 7%, about 4% to about 6%, about 4% to about 5%, about 5% to about 10%, about 5% to about 9%, about 5% to about 8%, about 5% to about 7%, about 5% to about 6%, about 6% to about 10%, about 6% to about 9%, about 6% to about 8%, about 6% to about 7%, about 7% to about 10%, about 7% to about 9%, about 7% to about 8%, about 8% to about 10%, about 8% to about 9%, or about 9% to about 10% DMSO. In some embodiments, said freeze media comprises about 1% to about 10% DMSO. In some embodiments, said freeze media comprises about 2.5% DMSO, about 5% DMSO, or about 10% DMSO.

In some embodiments, said electrolyte formulation is Plasmalyte A.

In various embodiments, a rinse medium and/or freeze medium lacks heparin.

In some embodiments, the rinse media is fresh.

In some cases, the freeze media is ≤25° C. before adding it to the bone marrow bulk bag.

The freeze media may be added to the bone marrow bulk bag at a predetermined rate (10% of the Freeze Media volume per minute) based on the following formula:

$$\text{Volume of Freeze Media to add per minute} = \text{Total Volume of Freeze Media (mL)} \times 0.1$$

Preferably, the elapsed time for adding the cryoprotectant to the bone marrow bulk bag does not exceed 9-11 minutes.

The freeze media is prepared by mixing the cryoprotectant and the rinse media according to the calculated total volume of freeze media needed for the volume of bone marrow collected. The bag containing the bone marrow is placed on a rocker for mixing and the freeze media is introduced into the bag by syringe. The freeze media is introduced at a particular rate over a predetermined time. In one embodiment, the freeze media is added at a rate of 10% of the media per minute, for a time of ten minutes. Once the media has been mixed with the concentrated bone marrow, a test sample is extracted by syringe. The remaining mixture of freeze media and bone marrow is injected in predetermined amounts into separate cryopreservation bags (and surrogate vials). In one embodiment, 70 ml of bone marrow mixture is introduced into each cryopreservation bag and air is drawn out with a syringe. At the end of the process, an 8 ml sample can be removed for sterility testing. Each cryopreservation bag is sealed to create four compartments, which are then separated for storage in cassettes to be stored in a cryo-freezer. In another embodiment, the separated compartments are stored in a passive cooling box, such as cooling box 200 shown in FIG. 5 or the cooling boxes described in U.S. Pat. No. 7,604,930, which is hereby incorporated by reference, in its entirety. A standard freezer box with or without a box rack may be used in these embodiments. In some embodiments, the cassettes are not stored in a passive cooling box. In some embodiments, the cassettes are arranged inside a cryo-freezer in a particular configuration to induce specific freezing rates. In some embodiments, the arrangement is the arrangement depicted in FIG. 14 or FIG. 15. As shown, the cassette are preferably not touching an internal wall of a freezer shelf. Also, it is preferable that cassettes are not stacked on top of each other.

Aspects of the present disclosure provide a cryopreserved cell product that is divided into two volumes, with a first volume (e.g., cryopreservation bag) for containing the cell product for transplant into a subject in need thereof and a second volume that acts as a surrogate for the first volume. As used herein, a surrogate vial is typically a smaller volume of the cell product and the surrogate can be thawed and assayed as needed, e.g., for cell viability (and especially "function viability" as determined by post-thaw proliferation). The assay results for the surrogate vial represent the expected assay results for the first (larger) volume; however, by using the surrogate it is unnecessary to thaw the first volume for assaying and, instead, it is thawed when needing to be used, e.g., for transplanting into a subject in need.

Without wishing to be bound by theory, for a given cell type, a specific, optimum cooling rate is required for that cell type or cell product to survive cryopreservation. This optimum cooling rate balances damage from intracellular ice formation (IIF) with damage from high solute concentration resulting from extracellular ice formation. If cells are cooled too fast, damaging IIF is likely; if cells are cooled too slowly, damaging solute effects are likely. For the surrogate vial to accurately represent the first volume, the cells in both volumes should be frozen at about the same rate, i.e., the optimized rate; this common rate results in equivalent survival and viability for cells in the two volumes. Importantly, the second volume may be stored in the same long-term storage system as the first volume, and will therefore be exposed to the same conditions over long-term storage durations; thus, promoting the ability of the surrogate vial to accurate represent the cryopreservation bag that contains cell for transplant. These ultimately allows the second volume to be tested to determine, at least, if storage of the cryopreservation bag was maintained appropriately and without having to manipulate and test the cells of the first volume. More specifically, by assaying the surrogate vial, the cryopreservation bag does not need to be warmed and/or handled prior to its immediate use. This feature is especially helpful to a subject's outcome and welfare in two ways. First, the cells for transplanting are thawed only when ready to be administered to the subject (and preferably at the site of administration) rather than being thawed two weeks or so before use so that assays can be performed to ensure that the cell product is suitable for use; this two week delay during which the cells are kept at room temperature, on ice, or at 37° C.—or worse refrozen and returned to cold storage—could adversely affect their viability and utility once transplanted. Second, since a subject likely undergoes myeloablative conditioning prior to transplant, the patient can forestall myeloablative conditioning until a cell product has been assayed and determined to be suitable for use, which usually takes about two weeks; by having an surrogate vial, a subject begins myeloablative conditioning once a suitable product has been identified, thereby shortening the length of time that the subject remains immune compromised.

The present disclosure provides methods for ensuring that the two volumes cool at the same rate. Based, at least, on laws of physics, a smaller volume of a cell product will cool at a faster rate than a larger volume of the cell product. And, the smaller volume, with a faster cooling rate should have increased IIF relative to the larger volume, which has a slower cooling rate. Methods of the present disclosure promote an equivalent rate of cell cooling between the first (larger) volume and the second (smaller) volume such that each volume will have similar amounts of IFF and, as such, the surrogate vial (smaller volume) will accurately represent the larger first volume. Without wishing to be bound by theory, methods of the present disclosure slow the rate of cooling for the second (smaller) volume to the rate experienced by the first (larger) volume based, in part, on use of different types of containers that directly holds or indirectly holds either a first volume or the second volume and/or positioning of containers within the same freezer, e.g., a static temperature freezer. As a result, cells in the smaller volume (i.e., the second volume/surrogate vial) and cells in the larger volume (i.e., the first volume/cryopreservation bag) experience similar rates of cooling (e.g., about −1° C./minute) when placed in the same static freezer, e.g., a −86° C. static freezer. Importantly, to slow the cooling rate of the smaller second volume, a surrogate vial is placed directly into an insulated vial container, e.g., CoolCell® freezing storage system, which when placed in a static freezer that is colder than −80° C., e.g., a −86° C. static freezer, the cells in the surrogate vial experience rate of freezing at the rate of about −1° C./minute; without use of the insulated vial container, the cells in the surrogate vial would experience rate of freezing at the rate of about −10° C./minute, which would likely cause damage from IIF On the other hand, the larger first volume, cryopreservation bag, does not need to be directly placed in an insulated container and instead, when the bags are placed in cassettes—which are not insulated (to avoid slowing the cooling rate of the bag)—and moved to −86° C. static freezer, the cells in the cryopreservation bag preferably experience freezing rate of about −1° C./minute. By "directly placed" means that each vial is in close proximity to the insulating material of the insulating container. These manipulation cause cells of the first and the second volumes to have roughly equivalent osmosis of intracellular water into the extracellular space for cells; this osmosis increases the solute concentration intracellularly, and helps avoid formation of (harmful) intracellular ice crystals and promotes extracellular ice formation (which is less harmful to the cell). Once the first step of freezing (in the −86° C. static freezer), the cryopreservation bag and the surrogate vial are placed in the same long-term storage device (e.g., a liquid nitrogen storage tank) and in a roughly similar position within the long-term storage device.

Accordingly, methods of the present disclosure allow production of a surrogate sample of the cell product that is expected to accurately represent the portion of the cell product that is to be administered to a subject in need thereof and provides a cell product that is, not only therapeutically beneficial to the subject, but promotes subject's outcome and welfare in ways that are not achievable when a cryopreserved cell product in merely contained in a single bag and without a surrogate vial.

In some cases, a first volume (i.e., a cryopreservation bag) and a second volume (i.e., a surrogate cryovials) are placed in −86° C. static freezer. The bags are placed in cassettes, which may lack insulation, while the surrogate vials are placed separately in a CoolCell® freezing storage system and then in front of the box of cassettes into the freezer.

When the test samples from the particular bone marrow batch have been validated for cell count and sterility, the cryopreservation bags and surrogate vials of cryopreserved bone marrow can be further cooled for long-term storage. In one embodiment, the bags and vials are cooled at a controlled rate to prevent damage to the bone marrow and cells. An optimal cooling scheme to yield an optimal amount of viable bone marrow and cells comprises varying the cool rate at various stages of the cooling process. In some embodiments, the stages of the cooling process are referred to as "Supra-Freeze" (about 17° C. to the point of nucleation) and "Sub-Freeze" (from about −10° C. to −40° C.). Typically, nucleation occurs from about 7° C. to about 15° C.

Once the first step of freezing (e.g., in the same −86° C. static freezer), the cryopreservation bag and the surrogate vial are placed in the same long-term storage device (e.g., a liquid nitrogen storage tank) and in a roughly similar position within the long-term storage device.

Aspects described in the present disclosure comprises a method for processing bone marrow or a derivative thereof (e.g. bone marrow derived cellular compositions), wherein the bone marrow or the derivative thereof is derived from a deceased donor, the method comprising: obtaining a bone or bone fragment from a deceased donor, optionally, processing the bone into bone fragments; extracting the bone marrow or the derivative thereof from the bone or bone fragment; and cryopreserving the bone marrow or the derivative thereof, wherein the cryopreserving comprises decreasing temperature of the bone marrow or the derivative thereof at a freeze rate of more than about −1° C./min in a static freezer. In some embodiments, the cryopreserving comprises cooling the bone marrow or the derivative thereof at a supra-freeze rate from about −2.5° C./min to about −5° C./min at least until at least one cell of the bone marrow or the derivative thereof is nucleated. In some embodiments, the cryopreserving comprises cooling the bone marrow or the derivative thereof at a supra-freeze rate from about −2.5° C./min to about −4° C./min at least until at least one cell of the bone marrow or the derivative thereof is nucleated. In some embodiments, the cryopreserving comprises cooling the bone marrow or the derivative thereof at a supra-freeze rate from about −2.5° C./min to about −3.5° C./min at least until at least one cell of the bone marrow or the derivative thereof is nucleated. In some embodiments, the cryopreserving comprises cooling the bone marrow or the derivative thereof at a sub-freeze rate from about −1° C./min to about −2° C./min. In some embodiments, the supra-freeze rate and the sub-freeze rate are maintained without the use of a passive cool box. In some embodiments, the cryopreserving comprises arranging one or more aliquots of the bone marrow or the derivative thereof inside the static freezer such that no aliquot contacts a wall of the static freezer. In some embodiments, the bone marrow or the derivative thereof comprises a population of CD34+ cells. In some embodiments, the population of CD34+ cells comprise at least 70% viable CD34+ cells after the bone marrow or the derivative thereof is thawed. In some embodiments, the population of CD34+ cells comprise at least 80% viable CD34+ cells after the bone marrow or the derivative thereof is thawed. In some embodiments, the static freezer is set at about −70° C. to −90° C. In some embodiments, the static freezer is set at −86° C. In some embodiments, the static freezer is set at less than −80° C.

In one specific embodiment, the cryopreservation bags and surrogate vials are cooled at a rate of −1 to −40° C. per minute until the bags have reached a temperature suitable for plunging the bags into liquid nitrogen. Preferably, the bags are cooled at a rate of −1° C. to −5° C. A suitable temperature is in the range of −40 to −100° C. Once that temperature has been reached, the bags are cooled further at a more rapid rate to a temperature of below −130° C. for storage. Once the first step of freezing (e.g., in the same −86° C. static freezer), the cryopreservation bag and the surrogate vial are placed in the same long-term storage device (e.g., a liquid nitrogen storage tank) and in a roughly similar position within the long-term storage device.

In some embodiments, the temperatures for freezing the bone marrow or bone marrow cells comprise the temperatures and freeze rates shown in Example 5. In some embodiments, the bone marrow or bone marrow cells can be cryopreserved at a supra-freeze rate or a supra-freeze range. In some embodiments, the bone marrow or bone marrow cells can be cryopreserved by freezing at both supra-freeze rate and sub-freeze rate. For example, the bone marrow or bone marrow cells can be cryopreserved by freezing at first with supra-freeze rate until a predetermined temperature is reached, which is then followed by switching freezing the bone marrow or bone marrow cells to a sub-freeze rate. In some embodiments, the nucleation temperature of the bone marrow or bone marrow cells can be reached during the supra-freeze. In some embodiments, the nucleation temperature of the bone marrow or bone marrow cells can be reached during the sub-freeze. In some embodiments the nucleation temperature of the bone marrow or bone marrow cells can be reached during the switching between the supra-freeze and the sub-freeze.

In some instances, the bone marrow or bone marrow cells can be cryopreserved first with supra-freeze. For example, the bone marrow or bone marrow cells can be cryopreserved while the bone marrow or bone marrow cells are just processed and at room temperature. In some instances, the supra-freeze rate is generally higher (e.g. decreasing of the temperature at a faster rate) compared to the sub-freeze rate. In some embodiments, the supra-freeze rate is from about −6° C./min to about −0.5° C./min. In some embodiments, the supra-freeze rate is from about −0.5° C./min to about −1° C./min, about −0.5° C./min to about −1.5° C./min, about −0.5° C./min to about −2° C./min, about −0.5° C./min to about −2.5° C./min, about −0.5° C./min to about −3° C./min, about −0.5° C./min to about −3.5° C./min, about −0.5° C./min to about −4° C./min, about −0.5° C./min to about −4.5° C./min, about −0.5° C./min to about −5° C./min, about −0.5° C./min to about −5.5° C./min, about −0.5° C./min to about −6° C./min, about −1° C./min to about −1.5° C./min, about −1° C./min to about −2° C./min, about −1° C./min to about −2.5° C./min, about −1° C./min to about −3° C./min, about −1° C./min to about −3.5° C./min, about −1° C./min to about −4° C./min, about −1° C./min to about −4.5° C./min, about −1° C./min to about −5° C./min, about −1° C./min to about −5.5° C./min, about −1° C./min to about −6° C./min, about −1.5° C./min to about −2° C./min, about −1.5° C./min to about −2.5° C./min, about −1.5° C./min to about −3° C./min, about −1.5° C./min to about −3.5° C./min, about −1.5° C./min to about −4° C./min, about −1.5° C./min to about −4.5° C./min, about −1.5° C./min to about −5° C./min, about −1.5° C./min to about −5.5° C./min, about −1.5° C./min to about −6° C./min, about −2° C./min to about −2.5° C./min, about −2° C./min to about −3° C./min, about −2° C./min to about −3.5° C./min, about −2° C./min to about −4° C./min, about −2° C./min to about −4.5° C./min, about −2° C./min to about −5° C./min, about −2° C./min to about −5.5° C./min, about −2° C./min to about −6° C./min, about −2.5° C./min to about −3° C./min, about −2.5° C./min to about −3.5° C./min, about −2.5° C./min to about −4° C./min, about −2.5° C./min to about −4.5° C./min, about −2.5° C./min to about −5° C./min, about −2.5° C./min to about −5.5° C./min, about −2.5° C./min to about −6° C./min, about −3° C./min to about −3.5° C./min, about −3° C./min to about −4° C./min, about −3° C./min to about −4.5° C./min, about −3° C./min to about −5° C./min, about −3° C./min to about −5.5° C./min, about −3° C./min to about −6° C./min, about −3.5° C./min to about −4° C./min, about −3.5° C./min to about −4.5° C./min, about −3.5° C./min to about −5° C./min, about −3.5° C./min to about −5.5° C./min, about −3.5° C./min to about −6° C./min, about −4° C./min to about −4.5° C./min, about −4° C./min to about −5° C./min, about −4° C./min to about −5.5° C./min, about −4° C./min to about −6° C./min, about −4.5° C./min to about −5° C./min, about −4.5° C./min to about −5.5° C./min, about −4.5° C./min to about −6° C./min, about −5° C./min to about −5.5° C./min, about −5° C./min to about −6° C./min, or about −5.5° C./min to about −6° C./min. In some embodiments, the supra-freeze rate is about −0.5° C./min, about −1° C./min, about −1.5° C./min, about −2° C./min, about −2.5° C./min, about −3° C./min, about −3.5° C./min, about −4° C./min, about −4.5° C./min, about −5° C./min, about −5.5° C./min, or about −6° C./min. In some embodiments, the supra-freeze rate is at least about −0.5° C./min, about −1° C./min, about −1.5° C./min, about −2° C./min, about −2.5° C./min, about −3° C./min, about −3.5° C./min, about −4° C./min, about −4.5° C./min, about −5° C./min, or about −5.5° C./min. In some embodiments, the supra-freeze rate is at most about −1° C./min, about −1.5° C./min, about −2° C./min, about −2.5° C./min, about −3° C./min, about −3.5° C./min, about −4° C./min, about −4.5° C./min, about −5° C./min, about −5.5° C./min, or about −6° C./min. In some embodiments, the supra-freeze rate is −3.2° C. In some embodiments, the supra-freeze rate is from about −2.54° C./min to about −4.09° C./min.

In some embodiments, the bone marrow or bone marrow cells can be cryopreserved at a sub-freeze rate or a sub-freeze range. In some embodiments, the sub-freeze rate is from about −2.5° C./min to about −0.1° C./min. In some embodiments, the sub-freeze rate is from about −0.1° C./min to about −0.2° C./min, about −0.1° C./min to about −0.4° C./min, about −0.1° C./min to about −0.6° C./min, about −0.1° C./min to about −0.8° C./min, about −0.1° C./min to about −1° C./min, about −0.1° C./min to about −1.2° C./min, about −0.1° C./min to about −1.4° C./min, about −0.1° C./min to about −1.6° C./min, about −0.1° C./min to about −1.8° C./min, about −0.1° C./min to about −2° C./min, about −0.1° C./min to about −2.5° C./min, about −0.2° C./min to about −0.4° C./min, about −0.2° C./min to about −0.6° C./min, about −0.2° C./min to about −0.8° C./min, about −0.2° C./min to about −1° C./min, about −0.2° C./min to about −1.2° C./min, about −0.2° C./min to about −1.4° C./min, about −0.2° C./min to about −1.6° C./min, about −0.2° C./min to about −1.8° C./min, about −0.2° C./min to about −2° C./min, about −0.2° C./min to about −2.5° C./min, about −0.4° C./min to about −0.6° C./min, about −0.4° C./min to about −0.8° C./min, about −0.4° C./min to about −1° C./min, about −0.4° C./min to about −1.2° C./min, about −0.4° C./min to about −1.4° C./min, about −0.4° C./min to about −1.6° C./min, about −0.4° C./min to about −1.8° C./min, about −0.4° C./min to about −2° C./min, about −0.4° C./min to about −2.5° C./min, about −0.6° C./min to about −0.8° C./min, about −0.6° C./min to about −1° C./min, about −0.6° C./min to about −1.2° C./min, about −0.6° C./min to about −1.4° C./min, about −0.6° C./min to about −1.6° C./min, about −0.6° C./min to about −1.8° C./min, about −0.6° C./min to about −2° C./min, about −0.6° C./min to about −2.5° C./min, about −0.8° C./min to about −1° C./min, about −0.8° C./min to about −1.2° C./min, about −0.8° C./min to about −1.4° C./min, about −0.8° C./min to about −1.6° C./min, about −0.8° C./min to about −1.8° C./min, about −0.8° C./min to about −2° C./min, about −0.8° C./min to about −2.5° C./min, about −1° C./min to about −1.2° C./min, about −1° C./min to about −1.4° C./min, about −1° C./min to about −1.6° C./min, about −1° C./min to about −1.8° C./min, about −1° C./min to about −2° C./min, about −1° C./min to about −2.5° C./min, about −1.2° C./min to about −1.4° C./min, about −1.2° C./min to about −1.6° C./min, about −1.2° C./min to about −1.8° C./min, about −1.2° C./min to about −2° C./min, about −1.2° C./min to about −2.5° C./min, about −1.4° C./min to about −1.6° C./min, about −1.4° C./min to about −1.8° C./min, about −1.4° C./min to about −2° C./min, about −1.4° C./min to about −2.5° C./min, about −1.6° C./min to about −1.8° C./min, about −1.6° C./min to about −2° C./min, about −1.6° C./min to about −2.5° C./min, about −1.8° C./min to about −2° C./min, about −1.8° C./min to about −2.5° C./min, or about −2° C./min to about −2.5° C./min. In some embodiments, the sub-freeze rate is about −0.1° C./min, about −0.2° C./min, about −0.4° C./min, about −0.6° C./min, about −0.8° C./min, about −1° C./min, about −1.2° C./min, about −1.4° C./min, about −1.6° C./min, about −1.8° C./min, about −2° C./min, or about −2.5° C./min. In some embodiments, the sub-freeze rate is at least about −0.1° C./min, about −0.2° C./min, about −0.4° C./min, about −0.6° C./min, about −0.8° C./min, about −1° C./min, about −1.2° C./min, about −1.4° C./min, about −1.6° C./min, about −1.8° C./min, or about −2° C./min. In some embodiments, the sub-freeze rate is at most about −0.2° C./min, about −0.4° C./min, about −0.6° C./min, about −0.8° C./min, about −1° C./min, about −1.2° C./min, about −1.4° C./min, about −1.6° C./min, about −1.8° C./min, about −2° C./min, or about −2.5° C./min. In some embodiments, the sub-freeze rate can be −1.36° C./min. In some embodiments, the sub-freeze rate comprises a range of −1.13° C./min to −1.62° C./min.

In some embodiments, the freeze rate for cryopreserving the bone marrow or the bone marrow cells described herein comprises determining the nucleation temperature. In some embodiments, the nucleation temperature is from about −24° C. to about −2° C. In some embodiments, the nucleation temperature is from about −2° C. to about −4° C., about −2° C. to about −6° C., about −2° C. to about −8° C., about −2° C. to about −10° C., about −2° C. to about −12° C., about −2° C. to about −14° C., about −2° C. to about −16° C., about −2° C. to about −18° C., about −2° C. to about −20° C., about −2° C. to about −22° C., about −2° C. to about −24° C., about −4° C. to about −6° C., about −4° C. to about −8° C., about −4°

C. to about −10° C., about −4° C. to about −12° C., about −4° C. to about −14° C., about −4° C. to about −16° C., about −4° C. to about −18° C., about −4° C. to about −20° C., about −4° C. to about −22° C., about −4° C. to about −24° C., about −6° C. to about −8° C., about −6° C. to about −10° C., about −6° C. to about −12° C., about −6° C. to about −14° C., about −6° C. to about −16° C., about −6° C. to about −18° C., about −6° C. to about −20° C., about −6° C. to about −22° C., about −6° C. to about −24° C., about −8° C. to about −10° C., about −8° C. to about −12° C., about −8° C. to about −14° C., about −8° C. to about −16° C., about −8° C. to about −18° C., about −8° C. to about −20° C., about −8° C. to about −22° C., about −8° C. to about −24° C., about −10° C. to about −12° C., about −10° C. to about −14° C., about −10° C. to about −16° C., about −10° C. to about −18° C., about −10° C. to about −20° C., about −10° C. to about −22° C., about −10° C. to about −24° C., about −12° C. to about −14° C., about −12° C. to about −16° C., about −12° C. to about −18° C., about −12° C. to about −20° C., about −12° C. to about −22° C., about −12° C. to about −24° C., about −14° C. to about −16° C., about −14° C. to about −18° C., about −14° C. to about −20° C., about −14° C. to about −22° C., about −14° C. to about −24° C., about −16° C. to about −18° C., about −16° C. to about −20° C., about −16° C. to about −22° C., about −16° C. to about −24° C., about −18° C. to about −20° C., about −18° C. to about −22° C., about −18° C. to about −24° C., about −20° C. to about −22° C., about −20° C. to about −24° C., or about −22° C. to about −24° C. In some embodiments, the nucleation temperature is about −2° C., about −4° C., about −6° C., about −8° C., about −10° C., about −12° C., about −14° C., about −16° C., about −18° C., about −20° C., about −22° C., or about −24° C. In some embodiments, the nucleation temperature is at least about −2° C., about −4° C., about −6° C., about −8° C., about −10° C., about −12° C., about −14° C., about −16° C., about −18° C., about −20° C., or about −22° C. In some embodiments, the nucleation temperature is at most about −4° C., about −6° C., about −8° C., about −10° C., about −12° C., about −14° C., about −16° C., about −18° C., about −20° C., about −22° C., or about −24° C. In some embodiments, the nucleation temperature can be about −12.31° C./min. In some embodiments, the nucleation temperature can comprise a range of from about −7.24° C. to about −17.52° C.

Figure 14:
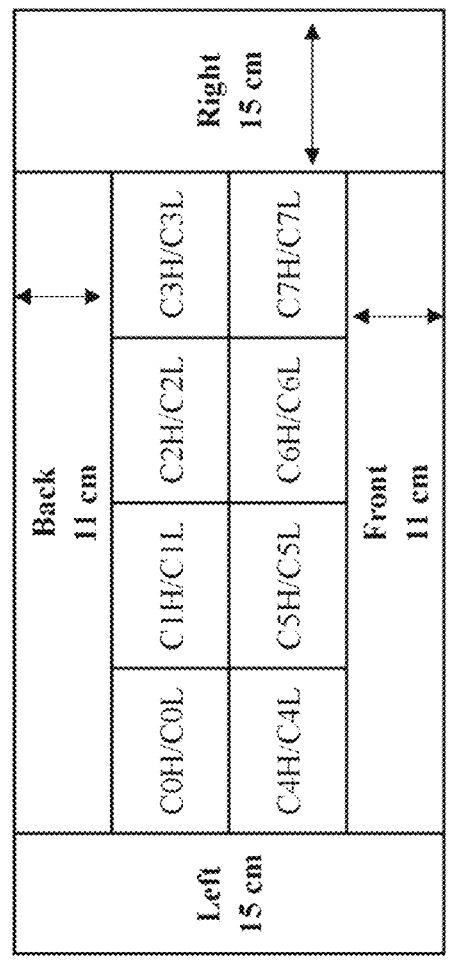
FIG. 14 illustrates HPC, Marrow experimental trials cassette location in shelf one of the −86° C. Eppendorf Cryocube Model F740hi.
Figure 15:
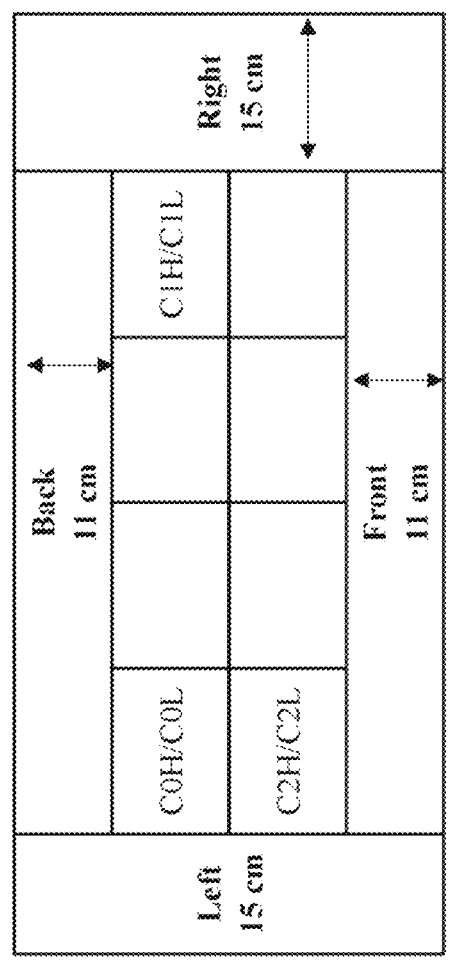
FIG. 15 illustrates an exemplary alternative arrangement of the cassette location in shelf one of the −86° C. Eppendorf Cryocube Model F740hi.

In some embodiments, the bone marrow or bone marrow cells to be cryopreserved can be placed in a container or bag such as a cryopreservation bag. In some cases, the cryopreservation bag can be subsequently placed into a cooling box which lacks insulation for freezing. Alternative, the cryopreservation bag is not placed in a cooling box. In some cases, the cryopreservation bag can be placed in a cassette and the subsequently placed in a freezing environment (e.g. placed in a freezer such as a −86° C. static freezer). In some cases, the cryopreservation bag can be placed in a freezing environment of liquid nitrogen or vapor stemmed from liquid nitrogen. In some cases, the cryopreservation bag can be placed in different compartments or different levels of shelfs in the freezer or the in the liquid nitrogen or liquid nitrogen vapor. In some embodiments, the cryopreservation bag containing the bone marrow or bone marrow cells can be placed in a position as depicted in FIG. 14 or FIG. 15.

A cryopreservation bag is placed within a corresponding compartment 201-203 of the cooling box 200 and the overlapping cover 205 is closed over the compartments to provide a sealed environment for cryo-preservation of the contents of the bags. The cooling box is placed within a cryo freezer such that the cooling box produces a cooling rate of −0.5 to −5° C./min, and typically −1° C./min, with nucleation temperatures above −20° C. The freezing process continues at the prescribed rate until the temperature of the bone marrow reaches a suitable temperature. The suitable temperature for storage of the bags is a temperature <−80° C. or <−150° C.

In another embodiment, the bags are cooled in a static chamber temperature as opposed to the controlled rate cryopreservation described above. In the passive cooling approach, the cooling box is placed in a −86° C. freezer until the bags reach a stable temperature. In some cases, the freezer can be set at a range of temperature from about −100° C. to about −60° C. In some cases, the freezer can be set at a range of temperature from about −60° C. to about −65° C., about −60° C. to about −70° C., about −60° C. to about −75° C., about −60° C. to about −80° C., about −60° C. to about −82° C., about −60° C. to about −84° C., about −60° C. to about −86° C., about −60° C. to about −88° C., about −60° C. to about −90° C., about −60° C. to about −95° C., about −60° C. to about −100° C., about −65° C. to about −70° C., about −65° C. to about −75° C., about −65° C. to about −80° C., about −65° C. to about −82° C., about −65° C. to about −84° C., about −65° C. to about −86° C., about −65° C. to about −88° C., about −65° C. to about −90° C., about −65° C. to about −95° C., about −65° C. to about −100° C., about −70° C. to about −75° C., about −70° C. to about −80° C., about −70° C. to about −82° C., about −70° C. to about −84° C., about −70° C. to about −86° C., about −70° C. to about −88° C., about −70° C. to about −90° C., about −70° C. to about −95° C., about −70° C. to about −100° C., about −75° C. to about −80° C., about −75° C. to about −82° C., about −75° C. to about −84° C., about −75° C. to about −86° C., about −75° C. to about −88° C., about −75° C. to about −90° C., about −75° C. to about −95° C., about −75° C. to about −100° C., about −80° C. to about −82° C., about −80° C. to about −84° C., about −80° C. to about −86° C., about −80° C. to about −88° C., about −80° C. to about −90° C., about −80° C. to about −95° C., about −80° C. to about −100° C., about −82° C. to about −84° C., about −82° C. to about −86° C., about −82° C. to about −88° C., about −82° C. to about −90° C., about −82° C. to about −95° C., about −82° C. to about −100° C., about −84° C. to about −86° C., about −84° C. to about −88° C., about −84° C. to about −90° C., about −84° C. to about −95° C., about −84° C. to about −100° C., about −86° C. to about −88° C., about −86° C. to about −90° C., about −86° C. to about −95° C., about −86° C. to about −100° C., about −88° C. to about −90° C., about −88° C. to about −95° C., about −88° C. to about −100° C., about −90° C. to about −95° C., about −90° C. to about −100° C., or about −95° C. to about −100° C. In some cases, the freezer can be set at a range of temperature from about −60° C., about −65° C., about −70° C., about −75° C., about −80° C., about −82° C., about −84° C., about −86° C., about −88° C., about −90° C., about −95° C., or about −100° C. In some cases, the freezer can be set at a range of temperature from at least about −60° C., about −65° C., about −70° C., about −75° C., about −80° C., about −82° C., about −84° C., about −86° C., about −88° C., about −90° C., or about −95° C. In some cases, the freezer can be set at a range of temperature from at most about −65° C., about −70° C., about −75° C., about −80° C., about −82° C., about −84° C., about −86° C., about −88° C., about −90° C., about −95° C., or about −100° C.

In some cases, freezing the cryopreservation bags and surrogate vials is less effective when placed in a static freezer set at −80° C. Instead, better results were obtained when the static freezer was set to temperatures less than −80° C., e.g., −86° C.

It is contemplated that the cryopreservation storage can be in many forms. For instance, the cryopreserved bone marrow can be contained in bags of 1 ml to 5 ml volume or vials of 0.1 to 15 ml volumes. In a preferred embodiment, the bags with 70 ml bone marrow are stored in a cooling box within a cryogenic freezer.

The cryopreserved bone marrow is cryobanked for later thawing and extraction of desired cells. The thawed bone marrow can be provided for a wide range of treatments including treatment for leukemias, brain tumors, breast cancer, Hodgkin's disease, multiple myeloma, neuroblastoma, non-Hodgkin's lymphoma, blood cancers, ovarian cancer, sarcoma, testicular cancer, other solid organ cancer, rheumatoid arthritis, multiple sclerosis, diabetes mellitus, cystic fibrosus, Alzheimer's disease, genetic immunodeficiencies, metabolic disorders, marrow failure syndromes, and HIV. Bone marrow can also be used for induction of immunotolerance to reduce the potential rejection of an implant obtained from an organ donor. Bone marrow treatments can also be indicated for casualties caused by radiation and certain biological weapons.

Another aspect of the present disclosure comprises a method for processing a biological sample comprising cells or a derivative thereof, the method comprising: generating a first volume of the biological sample comprising cells or a derivative thereof, wherein the first volume comprises a first concentration of cells or a derivative thereof; generating a second volume of the biological sample comprising cells or a derivative thereof, wherein the second volume is less than the first volume and comprises a second concentration of the cells wherein the second concentration of the cells is no more than 30% different than the first concentration of the cells; and cooling the first volume at a first cooling rate and cooling the second volume at a second cooling rate, wherein the first cooling rate is about the same than the second cooling rate; wherein a post-thaw cell proliferation rate of the cells in the first volume is no more than 30% different than a post-thaw proliferation rate of the cells in the second volume. In some embodiments, the first volume is contained in a first container, wherein the second volume is contained in a second container, and wherein the first container and the second container are exposed to a common temperature.

The preponderance of literature indicates cells stored below the glass transition temperature of water (−130° C.) are stable indefinitely, with estimates based on biophysical properties ranging from 200-30,000 years (see, e.g., Woods et al., "Off the shelf cellular therapeutics: Factors to consider during cryopreservation and storage of human cells for clinical use". *Cytotherapy* 18(6):697-711. (2016), the contents of which are incorporated by reference in its entirety). The major potential source of damage is through thermocycling due to inappropriate storage. Methods of the present disclosure allow detection of inappropriate storage and associated damage to the biological sample that is to be administered to a subject in need. Nonetheless, preferably storage units are alarm monitored 24 hours per day and manually checked weekly to ensure temperature is maintained.

Having at least two volumes of a biological sample allows testing a subset of the biological sample (the second volume) without having to manipulate the portion of the biological sample that is to be administered to a subject (the first sample), with the second volume acting as a surrogate for the first volume. As used herein, the surrogate vial is typically a smaller volume of the cell product and the surrogate can be thawed and assayed as needed, e.g., for cell viability. The assay results for the surrogate vial represent the expected assay results for the first (larger) volume; however, by using the surrogate it is unnecessary to thaw the first volume for assaying and, instead, it is thawed when needing to be used, e.g., for transplanting into a subject in need. For the surrogate vial to accurate represent the first volume, the cells in both volumes should be frozen at the same rate; this common rate results equivalent functional viability for cells in the two volumes. In some cases, a first volume (i.e., a cryopreservation bag) and a second volume (i.e., a surrogate cryovials) are placed in −86° C. static freezer. The bags are placed in cassettes, which may lack insulation, while the surrogate vials are placed separately in a CoolCell® freezing storage system and then in front of the box of cassettes into the freezer.

In some embodiments the second volume is less than about 0.5% of the first volume to about 50% of the first volume. In some embodiments the second volume is less than about 50% of the first volume to about 40% of the first volume, about 50% of the first volume to about 30% of the first volume, about 50% of the first volume to about 20% of the first volume, about 50% of the first volume to about 10% of the first volume, about 50% of the first volume to about 5% of the first volume, about 50% of the first volume to about 1% of the first volume, about 50% of the first volume to about 0.5% of the first volume, about 40% of the first volume to about 30% of the first volume, about 40% of the first volume to about 20% of the first volume, about 40% of the first volume to about 10% of the first volume, about 40% of the first volume to about 5% of the first volume, about 40% of the first volume to about 1% of the first volume, about 40% of the first volume to about 0.5% of the first volume, about 30% of the first volume to about 20% of the first volume, about 30% of the first volume to about 10% of the first volume, about 30% of the first volume to about 5% of the first volume, about 30% of the first volume to about 1% of the first volume, about 30% of the first volume to about 0.5% of the first volume, about 20% of the first volume to about 10% of the first volume, about 20% of the first volume to about 5% of the first volume, about 20% of the first volume to about 1% of the first volume, about 20% of the first volume to about 0.5% of the first volume, about 10% of the first volume to about 5% of the first volume, about 10% of the first volume to about 1% of the first volume, about 10% of the first volume to about 0.5% of the first volume, about 5% of the first volume to about 1% of the first volume, about 5% of the first volume to about 0.5% of the first volume, or about 1% of the first volume to about 0.5% of the first volume. In some embodiments the second volume is less than about 50% of the first volume, about 40% of the first volume, about 30% of the first volume, about 20% of the first volume, about 10% of the first volume, about 5% of the first volume, about 1% of the first volume, or about 0.5% of the first volume. In some embodiments the second volume is less than at least about 50% of the first volume, about 40% of the first volume, about 30% of the first volume, about 20% of the first volume, about 10% of the first volume, about 5% of the first volume, or about 1% of the first volume. In some embodiments the second volume is less than at most about 40% of the first volume, about 30% of the first volume, about 20% of the first volume, about 10% of the first volume, about 5% of the first volume, about 1% of the first volume, or about 0.5% of the first volume. In some embodiments the second volume is less than 50% of the first volume. In some embodiments the second volume is less than 40% of the first volume. In some embodiments the second volume is less than 37.5% of the first volume. In some embodiments the second volume is less than 35% of the first volume. In some embodiments the second volume is less than 30% of the first volume. In some embodiments the second volume is less than 20% of the first volume. In some embodiments the second volume is less than 15% of the first volume. In some embodiments the second volume is less than 10% of the first volume. In some embodiments the second volume is less than 5% of the first volume. In some embodiments the second volume is less than 1% of the first volume.

In some embodiments a post-thaw viability rate (e.g., the functional viability) of the cells in the first volume is no more than about 0.5% different than a post-thaw viability rate of the cells in the second volume to about 30% different than a post-thaw viability rate of the cells in the second volume. In some embodiments a post-thaw viability rate of the cells in the first volume is no more than about 30% different than a post-thaw viability rate of the cells in the second volume to about 25% different than a post-thaw viability rate of the cells in the second volume, about 30% different than a post-thaw viability rate of the cells in the second volume to about 20% different than a post-thaw viability rate of the cells in the second volume, about 30% different than a post-thaw viability rate of the cells in the second volume to about 15% different than a post-thaw viability rate of the cells in the second volume, about 30% different than a post-thaw viability rate of the cells in the second volume to about 10% different than a post-thaw viability rate of the cells in the second volume, about 30% different than a post-thaw viability rate of the cells in the second volume to about 5% different than a post-thaw viability rate of the cells in the second volume, about 30% different than a post-thaw viability rate of the cells in the second volume to about 1% different than a post-thaw viability rate of the cells in the second volume, about 30% different than a post-thaw viability rate of the cells in the second volume to about 0.5% different than a post-thaw viability rate of the cells in the second volume, about 25% different than a post-thaw viability rate of the cells in the second volume to about 20% different than a post-thaw viability rate of the cells in the second volume, about 25% different than a post-thaw viability rate of the cells in the second volume to about 15% different than a post-thaw viability rate of the cells in the second volume, about 25% different than a post-thaw viability rate of the cells in the second volume to about 10% different than a post-thaw viability rate of the cells in the second volume, about 25% different than a post-thaw viability rate of the cells in the second volume to about 5% different than a post-thaw viability rate of the cells in the second volume, about 25% different than a post-thaw viability rate of the cells in the second volume to about 1% different than a post-thaw viability rate of the cells in the second volume, about 25% different than a post-thaw viability rate of the cells in the second volume to about 0.5% different than a post-thaw viability rate of the cells in the second volume, about 20% different than a post-thaw viability rate of the cells in the second volume to about 15% different than a post-thaw viability rate of the cells in the second volume, about 20% different than a post-thaw viability rate of the cells in the second volume to about 10% different than a post-thaw viability rate of the cells in the second volume, about 20% different than a post-thaw viability rate of the cells in the second volume to about 5% different than a post-thaw viability rate of the cells in the second volume, about 20% different than a post-thaw viability rate of the cells in the second volume to about 1% different than a post-thaw viability rate of the cells in the second volume, about 20% different than a post-thaw viability rate of the cells in the second volume to about 0.5% different than a post-thaw viability rate of the cells in the second volume, about 15% different than a post-thaw viability rate of the cells in the second volume to about 10% different than a post-thaw viability rate of the cells in the second volume, about 15% different than a post-thaw viability rate of the cells in the second volume to about 5% different than a post-thaw viability rate of the cells in the second volume, about 15% different than a post-thaw viability rate of the cells in the second volume to about 1% different than a post-thaw viability rate of the cells in the second volume, about 15% different than a post-thaw viability rate of the cells in the second volume to about 0.5% different than a post-thaw viability rate of the cells in the second volume, about 10% different than a post-thaw viability rate of the cells in the second volume to about 5% different than a post-thaw viability rate of the cells in the second volume, about 10% different than a post-thaw viability rate of the cells in the second volume to about 1% different than a post-thaw viability rate of the cells in the second volume, about 10% different than a post-thaw viability rate of the cells in the second volume to about 0.5% different than a post-thaw viability rate of the cells in the second volume, about 5% different than a post-thaw viability rate of the cells in the second volume to about 1% different than a post-thaw viability rate of the cells in the second volume, about 5% different than a post-thaw viability rate of the cells in the second volume to about 0.5% different than a post-thaw viability rate of the cells in the second volume, or about 1% different than a post-thaw viability rate of the cells in the second volume to about 0.5% different than a post-thaw viability rate of the cells in the second volume. In some embodiments a post-thaw viability rate of the cells in the first volume is no more than about 30% different than a post-thaw viability rate of the cells in the second volume, about 25% different than a post-thaw viability rate of the cells in the second volume, about 20% different than a post-thaw viability rate of the cells in the second volume, about 15% different than a post-thaw viability rate of the cells in the second volume, about 10% different than a post-thaw viability rate of the cells in the second volume, about 5% different than a post-thaw viability rate of the cells in the second volume, about 1% different than a post-thaw viability rate of the cells in the second volume, or about 0.5% different than a post-thaw viability rate of the cells in the second volume. In some embodiments a post-thaw viability rate of the cells in the first volume is no more than at least about 30% different than a post-thaw viability rate of the cells in the second volume, about 25% different than a post-thaw viability rate of the cells in the second volume, about 20% different than a post-thaw viability rate of the cells in the second volume, about 15% different than a post-thaw viability rate of the cells in the second volume, about 10% different than a post-thaw viability rate of the cells in the second volume, about 5% different than a post-thaw viability rate of the cells in the second volume, or about 1% different than a post-thaw viability rate of the cells in the second volume. In some embodiments a post-thaw viability rate of the cells in the first volume is no more than at most about 25% different than a post-thaw viability rate of the cells in the second volume, about 20% different than a post-thaw viability rate of the cells in the second volume, about 15% different than a post-thaw viability rate of the cells in the second volume, about 10% different than a post-thaw viability rate of the cells in the second volume, about 5% different than a post-thaw viability rate of the cells in the second volume, about 1% different than a post-thaw viability rate of the cells in the second volume, or about 0.5% different than a post-thaw viability rate of the cells in the second volume. In some embodiments a post-thaw viability rate of the cells in the first volume is no more than 30% different than a post-thaw viability rate of the cells in the second volume. In some embodiments a post-thaw viability rate of the cells in the first volume is no more than 25% different than a post-thaw viability rate of the cells in the second volume. In some embodiments a post-thaw viability rate of the cells in the first volume is no more than 20% different than a post-thaw viability rate of the cells in the second volume. In some embodiments a post-thaw viability rate of the cells in the first volume is no more than 15% different than a post-thaw viability rate of the cells in the second volume. In some embodiments a post-thaw viability rate of the cells in the first volume is no more than 13.6% different than a post-thaw viability rate of the cells in the second volume. In some embodiments a post-thaw viability rate of the cells in the first volume is no more than 10% different than a post-thaw viability rate of the cells in the second volume. In some embodiments a post-thaw viability rate of the cells in the first volume is no more than 5% different than a post-thaw viability rate of the cells in the second volume. In some embodiments a post-thaw cell proliferation rate of the cells in the first volume is no more than 25% different than a post-thaw proliferation rate of the cells in the second volume. In some embodiments a post-thaw cell proliferation rate of the cells in the first volume is no more than 20% different than a post-thaw proliferation rate of the cells in the second volume. In some embodiments a post-thaw cell proliferation rate of the cells in the first volume is no more than 15% different than a post-thaw proliferation rate of the cells in the second volume. In some embodiments a post-thaw cell proliferation rate of the cells in the first volume is no more than 13.6% different than a post-thaw proliferation rate of the cells in the second volume. In some embodiments a post-thaw cell proliferation rate of the cells in the first volume is no more than 10% different than a post-thaw proliferation rate of the cells in the second volume. In some embodiments a post-thaw cell proliferation rate of the cells in the first volume is no more than 5% different than a post-thaw proliferation rate of the cells in the second volume. In some embodiments the post-thaw viability rate of the cells is at least 50%. Viability may relate to either or both of functional viability which measures the cells' ability to proliferate and routine viability which relates to the numbers or percentages of live cells, e.g., as measured by Trypan Blue.

In some embodiments the post-thaw proliferation rate of the cells (which represents the cells' functional viability) is at least 1 CFU-GM/$10^5$ cells. In some embodiments the post-thaw proliferation rate of the cells is at least about 1 CFU-GM/$10^5$ cells to about 200 CFU-GM/$10^5$ cells. In some embodiments the post-thaw proliferation rate of the cells is at least about 1 CFU-GM/$10^5$ cells to about 10 CFU-GM/$10^5$ cells, about 1 CFU-GM/$10^5$ cells to about 20 CFU-GM/$10^5$ cells, about 1 CFU-GM/$10^5$ cells to about 30 CFU-GM/$10^5$ cells, about 1 CFU-GM/$10^5$ cells to about 40 CFU-GM/$10^5$ cells, about 1 CFU-GM/$10^5$ cells to about 50 CFU-GM/$10^5$ cells, about 1 CFU-GM/$10^5$ cells to about 60 CFU-GM/$10^5$ cells, about 1 CFU-GM/$10^5$ cells to about 70 CFU-GM/$10^5$ cells, about 1 CFU-GM/$10^5$ cells to about 80 CFU-GM/$10^5$ cells, about 1 CFU-GM/$10^5$ cells to about 90 CFU-GM/$10^5$ cells, about 1 CFU-GM/$10^5$ cells to about 100 CFU-GM/$10^5$ cells, about 1 CFU-GM/$10^5$ cells to about 200 CFU-GM/$10^5$ cells, about 10 CFU-GM/$10^5$ cells to about 20 CFU-GM/$10^5$ cells, about 10 CFU-GM/$10^5$ cells to about 30 CFU-GM/$10^5$ cells, about 10 CFU-GM/$10^5$ cells to about 40 CFU-GM/$10^5$ cells, about 10 CFU-GM/$10^5$ cells to about 50 CFU-GM/$10^5$ cells, about 10 CFU-GM/$10^5$ cells to about 60 CFU-GM/$10^5$ cells, about 10 CFU-GM/$10^5$ cells to about 70 CFU-GM/$10^5$ cells, about 10 CFU-GM/$10^5$ cells to about 80 CFU-GM/$10^5$ cells, about 10 CFU-GM/$10^5$ cells to about 90 CFU-GM/$10^5$ cells, about 10 CFU-GM/$10^5$ cells to about 100 CFU-GM/$10^5$ cells, about 10 CFU-GM/$10^5$ cells to about 200 CFU-GM/$10^5$ cells, about 20 CFU-GM/$10^5$ cells to about 30 CFU-GM/$10^5$ cells, about 20 CFU-GM/$10^5$ cells to about 40 CFU-GM/$10^5$ cells, about 20 CFU-GM/$10^5$ cells to about 50 CFU-GM/$10^5$ cells, about 20 CFU-GM/$10^5$ cells to about 60 CFU-GM/$10^5$ cells, about 20 CFU-GM/$10^5$ cells to about 70 CFU-GM/$10^5$ cells, about 20 CFU-GM/$10^5$ cells to about 80 CFU-GM/$10^5$ cells, about 20 CFU-GM/$10^5$ cells to about 90 CFU-GM/$10^5$ cells, about 20 CFU-GM/$10^5$ cells to about 100 CFU-GM/$10^5$ cells, about 20 CFU-GM/$10^5$ cells to about 200 CFU-GM/$10^5$ cells, about 30 CFU-GM/$10^5$ cells to about 40 CFU-GM/$10^5$ cells, about 30 CFU-GM/$10^5$ cells to about 50 CFU-GM/$10^5$ cells, about 30 CFU-GM/$10^5$ cells to about 60 CFU-GM/$10^5$ cells, about 30 CFU-GM/$10^5$ cells to about 70 CFU-GM/$10^5$ cells, about 30 CFU-GM/$10^5$ cells to about 80 CFU-GM/$10^5$ cells, about 30 CFU-GM/$10^5$ cells to about 90 CFU-GM/$10^5$ cells, about 30 CFU-GM/$10^5$ cells to about 100 CFU-GM/$10^5$ cells, about 30 CFU-GM/$10^5$ cells to about 200 CFU-GM/$10^5$ cells, about 40 CFU-GM/$10^5$ cells to about 50 CFU-GM/$10^5$ cells, about 40 CFU-GM/$10^5$ cells to about 60 CFU-GM/$10^5$ cells, about 40 CFU-GM/$10^5$ cells to about 70 CFU-GM/$10^5$ cells, about 40 CFU-GM/$10^5$ cells to about 80 CFU-GM/$10^5$ cells, about 40 CFU-GM/$10^5$ cells to about 90 CFU-GM/$10^5$ cells, about 40 CFU-GM/$10^5$ cells to about 100 CFU-GM/$10^5$ cells, about 40 CFU-GM/$10^5$ cells to about 200 CFU-GM/$10^5$ cells, about 50 CFU-GM/$10^5$ cells to about 60 CFU-GM/$10^5$ cells, about 50 CFU-GM/$10^5$5 cells to about 70 CFU-GM/$10^5$5 cells, about 50 CFU-GM/$10^5$ cells to about 80 CFU-GM/$10^5$ cells, about 50 CFU-GM/$10^5$ cells to about 90 CFU-GM/$10^5$ cells, about 50 CFU-GM/$10^5$ cells to about 100 CFU-GM/$10^5$ cells, about 50 CFU-GM/$10^5$ cells to about 200 CFU-GM/$10^5$ cells, about 60 CFU-GM/$10^5$ cells to about 70 CFU-GM/$10^5$ cells, about 60 CFU-GM/$10^5$ cells to about 80 CFU-GM/$10^5$ cells, about 60 CFU-GM/$10^5$ cells to about 90 CFU-GM/$10^5$ cells, about 60 CFU-GM/$10^5$ cells to about 100 CFU-GM/$10^5$ cells, about 60 CFU-GM/$10^5$ cells to about 200 CFU-GM/$10^5$ cells, about 70 CFU-GM/$10^5$ cells to about 80 CFU-GM/$10^5$ cells, about 70 CFU-GM/$10^5$ cells to about 90 CFU-GM/$10^5$ cells, about 70 CFU-GM/$10^5$ cells to about 100 CFU-GM/$10^5$ cells, about 70 CFU-GM/$10^5$ cells to about 200 CFU-GM/$10^5$ cells, about 80 CFU-GM/$10^5$ cells to about 90 CFU-GM/$10^5$ cells, about 80 CFU-GM/$10^5$ cells to about 100 CFU-GM/$10^5$ cells, about 80 CFU-GM/$10^5$ cells to about 200 CFU-GM/$10^5$ cells, about 90 CFU-GM/$10^5$ cells to about 100 CFU-GM/$10^5$ cells, about 90 CFU-GM/$10^5$ cells to about 200 CFU-GM/$10^5$ cells, or about 100 CFU-GM/$10^5$ cells to about 200 CFU-GM/$10^5$ cells. In some embodiments the post-thaw proliferation rate of the cells is at least about 1 CFU-GM/$10^5$ cells, about 10 CFU-GM/$10^5$ cells, about 20 CFU-GM/$10^5$ cells, about 30 CFU-GM/$10^5$ cells, about 40 CFU-GM/$10^5$ cells, about 50 CFU-GM/$10^5$ cells, about 60 CFU-GM/$10^5$ cells, about 70 CFU-GM/$10^5$ cells, about 80 CFU-GM/$10^5$ cells, about 90 CFU-GM/$10^5$ cells, about 100 CFU-GM/$10^5$ cells, or about 200 CFU-GM/$10^5$ cells. In some embodiments the post-thaw proliferation rate of the cells is at least at least about 1 CFU-GM/$10^5$ cells, about 10 CFU-GM/$10^5$ cells, about 20 CFU-GM/$10^5$ cells, about 30 CFU-GM/$10^5$ cells, about 40 CFU-GM/$10^5$ cells, about 50 CFU-GM/$10^5$ cells, about 60 CFU-GM/$10^5$ cells, about 70 CFU-GM/$10^5$ cells, about 80 CFU-GM/$10^5$ cells, about 90 CFU-GM/$10^5$ cells, or about 100 CFU-GM/$10^5$ cells. In some embodiments the post-thaw proliferation rate of the cells is at least at most about 10 CFU-GM/$10^5$ cells, about 20 CFU-GM/$10^5$ cells, about 30 CFU-GM/$10^5$ cells, about 40 CFU-GM/$10^5$ cells, about 50 CFU-GM/$10^5$ cells, about 60 CFU-GM/$10^5$ cells, about 70 CFU-GM/$10^5$ cells, about 80 CFU-GM/$10^5$ cells, about 90 CFU-GM/$10^5$ cells, about 100 CFU-GM/$10^5$ cells, or about 200 CFU-GM/$10^5$ cells. Assays to determine functional viability may take about ten days to about two weeks of culturing. Method for culturing cell products relevant to the present disclosure are well-known in the art.

In some embodiments the first cooling rate and the second cooling rate comprise a supra-freeze rate from about −0.1° C./min to about −5° C./min at least until ice has nucleated in a freezing medium. In some instances, the biological sample or derivative thereof can be cryopreserved first with supra-freeze. For example, the biological sample or derivative thereof can be cryopreserved while the biological sample or derivative thereof are just processed and at room temperature. In some instances, the supra-freeze rate is generally higher (e.g. decreasing of the temperature at a faster rate) compared to the sub-freeze rate. In some embodiments, the supra-freeze rate is from about −6° C./min to about −0.5° C./min. In some embodiments, the supra-freeze rate is from about −0.5° C./min to about −1° C./min, about −0.5° C./min to about −1.5° C./min, about −0.5° C./min to about −2° C./min, about −0.5° C./min to about −2.5° C./min, about −0.5° C./min to about −3° C./min, about −0.5° C./min to about −3.5° C./min, about −0.5° C./min to about −4° C./min, about −0.5° C./min to about −4.5° C./min, about −0.5° C./min to about −5° C./min, about −0.5° C./min to about −5.5° C./min, about −0.5° C./min to about −6° C./min, about −1° C./min to about −1.5° C./min, about −1° C./min to about −2° C./min, about −1° C./min to about −2.5° C./min, about −1° C./min to about −3° C./min, about −1° C./min to about −3.5° C./min, about −1° C./min to about −4° C./min, about −1° C./min to about −4.5° C./min, about −1° C./min to about −5° C./min, about −1° C./min to about −5.5° C./min, about −1° C./min to about −6° C./min, about −1.5° C./min to about −2° C./min, about −1.5° C./min to about −2.5° C./min, about −1.5° C./min to about −3° C./min, about −1.5° C./min to about −3.5° C./min, about −1.5° C./min to about −4° C./min, about −1.5° C./min to about −4.5° C./min, about −1.5° C./min to about −5° C./min, about −1.5° C./min to about −5.5° C./min, about −1.5° C./min to about −6° C./min, about −2° C./min to about −2.5° C./min, about −2° C./min to about −3° C./min, about −2° C./min to about −3.5° C./min, about −2° C./min to about −4° C./min, about −2° C./min to about −4.5° C./min, about −2° C./min to about −5° C./min, about −2° C./min to about −5.5° C./min, about −2° C./min to about −6° C./min, about −2.5° C./min to about −3° C./min, about −2.5° C./min to about −3.5° C./min, about −2.5° C./min to about −4° C./min, about −2.5° C./min to about −4.5° C./min, about −2.5° C./min to about −5° C./min, about −2.5° C./min to about −5.5° C./min, about −2.5° C./min to about −6° C./min, about −3° C./min to about −3.5° C./min, about −3° C./min to about −4° C./min, about −3° C./min to about −4.5° C./min, about −3° C./min to about −5° C./min, about −3° C./min to about −5.5° C./min, about −3° C./min to about −6° C./min, about −3.5° C./min to about −4° C./min, about −3.5° C./min to about −4.5° C./min, about −3.5° C./min to about −5° C./min, about −3.5° C./min to about −5.5° C./min, about −3.5° C./min to about −6° C./min, about −4° C./min to about −4.5° C./min, about −4° C./min to about −5° C./min, about −4° C./min to about −5.5° C./min, about −4° C./min to about −6° C./min, about −4.5° C./min to about −5° C./min, about −4.5° C./min to about −5.5° C./min, about −4.5° C./min to about −6° C./min, about −5° C./min to about −5.5° C./min, about −5° C./min to about −6° C./min, or about −5.5° C./min to about −6° C./min. In some embodiments, the supra-freeze rate is about −0.5° C./min, about −1° C./min, about −1.5° C./min, about −2° C./min, about −2.5° C./min, about −3° C./min, about −3.5° C./min, about −4° C./min, about −4.5° C./min, about −5° C./min, about −5.5° C./min, or about −6° C./min. In some embodiments, the supra-freeze rate is at least about −0.5° C./min, about −1° C./min, about −1.5° C./min, about −2° C./min, about −2.5° C./min, about −3° C./min, about −3.5° C./min, about −4° C./min, about −4.5° C./min, about −5° C./min, or about −5.5° C./min. In some embodiments, the supra-freeze rate is at most about −1° C./min, about −1.5° C./min, about −2° C./min, about −2.5° C./min, about −3° C./min, about −3.5° C./min, about −4° C./min, about −4.5° C./min, about −5° C./min, about −5.5° C./min, or about −6° C./min. In some embodiments, the supra-freeze rate was −3.2° C. In some embodiments, the supra-freeze rate is from about −2.54° C./min to about −4.09° C./min. In some embodiments the first cooling rate and the second cooling rate comprise a supra-freeze rate from about −2.5° C./min to about −4° C./min at least until ice has nucleated in a freezing medium. In some embodiments the first cooling rate and the second cooling rate comprise a supra-freeze rate from about −2.5° C./min to about −3.5° C./min at least until ice has nucleated in a freezing medium. Preferably, the first cooling rate and the second cooling rate are from about −1° C. to about −5° C.

In some embodiments first cooling rate and the second cooling rate differ by from about 1% to about 500%. The first cooling rate and the second cooling rate may differ by from about 1% to about 100%, e.g., 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. The first cooling rate and the second cooling rate may differ by from about 100% to about 200%, e.g., 100%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, or 200%. The first cooling rate and the second cooling rate may differ by from about 200% to about 300%, e.g., 200%, 202%, 203%, 204%, 205%, 206%, 207%, 208%, 209%, 210%, 211%, 212%, 213%, 214%, 215%, 216%, 217%, 218%, 219%, 220%, 221%, 222%, 223%, 224%, 225%, 226%, 227%, 228%, 229%, 230%, 231%, 232%, 233%, 234%, 235%, 236%, 237%, 238%, 239%, 240%, 241%, 242%, 243%, 244%, 245%, 246%, 247%, 248%, 249%, 250%, 251%, 252%, 253%, 254%, 255%, 256%, 257%, 258%, 259%, 260%, 261%, 262%, 263%, 264%, 265%, 266%, 267%, 268%, 269%, 270%, 271%, 272%, 273%, 274%, 275%, 276%, 277%, 278%, 279%, 280%, 281%, 282%, 283%, 284%, 285%, 286%, 287%, 288%, 289%, 290%, 291%, 292%, 293%, 294%, 295%, 296%, 297%, 298%, 299%, or 300%. The first cooling rate and the second cooling rate may differ by from about 400% to about 500%, e.g., 300%, 302%, 303%, 304%, 305%, 306%, 307%, 308%, 309%, 310%, 311%, 312%, 313%, 314%, 315%, 316%, 317%, 318%, 319%, 320%, 321%, 322%, 323%, 324%, 325%, 326%, 327%, 328%, 329%, 330%, 331%, 332%, 333%, 334%, 335%, 336%, 337%, 338%, 339%, 340%, 341%, 342%, 343%, 344%, 345%, 346%, 347%, 348%, 349%, 350%, 351%, 352%, 353%, 354%, 355%, 356%, 357%, 358%, 359%, 360%, 361%, 362%, 363%, 364%, 365%, 366%, 367%, 368%, 369%, 370%, 371%, 372%, 373%, 374%, 375%, 376%, 377%, 378%, 379%, 380%, 381%, 382%, 383%, 384%, 385%, 386%, 387%, 388%, 389%, 390%, 391%, 392%, 393%, 394%, 395%, 396%, 397%, 398%, 399%, or 400%. %. The first cooling rate and the second cooling rate may differ by from about 400% to about 500%, e.g., 400%, 402%, 403%, 404%, 405%, 406%, 407%, 408%, 409%, 410%, 411%, 412%, 413%, 414%, 415%, 416%, 417%, 418%, 419%, 420%, 421%, 422%, 423%, 424%, 425%, 426%, 427%, 428%, 429%, 430%, 431%, 432%, 433%, 434%, 435%, 436%, 437%, 438%, 439%, 440%, 441%, 442%, 443%, 444%, 445%, 446%, 447%, 448%, 449%, 450%, 451%, 452%, 453%, 454%, 455%, 456%, 457%, 458%, 459%, 460%, 461%, 462%, 463%, 464%, 465%, 466%, 467%, 468%, 469%, 470%, 471%, 472%, 473%, 474%, 475%, 476%, 477%, 478%, 479%, 480%, 481%, 482%, 483%, 484%, 485%, 486%, 487%, 488%, 489%, 490%, 491%, 492%, 493%, 494%, 495%, 496%, 497%, 498%, 499%, or 500%.

In some embodiments the first cooling rate and the second cooling rate comprise a sub-freeze rate from about −1° C./min to about −2° C./min. In some embodiments, the sub-freeze rate is from about −2.5° C./min to about −0.1° C./min. In some embodiments, the sub-freeze rate is from about −0.1° C./min to about −0.2° C./min, about −0.1° C./min to about −0.4° C./min, about −0.1° C./min to about −0.6° C./min, about −0.1° C./min to about −0.8° C./min, about −0.1° C./min to about −1° C./min, about −0.1° C./min to about −1.2° C./min, about −0.1° C./min to about −1.4° C./min, about −0.1° C./min to about −1.6° C./min, about −0.1° C./min to about −1.8° C./min, about −0.1° C./min to about −2° C./min, about −0.1° C./min to about −2.5° C./min, about −0.2° C./min to about −0.4° C./min, about −0.2° C./min to about −0.6° C./min, about −0.2° C./min to about −0.8° C./min, about −0.2° C./min to about −1° C./min, about −0.2° C./min to about −1.2° C./min, about −0.2° C./min to about −1.4° C./min, about −0.2° C./min to about −1.6° C./min, about −0.2° C./min to about −1.8° C./min, about −0.2° C./min to about −2° C./min, about −0.2° C./min to about −2.5° C./min, about −0.4° C./min to about −0.6° C./min, about −0.4° C./min to about −0.8° C./min, about −0.4° C./min to about −1° C./min, about −0.4° C./min to about −1.2° C./min, about −0.4° C./min to about −1.4° C./min, about −0.4° C./min to about −1.6° C./min, about −0.4° C./min to about −1.8° C./min, about −0.4° C./min to about −2° C./min, about −0.4° C./min to about −2.5° C./min, about −0.6° C./min to about −0.8° C./min, about −0.6° C./min to about −1° C./min, about −0.6° C./min to about −1.2° C./min, about −0.6° C./min to about −1.4° C./min, about −0.6° C./min to about −1.6° C./min, about −0.6° C./min to about −1.8° C./min, about −0.6° C./min to about −2° C./min, about −0.6° C./min to about −2.5° C./min, about −0.8° C./min to about −1° C./min, about −0.8° C./min to about −1.2° C./min, about −0.8° C./min to about −1.4° C./min, about −0.8° C./min to about −1.6° C./min, about −0.8° C./min to about −1.8° C./min, about −0.8° C./min to about −2° C./min, about −0.8° C./min to about −2.5° C./min, about −1° C./min to about −1.2° C./min, about −1° C./min to about −1.4° C./min, about −1° C./min to about −1.6° C./min, about −1° C./min to about −1.8° C./min, about −1° C./min to about −2° C./min, about −1° C./min to about −2.5° C./min, about −1.2° C./min to about −1.4° C./min, about −1.2° C./min to about −1.6° C./min, about −1.2° C./min to about −1.8° C./min, about −1.2° C./min to about −2° C./min, about −1.2° C./min to about −2.5° C./min, about −1.4° C./min to about −1.6° C./min, about −1.4° C./min to about −1.8° C./min, about −1.4° C./min to about −2° C./min, about −1.4° C./min to about −2.5° C./min, about −1.6° C./min to about −1.8° C./min, about −1.6° C./min to about −2° C./min, about −1.6° C./min to about −2.5° C./min, about −1.8° C./min to about −2° C./min, about −1.8° C./min to about −2.5° C./min, or about −2° C./min to about −2.5° C./min. In some embodiments, the sub-freeze rate is about −0.1° C./min, about −0.2° C./min, about −0.4° C./min, about −0.6° C./min, about −0.8° C./min, about −1° C./min, about −1.2° C./min, about −1.4° C./min, about −1.6° C./min, about −1.8° C./min, about −2° C./min, or about −2.5° C./min. In some embodiments, the sub-freeze rate is at least about −0.1° C./min, about −0.2° C./min, about −0.4° C./min, about −0.6° C./min, about −0.8° C./min, about −1° C./min, about −1.2° C./min, about −1.4° C./min, about −1.6° C./min, about −1.8° C./min, or about −2° C./min. In some embodiments, the sub-freeze rate is at most about −0.2° C./min, about −0.4° C./min, about −0.6° C./min, about −0.8° C./min, about −1° C./min, about −1.2° C./min, about −1.4° C./min, about −1.6° C./min, about −1.8° C./min, about −2° C./min, or about −2.5° C./min. In some embodiments, the sub-freeze rate can be −1.36° C./min. In some embodiments, the sub-freeze rate comprises a range of −1.13° C./min to −1.62° C./min.

In some embodiments, wherein the supra-freezing rate, sub-freezing rate, and nucleation temperature for the given biological sample is not known, the cyrobanking methods described herein further comprise determining the supra-freezing rate, sub-freezing rate, and nucleation temperature for the biological sample. In some embodiments, the supra-freezing rate, sub-freezing rate, and nucleation temperature are derived from a freezing curve for the biological sample. In some embodiments, the freezing curve is modelled using a computer. In some embodiments, the freezing curve is determined empirically following the procedures and methods described herein (e.g. Example 5).

In some embodiments the post-thaw viability rate of the cells (e.g., the cells' functional viability) is at least about 60% to about 95%. In some embodiments the post-thaw viability rate of the cells is at least about 60% to about 70%, about 60% to about 80%, about 60% to about 90%, about 60% to about 95%, about 70% to about 80%, about 70% to about 90%, about 70% to about 95%, about 80% to about 90%, about 80% to about 95%, or about 90% to about 95%. In some embodiments the post-thaw viability rate of the cells is at least about 60%, about 70%, about 80%, about 90%, or about 95%. In some embodiments the post-thaw viability rate of the cells is at least at least about 60%, about 70%, about 80%, or about 90%. In some embodiments the post-thaw viability rate of the cells is at least at most about 70%, about 80%, about 90%, or about 95%. In some embodiments the post-thaw viability rate of the cells is at least 60%. In some embodiments the post-thaw viability rate of the cells is at least 70%. In some embodiments the post-thaw viability rate of the cells is at least 80%. In some embodiments the post-thaw viability rate of the cells is at least 90%. Viability may relate to either or both of functional viability which measures the cells' ability to proliferate and routine viability which relates to the numbers or percentages of live cells, e.g., as measured by Trypan Blue.

In some embodiments (c) occurs in one or more freezers. In some embodiments the first container and the second container are disposed in a first freezer of the one or more freezers. In some embodiments the first container is contained in a first freezer of the one or more freezers and the second container is contained in a second freezer of the one or more freezers. In some embodiments the one or more freezers comprise a static freezer. In some embodiments the first freezer, the second freezer, or both is a static freezer. method of any one of the preceding claims, wherein the one or more freezers comprise a controlled-rate freezer. In some embodiments the first freezer, the second freezer, or both is a controlled-rate freezer. In some embodiments the one or more freezers are set at about −70° C. to −90° C. In some embodiments the one or more freezers are set at −80° C. In some embodiments the one or more freezers are set at −86° C. In some cases, the one or more freezers can be set at a range of temperature from about −100° C. to about −60° C. In some cases, the freezer can be set at a range of temperature from about −60° C. to about −65° C., about −60° C. to about −70° C., about −60° C. to about −75° C., about −60° C. to about −80° C., about −60° C. to about −82° C., about −60° C. to about −84° C., about −60° C. to about −86° C., about −60° C. to about −88° C., about −60° C. to about −90° C., about −60° C. to about −95° C., about −60° C. to about −100° C., about −65° C. to about −70° C., about −65° C. to about −75° C., about −65° C. to about −80° C., about −65° C. to about −82° C., about −65° C. to about −84° C., about −65° C. to about −86° C., about −65° C. to about −88° C., about −65° C. to about −90° C., about −65° C. to about −95° C., about −65° C. to about −100° C., about −70° C. to about −75° C., about −70° C. to about −80° C., about −70° C. to about −82° C., about −70° C. to about −84° C., about −70° C. to about −86° C., about −70° C. to about −88° C., about −70° C. to about −90° C., about −70° C. to about −95° C., about −70° C. to about −100° C., about −75° C. to about −80° C., about −75° C. to about −82° C., about −75° C. to about −84° C., about −75° C. to about −86° C., about −75° C. to about −88° C., about −75° C. to about −90° C., about −75° C. to about −95° C., about −75° C. to about −100° C., about −80° C. to about −82° C., about −80° C. to about −84° C., about −80° C. to about −86° C., about −80° C. to about −88° C., about −80° C. to about −90° C., about −80° C. to about −95° C., about −80° C. to about −100° C., about −82° C. to about −84° C., about −82° C. to about −86° C., about −82° C. to about −88° C., about −82° C. to about −90° C., about −82° C. to about −95° C., about −82° C. to about −100° C., about −84° C. to about −86° C., about −84° C. to about −88° C., about −84° C. to about −90° C., about −84° C. to about −95° C., about −84° C. to about −100° C., about −86° C. to about −88° C., about −86° C. to about −90° C., about −86° C. to about −95° C., about −86° C. to about −100° C., about −88° C. to about −90° C., about −88° C. to about −95° C., about −88° C. to about −100° C., about −90° C. to about −95° C., about −90° C. to about −100° C., or about −95° C. to about −100° C. In some cases, the freezer can be set at a range of temperature from about −60° C., about −65° C., about −70° C., about −75° C., about −80° C., about −82° C., about −84° C., about −86° C., about −88° C., about −90° C., about −95° C., or about −100° C. In some cases, the freezer can be set at a range of temperature from at least about −60° C., about −65° C., about −70° C., about −75° C., about −80° C., about −82° C., about −84° C., about −86° C., about −88° C., about −90° C., or about −95° C. In some cases, the freezer can be set at a range of temperature from at most about −65° C., about −70° C., about −75° C., about −80° C., about −82° C., about −84° C., about −86° C., about −88° C., about −90° C., about −95° C., or about −100° C.

In some cases, freezing the cryopreservation bags and surrogate vials is less effective when placed in a static freezer set at −80° C. Instead, better results were obtained when the static freezer was set to temperatures less than −80° C., e.g., −86° C.

In some embodiments the second volume is placed directly in an insulating container, such that each vial is in close proximity to the insulating material of the insulating container. In some embodiments the method further comprises arranging the first volume inside the static freezer such that the first volume does not contact a wall of the one or more freezers. In some embodiments the biological sample comprising cells or a derivative thereof, in the first volume and the biological sample comprising cells or a derivative thereof, in the second volume experience a same cooling rate. In some embodiments the cells are stem cells or immune cells. In some embodiments the stem cells comprise hematopoietic stem cells (HSC), mesenchymal stem cells (MSC), or both. In some embodiments the biological sample comprises whole bone marrow. In some embodiments the biological sample comprises mobilized bone marrow cells, i.e., that result from treatment of a donor with a bone marrow mobilizing agent, e.g., a colony stimulating factors (CSFs)). In some embodiments the biological sample comprises one or more organs, blood, or both. In some embodiments the immune cells comprise T cells. In some embodiments the blood is cord blood or peripheral blood. In some embodiments the biological sample comprises plasma or blood serum. In some embodiments the HSCs comprise CD34+ cells. It is contemplated that the containers can be in many forms. For instance, the biological sample or derivative thereof can be contained in bags of 1 ml to 5 ml volume or vials of 0.1 to 15 ml volumes. In a preferred embodiment, the samples with less than 15 ml of biological sample are stored in an insulating container (e.g. a cooling box) within a freezer.

Described herein, in some embodiments, is a method for cryopreserving bone marrow or bone marrow cells. In some embodiments, the method utilizes the systems described herein. In some embodiments, the method comprises processing bone to obtain bone marrow or derivative thereof to obtain bone marrow cells. In some cases, the bone marrow cells can be any cells that can be isolated from bone marrow. In some embodiments, the bone marrow cells can be hematopoietic stem cells. In some embodiments, the bone marrow cells can be mesenchymal stem cells. In some embodiments, the bone marrow or bone marrow cells to be cryopreserved at a freeze rate comprising at least −0.1° C./min, −0.2° C./min, −0.5° C./min, −1° C./min, −1.5° C./min, −2° C./min, −2.5° C./min, −3° C./min, −3.5° C./min, −4° C./min, −4.5° C./min, −5° C./min, −5.5° C./min, −6° C./min, −7° C./min, −7.5° C./min, −8° C./min, −8.5° C./min, −9° C./min, −9.5° C./min, −10° C./min, −11° C./min, −12° C./min, −13° C./min, −14° C./min, −15° C./min, −20° C./min, or higher rate. Preferably, the cryopreservation bags and surrogate vials are cooled at a rate of −1° C. to −5° C.

In some embodiments, the freeze rate comprises the temperature decrease as measured by directly contacting the bone marrow or bone marrow cells with a thermometer. In some embodiments, the freeze rate comprises the temperature decrease as measured in the microenvironment or environment immediately adjacent the bone marrow or bone marrow cells. In some embodiments, the freeze rate comprises the temperature decrease as measured in the freezing apparatus (e.g. freezing bag, cryopreservation bag, cryotube, cryotank, freezing cassette, freezer, or vessel holding liquid nitrogen).

In some embodiments, the method of cryopreserving the bone marrow or bone marrow cells described herein increases the yield of the bone marrow cells after thawing compared to bone marrow cells that are not cryopreserved by the freezer rate described herein. In some instances, the yield of the bone marrow cells cryopreserved by the freezer rate described herein is increased by at least about 10%, 20%, 30%, 40%, 50%, 60%, 70%, 80%. 90%, 100%, 2 folds, 3 folds, 4 folds, 5 folds, 10 folds, 20 folds, 50 folds, or more compared to yield of bone marrow cells not cryopreserved by the freezer rate described herein. In some embodiments, the method of cryopreserving the bone marrow or bone marrow cells described herein increases the viability of the bone marrow cells after thawing compared to bone marrow cells that are not cryopreserved by the freezer rate described herein. In some instances, the viability of the bone marrow cells cryopreserved by the freezer rate described herein is increased by at least about 10%, 20%, 30%, 40%, 50%, 60%, 70%, 80%. 90%, 100%, 2 folds, 3 folds, 4 folds, 5 folds, 10 folds, 20 folds, 50 folds, or more compared to viability of bone marrow cells not cryopreserved by the freezer rate described herein. In some embodiments, the method of cryopreserving the bone marrow or bone marrow cells described herein increases the number of CD34+ bone marrow cells after thawing compared to the number of CD34+ bone marrow cells that are not cryopreserved by the freezer rate described herein. In some instances, the number of CD34+ the bone marrow cells cryopreserved by the freezer rate described herein is increased by at least about 10%, 20%, 30%, 40%, 50%, 60%, 70%, 80%. 90%, 100%, 2 folds, 3 folds, 4 folds, 5 folds, 10 folds, 20 folds, 50 folds, or more compared to the number of CD34+ the bone marrow cells not cryopreserved by the freezer rate described herein. In some embodiments, the method of cryopreserving the bone marrow or bone marrow cells described herein increases the number of CD45+ bone marrow cells after thawing compared to the number of CD45+ bone marrow cells that are not cryopreserved by the freezer rate described herein. In some instances, the number of CD45+ the bone marrow cells cryopreserved by the freezer rate described herein is increased by at least about 10%, 20%, 30%, 40%, 50%, 60%, 70%, 80%. 90%, 100%, 2 folds, 3 folds, 4 folds, 5 folds, 10 folds, 20 folds, 50 folds, or more compared to the number of CD45+ the bone marrow cells not cryopreserved by the freezer rate described herein.

In some embodiments, after thawing the samples frozen utilizing the schemes described herein (e.g. Example 5), the samples contain an increased amount of viable CD34+ cells as compared to known cryopreservation protocols. In some embodiments, the percentage of viable CD34+ cells in the thawed sample is at least about 70% to about 95%. In some embodiments, the percentage of viable CD34+ cells in the thawed sample is at least about 70% to about 75%, about 70% to about 80%, about 70% to about 85%, about 70% to about 90%, about 70% to about 95%, about 75% to about 80%, about 75% to about 85%, about 75% to about 90%, about 75% to about 95%, about 80% to about 85%, about 80% to about 90%, about 80% to about 95%, about 85% to about 90%, about 85% to about 95%, or about 90% to about 95%. In some embodiments, the percentage of viable CD34+ cells in the thawed sample is at least about 70%, about 75%, about 80%, about 85%, about 90%, or about 95%. In some embodiments, the percentage of viable CD34+ cells in the thawed sample is at least at least about 70%, about 75%, about 80%, about 85%, or about 90%. In some embodiments, the percentage of viable CD34+ cells in the thawed sample is at least at most about 75%, about 80%, about 85%, about 90%, or about 95%.

Illustrative methods for obtaining, manufacturing, cryopreserving, and/or storing bone marrow products comprising hematopoietic stem cells used in methods of the present disclosure may be described in PCT/US2020/025778 and in Woods et al., "Ischemia considerations for the development of an organ and tissue donor derived bone marrow bank." J Transl Med 18, 300 (2020); the contents of each of which is incorporated by reference in its entirety.

Automated System for Recovery of Bone Marrow

Figure 7B:
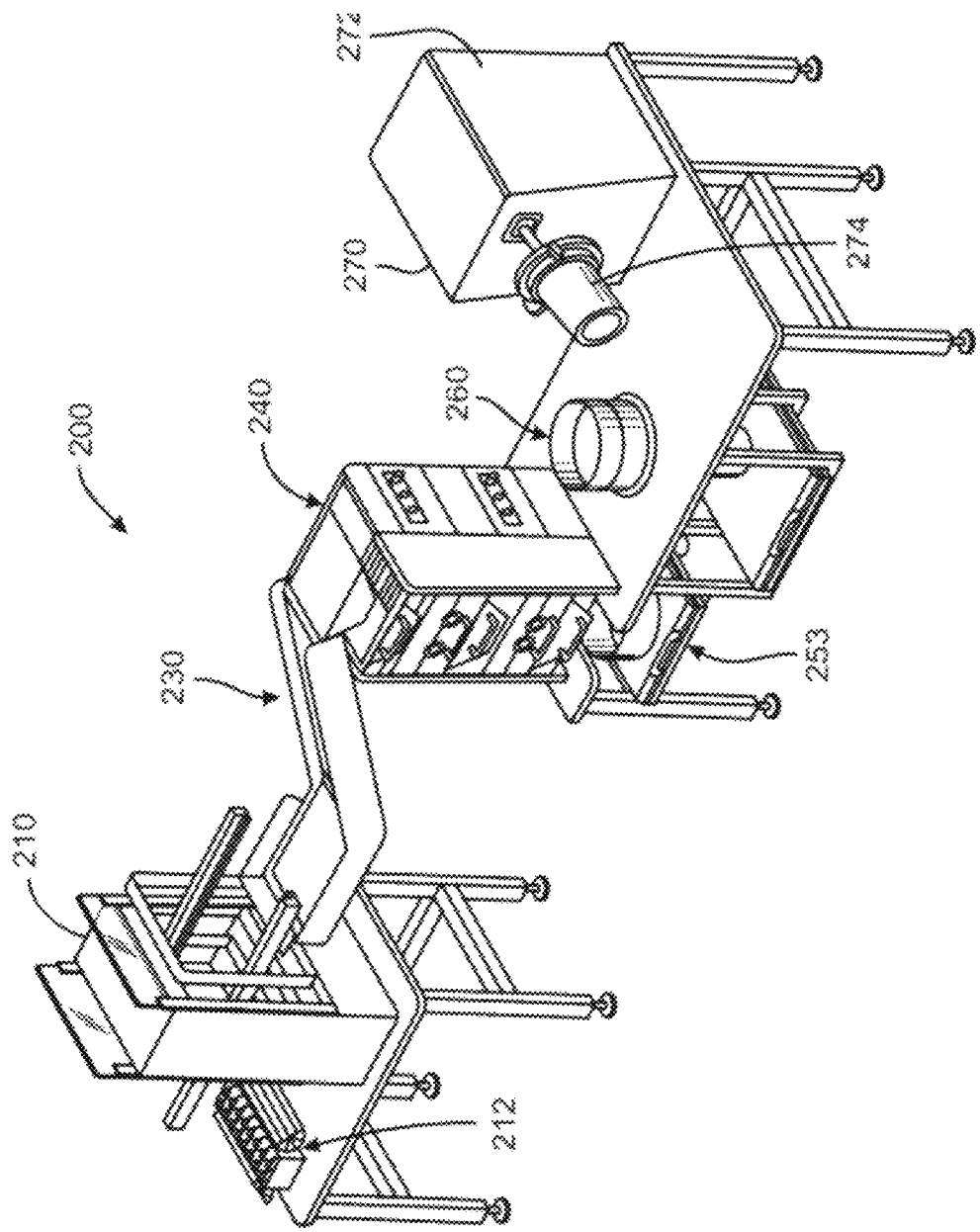
Figure 8A:
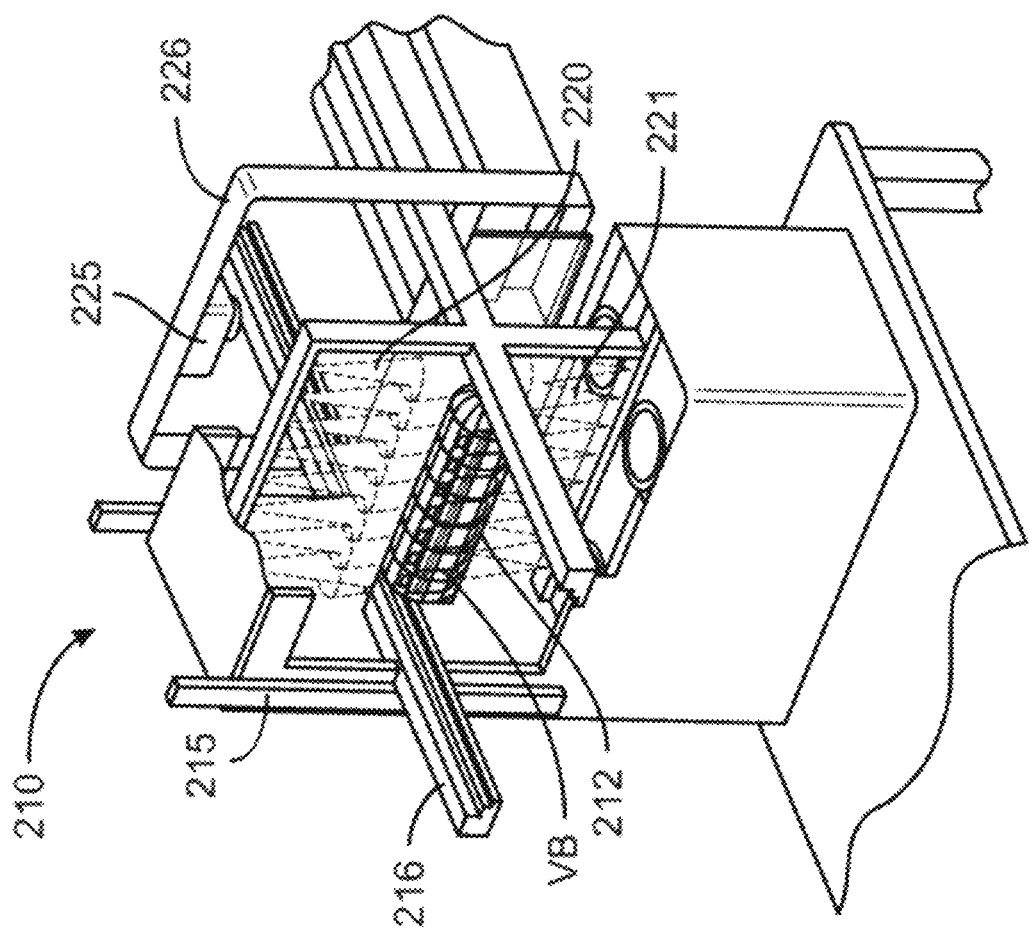
FIGS. 8A and 8B are perspective views of a bone debriding station of the system shown in FIGS. 7A and 7B.
Figure 8B:
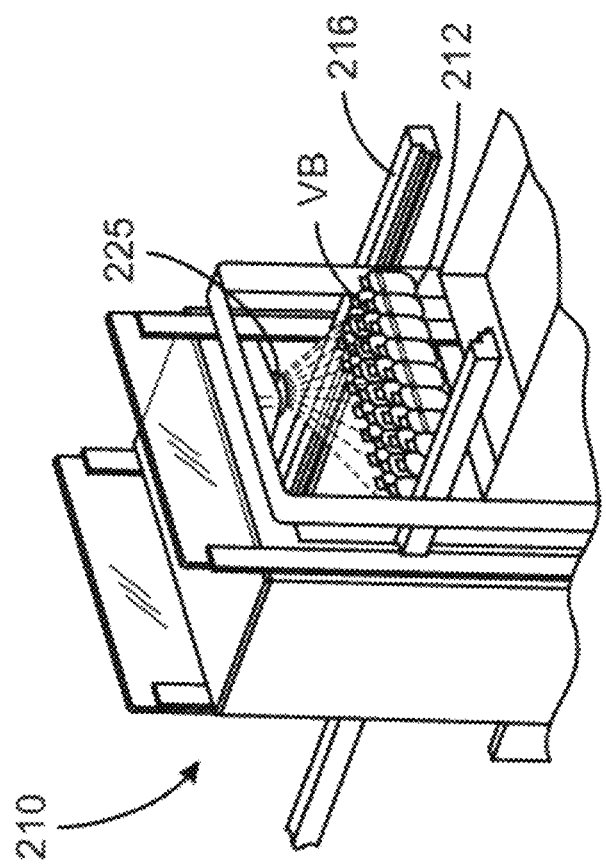

The present disclosure contemplates an automated process for recovery of the bone marrow, and even selection of cells from the bone marrow. In one aspect, an automated system 209 includes sequential stations, as depicted in FIGS. 7A-7B. The first station 210 of the automated process debrides the VBs to remove all soft tissue. In contrast to the manual process that operates on one VB at a time, the automated process is configured to debride an entire donor VB set (which can be at least ten vertebral bodies). The VBs are mounted on a rack or tray 212 that is configured to support the vertebral body set from a given donor. The tray 212 is placed on transfer rails 216 of a housing 215, as shown in FIGS. 8A-8B, with the tray advanced automatically or manually into the interior of the housing. The housing 215 supports a plurality of hydrojets 220 that direct high pressure and high velocity jets of saline onto the VBs. In the known manual process, a manual hydrojet, operating at lower velocities and pressures, directs a stream of detergent onto the VB. In the manual process, the detergent is needed to clean the VBs of the soft tissue. In contrast, the automated cleaning station 210 of the present disclosure uses a saline medium, with the velocity and pressure of the water jets being sufficient to dislodge all soft tissue from the VBs. The automated cleaning station of the present disclosure includes jets configured to produce a direct stream or narrow "V" water/saline jet that generates a high concentrated impact force at varying distances. To achieve good coverage of the VBs, the device includes many direct jets at close spacing at different orientations relative to the VBs, which allows for uniform cleaning independent of position of the VB in the device. In the illustrated embodiment of FIG. 8A, the hydrojets are provided in an upper 220 and a lower row 221. The "V" jets are aligned at different angles to achieve full coverage of the surfaces of the VBs. In addition, or alternatively, the hydrojets 220, 221 can be configured to oscillate over the tray of VBs to ensure complete coverage.

A visualization device 225 is arranged at the outlet of the debridement station 210 that is operable to visualize and interpret the VBs exiting the station to determine if all of the soft tissue has been removed, as shown in FIG. 8B. If not, then the VBs are returned along the rails 216 back into the housing for further hydrojet processing. It is contemplated that a controller (not shown) can be provided to control the movement of the tray 212 along the rails 216 and to interpret the signals generated by the visualization device 225. The visualization device can include a camera that obtains an image of the VBs and the controller can include imaging software capable of recognizing the soft tissue in the acquired image. A dye can be applied to the cleaned VBs at the end of the hydrojet debridement process, in which the dye is absorbed by soft tissue but not bone. The dye can thus provide contrast to facilitate differentiation of any remaining soft tissue from the bone. The visualization device 225 can be configured to pan across the VBs, such as by translating along a frame 226 and by translating the frame in order to view the VBs at all angles.

Figure 9A:
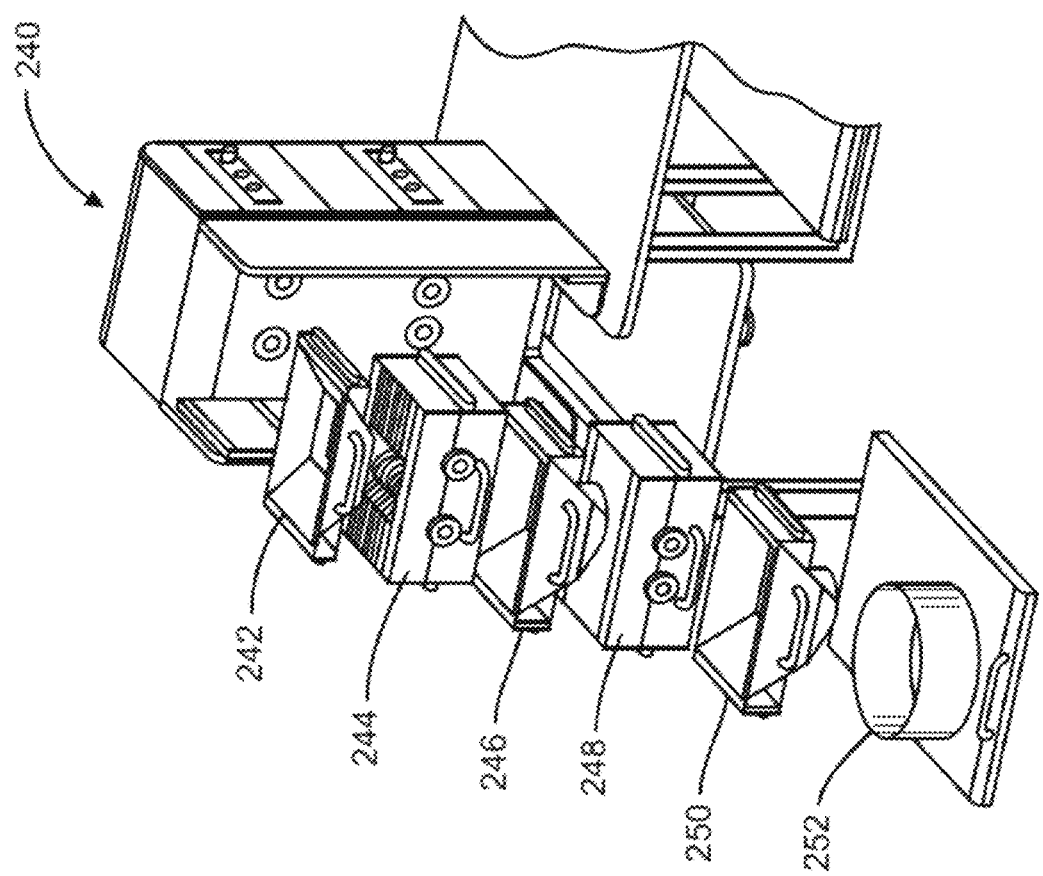

Returning to FIGS. 9A-9B, once it is determined that the VBs are cleaned of all soft tissue, the debrided VBs are then fed by a conveyor 230 to an automated grinding station 240 to produce appropriately sized pieces for tumbling and final cell extraction. The manual "cubing" process described above can be variable, time consuming, and potentially not safe for the operator. The automated system includes a grinding station that combines "cubing" the VBs (i.e., cutting the VBs into small pieces) and grinding the cubed VBs to reduce the VBs to 2-3 mm pieces. The rails 216 and tray 212 can be con0d to deposit the debrided VBs onto the conveyor 230 which then automatically transfers the VBs to an input hopper 242 of the grinding station 240, shown in more detail in FIGS. 9A-9B. The VBs are directed through an initial mill cutter module 244, then through a funnel 246 to a fine mill cutter module 248, as shown in FIG. 9A. As shown in FIG. 9B the initial mill cutter module 242 includes opposed rotating grinding mills 245 that are separated by a predetermined gap, such as a 5-8 mm gap, so that the incoming VBs are ground into coarse-sized segments. The coarse ground segments are fed to the fine mill cutter module 248 in which smaller diameter grinding mills 249 are provided. The fine grind mills 249 are separated by a smaller gap, on the order of 2-3 mm, to produce finely ground VB segments. As shown in FIG. 9A, a funnel 246 conveys the coarse ground segments to the second grinding mill 248, and a funnel 250 directs the finely ground VB segments to a collection pan 252 supported on a plate 253. During the milling operation, a measured volume of processing/resuspension medium with DNAse can be directed through the upper hopper, onto grinding cutters. This medium can be manually introduced during the operation of the grinding station 240, or can be automatically implemented through nozzles incorporated into the hopper 242.

Figure 10:
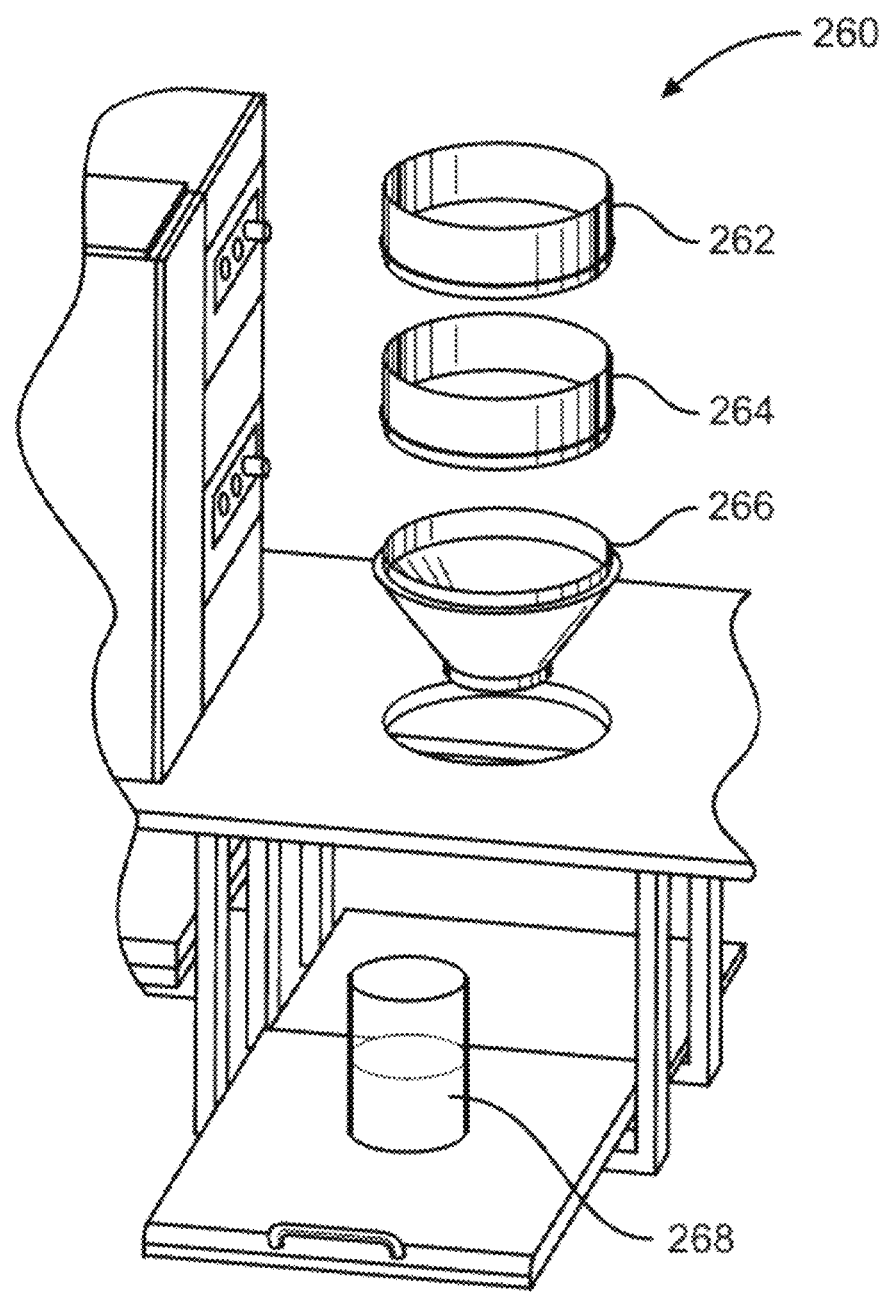
FIG. 10 is a perspective view of a sieve station of the system shown in FIG. 7A and FIG. 7B.

The finely ground VB segments and processing medium are collected in the collection pan 252 and the plate 253 can be moved to a sieve station 260 (FIGS. 8A-8B), whether manually or automatically. Once at the sieve station 260 the contents of the pan 252 are dropped into a sieve cartridge unit which includes two 12" diameter filter sieves—a #40 sieve 262 on top followed by a finer #80 sieve 264, as depicted in FIG. 10. A funnel 266 directs the filtered contents to a collection container 268. The grindings retained by the filters are rinsed within the sieve station 260 with processing/resuspension medium that does not include DNAse. The liquid bone marrow product in the collection container 268 can be analyzed to determine cell content and then concentrated and packaged in appropriate volumes for cryopreservation, as described below. Alternatively, some or all of the processed bone marrow can be further processed using automated cell selection approaches for specialized cell products such as CD34+ cells. Because large volumes of cells can be recovered from a single organ donor with this approach, one donor could yield multiple product types. Moreover, since the source is primary bone marrow (as opposed to G-CSF mobilized peripheral blood) the cell product will endure cryopreservation processing.

In one modification, the output from the grinding station 240 or the sieve station 260 can be automatically fed to a collection bag for cryogenic treatment. In this modification, the lower funnel 250 can be configured to direct the contents to a fluid line connected to a sterile bag. A peristaltic pump can engage the fluid line to pump the output from the grinding station to the sterile bag. A similar arrangement can be engaged to the funnel 266 of the sieve station.

The content of the collection container 268, which is essentially a bone marrow slurry, is conveyed, either manually or automatically, to an adjacent tumbler station 270 that includes a mechanical tumbler 272 and a large disposable vessel 274 that can contain the entire contents of ten processed VBs and associated processing/resuspension medium. The tumbler 272 has a paddle for agitation of the grinding slurry to mechanically liberate cells. When the tumbling cycle is complete, the contents of the tumbler are poured through a sieve magazine into the vessel 274. The contents of the vessel 274 can be processed further or prepared for cryogenic storage.

Additional teachings regarding packaging is disclosed in Woods, E. J. and S Thirumala. "Packaging considerations for biopreservation." *Transfusion Medicine and Hemotherapy* 38:149-156 (2011); the contents of which is incorporated by reference in its entirety.

Isolation of CD34+ Cells

Described herein, in some aspects, is a method for processing (e.g. isolating) CD34+ cells obtained from bone marrow or bone marrow derivative. In some cases, the bone marrow or bone marrow derivative can be fresh (e.g. never frozen) or thawed from being previously frozen. In some embodiments, the bone marrow or bone marrow derivative can be ground by the methods and systems described herein. In some embodiments, ground bone marrow or bone marrow cells can be contacted with the stabilization buffer described herein. In some embodiments, the stabilization prevents formation of aggregates of the bone marrow cells. In some instances, the bone marrow cells contacted and suspended in the stabilization buffer can be isolated by attaching to antibody such as a conjugated antibody. For example, bone marrow cells expressing CD34+ can be isolated and enriched by contacting the bone marrow cells with the CD34 antibody conjugated with iron, where the bone marrow cells expressing CD34 are then trapped a magnetic separation column (e.g. "CliniMACS®"). The bone marrow cells not expressing CD34 are can be washed away. The trapped CD34+ bone marrow cells can be harvested by removing the magnetic field and eluting the targeted CD34+ bone marrow cells. Such approach does not require isolating the bone marrow cells with a Ficoll gradient.

Aspect described in the present disclosure comprises a method for processing a population of CD34+ cells obtained from bone marrow or a derivative thereof, wherein the bone marrow or the derivative thereof is derived from a deceased donor, the method comprising: obtaining a bone or bone fragment from a deceased donor, optionally, processing the bone into bone fragments; extracting the bone marrow or derivative thereof from the bone or bone fragment; and contacting the bone marrow or derivative thereof with a stabilization buffer, wherein the stabilization buffer comprises more than about 3 U/ml of a nuclease; performing a CD34+ cell isolation assay to generate a cellular composition comprising the population of CD34+ cells, wherein the composition comprising the population of CD34+ cells comprises at least about 80,000 CD34+ cells/750 µl of the bone marrow or the derivative thereof contacted with the stabilization buffer. In some embodiments, the at least about 80,000 CD34+ cells/750 µl of the bone marrow or the derivative thereof contacted with the stabilization buffer comprise at least 70% viable CD34+ cells. In some embodiments, the at least about 80,000 CD34+ cells/750 µl of the bone marrow or the derivative thereof contacted with the stabilization buffer comprise at least 80% viable CD34+ cells. In some embodiments, the at least about 80,000 CD34+ cells/750 µl of the bone marrow or the derivative thereof contacted with the stabilization buffer comprise at least 90% viable CD34+ cells.

Another aspect of the present disclosure comprises a stabilization buffer comprising: at least 5 U/ml of an anticoagulant; and more than 3 U/ml of a nuclease. In some embodiments, stabilization buffer comprises more than about 5 U/ml of a nuclease. In some embodiments, the stabilization buffer comprises more than about 10 U/ml of a nuclease. In some embodiments, the stabilization buffer comprises more than about 15 U/ml of a nuclease. In some embodiments, the stabilization buffer comprises more than about 20 U/ml of a nuclease. In some embodiments, the stabilization buffer comprises about 20 U/ml of a nuclease. In some embodiments, the nuclease is Benzonase® or Denarase®. In some embodiments, the stabilization buffer further comprises more than about 10 U/ml of an anticoagulant. In some embodiments, the stabilization buffer further comprises about 10 U/ml of an anticoagulant. In some embodiments, the anticoagulant is heparin. In some embodiments, the stabilization buffer further comprises human serum albumin (HSA). In some embodiments, the stabilization buffer comprises 0.5% HSA.

In some embodiments, the stabilization buffer comprises nuclease. In some embodiments, the nuclease is Benzonase® or Denarase®. In some embodiments, the stabilization buffer comprises nuclease at about 3 U/ml, 4 U/ml, 5 U/ml, 6 U/ml, 7 U/ml, 8 U/ml, 9 U/ml, 10 U/ml, 11 U/ml, 12 U/ml, 13 U/ml, 14 U/ml, 15 U/ml, 16 U/ml, 17 U/ml, 18 U/ml, 19 U/ml, 20 U/ml, 21 U/ml, 22 U/ml, 23 U/ml, 24 U/ml, 25 U/ml, 26 U/ml, 27 U/ml, 28 U/ml, 29 U/ml, 30 U/ml, 50 U/ml, 100 U/ml, 200 U/ml, or more U/ml. In some embodiments, the stabilization buffer comprises an anticoagulant. In some cases, the anticoagulant is Heparin. In some instances, the stabilization buffer comprises anticoagulant at about 0.1 U/ml, 0.2 U/ml, 0.3 U/ml, 0.4 U/ml, 0.5 U/ml, 0.6 U/ml, 0.7 U/ml, 0.8 U/ml, 0.9 U/ml, 1.0 U/ml, 2.0 U/ml, 3.0 U/ml, 4.0 U/ml, 5.0 U/ml, 6.0 U/ml, 7.0 U/ml, 8.0 U/ml, 9.0 U/ml, 10 U/ml, 11 U/ml, 12 U/ml, 13 U/ml, 14 U/ml, 15 U/ml, 16 U/ml, 17 U/ml, 18 U/ml, 19 U/ml, 20 U/ml, 21 U/ml, 22 U/ml, 23 U/ml, 24 U/ml, 25 U/ml, 26 U/ml, 27 U/ml, 28 U/ml, 29 U/ml, 30 U/ml, 50 U/ml, 100 U/ml, 200 U/ml, or more U/ml.

In various embodiments, a stabilization buffer lacks heparin.

In some embodiments, the stabilization buffer comprises about 0.001%, 0.002%, 0.003%, 0.004%, 0.005%, 0.01%, 0.02%, 0.03%, 0.04%, 0.05% HSA, 0.1% HSA, 0.2% HSA, 0.3% HSA, 0.4% HSA, 0.5% HSA, 0.6% HSA, 0.7% HSA, 0.8% HSA, 0.9% HSA, 1.0% HSA, 1.5% HSA, 2% HSA, 2.5% HSA, 5% HSA, 10% HSA, 20% HSA, or more HSA.

Described herein, in some embodiments, is a method of processing bone marrow to obtain bone marrow cells. In some embodiments, the method comprises contacting the bone marrow or the bone marrow cells with the stabilization buffer described herein.

Another aspect of the present disclosure comprises a method for processing a population of CD34+ cells comprised in bone marrow or a derivative thereof, wherein the bone marrow or the derivative thereof is derived from a deceased donor, the method comprising: obtaining a bone or bone fragment from a deceased donor, optionally, processing the bone into bone fragments; extracting the bone marrow or derivative thereof from the bone or bone fragment; and contacting the bone marrow or derivative thereof with a stabilization buffer, wherein the stabilization buffer comprises more than about 3 U/ml of a nuclease; performing a CD34+ cell isolation assay to generate a cellular composition comprising the population of CD34+ cells, wherein the composition comprising the population of CD34+ cells comprises at least about 80,000 CD34+ cells/750 ul of the bone marrow or the derivative thereof contacted with the stabilization buffer.

In some embodiments, processing or contacting the bone marrow or bone marrow cells described herein with the stabilization buffer increases the yield of the bone marrow cells obtained from the methods described herein compared to the yield of the bone marrow cells processed in the absence of the stabilization buffer. In some instances, processing or contacting the bone marrow or bone marrow cells described herein with the stabilization buffer increases the yield of the bone marrow cells by at least about 10%, 20%, 30%, 40%, 50%, 60%, 70%, 80%. 90%, 100%, 2 fold, 3 fold, 4 fold, 5 fold, 10 fold, 20 fold, 50 fold, or more compared to yield of bone marrow cells processed in the absence of the stabilization buffer. In some embodiments, processing or contacting the bone marrow or bone marrow cells described herein with the stabilization buffer increases the viability of the bone marrow cells obtained from the methods described herein compared to the viability of the bone marrow cells processed in the absence of the stabilization buffer. In some instances, processing or contacting the bone marrow or bone marrow cells described herein with the stabilization buffer increases the viability of the bone marrow cells by at least about 10%, 20%, 30%, 40%, 50%, 60%, 70%, 80%. 90%, 100%, 2 fold, 3 fold, 4 fold, 5 fold, 10 fold, 20 fold, 50 fold, or more compared to viability of bone marrow cells processed in the absence of the stabilization buffer.

In some embodiments, processing or contacting the bone marrow or bone marrow cells described herein with the stabilization buffer increases the number of CD34+ bone marrow cells compared to the number of CD34+ bone marrow cells processed in the absence of the stabilization buffer. In some cases, the number of CD34+ bone marrow obtained from processing with the stabilization buffer is increased by at least about 10%, 20%, 30%, 40%, 50%, 60%, 70%, 80%. 90%, 100%, 2 fold, 3 fold, 4 fold, 5 fold, 10 fold, 20 fold, 50 fold, or more compared to the number of CD34+ bone marrow obtained from processing in the absence of stabilization buffer. In some embodiments, processing or contacting the bone marrow or bone marrow cells described herein with the stabilization buffer increases the number of CD45+ bone marrow cells compare to the number of CD45+ bone marrow cells processed in the absence of the stabilization buffer. In some cases, the number of CD45+ bone marrow obtained from processing with the stabilization buffer is increased by at least about 10%, 20%, 30%, 40%, 50%, 60%, 70%, 80%. 90%, 100%, 2 fold, 3 fold, 4 fold, 5 fold, 10 fold, 20 fold, 50 fold, or more compared to the number of CD45+ bone marrow obtained from processing in the absence of stabilization buffer.

In some embodiments, cellular compositions comprising CD34+ cells derived from bone marrow samples processed with the stabilization buffers described herein have an increased amount of CD34+ cells, as compared to cellular compositions generated from known CD34+ isolation methods. In some embodiments. The amount of CD34+ cells isolated from the bone marrow samples contacted with the stabilization buffers described herein is at least about 70,000 CD34+ cells/750 ul of bone marrow or a derivative thereof contacted with the stabilization buffers described herein. In some embodiments, the amount of CD34+ cells isolated from the bone marrow samples contacted with the stabilization buffers described herein is at least about 70,000 cells/750 ul to about 100,000 cells/750 ul. In some embodiments, the amount of CD34+ cells isolated from the bone marrow samples contacted with the stabilization buffers described herein is at least about 70,000 cells/750 ul to about 75,000 cells/750 ul, about 70,000 cells/750 ul to about 80,000 cells/750 ul, about 70,000 cells/750 ul to about 85,000 cells/750 ul, about 70,000 cells/750 ul to about 90,000 cells/750 ul, about 70,000 cells/750 ul to about 95,000 cells/750 ul, about 70,000 cells/750 ul to about 100,000 cells/750 ul, about 75,000 cells/750 ul to about 80,000 cells/750 ul, about 75,000 cells/750 ul to about 85,000 cells/750 ul, about 75,000 cells/750 ul to about 90,000 cells/750 ul, about 75,000 cells/750 ul to about 95,000 cells/750 ul, about 75,000 cells/750 ul to about 100,000 cells/750 ul, about 80,000 cells/750 ul to about 85,000 cells/750 ul, about 80,000 cells/750 ul to about 90,000 cells/750 ul, about 80,000 cells/750 ul to about 95,000 cells/750 ul, about 80,000 cells/750 ul to about 100,000 cells/750 ul, about 85,000 cells/750 ul to about 90,000 cells/750 ul, about 85,000 cells/750 ul to about 95,000 cells/750 ul, about 85,000 cells/750 ul to about 100,000 cells/750 ul, about 90,000 cells/750 ul to about 95,000 cells/750 ul, about 90,000 cells/750 ul to about 100,000 cells/750 ul, or about 95,000 cells/750 ul to about 100,000 cells/750 ul. In some embodiments, the amount of CD34+ cells isolated from the bone marrow samples contacted with the stabilization buffers described herein is at least about 70,000 cells/750 ul, about 75,000 cells/750 ul, about 80,000 cells/750 ul, about 85,000 cells/750 ul, about 90,000 cells/750 ul, about 95,000 cells/750 ul, or about 100,000 cells/750 ul. In some embodiments, the amount of CD34+ cells isolated from the bone marrow samples contacted with the stabilization buffers described herein is at least at least about 70,000 cells/750 ul, about 75,000 cells/750 ul, about 80,000 cells/750 ul, about 85,000 cells/750 ul, about 90,000 cells/750 ul, or about 95,000 cells/750 ul. In some embodiments, the amount of CD34+ cells isolated from the bone marrow samples contacted with the stabilization buffers described herein is at least at most about 75,000 cells/750 ul, about 80,000 cells/750 ul, about 85,000 cells/750 ul, about 90,000 cells/750 ul, about 95,000 cells/750 ul, or about 100,000 cells/750 ul.

In some embodiments, the CD34+ cells derived from bone marrow samples processed with the stabilization buffers described herein also exhibit higher viability as compared to cellular compositions generated from known CD34+ isolation methods.

In some embodiments, the amount of CD34+ cells isolated from the bone marrow samples contacted with the stabilization buffers described herein comprise a percent viability of at least about 70% to about 95%. In some embodiments, the amount of CD34+ cells isolated from the bone marrow samples contacted with the stabilization buffers described herein comprise a percent viability of at least about 70% to about 95%. In some embodiments, the amount of CD34+ cells isolated from the bone marrow samples contacted with the stabilization buffers described herein comprise a percent viability of at least about 70% to about 75%, about 70% to about 80%, about 70% to about 85%, about 70% to about 90%, about 70% to about 95%, about 75% to about 80%, about 75% to about 85%, about 75% to about 90%, about 75% to about 95%, about 80% to about 85%, about 80% to about 90%, about 80% to about 95%, about 85% to about 90%, about 85% to about 95%, or about 90% to about 95%. In some embodiments, the amount of CD34+ cells isolated from the bone marrow samples contacted with the stabilization buffers described herein comprise a percent viability of at least about 70%, about 75%, about 80%, about 85%, about 90%, or about 95%. In some embodiments, the amount of CD34+ cells isolated from the bone marrow samples contacted with the stabilization buffers described herein comprise a percent viability of at least at least about 70%, about 75%, about 80%, about 85%, or about 90%. In some embodiments, the amount of CD34+ cells isolated from the bone marrow samples contacted with the stabilization buffers described herein comprise a percent viability of at least at most about 75%, about 80%, about 85%, about 90%, or about 95%. Viability may relate to either or both of functional viability which measures the cells' ability to proliferate and routine viability which relates to the numbers or percentages of live cells, e.g., as measured by Trypan Blue.

In an aspect of the present disclosure, a method is provided for selecting CD34 expressing (CD34+) cells from deceased donor bone marrow using density reduced Ficoll and an immunomagnetic CD34+ cell isolation kit. Surprisingly, it has been found that cell isolation using density reduced Ficoll prior to CD34 selection is beneficial to obtain high purity and viability CD45/CD34+ cells from freshly prepared deceased donor bone marrow. On the other hand, Ficoll at conventional density has been found to be optimal for CD45/CD34+ cell selection from thawed cryopreserved deceased donor bone marrow.

Vertebral sections obtained from a recently deceased donor were processed as described above. Thus, in one embodiment, the bone is cleaned of all soft tissue and then cut into small pieces that were immediately submerged into 500 ml of grinding media. The grinding media can be PLASMA-LYTE™ A injection pH 7.4, multiple electrolytes, injection type 1 USP (PLASMA-LYTE™) containing 2.5% human serum albumin (HSA), 3 U/ml denarase, and 10 U/ml heparin. The sectioned VB are ground using a bone grinder, filtered and rinsed with rinse media (such as PLASMA-LYTE™ with 2.5% HSA). The entire cell suspension is centrifuged to concentrate cells to $2-3\times10^8$/ml and the cell concentration is extracted. A portion or all of the resulting BM preparation can be used immediately for CD34 selection, while the remainder can be prepared for cryopreservation. The cryopreserved portion involves adding a final concentration of 10% DMSO and 5% HSA to the BM cells and bringing the preparation to −86° C., either by passive cooling or by controlled cooling at a rate of approximately −1° C./min, after which the cryopreserved portion is plunged into liquid nitrogen.

For selection of CD34+ cells, either the newly processed BM preparation is used or a previously cryopreserved portion is thawed for use. Ficoll-Paque PLUS is added to the BM preparation to separate the desired CD34+ cell component of the bone marrow. It has been found for cell selection from cryopreserved bone marrow that the conventional density for the Ficoll of 1.077 g/ml produces acceptable results. However, in one aspect of the present disclosure, for cell selection from freshly prepared deceased donor bone marrow the Ficoll density is reduced from the conventional density. In particular, the density is reduced by mixing Ficoll-Paque PLUS (density 1.077 g/mL, GE Company)

with Plasma Lyte-A Injection pH 7.4 (Baxter Healthcare 2B2544X) in specific proportions to obtain an overall density of less than 1.077 g/ml, particularly 1.063-1.052 g/ml. In one specific embodiment, the density of 1.063 g/ml was found to be optimal for isolation of CD34+ cells, taking into account quantity, viability and purity of the CD34+ cells.

In one embodiment, 5 ml of the 1.063 g/ml density Ficoll solutions is pipetted into 15-ml centrifuge tubes, and the BM solution generated from VBs of deceased donors is carefully layered over the Ficoll gradient. The tubes are centrifuged for 30 min at 400 g without break at room temperature. After centrifugation, buffy coat cells are harvested carefully, and the cells are washed in phosphate-buffered saline (PBS) containing 0.5% HSA and 2 mM Ethylenediaminetetraacetic acid (EDTA) (MACS buffer, Miltenyi). In one specific embodiment, centrifugation is performed for 5 min at 400 g, and the resulting cell pellets are resuspended in 10 ml PBS, followed by a second centrifugation for 5 min at 400 g.

Nucleated cells in the isolated buffy coat can be counted using a Sysmex XP-300. A Cellometer Vision (Nexcellom) or flow cytometer can be used to determine cell counts of purified CD34 cells. 20 microliters of AOPI can be added to 20 microliters of cells and after mixing total viable cells can be determined. The CD34+ cells can be selected by a positive immune separation method using a CliniMACS system (Miltenyi, Bergisch Gladbach, Germany) or an EasySep CD34 kit (Stemcell Technologies, Vancouver, BC, Canada) in accordance with the protocol of the manufacturer. From testing at various Ficoll densities it has been surprisingly determined that the lower Ficoll density contemplated in the present disclosure (i.e., 1.063-1.052 gm/ml vs. the conventional 1.077 gm/ml density) leads to more optimum cell recovery. Optimization is based on purity, viability and yield of selected CD34 cells. A target of >90% purity and >90% viable CD34+ cells is preferred. While lower Ficoll densities resulted in greater purity and fewer dead cells, it was surprisingly found that a greater portion of the CD34+ cells present in the deceased donor whole bone marrow before selection are lost using the lower Ficoll densities to prepare buffy coat. Thus, the high viability and purity of CD45/CD34+ cells achieved at the conventional Ficoll density gradient also leads to a large loss in yield (approximately 60% loss of input CD34+ cells).

Thus, in accordance with one aspect of the present disclosure, for freshly prepared the optimal density of Ficoll for selection of CD45/CD34+ cells at >90% purity and viability is less than 1.077 and particularly 1.063-1.052. This Ficoll density provides a higher yield of CD45/CD34+ cells with similar purity and cell viability to the conventional Ficoll density approach.

In another aspect of the present disclosure, the CD34+ cells can be initially acquired from a freshly prepared deceased donor bone marrow using the reduced density Ficoll-Paque described above. The BM can be cryogenically frozen and then the CD34+ cells can be acquired later using conventional density Ficoll-Paque. This approach essentially allows selective recovery of cells from deceased donor bone marrow—either before freezing using the modified Ficoll density or after freezing and thawing using conventional Ficoll density.

Recovery of MSCs from Processed Bone Marrow

Bone marrow is a well-known source for mesenchymal stromal/stem cells (MSCs) which can be harvested from bone marrow obtained using the methods described above. MSCs are self-renewing, multipotent progenitor cells with multilineage potential to differentiate into cell types of mesodermal origin, such as adipocytes, osteocytes, and chondrocytes. In addition, MSCs can migrate to sites of inflammation and exert potent immunosuppressive and anti-inflammatory effects through interactions between lymphocytes associated with both the innate and adaptive immune system. MSCs can be used in treating osteogenesis imperfect, cartilage defects, myocardial infarction, Crohn's disease, multiple sclerosis, autoimmune disease such as Lupus, liver cirrhosis, osteo arthritis, and rheumatoid arthritis. Matched HSC/MSC units which can be used in co-transplant for treatment of graft vs. host disease (GVHD), and for hematopoietic stem cell transplant support.

In another feature of the systems and methods disclosed herein, a method is provided for recovering mesenchymal stem cells (MSCs) from enzymatically digested vertebral body (VB) bone fragments that are the byproduct of the VB grinding and elution of the methods described herein. In this method, a mixture of both collagenase and neutral protease is used to obtain the highest possible yields of vertebral bone adherent MSC (vBA-MSC). The MSCs can be recovered from cryopreserved VB bone fragments that are later processed according to the present disclosure. In one specific aspect, recombinant *Clostridium histolyticum* collagenase, comprised of the two active isoforms, is used in effective amounts in the MSC extraction process. The mixture of cells liberated by digesting VB bone fragment is cultured on tissue-coated plastic in the presence of Mesencult medium to select proliferative vBA-MSC. Freshly digested preparations as well as different passages of vBA-MSC can be characterized by flow cytometry, colony forming unit-fibroblast (CFU-F) potential, population doubling time (PDT) and trilineage (adipogenic, chondrogenic and osteogenic) differentiation in vitro. In some embodiments, the mesenchymal stem cells can be recovered or cultured in Alpha-MEM supplemented with human platelet lysate and epidermal growth factor and/or fibroblast growth factor.

The present disclosure thus contemplates a method for optimizing digestion and MSC recovery from vertebral bone fragments using a combination of purified collagenase and neutral protease. In one specific embodiment, the collagenase is DE collagenase (Vitacyte), which is comprised of purified *Clostridium histolyticum* collagenase and *Paneibacillus polymyxa* neutral protease. In accordance with one aspect of the disclosure, optimal neutral protease concentration and collagenase concentrations (C1 and C2 collagenase) and optimal ratio of solution volume (mls) to bone fragment weight (mgs) are determined.

In some embodiments, a collagenase may include *Clostridium histolyticum* further comprising two active isoforms, C1 and C2. In some embodiments, one or more collagenases comprising isoforms C1 and C2 may be present in the digestion solution at a ratio comprising more collagenase isoform C1 than collagenase isoform C2. In some embodiments, the ratio of collagenase isoform C1 to collagenase isoform C2 may be about 30 to about 70: about 10 to about 29. In some embodiments, the ratio of collagenase isoform C1 to collagenase C2 may be 35:15. In some embodiments, the mass ratio of C1 and C2 for each concentration may be 70:30, 54:46, 37:63, 82:18, 54:46, and 90:10.

In some embodiments, the neutral protease may be *Paneibacillus polymyxa* neutral protease. In some embodiments, the neutral protease concentration may be about 2 U/ml to about 21 U/ml. In some embodiments, the neutral protease concentration may be about 2 U/ml to about 7 U/ml, about 2 U/ml to about 12 U/ml, about 2 U/ml to about 17 U/ml, about 2 U/ml to about 21 U/ml, about 7 U/ml to about 12 U/ml, about 7 U/ml to about 17 U/ml, about 7 U/ml to about 21 U/ml, about 12 U/ml to about 17 U/ml, about 12 U/ml to about 21 U/ml, or about 17 U/ml to about 21 U/ml. In some embodiments, the neutral protease concentration may be about 2 U/ml, about 7 U/ml, about 12 U/ml, about 17 U/ml, or about 21 U/ml. In some embodiments, the neutral protease concentration may be at least about 2 U/ml, about 7 U/ml, about 12 U/ml, or about 17 U/ml. In some embodiments, the neutral protease concentration may be at most about 7 U/ml, about 12 U/ml, about 17 U/ml, or about 21 U/ml. In some embodiments, the digestion solution may comprise the neutral protease at an activity of about 19.6 U/ml.

In some embodiments, the collagenase concentration is about 0.05 U/ml to about 1.6 U/ml. In some embodiments, the collagenase concentration is about 0.05 U/ml to about 0.1 U/ml, about 0.05 U/ml to about 0.15 U/ml, about 0.05 U/ml to about 0.2 U/ml, about 0.05 U/ml to about 0.25 U/ml, about 0.05 U/ml to about 0.3 U/ml, about 0.05 U/ml to about 0.35 U/ml, about 0.05 U/ml to about 0.4 U/ml, about 0.05 U/ml to about 0.8 U/ml, about 0.05 U/ml to about 1.2 U/ml, about 0.05 U/ml to about 1.6 U/ml, about 0.1 U/ml to about 0.15 U/ml, about 0.1 U/ml to about 0.2 U/ml, about 0.1 U/ml to about 0.25 U/ml, about 0.1 U/ml to about 0.3 U/ml, about 0.1 U/ml to about 0.35 U/ml, about 0.1 U/ml to about 0.4 U/ml, about 0.1 U/ml to about 0.8 U/ml, about 0.1 U/ml to about 1.2 U/ml, about 0.1 U/ml to about 1.6 U/ml, about 0.15 U/ml to about 0.2 U/ml, about 0.15 Um' to about 0.25 U/ml, about 0.15 U/ml to about 0.3 U/ml, about 0.15 U/ml to about 0.35 U/ml, about 0.15 U/ml to about 0.4 U/ml, about 0.15 U/ml to about 0.8 U/ml, about 0.15 U/ml to about 1.2 U/ml, about 0.15 U/ml to about 1.6 U/ml, about 0.2 U/ml to about 0.25 U/ml, about 0.2 U/ml to about 0.3 U/ml, about 0.2 U/ml to about 0.35 U/ml, about 0.2 U/ml to about 0.4 U/ml, about 0.2 U/ml to about 0.8 U/ml, about 0.2 U/ml to about 1.2 U/ml, about 0.2 U/ml to about 1.6 U/ml, about 0.25 U/ml to about 0.3 U/ml, about 0.25 U/ml to about 0.35 U/ml, about 0.25 U/ml to about 0.4 U/ml, about 0.25 U/ml to about 0.8 U/ml, about 0.25 U/ml to about 1.2 U/ml, about 0.25 U/ml to about 1.6 U/ml, about 0.3 U/ml to about 0.35 U/ml, about 0.3 U/ml to about 0.4 U/ml, about 0.3 U/ml to about 0.8 U/ml, about 0.3 U/ml to about 1.2 U/ml, about 0.3 U/ml to about 1.6 U/ml, about 0.35 U/ml to about 0.4 U/ml, about 0.35 U/ml to about 0.8 U/ml, about 0.35 U/ml to about 1.2 U/ml, about 0.35 U/ml to about 1.6 U/ml, about 0.4 U/ml to about 0.8 U/ml, about 0.4 U/ml to about 1.2 U/ml, about 0.4 U/ml to about 1.6 U/ml, about 0.8 U/ml to about 1.2 U/ml, about 0.8 U/ml to about 1.6 U/ml, or about 1.2 U/ml to about 1.6 U/ml. In some embodiments, the collagenase concentration is about 0.05 U/ml, about 0.1 U/ml, about 0.15 U/ml, about 0.2 U/ml, about 0.25 U/ml, about 0.3 U/ml, about 0.35 U/ml, about 0.4 U/ml, about 0.8 U/ml, about 1.2 U/ml, or about 1.6 U/ml. In some embodiments, the collagenase concentration is at least about 0.05 U/ml, about 0.1 U/ml, about 0.15 U/ml, about 0.2 U/ml, about 0.25 U/ml, about 0.3 U/ml, about 0.35 U/ml, about 0.4 U/ml, about 0.8 U/ml, or about 1.2 U/ml. In some embodiments, the collagenase concentration is at most about 0.1 U/ml, about 0.15 U/ml, about 0.2 U/ml, about 0.25 U/ml, about 0.3 U/ml, about 0.35 U/ml, about 0.4 U/ml, about 0.8 U/ml, about 1.2 U/ml, or about 1.6 U/ml.

In accordance with one aspect of the disclosure, neutral protease concentration and collagenase concentrations (C1 and C2 collagenase) and ratio of solution volume (mls) to bone fragment weight (mgs) are determined.

In some embodiments, the total collagenase concentrations (C1 and C2 collagenase) are about 25 µg/ml to about 100 µg/ml. In some embodiments, the total collagenase concentrations are about 25 µg/ml to about 32.5 µg/ml, about 25 µg/ml to about 47.5 µg/ml, about 25 µg/ml to about 42.5 µg/ml, about 25 µg/ml to about 50 µg/ml, about 25 µg/ml to about 65 µg/ml, about 25 µg/ml to about 77.5 µg/ml, about 25 µg/ml to about 85 µg/ml, about 25 µg/ml to about 100 µg/ml, about 32.5 µg/ml to about 47.5 µg/ml, about 32.5 µg/ml to about 42.5 µg/ml, about 32.5 µg/ml to about 50 µg/ml, about 32.5 µg/ml to about 65 µg/ml, about 32.5 µg/ml to about 77.5 µg/ml, about 32.5 µg/ml to about 85 µg/ml, about 32.5 µg/ml to about 100 µg/ml, about 47.5 µg/ml to about 42.5 µg/ml, about 47.5 µg/ml to about 50 µg/ml, about 47.5 µg/ml to about 65 µg/ml, about 47.5 µg/ml to about 77.5 µg/ml, about 47.5 µg/ml to about 85 µg/ml, about 47.5 µg/ml to about 100 µg/ml, about 42.5 µg/ml to about 50 µg/ml, about 42.5 µg/ml to about 65 µg/ml, about 42.5 µg/ml to about 77.5 µg/ml, about 42.5 µg/ml to about 85 µg/ml, about 42.5 µg/ml to about 100 µg/ml, about 50 µg/ml to about 65 µg/ml, about 50 µg/ml to about 77.5 µg/ml, about 50 µg/ml to about 85 µg/ml, about 50 µg/ml to about 100 µg/ml, about 65 µg/ml to about 77.5 µg/ml, about 65 µg/ml to about 85 µg/ml, about 65 µg/ml to about 100 µg/ml, about 77.5 µg/ml to about 85 µg/ml, about 77.5 µg/ml to about 100 µg/ml, or about 85 µg/ml to about 100 µg/ml. In some embodiments, the total collagenase concentrations are about 25 µg/ml, about 32.5 µg/ml, about 47.5 µg/ml, about 42.5 µg/ml, about 50 µg/ml, about 65 µg/ml, about 77.5 µg/ml, about 85 µg/ml, or about 100 µg/ml. In some embodiments, the total collagenase concentrations are at least about 25 µg/ml, about 32.5 µg/ml, about 47.5 µg/ml, about 42.5 µg/ml, about 50 µg/ml, about 65 µg/ml, about 77.5 µg/ml, or about 85 µg/ml. In some embodiments, the total collagenase concentrations are at most about 32.5 µg/ml, about 47.5 µg/ml, about 42.5 µg/ml, about 50 µg/ml, about 65 µg/ml, about 77.5 µg/ml, about 85 µg/ml, or about 100 µg/ml.

In some embodiments, the mass ratio of C1 and C2 for each concentration are 70:30, 54:46, 37:63, 82:18 and 90:10, respectively.

The volume to weight ratio of digestion solution to captured ground bone is about 1:1 to about 15:1, e.g., about 5:1. In some embodiments, the ratio may be 1:1, 2.5:1, 5:1, 7.5:1, 10:1 and 15:1 (volume:weight). In some embodiments, the incubation period is about 1 hour to about 4 hours. In some embodiments, the incubation period is about 1 hour to about 1.5 hours, about 1 hour to about 2 hours, about 1 hour to about 2.5 hours, about 1 hour to about 3 hours, about 1.5 hours to about 2 hours, about 1.5 hours to about 2.5 hours, about 1.5 hours to about 3 hours, about 2 hours to about 2.5 hours, about 2 hours to about 3 hours, or about 2.5 hours to about 3 hours. In some embodiments, the incubation period is about 1 hour, about 1.5 hours, about 2 hours, about 2.5 hours, or about 3 hours. In some embodiments, the incubation period is at least about 1 hour, about 1.5 hours, about 2 hours, or about 2.5 hours. In some embodiments, the incubation period is at most about 1.5 hours, about 2 hours, about 2.5 hours, about 3 hours, or about 4 hours. In some cases, the digestion solution is contacted with the captured ground bone for up to about 4 hours.

In some cases, the optimal volume-to-weight ratio has been found to be 5:1 at an optimal incubation time of 2.5 hours. The optimal protease produced neutral protease activity of 19.6 U/ml. On the other hand, it was found that total viable MSC cell count is generally insensitive to collagenase concentration. It was also found that the yields produced by recombinant collagenase isoforms C1 and C2 are similar to the yields with purified collagenase, regardless of the C1/C2 ratio. Further details of the MSC recovery process of the present disclosure are found in the technical article in Johnstone et al., "Identification and characterization of a large source of primary mesenchymal stem cells tightly adhered to bone surfaces of human vertebral body marrow cavities" bioRxiv 2020.05.04.076950; doi.org/10.1101/2020.05.04.076950, the entire disclosure of which is incorporated herein by reference.

According to the process, fragments of VB bone (either fresh fragments or cryopreserved fragments) are placed in cryoprotectant solution comprised of PLASMA-LYTE™, 2.5% human serum albumin and 10% dimethyl sulfoxide (DMSO) and incubated for 1 hour at 4° C. The solution is removed and the bone fragments cooled at a rate of −1°/min to −86° C. and then plunged into liquid nitrogen. After 24-48 hours in liquid nitrogen, the bone fragments are thawed rapidly in a water bath set at 37° C. and then washed in saline and digested using the collagenase/protease solution described above.

Predicting Cell Viability Based on Ischemia Time

As discussed above, ischemia time of the donor bone impacts the viability of the cells extracted using the processes described above. According to the present disclosure, total ischemia is defined as the interval starting at time of death (the point at which the donor's arterial system was cross-clamped and circulation ceased) and ending with the start of the recovery of cells from the bone. For purposes of statistical modeling, this total interval can be separated into three successive and mutually exclusive time components: (a) Warm Ischemia Time (WIT)—beginning at time of death and ending either when bones are recovered and packed on ice or when the body is placed in a cooler; (b) Body Cooling Time (BCT)—beginning when the body is placed in the cooler and ending when bones are packed on ice; and (c) Cold Ischemia Time (CIT)—beginning when bones are packed on ice and ending when processing begins for extraction of cells, such as HSPCs. Thus, Total Ischemia Time=(WIT)+(BCT)+(CIT). For cases where whole-body cooling is not used, BCT is zero and Total Ischemia Time=(WIT)+(CIT).

In addition to Total Ischemia Time, a variable corresponding to processing experience can be incorporated into the viability determination. It is known that learning curves exert significant effects on outcomes, so to control for this fact a variable EXP can be defined as the number of donors processed prior to the current donor—i.e., for the $i^{th}$ donor, EXP=i−1. Other variables can include bone type (such as vertebral bodies and ilia), donor sex and donor age.

In one aspect, the outcome variables are: the proportion of a particular cell population, such as CD34+ cells, that are viable, the total number of colony forming units (CFUs) per $10^5$ nucleated cells detected following cell processing, and the number of CFU granulocyte macrophages (CFU-GM) detected per $10^5$ nucleated cells.

According to the present disclosure, an ordinary least squares (OLS) beta regression model can be used to predict the outcome variables, with linear regression models used for CFU and CFU-GM and a beta regression model used for the proportion of viable CD34+ cells, or % CD34+, where 0<(% CD34+)<1. The beta regression equation for predicting % CD34+ is:

The regression models are based on un-adjusted models that only account for the ischemia-based variables and not the experience, bone type, donor sex and donor age variables. A fully adjusted model for % CD34+ that accounts for all of the variables. The results of these models are depicted in Tables 1-3.

TABLE 1

% CD34+ values for the coefficients

| | |
|---|---|
| $\beta_0$ Constant | 3.112681 |
| $\beta_1$ Experience | 0.0095651 |
| $\beta_2$ Bone Type (VB = 1) | 0.0351495 |
| $\beta_3$ Warm Ischemia (WIT) (hrs)$^a$ | −0.0229737 |
| $\beta_4$ Body Cooling (BCT) (hrs) | −0.176881 |
| $\beta_5$ Body Cooling Squared (BCT$^2$) | 0.0062293 |
| $\beta_6$ Cold Ischemia (CIT) (hrs) | −0.101344 |
| $\beta_7$ Cold Ischemia Squared (CIT$^2$) | 0.0013874 |

TABLE 2

CFU values for the coefficients

| | |
|---|---|
| $\beta_0$ Constant | 160.6034 |
| $\beta_1$ Experience | 2.60499 |
| $\beta_2$ Facility × Experience | 5.36988 |
| $\beta_3$ Bone Type (VB = 1) | 206.9969 |
| $\beta_4$ Warm Ischemia (hrs) | −3.73481 |
| $\beta_5$ Body Cooling (hrs) | −82.49506 |
| $\beta_6$ Body Cooling Squared | 2.95994 |
| $\beta_7$ Cold Ischemia (hrs) | 9.55975 |
| $\beta_8$ Cold Ischemia Squared | −0.12535 |

The coefficient $\beta_1$ attempts to quantify the effect of the number of donors processed (i.e., experience) on cell quantity and viability. In the fully adjusted CFU model, coefficient $\beta_2$ corresponds to the experience at a particular facility based on the assumption that facilities can have different learning trajectories. Either or both of these coefficients may be modified or even eliminated.

TABLE 3

CFU-GM values for the coefficients

| | |
|---|---|
| $\beta_0$ Constant | 88.3589 |
| $\beta_1$ Bone Type (VB = 1) | 16.71592 |
| $\beta_2$ Warm Ischemia (hrs) | −7.19329 |
| $\beta_3$ Body Cooling (hrs) | −5.24410 |
| $\beta_4$ Cold Ischemia (hrs) | 0.10750 |

Figure 11A:
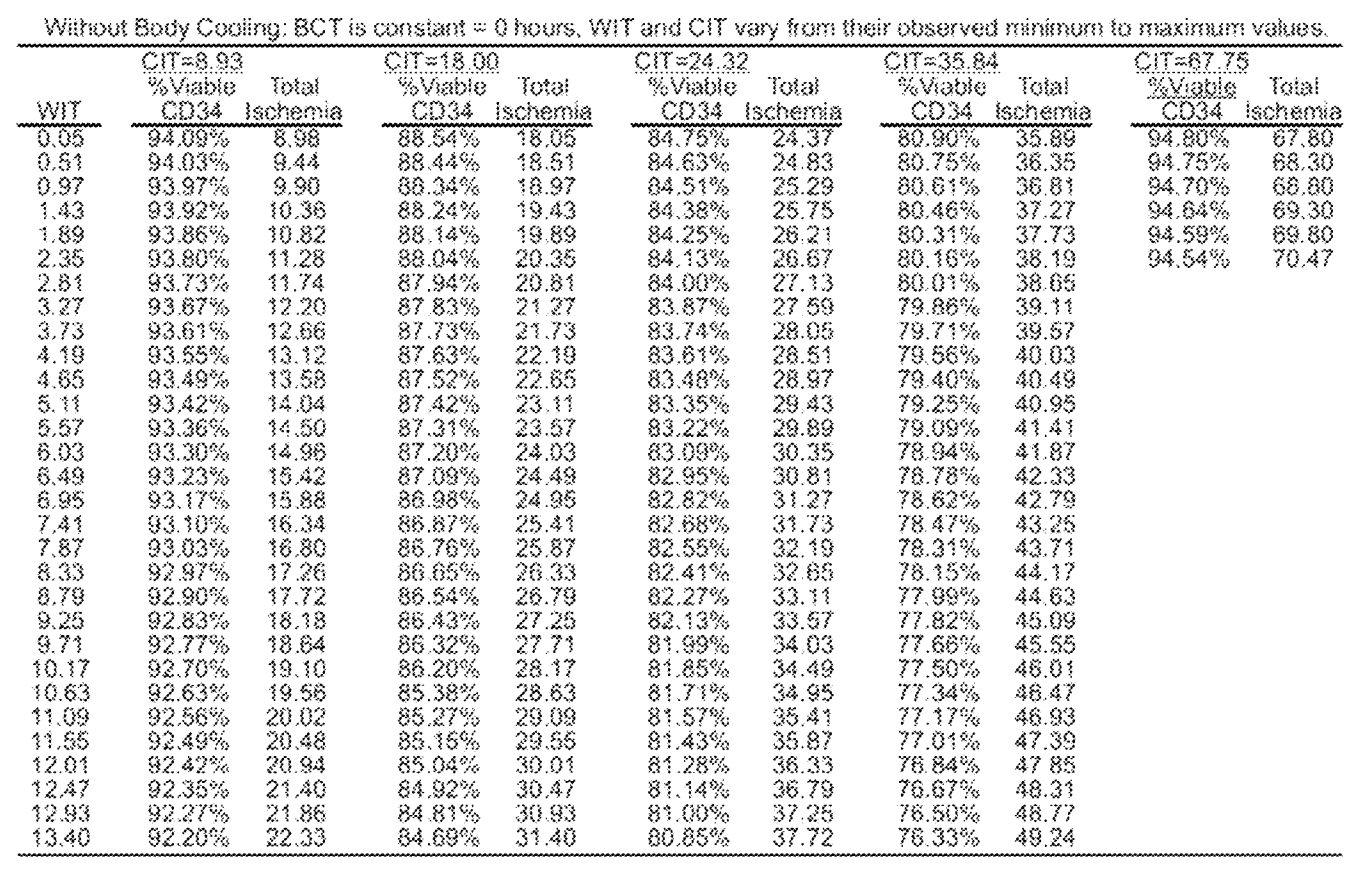
Figure 11C:
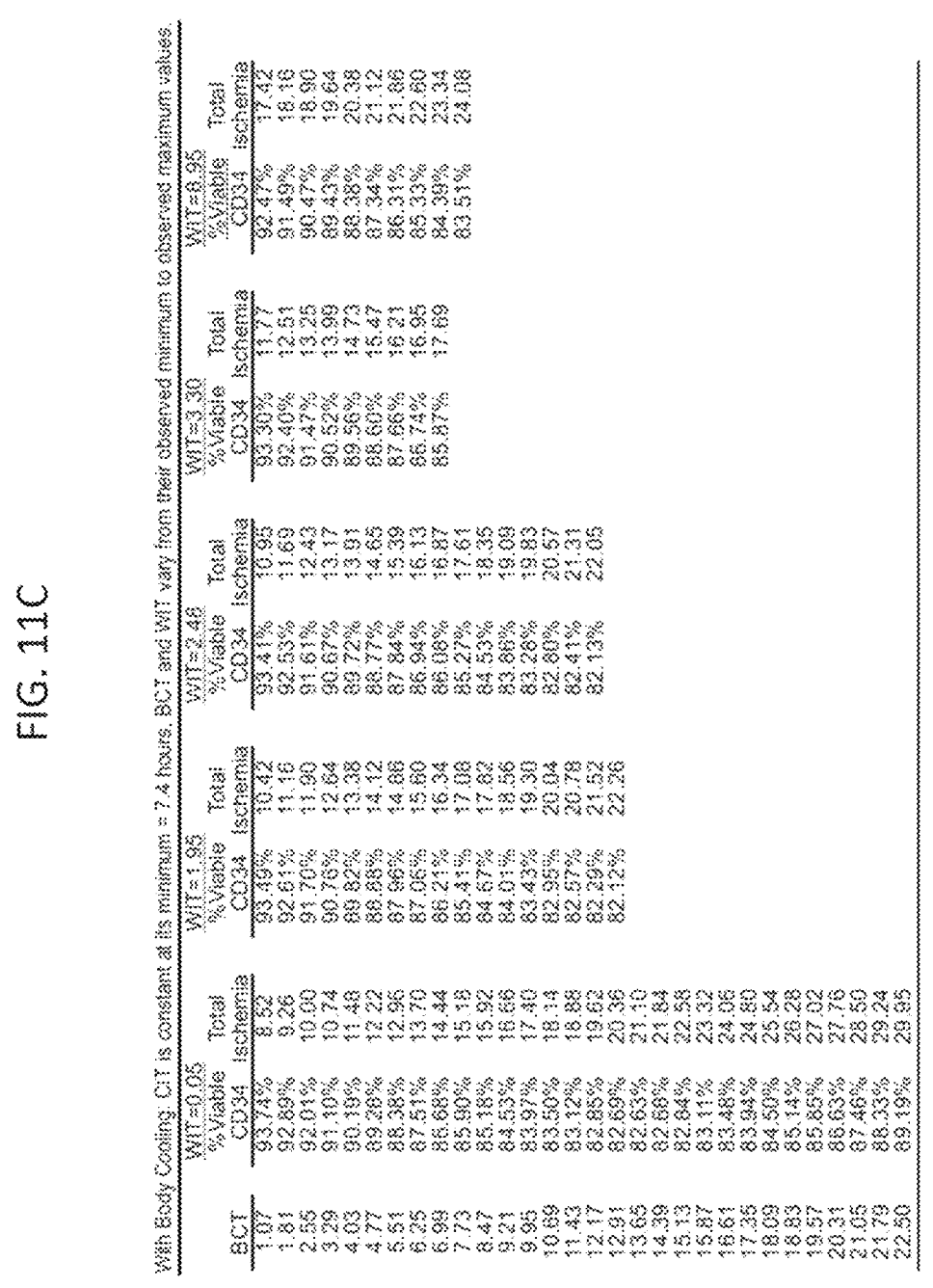

Applying these models to observed data can be used to determine the effect of ischemia time variables on % CD34+, as reflected in the tables shown in FIGS. 11A-11C, on total CFU, as shown in the tables of FIGS. 12A-12C, and on the amount of CFU-GM, as shown in the tables of FIGS. 13A-13C. The data in these tables can be used to decide whether a particular donor bone can yield sufficient cells to warrant further processing of the donor bone. In other words, the predictive models can be used to establish ischemia tolerance limits and HSPC quality acceptance criteria. For instance, with respect to the % CD34+ outcome variable, predicted values of over 80% may be required in order to consider the particular donor bone.

The models described above and the examples shown in the tables of FIGS. 11A-11C suggest that acceptable levels of HSPC quality are achievable despite the prolonged ischemia times that are inevitable when bones must be procured by geographically-dispersed OPOs and shipped long distances to processing centers. Even under such conditions, favorable combinations of warm- and cold-ischemia times can be achieved, enabling % CD34+ viabilities in the range of 80-90%. The models also suggest that refrigerating the body prior to bone recovery, a practice that is common in the recovery of tissues, is less beneficial in the context of bone marrow recovery. For instance, when whole-body cooling was used, CD34+ viability averaged 72.75%, whereas when body cooling was not used, the average was just under 90%. These models suggest that an optimal practice would be to dispense with body cooling and move recovered bone as quickly as possible to a cold ischemic environment. The models further suggest that limiting WIT (warm ischemia time) to less than eight (8) hours and CIT (cold ischemia time) to less than 40 hours optimizes the opportunity to recover meaningful quantities of viable cells from donor bone.

The models disclosed herein predict viability in which an 80% CD34+ cell viability threshold is determined to be acceptable. As reflected in the chart, the relationship between warm and cold ischemia times follows a curve from a point at which the WIT is 10 hours and the CIT is 18 hours, to a point at which the WIT is 1 hour and the CIT is 27 hours.

Further details of the method for predicting cell viability of the present disclosure are found in Woods et al., "Ischemia considerations for the development of an organ and tissue donor derived bone marrow bank." J Transl Med 18, 300 (2020). doi.org/10.1186/s12967-020-02470-1, the entire disclosure of which is incorporated herein by reference.

Banking Cadaveric BM

Typically, less than one-half of the patients waiting for an allo-bone marrow (BM) transplant receive the need transplant. The living donor BM registry, BM cryopreservation and auto-transplantation, and umbilical cord blood banking have provided lifesaving solutions for thousands of patients with, at least, hematologic diseases; however, these methods still suffer from severe limitations tied to supply and logistics and would benefit from the systems and methods of the present disclosure. Additionally, though rare, adverse events are possible from living bone marrow donation (i.e., the risk of death associated with bone marrow donation is 1:10, 000)), and while peripheral blood stem cell donation is currently much more utilized, nearly all of those donors will experience bone pain, 1 in 4 will have significant headache, nausea, or citrate toxicity, and 1 in 5,000 will experience splenic rupture or other fatal complication. Additionally, the long-term effects of stem cell mobilizing agents administered to a donor during donation are not yet known. The technical feasibility of cadaveric BM banking has been demonstrated in principle; however, numerous challenges in this remain. These challenges are directly addressed by this disclosure.

Banking BM as disclosed herein provides a ready mechanism to provide BM to patients for whom living donor match has not been identified. Additionally, it provides a more efficient method for providing BM to the patient for whom a living donor match exists, in that there is reduced delay associated with, at least, identifying a donor match, locating the donor match, and arranging for the donation. Accordingly, banking BM can greatly increase post-transplant survival rates for many patients with rapidly progressing diseases and poor prognosis by allowing on-demand transplantation and reducing waiting times for these patients from many months to only 1-2 days. And importantly, this approach provides large quantities of BM from a single donor, sufficient to allow engraftment of hematopoietic stem and progenitor cells (HSPCs) for several patients and enabling immediate repeat BM transplantation when needed. Furthermore, since a single donor provides sufficient BM for transplantation, it is unnecessary to pool BM from multiple donors or provide a subsequent donations for different donors, each of which increases the likelihood of adverse reaction due to allografting.

The methods and systems disclosed herein enable large supplies of on-demand bone marrow (BM) for national emergency preparedness efforts. The urgent unmet need for on-demand BM and stem cell transplants as a medical countermeasure for nuclear accidents or attacks has been well documented by HHS, BARDA's multi-billion-dollar Project Bioshield, and the United States Dept. of Defense. The present disclosure also provides needed BM for emerging applications such as immune tolerance induction and beyond. A protocol for processing and the banking of BM from deceased organ donors that preserves the BM for extended periods of time is critical to this approach. Additionally, patients who receive deceased donor organ transplants today could benefit from this therapy when it becomes available in the future, if BM from these donors is banked—making this method immediately beneficial to vital organ transplant recipients. In other words, the systems and methods described in the present disclosure allows harvesting and banking of increased number of bone marrow or bone marrow cells compared to methods currently utilized. If successful, other promising methods and treatments being researched have the potential to greatly enhance the value of cadaveric BM procurement and banking using the proposed method for making large supplies of banked bone marrow immediately usable for most recipients who need a BM transplant quickly, particularly to address severe forms of autoimmune disorders, genetic diseases, Multiple Sclerosis, and Type 1 Diabetes.

The present disclosure provides a clinically oriented research protocol and system that is modified to be implemented in an industrial context within state-of-the-art clean rooms. One aspect of the disclosed system involves, among other things, debridement of the incoming donor bone, initial fragmentation using a custom-made surgical stainless-steel cutter, and grinding of the fragmented bone to approximately 3 mm-sized bone fragments. These refinements provide a system in which skilled tissue processing technicians can process sets of donor bones within a 6-hour window to yield meaningful quantities of viable marrow.

In the process described herein is the evaluation of potential sources of deceased donor bone marrow. In processing long bones from a donor, such as the tibia, it has been found that due to conversion of red marrow to yellow with age, red marrow is limited to the ends of the long bones and varies dramatically from donor to donor. It has also been determined that mixed yellow-red marrow is poor quality, compared to wholly red marrow, such as marrow from the vertebral bodies or the ilium, and mixed yellow-red marrow contains fatty infiltrate that complicates subsequent processing. The best donor long bone in certain clinical experiments yielded only $1/100^{th}$ BM cells/kg compared to cells obtained from the ilia of the same donor. It has been determined, then, that long bone processing is preferably only performed in special cases, such as involving extra valuable "universal" HLA types or bone marrow with the HIV resistant delta 32 (CCR5-delta 32) mutation.

In contrast, the vertebral body and the ilium represent the largest consistent reservoirs of high-quality red marrow. Utilizing one or both sources has optimized the recovery of bone marrow, particularly with the implementation of the industrialized, scalable, GMP process disclosed herein. The completion of the process disclosed herein results in cryopreservation of a final product configuration of storing a 60-70 ml volume at a target of 100-150 million total nucleated cell (TNC)/ml in standard blood bags, similar to the product configuration already used for cryopreserved BM for autologous transplants.

The present disclosure should be considered as illustrative and not restrictive in character. It is understood that only certain embodiments have been presented and that all changes, modifications and further applications that come within the spirit of the disclosure are desired to be protected.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

Any aspect or embodiment described herein can be combined with any other aspect or embodiment as disclosed herein.

Definitions

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Use of absolute or sequential terms, for example, "will," "will not," "shall," "shall not," "must," "must not," "first," "initially," "next," "subsequently," "before," "after," "lastly," and "finally," are not meant to limit scope of the present embodiments disclosed herein but as exemplary.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

As used herein, "or" may refer to "and", "or," or "and/or" and may be used both exclusively and inclusively. For example, the term "A or B" may refer to "A or B", "A but not B", "B but not A", and "A and B". In some cases, context may dictate a particular meaning.

Any systems, methods, software, and platforms described herein are modular. Accordingly, terms such as "first" and "second" do not necessarily imply priority, order of importance, or order of acts.

The term "about" when referring to a number or a numerical range means that the number or numerical range referred to is an approximation within experimental variability (or within statistical experimental error), and the number or numerical range may vary from, for example, from 1% to 15% of the stated number or numerical range. In examples, the term "about" refers to ±10% of a stated number or value.

The term "from" as in "from 1 to 10" includes the initial and final number recited. Therefore, "from 1 to 10" includes the whole numbers 1, 2, 3, 4, 5, 6, 7, 8, 9, and 10 and includes fractions thereof, (e.g., about 0.1, 0.2, 0.3, 0.4, 0.5, 0.6, 0.7, 0.8, and about 0.9).

The terms "increased", "increasing", or "increase" are used herein to generally mean an increase by a statically significant amount relative to a reference level or a historical control. A historical control relates to data obtained from another subject or population of subjects who have not received a treatment according to methods of the present disclosure and are similar to the subject in various characteristics (e.g., age, sex, health status, comorbidities, hematologic cancer type, and cancer severity). In some aspects, the terms "increased," or "increase," mean an increase of at least 10% as compared to a reference level or a historical control, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, standard, or historical control. Other examples of "increase" include an increase of at least 2-fold, at least 5-fold, at least 10-fold, at least 20-fold, at least 50-fold, at least 100-fold, at least 1000-fold or more as compared to a reference level or a historical control.

The terms "decreased", "decreasing", or "decrease" are used herein generally to mean a decrease in a value relative to a reference level or a historical control. A historical control relates to data obtained from another subject or population of subjects who have not received a treatment according to methods of the present disclosure and are similar to the subject in various characteristics (e.g., age, sex, health status, comorbidities, hematologic cancer type, and cancer severity). In some aspects, "decreased" or "decrease" means a reduction by at least 10% as compared to a reference level or a historical control, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level or a historical control. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

An "effective amount" or "therapeutically-effective amount" refers to that amount of a bone marrow product and/or HSCs contained in a bone marrow product as described herein which, when administered to a subject (e.g., human), that sufficient to promote treating a disease, e.g., a hematologic cancer. The amount of a bone marrow product and/or HSCs contained in the bone marrow product that constitutes a "therapeutically-effective amount" will vary depending on the cell preparations, the condition and its severity, the manner of administration, and the age of the subject to be treated, but can be determined routinely by one of ordinary skill in the art having regard to his own knowledge and to this disclosure.

CD34: Antigen present on immature hematopoietic precursor cells and all hematopoietic colony-forming cells in bone marrow and blood. Certain populations of non-hematopoietic (i.e., CD45 negative) cells also express CD34. Of hematopoietic (i.e., CD45+ cells), the CD34 antigen expression is highest on early progenitor cells and decreases with the maturation of cells. The CD34 antigen is absent on fully differentiated hematopoietic cells. Normal peripheral blood lymphocytes, monocytes, granulocytes, and platelets do not express the CD34 antigen.

The section headings used herein are for organizational purposes only and are not to be construed as limiting the subject matter described.

ADDITIONAL EMBODIMENTS

In another aspect, a method of the present disclosure provides for recovering cells from deceased donor bone marrow that comprises the steps of: obtaining bone from a deceased donor; processing the bone to extract bone marrow cells from the bone; obtaining a reduced density Ficoll solution having a density of 1.063-1.052 gm/mL; introducing the reduced density Ficoll solution into a centrifuge tube to form a Ficoll gradient; layering the extracted bone marrow cells over the Ficoll gradient in the centrifuge tube; centrifuging the tubes containing the Ficoll gradient and bone marrow cells; harvesting the buffy coat cells from within the centrifuge tubes; and washing the harvested cells for subsequent use or processing. In some embodiments, the bone is a vertebral body. In some embodiments, the harvested cells are CD34+ cells. In some embodiments, the processing of the bone comprises: cleaning the bone of soft tissue; cutting the bone into pieces and grinding the pieces; filtering and rinsing the ground pieces of bone; and centrifuging a suspension of the filtered and rinsed pieces of bone to concentrate bone marrow cells. In some embodiments, the obtaining of a reduced density Ficoll comprises mixing Ficoll-Paque at a density of 1.077 g/mL with PLASMA-LYTE™ in a proportion to obtain a density of 1.063-1.052 g/mL. In some embodiments, the centrifuging of the tubes includes centrifuging the tubes for 30 minutes at 400 g. In some embodiments, the washing of the harvested cells includes washing the cells in phosphate-buffered saline (PBS) containing 0.5% human serum albumin (HSA) and 2 mM Ethylenediaminetetraacetic acid (EDTA).

Another aspect of the present disclosure comprises a method for obtaining bone marrow cells from deceased donor bone comprising: obtaining a bone from a deceased donor; cleaning the bone of soft tissue; grinding the bone into bone pieces; filtering and rinsing the ground bone to produce a liquid composition; centrifuging the liquid composition of the filtered and rinsed ground bone to concentrate bone marrow cells into a bone marrow cell composition; and extracting the bone marrow cell composition into a sterile container. In some embodiments, the donor bone is one or more vertebral bodies and/or the ilium of the deceased donor. In some embodiments, the donor bone is freshly obtained and not frozen. In some embodiments, the donor bone is thawed after being frozen for transfer to a processing facility. In some embodiments, the cleaning of the bone of soft tissue comprises: removing soft tissue from the bone using a tool; and submerging the bone in one or more solutions adapted to remove soft tissue and soft tissue cells from the bone. In some embodiments, the submerging of the bone in one or more solutions comprising: submerging the bone in a bleach solution; and submerging the bone in a hydrogen peroxide solution. In some embodiments, the submerging of the bone in one or more solutions includes; submerging the bone in a container; detecting a level of foam within the container; and repeating at least the step of submerging the bone in a hydrogen peroxide solution until no foam is detected. In some embodiments, an inert contrast dye is added to the hydrogen peroxide solution to enhance the visibility of any foam in the container. In some embodiments, the grinding of the bone comprises: cutting the bone into fragments; and grinding the bone fragments in a bone grinder with a grind media. In some embodiments, the grind media comprises PLASMA-LYTE™ as a base with 10 U/mL heparin, 2.5% human serum albumin (HSA), and 3 U/mL Benzonase® reagent. In some embodiments, the filtering and rinsing the ground bone comprises: submerging the ground bone in grind media; passing the ground bone and grind media through a series of sieves; thereafter rinsing the sieves with grind media; receiving the liquid composition passing through the sieves in a container; and transferring the liquid composition to a sterile container. In some embodiments, the series of sieves includes a first No. 40 sieve (425 μm) followed by a second No. 80 sieve (177 μm). In some embodiments, the filtering and rinsing the ground bone comprises: submerging the ground bone in grind media within a first collection bag; suspending the first collection bag and connecting the bottom of the first collection bag to a series of in-line filters and a second collection bag; and passing the contents of the first collection bag through the in-line filters into the second collection bag. In some embodiments, the bone marrow passes first through an 800 μm pre-filter. In some embodiments, a series of in-line filters includes two filters having either a 200 μm filter or a 500 μm filter. In some embodiments, a first pass of the contents of the first collection bag the two filters are 200 μm filters and in a second pass of the contents of the second collection bag into a third collection bag the two filters are 500 μm filters. In some embodiments, the filtering and rinsing of the ground bone includes removing the fat content of the ground bone. In some embodiments, the removing of the fat content of the ground bone includes: placing a suspension of the ground bone in a collection bag; centrifuging the collection bag so that a fat layer is formed at the top of the collection bag when suspended; and removing a pellet of the bone marrow from the bottom of the suspended collection bag. In some embodiments, the prior to removing the pellet a clip is placed on the bag below the fat layer to pinch the bag and prevent passage of the fat layer as the pellet is removed. In some embodiments, the method further comprises cryopreserving the bone marrow cell composition. In some embodiments, the cryopreserving of the bone marrow cell composition comprises: preparing a predetermined volume of freeze media as a solution of a rinse media and a cryopreservation composition; and introducing the freeze media into the sterile container containing the bone marrow cell composition at a predetermined rate. In some embodiments, the sterile container contains 60-70 mL of bone marrow cell composition and the predetermined volume of freeze media is calibrated for the volume of bone marrow cell composition. In some embodiments, the predetermined rate is ten percent (10%) of the predetermined volume of the freeze media per minute. In some embodiments, the cryoprotectant can be one or more compositions selected from group including: dimethyl sulfoxide (DMSO); 1, 2 propane diol (also known as propylene glycol); ethylene glycol; glycerol; foramamide; ethanediol or butane 2, 3 diol; hydroxyethyl starch (HES), dextran, sucrose, trehalose, lactose, raffinose, ribotol, mannitol and polyvinylpyrrolidone (PVP). In some embodiments, the rinse media can be one or more compositions selected from the group including: PlasmaLyte; Isolyte; and IMDM. In some embodiments, the freeze media further includes oxyrase.

Another aspect of the present disclosure comprises a bone cutting tool comprising: a fixed handle having an end configured to be gripped by a user and an opposite jaw end, the fixed handle defining a bone engaging recess at the jaw end; a lever handle pivotably connected at a first pivot to the fixed handle to pivot toward and away from the fixed handle and configured to be gripped by the user while gripping the fixed handle to successively pivot the lever handle toward the fixed handle; a knife element pivotably connected at a second pivot to the fixed handle and including a knife edge facing the bone engaging recess at the jaw end of the fixed handle, the knife element including a ratchet component disposed between the fixed handle and the lever handle, the ratchet component including a plurality of teeth; a pawl component pivotably connected at a third pivot to the lever handle and arranged to engage each of the plurality of teeth at each successive pivot of the lever handle to the fixed handle by the user, wherein each of the first pivot includes an elongated pin passing through openings in the fixed handle and the lever handle, the second pivot includes an elongated pin passing through openings in the fixed handle and the knife element, and the third pivot includes an elongated pin passing through openings in the pivot handle and the pawl component, and wherein each pin is removably retained within the respective first, second and third pivot by at least one removable retaining ring such that the fixed handle, pivot handle, knife element and pawl component can be readily disassembled for cleaning and re-assembled after cleaning. In some embodiments, the knife element includes an integral link; and the tool further includes a free link pivotably connected to the lever handle at a fourth pivot and pivotably connected to the integral link, the fourth pivot including an elongated pin passing through openings in the pivot handle and the free link for ready disassembly. In some embodiments, the fixed handle, knife element, pivot handle, pawl component and free link are formed of stainless steel and the surfaces thereof are passivated. In some embodiments, the stainless steel is a hardened stainless steel.

Another aspect of the present disclosure comprises a method for high-yield recovery of stem cells from cadaver bone or cadaver bone fragments, the method comprising: obtaining cadaver bone or cadaver bone fragments; processing the bone or bone fragments to extract bone marrow cells; combining the extracted bone marrow cells with a reduced density Ficoll solution having a density of 1.063-1.052 gm/mL; centrifuging the extracted bone marrow cells, thereby separating out buffy coat cells comprising stem cells; and harvesting the buffy coat cells, thereby recovering stem cells.

Another aspect of the present disclosure comprises a method for high-yield recovery of stem cells from cadaver bone or cadaver bone fragments, the method comprising: obtaining cadaver bone or cadaver bone fragments, optionally, processing the cadaver bone into cadaver bone fragments; combining the cadaver bone fragments with a medium comprising two or more of a nuclease, human serum albumin (HSA), heparin, an electrolyte medium, and a growth media, thereby obtaining medium-treated cadaver bone fragments; processing the medium-treated cadaver bone fragments to extract bone marrow cells; and collecting the extracted bone marrow cells, thereby recovering the stem cells. In some embodiments, the nuclease is Benzonase®, Denarase®, or a DNase. In some embodiments, the electrolyte medium is Plasma-Lyte A or Isolyte. In some embodiments, the growth media is Iscove's Modified Dulbecco's Media (IMDM). In some embodiments, the processing medium comprising three or more of a nuclease, HSA, heparin, an electrolyte medium, and a growth media. In some embodiments, the processing medium comprising four or more of a nuclease, HSA, heparin, an electrolyte medium, and a growth media. In some embodiments, the processing medium comprises Benzonase®, HSA, heparin, and Plasma-Lyte A.1. A method for high-yield recovery of stem cells from cadaver bone or cadaver bone fragments, the method comprising: obtaining cadaver bone or cadaver bone fragments; processing the bone or bone fragments to extract bone marrow cells; combining the extracted bone marrow cells with a reduced density Ficoll solution having a density of 1.063-1.052 gm/mL; centrifuging the extracted bone marrow cells, thereby separating out buffy coat cells comprising stem cells; and harvesting the buffy coat cells, thereby recovering stem cells.

Another aspect of the present disclosure comprises a method for optimizing recovery of stem cells from cadaver bone, the method comprising: limiting warm ischemia time (WIT) to less than eight hours and limiting cold ischemia time (CIT) to less than 40 hours. In some embodiments, the WIT begins at the time of death and ends either when the cadaver bone is recovered and placed in a cooling environment or condition or when the cadaver is placed in a cooling environment or condition. In some embodiments, the CIT begins at the time when the cadaver bone is placed in a cooling environment and ends when processing to extraction of cells from the cadaver begins. In some embodiments, the bone was obtained from the cadaver prior to placing the cadaver in a cooling environment or condition.

Another aspect of the present disclosure comprises a method for recovering vertebral bone adherent mesenchymal stromal/stem cells (vBA-MSC) from cadaver bone or cadaver bone fragments, the method comprising: obtaining cadaver bone, cadaver bone fragments, or ground cadaver bone, optionally, preparing ground cadaver bone from the cadaver bone or cadaver bone fragments; incubating the ground cadaver bone in a digestive solution comprising collagenase or neutral protease thereby obtaining a digested bone product; processing the digested cadaver bone product to extract bone marrow cells; and collecting the extracted bone marrow cells, thereby recovering the vBA-MSC. In some embodiments, the volume to weight ratio of solution to weight of ground cadaver bone is about 5 to about 1. In some embodiments, the incubating is up to about 2.5 hours. In some embodiments, the amount of neutral protease amount is about 19.6 U/ml. In some embodiments, the digestive solution comprises collagenase and neutral protease. In some embodiments, the bone marrow has been isolated from the ground cadaver bone prior to incubating the ground cadaver bone in the digestive solution.

Another aspect of the present disclosure comprises a method for optimizing recovery of stem cells from cadaver bone or cadaver bone fragments, the method comprising: obtaining cadaver bone or cadaver bone fragments; optionally, processing the cadaver bone into cadaver bone fragments; submerging the cadaver bone or cadaver bone fragments in a solution comprising bleach, thereby obtaining a bleached bone product; and then submerging the bleached bone product in a solution comprising hydrogen peroxide, thereby obtaining a treated bone product; processing the treated bone product to extract bone marrow cells; and collecting the extracted bone marrow cells, thereby recovering the stem cells.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

EXAMPLES

The following illustrative examples are representative of embodiments of the stimulation, systems, and methods described herein and are not meant to be limiting in any way.

Example 1. Tissue Processing

Described herein is an exemplary tissue processing protocol. In some cases, the tissue being processed can be vertebral bodies. In some cases, the tissue processing protocol can yield the bone marrow cells described herein.
A. Tissue Debriding
1. Spray down the surface of the exterior bag of fresh VBs with 70% isopropanol. In hood, remove outer nonsterile bag and dispose. Open inner bag and dispose of bag.
2. Unwrap specimen from blue towel and lap sponges. Record presence of packing materials and condition of the spine for: minimum 2 layers of sterile bas; blue towel; lap sponges; tissue moisture maintenance; and presence of pedicles.
3. Record the start time for tissue debriding.
4. Remove soft tissue surrounding pedicles to reveal correct sawing location. Scrape off exterior tissue with osteotomes.
5. If present, saw through pedicles. Retain anterior VBs and discard pedicles and posterior elements. Avoid exposing cancellous tissue.
6. Separate VBs by slicing through discs using the boning knife.
7. Remove remaining soft tissue from each individual VB surface, using a combination of scissors, knives, and osteotomes. Make note of any anatomical pathologies or injury during recovery (e.g. bone spurs, herniated discs, and degenerative discs, cuts into VBs from recovery, or others such as brittle bones).
8. Count the number of intact VBs and determine the levels recovered (e.g. T8-L5) Discard any VBs that were damaged during recovery and have cancellous tissue exposed.
9. Spray balance (CS-5000 model) with 70% IPA and place in a clean area inside the Biosafety cabinet (BSC). Tare balance with the sterile bag. Place VBs that will be processed further into the sterile bag, and record mass. Record the #of VBs used for BM extraction.
B. Surface Decontamination
1. Record the temperature of the VBs.
2. Place VBs into a sterile bag, then add 1 L of 10% bleach solution to the bag and ensure all VBs are submerged. Once bleach is added to the VB bag, immediately start a timer for 10 minutes. Allow 10 minutes of contact time before proceeding to B.4.
3. Remove all used processing equipment and drapes from the hood and remove soiled gloves. Clean BSC with 70% IPA and allow to dry before proceeding.
4. After 10 minutes of bleach solution contact time, immediately begin transfer of the VBs into a new sterile bag using a pair of sterile, long handled forceps.
5. Add 1 L of 3% hydrogen peroxide solution to the bag. Ensure VBs are completely submerged. Close the bag and shake briefly.
6. Transfer the VBs into a new sterile bag using new, sterile, long handled forceps.
7. Fill the bag with 1 L of Plasma-Lyte. Close the bag and shake briefly.
8. Transfer the VBs into a new sterile bag using new, sterile long handled forceps.
9. Fill the bag with 1 L of Plasma-Lyte. Close the bag and shake briefly.
10. Transfer the VBs to a sterile pan using long handled forceps. Use sterile gauze or lap sponges to absorb excessive liquid if needed.
11. Record the end time for surface decontamination.
C. Bone Grinding
1. Document the device used for grinding VBs and set up per Bone Grinder Operation and Maintenance or CCF Bone Grinder.
2. Record the grinding start time.
3. Obtain 1 L Grind media prepared at the beginning of the process.
4. Pour—300 mL of Grind Media into one sterile, stainless-steel pitcher. This pitcher will be called "Pitcher 1" and will contain cut VB pieces. Pour—300 mL of Grind Media into another pitcher or catch pan named "Pitcher 2", to catch grindings. An additional—300 mL will be used for rinsing through grinder while grinding. The remaining—100 mL of Grind Media will be set aside for final rinsing of grinder and Pitcher 2 after all pieces are ground.
5. Place Pitcher 2 underneath the grinder head.
6. Using a clean drape and gloves donned, cut VBs into pieces of adequate size for the grinder using hand cutting tool. Cut pieces should immediately be submerged in Pitcher 1 with Grind Media.

7. Verify that 1 L of grind media was used and is in Pitcher 2. Turn off grinder and record the grinding end time.

D. Filtration

1. Open a Bone Marrow Collection Kit and record the mass of one empty, 600 mL TRANSFER-PACK using the VWR-3000P balance. Empty Mass of 600 mL TRANSFER-PACK.
2. Assemble the bone marrow filtration kit and perform the bone marrow extraction following Bone Marrow Collection and Filtration of Example 1 using a total of 1000 mL of Rinse Media (2×500 mL). Note: Total media volume after is 2 L (1 L Grind media and 1 L Rinse Media).
3. Document the mass (g) of each filled 600 mL TRANSFER-PACK and calculate the total mass of all 6 TRANSFER-PACKs.
4. Calculate the total mass of bone marrow (BM) extract: Total Mass (g) (D.3 [B]), Empty Mass (g) (D.1 [A]), Empty Mass of all TRANSFER-PACKS (g) (A×6), and Total Mass of BM Extract (g) (B-C).
5. Intermediate Accountability: Total Mass of BM Extract >1800 g (if yes, proceed; if no alert supervisor).
6. Close the clamp on the extra 2000 mL TRANSFER-PACK and save for later use.
7. Visually inspect the bone marrow (BM) in each TRANSFER-PACK to confirm there are no visible grindings or soft tissue. If excessive clumping is observed during filtration, notify area management.
8. Identify the first TRANSFER-PACK filtered. Mix TRANSFER-PACK by inversion and then remove 0.3 mL of BM using a 1 mL syringe inside BSC. Place sample in a pre-labeled tube with the ISBT #and "QC 1" along with the date and time. Submit sample to QC for testing on the Sysmex Hematology Analyzer. Record results below and calculate the TNC (use same number of significant figures from QC1 Sysmex WBC concentration). Processing may proceed prior to obtaining this result. Note: Assume density of 1 g/ml.
9. Seal the tubing near the connector on the end of each of the six TRANSFER-PACKs collected and label with the ISBT #.
10. Record the filtration end time.

E. Removal of Fat

1. Pair up TRANSFER-PACKs and use taring sticks so that the centrifuge is balanced prior to operation. Use volume compensating plates to prevent creasing of bags during centrifugation.
2. Set the centrifuge to 500×g for 15 minutes at room temperature, with a brake setting of 4. Centrifuge TRANSFER-PACKs with tubing down.
3. While TRANSFER-PACKS are in the centrifuge, remove all drapes and supplies from the BSC nd clean all surfaces with 70% isopropyl alcohol (IPA).
4. Carefully remove TRANSFER-PACK, one at a time, from the centrifuge and hang on a ring stand.
5. Weld on an empty, new 600 mL Fenwal bag (post-fat intermediate bag) to the centrifuged TRANSFER-PACK. Label the new post-fat intermediate bag with the ISBT #. Inspect the weld prior to proceeding.
6. With the centrifuged TRANSFER-PACK hanging on one ring stand, place a bag clamp just below the fat, and open the weld on the tubing and drain pellet into new post-fat intermediate bag. Agitate the pellet and spike ports gently to resuspend all pellet. Allow at least half of the volume from the centrifuged bag to drain into the post-fat intermediate bag before proceeding. Note: It is best practice to not allow all the liquid to drain out from above the clamp. If liquid seems to be draining quickly, use one hand to press the clamp closed to slow the draining of liquid.
7. Close the tubing with a hemostat or tube sealer.
8. Weld the next centrifuged TRANSFER-PACK onto the same post-fat intermediate bag used to collect the pellet in E.6. Leave enough tubing on this bag for future welds.
9. Repeat E.6.-E.7.
10. For the next two centrifuged TRANSFER-PACKs, repeat E.4.-E.9. creating the second post-fat intermediate bag.
11. Repeat E.4.-E.9. for the final two centrifuged bags creating a third post-fat intermediate bag.

F. Concentrate

1. Set the centrifuge to 500×g for 15 minutes at room temperature, with a brake setting of 4. Centrifuge post-fat intermediate bags with tubing up. Use volume compensating plates to prevent creasing of bags during centrifugation.
2. Carefully remove a post-fat intermediate bag from the centrifuge and hang on the plasma press. Only remove one bag at a time from the centrifuge.
3. For each bag centrifuged, weld on a 1000 mL waste bag (label as "Waste") and use the plasma extractor to remove the supernatant into the waste bag. Use a hemostat to clamp tubing as soon as the pellet breaks or when the pellet rises close to the top.
4. Seal the tubing and cut through to remove the post-fat intermediate bag from the waste bag, leaving enough tubing attached for welding. Weld on a female luer extension.
5. Repeat F.2.-F.4. for each post-fat intermediate bag.
6. Discard waste bags in biohazard trash bag.
7. Label a new, empty 2 L bulk bag from the BM filtration kit with the ISBT #, then measure and record the mass. If the bag is removed from the BSC for weighting, clean the luer connection with sterile alcohol after returning to the BSC. Wait until dry before proceeding.
8. For the following materials, spray with 70% IPA, place inside the BSC and wait until dry before proceeding: 50 mL syringes (3), 30 mL syringe, 50 mL conical tube and rack, Rinse Media.
9. Combine pellets from each of the three small bags into the pre-weighed bulk bag using a new 50 mL syringe for each small bag. Note: Press down on the plunger of the syringe slowly and avoid creating bubbles.
10. Aseptically transfer 25 mL of rinse media into a 50 mL conical tube. Use a new 30 mL syringe to rinse each bag serially with −20 mL of Rinse Media and add to the bulk bag. Note: A 50 mL syringe may be used to carry volume between bags if 30 mL syringe is too small.

G. Sampling and Accountability

1. On the bulk bag, open the clamp and drain BM extract in the tubing back into the bag. Invert bag three times minimum to mix, ensuring all pellet is resuspended. Remove about 0.5 mL of BM extract using a 1 mL syringe inside BSC. Place sample volume in a pre-labeled sterile sample tube with the ISBT #and "QC2" along with the date and time of sample collection. Submit sample to QC for testing, along with at least 50 mL of Rinse Media. Record the time samples were submitted for testing.
2. Measure and record the mass of the bulk bag of bone marrow extract. Subtract the empty mass from the filled mass to get the mass of BM extract (one decimal place), including empty mass [G] (g), filled mass [H] (g), and mass of BM extract [H-G] (g).
3. Record results from QC2 printout below and calculate the QC2 concentration and the QC2 TNC Count (use the same number of significant figures from QC2 Sysmex WBC concentration for QC2 TNC Count). Note: Assume density of 1 g/mL, including QC2 Sysmex WBC Concentration (cells/4); QC2 Dilution Factor; QC2 Concentration (cells/mL) (K×L×1000); and QC2 TNC Count [M×G.2 (J)].
4. Calculate the TNC % Yield to one decimal place for QC2 TNC Count (G.3 [N]); QC1 (D.8 [F]); and % Yield=(N÷F)×100.

H. Determining the Number of Bags
1. Record the QC2 TNC count from [G.3 (N)]. Calculate the total volume needed (one decimal place), Total Volume Needed (mL) [N÷(140×106)]. NOTE: If the volume is less than 228.9 mL, alert production supervisor.
2. Determine the number of bags and vials to prepare using the total volume needed previously.
3. Calculate the volume of freeze media needed, volume of Rinse Media, and volume of DMSO to add. Round calculated numbers to one decimal place (Total Volume Needed (H.1 [P]); Mass of BM Extract [G.2.J] (g is approximately ml); Total Vol. Freeze Media (Q-R); Vol. of DMSO (Q×0.1); and Vol. of Rinse Media (S-T). Note: Assume density of BM extract is 1 g/ml.

I. Cryoprotectant Addition
1. Prepare the freeze media using rinse media prepared per B-6 of and 100% DMSO. Add the volume of rinse media calculated in H.3 [U] to a sterile bottle labeled "Freeze Media" with the date prepared.
2. Add the volume of DMSO calculated in H.3 [T] to the freeze media bottle. Gently invert the bottle once to mix.
3. Record the temperature of the Freeze Media.
4. If temperature of the Freeze Media is >25.0° C., wait until the temperature of the Freeze media decreases to <25.0° C. Record the new temperature of the Freeze Media prior to use if applicable.
5. Inside BSC place the BM bulk bag on a rocker for mixing. Remove the plunger of a large syringe and connect to the lure port on the bulk bag. Keep the syringe upright during the entire addition.
6. Calculate the volume of Freeze media to add per minute to the bulk bag as determined by volume of Freeze Media (H.3. [S]) and volume to add per Minute (S×0.1).
7. Set a timer for 10 minutes and begin adding freeze media through the syringe at a rate of 10% of the freeze media volume per minute, calculated in 1.6.
8. Record the start and end time of the DMSO addition. Aim for elapsed time from about 9 minutes to about 11 minutes.

J. Cryopreservation
1. Refer to H.2. to determine the number of cryopreservation bags and surrogate vials needed. Close clamps and label cryopreservation bags with the prepared product labels, containing the ISBT number, product name, and date processed. Note: Label is placed inside the pocket on the top right of each bag. Use the tube sealer to tack the pocket so that the label will not fall out.
2. Use a 10 ml syringe to pull the entire volume for surrogate vials needed and fill with bone marrow (1 ml per vial).
3. For each cryopreservation bag, inside the BSC, use a new 100 ml syringe to fill the bag with 65 ml of bone marrow.
4. Unscrew the syringe to allow the tubing to drain back into the bag, then re-attach the syringe and draw air out of the bag while holding system upright.
5. Clamp tubing when bone marrow fills tubing, just before passing the Y connector. Discard syringe and replace cap.
6. Mix the bulk bag by inversion before removing more volume. Repeat J.3-J.5 for each cryopreservation bag of product to prepare.
7. Record the actual number of bags prepared.
8. If there is bone marrow left in the bulk bag, vials for research use may be prepared. Label the required number of 5 mL cryovials and fill each one with 5 mL of BM by syringe or pipette.
9. Use the tube sealer to seal the tubing to create four segments on each product bag for cryopreservation.
10. Record the end time for bagging. Note: Product and samples must be frozen as quickly as possible after addition of DMSO.
11. Notify QC that bags are ready for cryopreservation. Note: QC will perform a packaging inspection prior to freezing product bags.
12. For each cryopreservation bag, cut through the seal in the tubing to remove 4 segments.
13. Cryopreservation bags are placed in cassettes and/or directly onto shelves (see FIG. 14 and FIG. 15) into Styrofoam boxes and surrogate vials placed separately in a CoolCell® freezing storage system and then in front of the box of cassettes into the freezer.
14. Record the date and time the cassettes and samples were placed in the freezer.
15. Record the date and time vials were placed in the freezer.

K. Inventory
1. Enter donor material into Freezerworks in a Quarantine status, according to Freezerworks Inventory Management. Note: Ensure the numbers on each passive cooling container match the box number in Freezerworks.

Example 2. Bleach Soak of Vertebral Bodies

The scope of this experiment encompassed the testing of bone marrow extract after soaking the vertebral bodies in a 5,000 ppm bleach solution for different lengths of time to evaluate the potential impact of variation of cell viability in the process, specifically, the described bleaching protocol will be utilized prior to the "bone grinding" step of Example 1. The viability of the cells was determined by cell sorting based on cell surface expression of CD45 and CD34. CD45 is an antigen present on all human leukocytes, including lymphocytes, monocytes, granulocytes, eosinophils, and basophils. It has a role in signal transduction and is weakly expressed on hematopoietic progenitor cells. CD34 is an antigen present on immature hematopoietic precursor cells and all hematopoietic colony-forming cells in bone marrow and blood. Certain populations of non-hematopoietic (i.e., CD45 negative) cells also express CD34. Of hematopoietic (i.e., CD45+ cells), the CD34 antigen expression is highest on early progenitor cells and decreases with the maturation of cells. The CD34 antigen is absent on fully differentiated hematopoietic cells. Normal peripheral blood lymphocytes, monocytes, granulocytes, and platelets do not express the CD34 antigen.

Vertebral bodies were debrided according to B-2 of the tissue processing of Example 1. 10% bleach solution and 3% hydrogen peroxide solution were prepared. VBs were separated for each time point of 10, 15, 20 and 25 minutes to sterile bags and soaked in the allotted time in bleach. After the set time passed, the VBs were quickly transferred into a hydrogen peroxide sterile bag then shaken briefly. VBs were then transferred into a Plasma-Lyte bag, shaken briefly and then a final Plasma-Lyte bag. VBs were grinded according to B-3 of tissue processing of Example 1. Grindings for each time point were then placed in separate sieves and 3 ml samples of bone marrow were used for testing.

Bone marrow from each group of VBs processed were tested by flow cytometry to assess viability. As shown in Table 4, the results from this experiment showed that there was no significant difference in cell viability when the vertebrae were soaked up to 25 minutes. Increasing the time from the current protocol of ten minutes would not affect the viability of the cells.

TABLE 4

Bleach Soak of Vertebral Bodies

| Time Point (min) | CD45+ % Viability | CD34+ % Viability | CD3+ % Viability |
|---|---|---|---|
| 10 | 88.59 | 95.92 | 80.50 |
| 15 | 88.78 | 97.95 | 75.61 |
| 20 | 87.12 | 96.85 | 71.14 |
| 25 | 86.81 | 96.75 | 71.67 |
| Avg. | 87.825 | 96.8675 | 74.73 |
| SD | 0.869554 | 0.721747 | 3.752299 |

Example 3. CD34 Selection from Fresh or Thawed BM from Deceased Donors Using CliniMACS Plus Described herein is protocol for isolating cells expressing CD34 from fresh or thawed bone marrow (BM) from diseased donors.

Buffer and Bags Preparation

Label five 600 ml Transfer-Pack bags as follows, and record the weight of each bag:
1) Cell Prep Bag 1 (can be more than 1 bag)
2) Plasma Waste
3) Waste 1
4) Waste 2

Buffers:
A. Prepare in Biosafety cabinet (BSC)
B. Labeling Buffer (2 bags):
   1) Obtain 2 bags of Plasma Lyte (1 L)
   2) Obtain 2 30 cc syringes with 18-gauge needles affixed.
   3) Using syringe and needle, inject 20 ml Benzonase (1000 U/ml) and 20 ml HSA (25%) to each 1 L Plasma Lyte bag.
   4) Use a new syringe and needle for each injection.
   5) Mix well by inverting at least 5 times.
   6) Label each bag with "Labeling buffer".
   7) Final concentrations are 20 U/ml Benzonase and 0.5% HSA.
C. Selection Buffer:
   1) Obtain a 1 L bag of Plasma Lyte.
   2) Obtain a 30 cc syringe with an 18 gauge needle affixed.
   3) Using syringe and needle, inject 20 ml HSA (25%) into a 1 L Plasma Lyte bag.
   4) Mix well by inverting at least 5 times.
   5) Label the bag with "Selection buffer".
   6) Final concentration is 0.5% HAS Preparation for Labeling of Fresh (A) or Frozen (B) Bone Marrow Products A. Protocol for fresh bone marrow product:
   1) After grinding and removing fat, centrifuge bone marrow cell suspension in blood collection bags at 300×g for 15 minutes
   2) Perform following in a BSC.
   3) Combine all bone marrow cell pellets into the Cell Prep Bag 1
   4) Rinse all blood collection bags with 50 ml of Rinse media and transfer to Cell Prep Bag 1.
   5) Weigh bag.
   6) Determine total volume of cell suspension in the Cell Prep Bag 1 by subtracting original weight from that obtained in step 5 of this section. Use the following formula to convert weight to volume: 1 gram=1 ml.
   7) Gently mix Cell Prep Bag 1 with a rotating motion.
   8) Use a 1.0 ml syringe to withdraw 0.5 ml bone marrow through a sampling site coupler and transfer to a 1.5 ml Eppendorf tube for CD34+ cell and T cell enumeration using flow cytometry.
   9) Fill the Cell Prep Bag 1 with approximately 400 ml Labeling buffer and centrifuge at 300 g for 15 minutes with a brake setting of 4 at room temperature.
   10) Reduce volume in Cell Prep Bag 1 to desired volume based on total T cell and CD34+ cell counts as indicated in Table 5.

TABLE 5

Optimal labeling volume and tubing set determination for the selection of CD34+ cells

| | Total Leukocytes [D] | Total CD34+ [E] | Volume of Cell solution before labelling (ml) |
|---|---|---|---|
| Standard-scale (TS) | ≤60 × 10$^9$ | ≤0.6 × 10$^9$ | 93.5 |
| Large-scale (LS) | ≤60 × 10$^9$ | >0.6 × 10$^9$ | 187 |
| Large-scale (LS) | >60 × 10$^9$ – 120 × 10$^9$ | ≤0.6 × 10$^9$ | 187 |
| Large-scale (LS) | >60 × 10$^9$ – 120 × 10$^9$ | >0.6 × 10$^9$ | 187 |

B. Protocol for thawed bone marrow:
   1) Thaw cells in 2 cryopreservation bags in a 37° C. water bath
   2) Transfer all bags to a BSC
   3) Aseptically clean the ports and spike of each bag.
   4) Using a 5 cc syringe with affixed needle, immediately inject Benzonase (1000 U/ml) into each cryopreservation bag to achieve a final concentration of 20 U/mL (e.g., for 70 ml of bone marrow product, inject 1.4 mL Benzonase) and mix well.
   5) Combine contents from the 2 thawed cryopreservation bags into Cell prep Bag 1 by withdrawing using a 100 mL syringe attached to the transfer port.
   6) Rinse each bag with 50 ml of Labeling buffer and slowly transfer to same Cell Prep Bag 1.
   7) Record weight of Cell Prep Bag 1.
   8) Record total volume of cell suspension in the Cell Prep Bag 1 (should no more than 200 mL) by subtracting the original weight from the weight obtained in step 7 (1 gram=1 mL).

9) Slowly fill Cell Prep Bag 1 with an equal volume of Labeling buffer by adding 10% of the volume per minute while shaking on a shaker.
10) Quickly add another volume of Labeling buffer to Cell Prep Bag 1.
11) After mixing well, remove 0.5 ml sample for T cell and CD34+ cell enumeration by flow cytometry.
12) Optional step: If clumps are present, insert standard blood filter, filter the cells and transfer to the second Cell Prep Bag.
13) Centrifuge at 300 g for 15 minutes with a brake setting of 4 at room temperature.
14) Express supernatant, gently mix cell pellet and combine all cells into one bag.
15) Wash bags and adjust volume to target volume with Labeling buffer according to Table 5.

Cell Labeling and Selection

A. Add human IVIG to Cell Prep Bag at final concentration 1.5 mg/ml.
B. The calculated volume of IVIG added should be included in the final labeling weight, not to exceed 95 g or 190 g, depending on scale of preparation (Table 5).
C. Inject 100 ml of sterile air into the bag using a 100 ml syringe with affixed 0.2 micron filter
D. Place the Cell Prep Bag on an orbital rotator and gently shake for 5 minutes at room temperature.
E. After 5 minutes, using a 20 ml syringe, inject 1 vial (7.5 ml) of CD34+ Reagent for Standard-scale or 2 vials (15 ml) for Large-scale into the Cell Prep Bag through the sampling site coupler.
F. Incubate bag on the orbital rotator for 30 minutes at room temperature.
G. In BSC, remove air in Cell Prep Bag using a 100 ml syringe. Add 500±10 ml (g) of Labeling buffer to the Cell Prep Bag. Centrifuge at 300 g for 15 minutes, with a brake setting of 4 at room temperature.
H. Remove as much of the supernatant as possible (at least 500 ml for standard-scale and 450 ml for Large-scale) from the Cell Prep Bag using a plasma press. Be careful not to remove cells.
I. Record the amount of supernatant removed.
J. Add 500±10 ml (g) of Labeling buffer to the Cell Prep Bag.
K. Centrifuge at 300 g for 15 minutes, with a brake setting of 4 at room temperature.
L. Remove as much of the supernatant as possible (at least 500 ml for standard-scale and 450 ml for Large-scale) from the Cell Prep Bag using a plasma press.
M. Gently mix cell pellet and resuspend pellet with Labeling buffer 1 to target volume 140 ml for standard-scale preparation or 265 ml for large-scale.
N. Inside the BSC, transfer 0.5 ml bone marrow using a 1 mL syringe to a 1.5 ml Eppendorf tube to perform pre-CliniMACS QC including cell count, T cell and CD34+ cell enumeration.
O. The product is ready to process on the CliniMACS plus instrument according to the Manufacture's instruction with the exception that custom Selection buffer is used instead MACS buffer.
P. The volume of the selected cells at the end is expected to be ~40-50 ml for the standard selection tubing set and ~75-80 ml for large selection.
Q. Obtain samples for product QC.
R. Selected cells are ready for immediate infusion or cryopreservation.

Example 4. HPC, Marrow Shaker Grindings

The scope of this experiment encompassed the testing of the bone marrow extract using a different grinding and filtration method, with the addition of a shaker to determine and compare the cell concentration to evaluate the cell concentration (WBC) of bone marrow extract with the use of a shaker prior to filtration. "Quality Control 1" (QC1) was taken after the second filtration from the first 600 mL bag that is filled. "CD34+ HSC" were cells which had forward scatter and side scatter characteristics similar to lymphocytes; expressing both CD45 and CD34 and exhibiting dim CD45 expression and low side scatter characteristics. (also referred to as "True Blasts" by ISHAGE.) CD45 is an antigen present on all human leukocytes, including lymphocytes, monocytes, granulocytes, eosinophils, and basophils. It has a role in signal transduction and is weakly expressed on hematopoietic progenitor cells.

Bone marrow extract was produced from cadaveric vertebral bodies (VBs) per B-2 and B-3 of Example 1. and using the attached protocol for grinding and filtration. Grinding protocol involved:

A. Separate the VBs into two separate, sterile bags at decontamination. Record the weight. Label bags #1 and #2.
B. Grinding Protocol:
1) Separate the VBs into two separate, sterile bags at decontamination. Record the weight. Label bags #1 and #2.
2) Assemble the grinder. Depress foot pedal to start.
3) Pour—133 mL of Grind Media into one sterile, stainless-steel pitcher. This pitcher will be called "Pitcher 1" and will contain cut VB pieces. Pour—133 mL of Grind Media into another pitcher, "Pitcher 2", to catch grindings. An additional—133 mL will be used for rinsing through grinder while grinding. The remaining—100 mL of Grind Media will be set aside for the final rinsing of the grinder after all pieces are ground.
4) Using the hand cutting tool, cut the VBs no larger than 1.5 cm. Place the VB pieces into "Pitcher 1."
5) Using sterile forceps, carefully grab one VB piece and drop it in the inlet container of the grinder. Do not force VB pieces into the grinder with forceps. Use plunger as needed.
6) The grindings will be caught in "Pitcher 2." Occasionally rinse the grinder head with additional—133 mL of Grind Media. Make sure that all the grindings are fully covered in Grind Media.
7) Carefully pour the remaining 100 mL of Grind Media into the inlet container to rinse the grindings.
8) When all grindings have been washed through the grinder, stop grinder by depressing foot pedal.
9) Repeat B.3-B.7 for the experiment (Bag #2) using the remaining 500 mL of Grind Media.
C. Filtration Protocol Included:
1) Spray the sterile, white-capped container or stainless-steel jar and 2 bone marrow (BM) filtering kits thoroughly with 70% IPA and place it inside the BSC.
2) For bag #1 (control), perform the same BM extraction following Bone Marrow Collection & Filtration of Example 1 using a total of 500 ml Rinse Media (2×250 ml).
3) For bag #2 (experiment), aseptically pour the grind media and BM grindings from the pitcher to the white-capped container or stainless-steel jar.
4) Place the sterile container on the shaker plate at 150 RPM for 10 minutes.
5) Open the collection container cap and insert the large sterile funnel.

6) Using a large sterile funnel, carefully pour grind media and BM grindings into the collection container (do not add the bone into the collection container).
7) Remove the sterile funnel. Close the collection container cap.
8) Pour 250 mL of the Rinse Media into the white-capped container or the stainless-steel jar with the bone grindings. Swirl slightly.
9) Place sterile container on the shaker plate at 120 RPM for 5 minutes.
10) While the shaker is running, open the clamps on the collection container and the TRANSFER-PACK container. Allow bone marrow to flow into TRANSFER-PACK by gravity.
11) Once all the media has been drained into the TRANSFER-PACK, close all clamps.
12) Open the collection container cap and insert the sterile funnel. Carefully pour the Rinse Media and BM grindings into the collection container funnel (do not add the bone into the collection container).
13) Repeat C.8-C.12.
14) Carefully pour the Rinse Media and bone grindings into the collection container funnel, using the forceps to help push the grindings into the collection container.
15) Close clamps and remove the 2000 mL TRANSFER-PACK from the filter set. Discard the used filters and collection container.
16) Spray container of microcentrifuge tubes with 70% IPA and two 1 mL syringes. Place it in the BSC and take out 2 microcentrifuge tubes. Label one tube #1 and the other #2.
17) Sterile weld a male luer extension onto the 2000 mL TRANSFER-PACK, following TSCD II Sterile Tubing Welder Operation.
18) Using the sterile 1 mL syringes, take out 1 mL of BM from the Bag #1 bag. Label bag #1 microcentrifuge tube with the time and date. Repeat step for bag #2.
19) Continue BM extraction and filtration #2 following Bone Marrow Collection & Filtration of Example 1.
D. Perform Sysmex and Flow testing on QC1 sample for bags #1 and #2. One of the donors, W437520000047, went against the original protocol. Only one filtration kit was used and filtration #2 was not performed. Instead of having two 500 gm filtering units connected to each other, the single filtration kit that was used for this donor was set up to where it had one 500 gm filter and one 200 gm filter connected to each other. Despite using only one filtering kit, there was no signs of clumping in the 500 and 200 gm filtering units.

Results

Bone marrow from 3 different donors was collected for this experiment, all of which ranged from different ages. All donors were processed in the research lab for non-clinical development purposes. Data was collected from QC1. (Table 6) The average cell concentration of the controlled concentrated bone marrow extract was $17.3 \times 10^3$ g/ml, while the cell concentration of the experimental bone marrow extract was $26.4 \times 10^3$ g/ml. The difference between the cell concentration of the control and experiment is $9.1 \times 10^3$ g/ml. The p-value calculated between the two groups were 0.0237.

TABLE 6

Summary of HPC Marrow Shaker Grindings

| Donor ID | Age/Gender | Warm Ischemia Time (min) | Cold Ischemia Time (min) | WBC (PimL)-Control | WBC (μ/mL)-Experiment |
|---|---|---|---|---|---|
| 437520000044 | 49/F | 107 | 1076 | $17.3 \times 10^3$ | $29.6 \times 10^3$ |
| 437520000045 | 51/F | 163 | 1503 | $17.7 \times 10^3$ | $22.5 \times 10^3$ |
| 437520000047 | 20/M | 78 | 1697 | $17.0 \times 10^3$ | $27.2 \times 10^3$ |
| Average | | 116 | 1425.3 | $17.3 \times 10^3$ | $26.4 \times 10^3$ |
| SD | | | | 0.351 | 3.61 |

From the 3 different donors, flow cytometry was performed and analyzed between the control and experiment (Table 7). Specific data from abs CD45+ and CD34+ and the viability percentage of both CD45+ and CD34+ were examined.

TABLE 7

Flow cytometry examining CD45 and CD34+ cells

| Donor ID | Abs CD45+/mL-Control | Abs CD45-1-/mL-Experiment | Abs CD34+ HSPC/mL-Control | Abs CD34+ HSPC/mL-Experiment | Viable CD45+-Control | Viable CD45+-Experiment | Viable CD34+ HSPC-Control | Viable CD34+ HSPC-Experiment |
|---|---|---|---|---|---|---|---|---|
| 437520000044 | $1.80 \times 10^7$ | $2.30 \times 10^7$ | $1.90 \times 10^5$ | $2.30 \times 10^5$ | 85.93% | 89.40% | 97.23% | 96.80% |
| 437520000045 | $1.20 \times 10^7$ | $1.80 \times 10^7$ | $1.30 \times 10^5$ | $2.20 \times 10^5$ | 91.76% | 92.56% | 95.31% | 97.05% |
| 437520000047 | $1.20 \times 10^7$ | $2.10 \times 10^7$ | $1.80 \times 10^5$ | $2.90 \times 10^5$ | 88.89% | 88.76% | 97.08% | 97.33% |
| Average | $1.40 \times 10^7$ | $2.07 \times 10^7$ | $1.67 \times 10^5$ | $2.47 \times 10^5$ | 88.86% | 90.24% | 96.54% | 97.06% |
| SD | 0.346 | 0.252 | 0.321 | 0.379 | 2.92 | 2.00 | 1.07 | 0.265 |

Table 8 illustrates comparison between bone marrow cells isolated with the processing techniques described herein with added shaking or added shaking and spinning. The cells isolated from shaking only or from shaking and spinning exhibited similar characteristics such as viability, CD34 expression, CD45 expression, or CD3 expression.

TABLE 8

Shake or Shaker and Spin Comparison

| ID | Purpose/ Expt | Date Tested | Mass processed (g) | # VBs | QC1 Sysmex TNC/ donor | QC1 Sysmex TNC/g bone | Abs CD45+/mL | CD45+/ donor | CD45+/VB | Abs CD34+ HSPC/mL |
|---|---|---|---|---|---|---|---|---|---|---|
| W437520000122 | shaker | 21 Jul. 2020 | 290.0 | 9 | 5.38E+10 | 1.86E+08 | 230000000 | 3.35E+10 | 3.72E+09 | 2700000 |
| W437520000131 | shaker | 2 Aug. 2020 | 218.0 | 7 | 4.99E+10 | 2.29E+08 | 320000000 | 2.83E+10 | 4.04E+09 | 1700000 |
| W437520000133 | shaker | 11 Aug. 2020 | 258.0 | 10 | 5.80E+10 | 2.25E+08 | 330000000 | 3.22E+10 | 3.22E+09 | 5700000 |
| W437520000137 | shaker + spin | 17 Aug. 2020 | 244.0 | 6 | 5.63E+10 | 2.31E+08 | 440000000 | 4.01E+10 | 6.69E+09 | 1860000 |
| W437520000139 | shaker + spin | 21 Aug. 2020 | 164.0 | 6 | 3.54E+10 | 2.16E+08 | 330000000 | 2.5E+10 | 4.17E+09 | 3300000 |
| W437520000149 | shaker + spin | 2 Sep. 2020 | 308.0 | 10 | 5.87E+10 | 1.91E+08 | 304000000 | 3.17E+10 | 3.17E+09 | 2720000 |

| ID | Abs Total CD34+ HSC/ donor | Abs CD34+ HSC/g bone | Abs CD3+/mL | Abs CD3+/ donor | Viable CD45+ | Viable CD34+ HSPC | Viable CD3+ | CD34+ HSPC % | Viable CD34+ HSC/ unit | Viable CD3+/ donor |
|---|---|---|---|---|---|---|---|---|---|---|
| W437520000122 | 393120000 | 1355586.2 | 7500000 | 1.09E+09 | 0.9207 | 0.9085 | 0.6451 | 1.17% | 1.59E+08 | 7.04E+08 |
| W437520000131 | 150280000 | 689357.8 | 26000000 | 2.3E+09 | 0.9055 | 0.8647 | 0.7819 | 0.53% | 95549350 | 1.8E+09 |
| W437520000133 | 555750000 | 2154069.8 | 39000000 | 3.8E+09 | 0.9095 | 0.9443 | 0.8786 | 1.73% | 3.5E+08 | 3.34E+09 |
| W437520000137 | 169632000 | 695213.11 | 26000000 | 2.37E+09 | 0.9375 | 0.9276 | 0.7627 | 0.42% | 1.12E+08 | 1.81E+09 |
| W437520000139 | 250470000 | 1527256.1 | 27400000 | 2.08E+09 | 0.924 | 0.953 | 0.7954 | 1.00% | 2.04E+08 | 1.65E+09 |
| W437520000149 | 283424000 | 920207.79 | 14100000 | 1.47E+09 | 0.8697 | 0.9398 | 0.6668 | 0.89% | 1.66E+08 | 9.8E+08 |

In this study, the vertebral bodies were split into two groups to test a new method during grinding and filtration. The method will include the use of a shaker for the bone grindings. Prior to this protocol, no agitation was used other than massaging the grindings in the collection container. The purpose of this study was to increase the cell yield in the bone marrow extract with the use of a shaker. It was expected that the cell concentration would increase due to the agitation of the bone grindings in three different stages at a consistent speed. A similar study was done at the University of Pittsburgh Cancer Institute's Hematopoietic Stem Cell Laboratory (Donnenberg et al., 2011). The idea with agitating the bone grindings was to extract as much marrow from the donor into the medium.

The HPC, Marrow extract was tested using the Sysmex and flow cytometry. When comparing the protocol to the control, the data presents a consistent pattern of a higher cell concentration count, increase in abs CD45+ and CD34+ HSPC, and a higher percent viability of CD45+ and CD34+ HSPC with the method using the shaker. The t-test was done to represent the difference between the two tested groups. With a small calculated p-value, it indicates that there is only a 2.37% probability that the results from the experiment happening by chance. The purpose of using the Sysmex was to obtain the in-process blood count per donor, but this count includes nucleated red blood cells. Here, the focus was on the white blood cell (leukocyte) count obtained by flow cytometry, specifically the number of CD34+ cells since they are the stem cells that will engraft in the patient.

Flow cytometry was performed to evaluate and analyze the CD45+ and CD34+ cell count and viability. CD45+ displayed an increase in count and viability in the experimental method, however, there could be variability in the type of cells, such as granulocytes that sharply decline during cryopreservation. Similarly, CD34+ increased in count, cell concentration, and in its percent viability. Based on literature from the University of Pittsburgh, a procedure like this could be used during clinical applications. In addition, with the increase in the number of CD45 and CD34+ cells, it will increase the number of units that can be banked.

Example 5. HPC, Marrow Passively Cooled Using Cassettes Only at a Plunging Temperature of −86° C.

The objective this study was to evaluate the cooling profiles of simulated HPC, Marrow and HPC, Marrow products to improve cryopreservation processing. By Passive Cryopreservation of Example 1, 65 ml HPC, Marrow in Cryostore 250 EVA Freezing Bags were placed in freezing cassettes for a 2-step cryopreservation process involving passive cooling to −86° C. in a mechanical freezer followed by plunging into LN2 vapor phase for intracellular vitrification and long term storage. While this method had been validated and delivered satisfactory results, it had been noted that the QC vials often outperformed bags post thaw with respect to viability testing. In the initial validation, it was noted that thermal resistance of the box results in slower cooling rates than the vials. For CD34+ cells, which are relatively solute insensitive, this was not identified as a concern. This process improvement work was based on observations that the other cells in the HPC, Marrow product (i.e. neutrophils) could be more solute sensitive and therefore may not do as well with very slow cooling rates and may be collaterally damaging the CD34+ cells as a result of spilling intracellular contents.

The purpose of this experiment was therefore to determine if the −86° C. static chamber temperature could result in a passive cooling approach that yield cooling rates consistently that could product higher viability post thaw, by eliminating the box. For the first experiment, simulated HPC, Marrow (freeze media) would be loaded into the −86° C. with cassettes only and cooling profiles would be measured with thermocouples inside the bag. The second experiment would evaluate cooling profiles of HPC, Marrow at −86° C. with cassettes only with thermocouples on the outside of the bag. If cooling rates were successfully achieved at approximate −1° C./min from below initial ice nucleation to −40° C., a subsequent, separate evaluation would consider cell viability post thaw based on flow cytometry to determine how cooling with cassettes only affects post-thaw viability of the CD34+ cells.

DEFINITIONS: CD34: Antigen present on immature hematopoietic precursor cells and all hematopoietic colony-forming cells in bone marrow and blood. Certain populations of non-hematopoietic (i.e., CD45 negative) cells also express CD34. Of hematopoietic (i.e., CD45+ cells), the CD34 antigen expression is highest on early progenitor cells and decreases with the maturation of cells. The CD34 antigen is absent on fully differentiated hematopoietic cells. Normal peripheral blood lymphocytes, monocytes, granulocytes, and platelets do not express the CD34 antigen. CD45: Antigen present on all human leukocytes, including lymphocytes, monocytes, granulocytes, eosinophils, and basophils. It has a role in signal transduction and is weakly expressed on hematopoietic progenitor cells. DMSO ($C_2H_6OS$): Dimethyl sulfoxide. Used as a cryoprotectant. Plasma Lyte-A: A sterile, nonpyrogenic isotonic solution which closely mimics human plasma. Human Serum Albumin (HSA): A water soluble, monomeric protein that transports hormones, fatty acids and other compounds, buffers pH, and maintains oncotic pressure, among other functions. It is the primary protein present in human blood plasma. Rinse Media: A solution consisting of Plasma Lyte-A with 2.5% HSA. Freeze Media: A solution consisting of rinse media with 10% DMSO. BSC: Biosafety cabinet.

A bank of HPC was being developed for bone marrow derived from deceased organ and tissue donors. The HPC bone marrow was stored in freezing bags (Cryostore 250 EVA Freezing Bags) placed in cassettes. Cryopreservation of this material involved passively cooling HPC, bone marrow in a dedicated −86° C. Eppendorf CryoCube Model F740hi before transferring to cryogenic storage in a permanent location in a vapor nitrogen cryotank. For the first phase of the experiment, freeze media was used to simulate HPC, Marrow. To prepare the freezing bags for the experiment, a heated screwdriver was used to bore a hole in the most central spike port of the bags. Type-T thermocouples were inserted through the newly bored hole until halfway into the freezing bags. The hole was then sealed using a low temperature heat gun and epoxy glue sticks which also held thermocouples in place. The freezing bags were then filled with 65±5 mL freeze media. Excess air was removed from the bag and all ports sealed. These freezing bags were then placed in freezing cassettes and labeled with each corresponding port (COH/COL-C7H/C7L) on the temperature board. The temperature board used for this experiment was an Omega OM-USB-TC temperature board.

The software used in conjunction with the temperature board was TracerDAQ, software version 2.3.4.0. The computer model used with the temperature board was a Lenovo Desktop, model 20F13CT01WW with Microsoft Windows Home 10 installed. The settings used in TracerDAQ were as set with the scanning rate adjusted to 0.05 Hz, resulting in one data point per 20 seconds. In the, "display settings," Celsius was selected as the label. The upper and lower limit was selected at 30° C. and −190° C., respectively. The duration of the data acquisition was 6 hours and ten minutes.

Preliminary experiments indicated that cooling rates would be faster if cassettes were placed directly against the walls of the freezer, but were consistent across the bulk of the shelves (data not shown). For these reasons, the cassettes were placed in the top shelf of the dedicated −86° C. Eppendorf CryoCube Model F740hi (asset 0144) in specific locations of the shelf. Per the user manual, the length and width of the shelves in the −86° C. Eppendorf Cryocube Model F740hi are 86.5×62.1 cm, respectively. The length and width of the cassettes are 20.0×14.0 cm, respectively. The cassettes were placed in two rows of four 15 cm away from both sides of the freezer and 11 cm from the back of the freezer (FIG. 15). This put the cassettes in the most central location of the freezer. Care was taken not to pull on thermocouple wires during placement and closing the freezer door to maintain their positioning. Upon completion, the data was saved as an excel csv file and then formatted as an xlsx file. All Excel sheets were printed and filed in the *Process Improvement Experimental Report: HPC, Marrow Passively Cooled Using Cassettes Only Binder.*

The second experiment was performed using HPC, Marrow from donors ISBT: W437520000044-W437520000046. All donor batch records and testing records can be found in the donor file. The age, gender, warm ischemia, and cold ischemia times are summarized in Table 9.

TABLE 9

Age, gender, and ischemia times for donors used.

| ISBT # | Age | Gender | Warm Ischemia (minutes) | Cold Ischemia at Process Start (minutes) |
| --- | --- | --- | --- | --- |
| W437520000044 | 49 | F | 107 | 2415 |
| W437520000045 | 51 | F | 163 | 1503 |
| W437520000046 | 54 | M | 205 | 2263 |

To track the temperature of the freeze media, an Omega OM-USB-TC temperature board was used with Type-T thermocouples. Before receiving the HPC, Marrow, the auto-update settings for the computer were suspended to avoid interruptions in data acquisition. The power saving settings were also set to not allow the computer to shut down or go to sleep during data acquisition.

Three cryopreservation bags containing 65±5 mL HPC, Marrow were collected from each donor per current processing methods. A thermocouple was centrally placed on the external surface of the bags and held in place by tape. Each bag was then placed in a cassette and thermocouples placed into the port of thermocouple in ascending order starting from COH/COL and ending with C2H/C2L. The cassettes were then labeled with the donor ID, date, bag number, and the temperature board port thermocouples were inserted in.

The software used in conjunction with the temperature board was TracerDAQ. The settings used in TracerDAQ were as set with the scanning rate adjusted to 0.05 Hz, resulting in one data point per 20 seconds. In the, "display settings," Celsius was selected as the label. The upper and lower limit was selected at 30° C. and −190° C., respectively. The duration of the data acquisition was 6 hours and ten minutes.

Upon pressing play in TracerDaq to begin data acquisition, the cassettes were placed on the top shelf (shelf 1) of the −86° C. Eppendorf Cryocube Model F740hi. Their positions relative to the shelf are represented in FIG. 14 or FIG. 15. For donor W437520000044, the cryovials were plunged at −86° C. along with the cassettes on the top shelf. For the remaining donors, cryovials were plunged at −86° C. on the bottom shelf (shelf 3). The positioning of the cassettes for all donors remained the same to maintain consistency.

The HPC, Marrow vials consisting of 1 PT QC vial, 2 Reserve Vials, and 1 Surrogate Vial per freezing bag were cryopreserved via Passive Cryopreservation of Example 1. Donors W437520000045-W437520000046 deviated from Passive Cryopreservation of Example 1 by being plunged in the bottom shelf of the −86° C. Eppendorf CryoCube Model F740hi instead of the top shelf.

Upon completion of data acquisition, the cassettes were transferred from the top shelf (shelf 1) of the −86° C. Eppendorf CryoCube Model F740hi to the central shelf (shelf 2). Upon allowing a minimum of six hours to elapse with the cassettes in the central shelf, the cassettes and cryovials were transferred to a vapor phase nitrogen cryotank where they were stored until post-thaw viability testing. See Tables 16-18 for post thaw results for donors W437520000044, W437520000045, and W437520000046.

Figure 16:
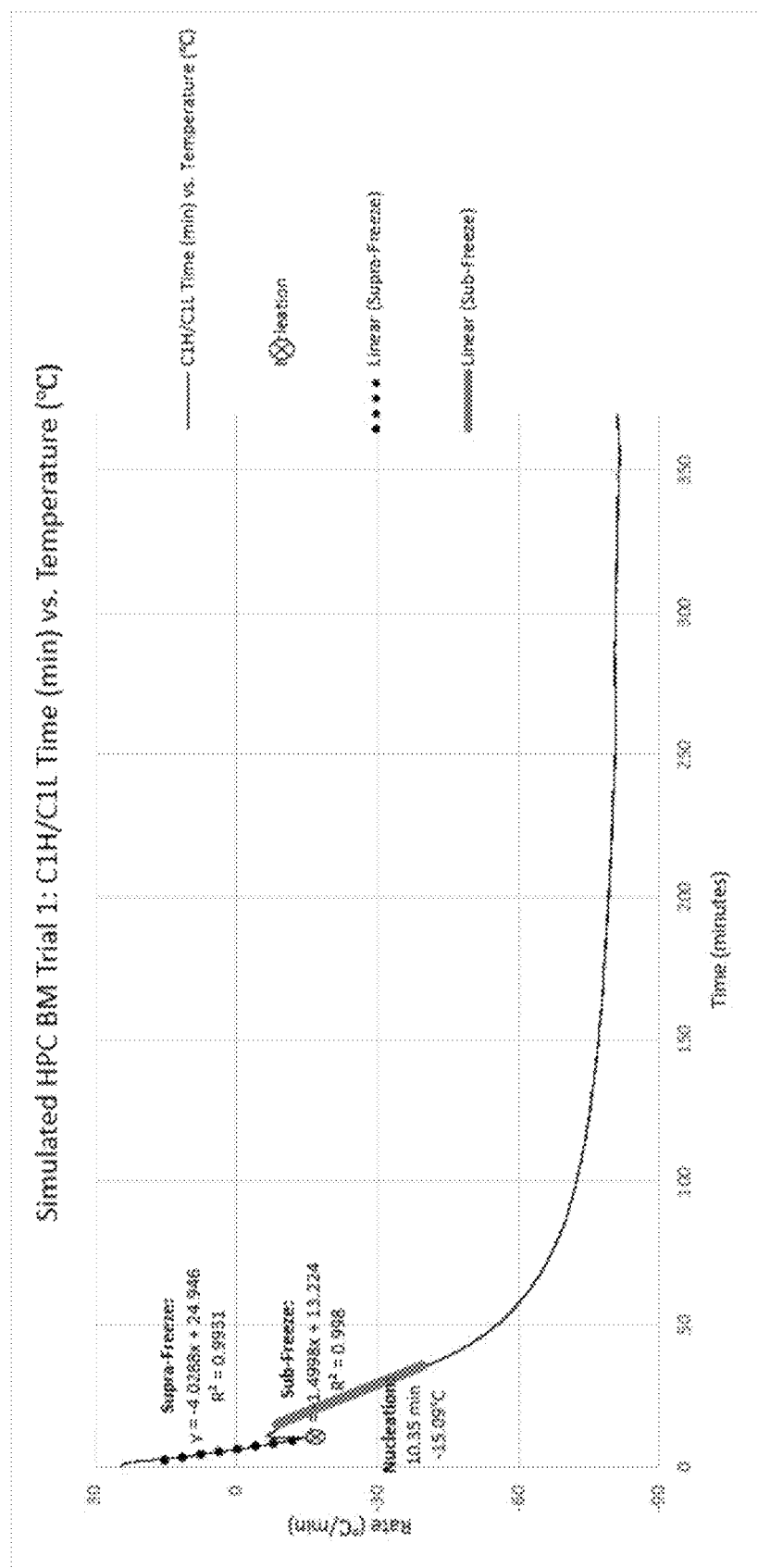
FIG. 16 illustrates an example of graph used to determine supra/sub-freeze cooling rates and nucleation temperatures.

The data acquiesced via the Omega OM-USB-TC temperature board was saved as an excel.csv file and then reformatted as an excel.xlsx file. To give a visual representation of the overall data for each cassette, a scatter plot was made consisting of temperature (° C.) vs. time (min), the supra and sub-freeze data, and nucleation points. See FIG. 16 for an example freeze curve. The supra and sub-freeze plots and the point of nucleation are superimposed on the scatter plot for the overall data for each port (C0H/C0L-C7H/C7L).

To determine the supra-freeze check/cooling rate, a scatter plot was made (° C./min) from approximately 17° C. to the point of nucleation. Using excel, a linear trendline was used to determine the slope as well as the coefficient of determination. This method was used to determine all supra-freeze cooling rates.

To determine the sub-freeze check/cooling rate, a scatter plot was made (° C./min) from −10° C. to −40° C. Using excel, a linear trendline was used to determine the slope as well as the coefficient of determination. This method was used to determine all sub-freeze cooling rates.

As ice forms, latent heat of fusion is released resulting in an increase in temperature. Therefore, to determine the temperature at nucleation, the lowest temperature recorded before the increase in temperature is the nucleation temperature. The statistical analysis was performed using the Data Analysis Tools provided by Microsoft Excel, version 2004. The results for experiment 1 are reported in Tables 10-12. For all three simulated marrow trials in Table 10, the average supra-freeze cooling rate was −3.2° C. (over a range of −2.54 to −4.09° C./min). For all three simulated marrow trials in Table 11, the average sub-freeze cooling rate was and −1.36° C./min (over a range of −1.13 to −1.62° C./min). For all three simulated trials in Table 12, the average nucleation temperature was −12.31 (over a range of −7.24 to −17.52° C.).

TABLE 10

Simulated HPC, Marrow Supra-Freeze Rates (° C./min)

| Channel | Trial 1 | Trial 2 | Trial 3 |
|---|---|---|---|
| C0H/C0L | −3.49 | −3.53 | −3.37 |
| C1H/C1L | −3.11 | −3.62 | −3.1 |
| C2H/C2L | −2.59 | −2.54 | −2.91 |
| C3H/C3L | −3.49 | −3.24 | −3.28 |
| C4H/C4L | −3.02 | −3.45 | −3.36 |
| C5H/C5L | −3.3 | −4.09 | −3.1 |
| C6H/C6L | −2.95 | −2.85 | −3.16 |
| C7H/C7L | −3.57 | −3.52 | −3.16 |

TABLE 11

Simulated HPC, Marrow Sub-Freeze Rates

| Channel | Simulated HPC, Marrow Trial 1 (° C./min) | Simulated HPC, Marrow Trial 2 (° C./min) | Simulated HPC, Marrow Trial 3 (° C./min) |
|---|---|---|---|
| C0H/C0L | −1.47 | −1.52 | −1.52 |
| C1H/C1L | −1.23 | −1.24 | −1.28 |
| C2H/C2L | −1.59 | −1.47 | −1.26 |
| C3H/C3L | −1.45 | −1.30 | −1.49 |
| C4H/C4L | −1.44 | −1.62 | −1.32 |
| C5H/C5L | −1.19 | −1.18 | −1.13 |
| C6H/C6L | −1.35 | −1.22 | −1.15 |
| C7H/C7L | −1.43 | −1.48 | −1.25 |

TABLE 12

Simulated HPC, Marrow Nucleation Temperatures (° C.)

| Channel | Trial 1 | Trial 2 | Trial 3 |
|---|---|---|---|
| C0H/C0L | −13.34 | −11.93 | −7.53 |
| C1H/C1L | −15.68 | −12.32 | −15.62 |
| C2H/C2L | −17.52 | −16.65 | −9.93 |
| C3H/C3L | −12.75 | −13.42 | −7.24 |
| C4H/C4L | −9.20 | −11.21 | −9.87 |
| C5H/C5L | −14.78 | −11.17 | −10.32 |
| C6H/C6L | −8.27 | −11.63 | −14.26 |
| C7H/C7L | −14.75 | −11.97 | −14.00 |

The temperature board data was not recorded for C2H/C2L for W437520000045 and W437520000046.

For all three donors of the HPC, Marrow, the average supra-freeze rate was −3.90° C./min (over a range of −3.52 to −4.23° C./min, Table 13).

TABLE 13

HPC, Marrow Supra-Freeze Rates (° C./min)

| Channel | W437520000044 | W437520000045 | W437520000046 |
|---|---|---|---|
| C0H/C0L | −3.78 | −3.52 | −4.12 |
| C1H/C1L | −4.23 | −3.84 | −3.77 |
| C2H/C2L | −4.01 | | |

For all three donors of the HPC, Marrow, the average sub-freeze rate was −1.5157° C./min (over a range of −1.3178 to −1.6448° C./min, Table 14).

TABLE 14

HPC, Marrow Sub-Freeze Rates (° C./min)

| Channel | W437520000044 | W437520000045 | W437520000046 |
|---|---|---|---|
| C0H/C0L | −1.5553 | −1.3178 | −1.6339 |
| C1H/C1L | −1.6448 | −1.3693 | −1.5309 |
| C2H/C2L | −1.5578 | | |

For all three donors of the HPC, Marrow, the average nucleation temperature was −13.7032° C. (over a range of −10.9017° C. to −18.3652° C., Table 15).

TABLE 15

HPC, Marrow Nucleation Temperatures (° C.)

| Channel | W437520000044 | W437520000045 | W437520000046 |
|---|---|---|---|
| C0H/C0L | −10.9017 | −12.7773 | −18.3652 |

TABLE 15-continued

| | | | |
|---|---|---|---|
| C1H/C1L | −12.3823 | −13.2287 | −17.005 |
| C2H/C2L | −11.2624 | | |

The preponderance of the literature regarding successful cryopreservation of hematopoietic stem/progenitor cell products indicates that cooling rates from −1 to −5° C. result in equivalent, optimized yields. If the static chamber passive freezing system is used with the bags in cassettes but without using a further insulator (and the bags are not placed directly against the walls of the freezer) the cooling profiles look consistent and meet the cooling rate requirements for high viability. The method tested in these experiments is suitable for subsequent validation.

Example 6. Post-Thaw Results for HPC, Marrow Frozen without SmartCool Box

To evaluate how freezing HPC, Marrow in Cryostore 250 EVA Freezing Bags without a SmartCool Box impacts post-thaw viability and proliferation. Post thaw viability for vials frozen in CoolCells and bags frozen without a Smart-Cool Box should meet a post-thaw CD34+ HSC viability of 50% and at least 1 CFU-GM/$10^5$. The removal of the SmartCool box should eliminate the systematic difference between bags and vials, so that vials can be used as a surrogate for bags post-thaw. The variability observed between bags and vials should be comparable to the variability expected with testing human donor samples. The experiment and its data will be used in determining if it is suitable to freeze HPC, Marrow bags in Cryostore 250 EVA Freezing Bags without the use of a passive cooling box and if a vial can be a surrogate for the bag post-thaw.

Three donors were processed, frozen without a passive cooling box, thawed, and tested according to current batch records and testing methods (Tables 16-18). Samples were thawed as described herein.

Example 7. Colony Forming Unit Assay was Performed Per Methods Described Herein

All vials frozen in CoolCells and bags frozen without a SmartCool Box meet a post-thaw CD34+ HSC viability of 50% and have at least 1 CFU-GM/$10^5$. The variability between bags frozen without a SmartCool box and vials frozen in CoolCells is the variability expected from testing human donors. The removal of the SmartCool box does not show a systematic difference between bags and vials. Thus, the removal of the SmartCool box would be a positive change that would allow post thaw vials to be used as surrogates for the bags.

TABLE 16

Donor W437520000044 Thaw Data

Flow Cytometry

| Sample ID | Sample ID | Abs CD45+/mL | Abs CD34+ HSPC/mL | Abs CD3+/mL | Viable CD45+ | Viable CD34+ HSC | Viable CD3+ |
|---|---|---|---|---|---|---|---|
| W-44 Fresh | QC2 | 3.20E+08 | 3.68E+06 | 3.36E+07 | 90.17% | 96.86% | 60.65% |
| | QC3 | 1.28E+08 | 1.36E+06 | 1.04E+07 | 78.42% | 97.92% | 55.92% |
| W-44 Thaw 2 mL Vials | Vial 1 | 4.50E+07 | 6.84E+05 | 5.13E+06 | 55.46% | 95.08% | 70.53% |
| | Vial 2 | 4.14E+07 | 6.30E+05 | 4.59E+06 | 46.74% | 94.74% | 74.00% |
| | Vial 3 | 4.41E+07 | 6.66E+05 | 4.77E+06 | 43.86% | 94.91% | 74.04% |
| W-44 Thaw Bags | Bag 1 | 3.47E+07 | 7.79E+05 | 4.90E+06 | 62.63% | 96.91% | 71.15% |
| | Bag 2 | 4.41E+07 | 7.74E+05 | 5.58E+06 | 57.00% | 97.51% | 79.03% |
| | Bag 3 | 4.41E+07 | 7.29E+05 | 5.40E+06 | 63.39% | 97.69% | 81.24% |

Colony Forming Unit Assay

| Sample | Concentration | Average BFU-E/ 10^5 | Average CFU-GM/ 10^5 | Average CFU-GEMM/ 10^5 | Average Total/ 10^5 | Comments |
|---|---|---|---|---|---|---|
| W-44 Fresh | Low | 130 | 150 | 20 | 300 | N/A |
| | High | — | — | — | — | Over-plated |
| W-44 Thaw Vial 1 | Low | 50 | 100 | 0 | 150 | N/A |
| | High | 30 | 80 | 0 | 110 | N/A |
| W-44 Thaw Vial 2 | Low | 0 | 50 | 0 | 50 | N/A |
| | High | 55 | 45 | 0 | 100 | N/A |
| W-44 Thaw Vial 3 | Low | 0 | 0 | 0 | 0 | N/A |
| | High | 40 | 40 | 0 | 80 | N/A |
| W-44 Thaw Bag 1 | Low | 100 | 100 | 0 | 100 | N/A |
| | High | 65 | 45 | 5 | 115 | N/A |
| W-44 Thaw Bag 2 | Low | 100 | 50 | 0 | 150 | N/A |
| | High | 55 | 50 | 0 | 105 | N/A |
| W-44 Thaw Bag 3 | Low | 0 | 100 | 0 | 100 | N/A |
| | High | 55 | 40 | 0 | 95 | N/A |

TABLE 17

Donor W437520000045 Thaw Data

Flow Cytometry

| ID | Date Tested | Sample ID | Abs CD45+/mL | Abs CD34+ HSPC/mL | Abs CD3+/mL | Viable CD45+ | Viable CD34+ HSC | Viable CD3+ |
|---|---|---|---|---|---|---|---|---|
| W-45 Fresh | 31 Mar. 2020 | QC2 | 3.20E+08 | 4.00E+06 | 2.72E+07 | 90.42% | 96.93% | 85.13% |
| | | QC3 | 8.80E+07 | 9.60E+05 | 6.88E+06 | 73.77% | 97.31% | 63.13% |
| W-45 Thaw 2 mL Vials | 27 Apr. 2020 | Vial 1 | 6.90E+07 | 4.04E+05 | 7.19E+06 | 45.92% | 69.39% | 45.07% |
| | | Vial 2 | 6.48E+07 | 4.24E+05 | 7.69E+06 | 45.46% | 73.75% | 46.87% |
| | | Vial 3 | 5.97E+07 | 3.77E+05 | 7.24E+06 | 43.93% | 71.89% | 44.91% |
| | | Vial 4 | 6.97E+07 | 4.17E+05 | 8.47E+06 | 46.02% | 75.25% | 45.69% |
| | | Vial 5 | 6.39E+07 | 6.24E+05 | 7.25E+06 | 47.18% | 72.02% | 44.49% |
| W-45 Thaw Bags | 5 May 2020 | Bag 1 | 4.86E+07 | 1.40E+06 | 7.83E+06 | 50.04% | 90.04% | 33.56% |
| | | Bag 2 | 2.07E+07 | 5.49E+05 | 3.24E+04 | 47.54% | 88.05% | 28.15% |
| | | Bag 3 | 1.89E+07 | 4.41E+05 | 3.15E+06 | 44.51% | 82.06% | 24.09% |

Colony Forming Unit Assay

| Sample | Concentration | Average BFU-E/10^5 | Average CFU-GM/10^5 | Average CFU-GEMM/10^5 | Average Total/10^5 | Comments |
|---|---|---|---|---|---|---|
| W-45 Fresh | Low | 130 | 290 | 35 | 455 | N/A |
| | High | — | — | — | — | Over-plated |
| W-45 Thaw Vial 1 | Low | 0 | 0 | 0 | 0 | N/A |
| | High | 85 | 80 | 0 | 165 | N/A |
| W-45 Thaw Vial 2 | Low | 0 | 0 | 0 | 0 | N/A |
| | High | 55 | 65 | 15 | 135 | N/A |
| W-45 Thaw Vial 3 | Low | 50 | 0 | 0 | 50 | N/A |
| | High | 65 | 60 | 0 | 125 | N/A |
| W-45 Thaw Vial 4 | Low | 0 | 0 | 0 | 0 | N/A |
| | High | 95 | 60 | 5 | 160 | N/A |
| W-45 Thaw Vial 5 | Low | 0 | 50 | 0 | 50 | N/A |
| | High | 65 | 65 | 5 | 135 | N/A |
| W-45 Thaw Bag 1 | Low | 50 | 0 | 0 | 50 | N/A |
| | High | 40 | 45 | 0 | 85 | N/A |
| W-45 Thaw Bag 2 | Low | 100 | 50 | 0 | 150 | N/A |
| | High | 75 | 95 | 10 | 180 | N/A |
| W-45 Thaw Bag 3 | Low | 0 | 150 | 0 | 150 | N/A |
| | High | 80 | 60 | 15 | 145 | N/A |

TABLE 18

Donor W437520000046 Thaw Data

Flow Cytometry

| ID | Date Tested | Sample ID | Abs CD45+/mL | Abs CD34+ HSPC/mL | Abs CD3+/mL | Viable CD45+ | Viable CD34+ HSC | Viable CD3+ |
|---|---|---|---|---|---|---|---|---|
| W-46 Fresh | 28 Mar. 2020 | QC2 | 3.20E+08 | 3.68E+06 | 3.36E+07 | 90.17% | 96.86% | 60.65% |
| | | QC3 | 1.28E+08 | 1.36E+06 | 1.04E+07 | 78.42% | 97.92% | 55.92% |
| W-46 Thaw 2 mL Vials | 19 May 2020 | Vial 1 | 5.13E+07 | 4.68E+05 | 5.49E+06 | 81.32% | 95.51% | 80.43% |
| | | Vial 2 | 5.22E+07 | 4.59E+05 | 5.94E+06 | 43.88% | 94.40% | 64.17% |
| | | Vial 3 | 3.51E+07 | 2.43E+05 | 4.41E+06 | 45.05% | 93.54% | 54.71% |
| | | Vial 4 | 4.41E+07 | 4.50E+05 | 5.13E+06 | 37.95% | 79.42% | 37.97% |
| | | Vial 5 | 4.05E+07 | 5.13E+05 | 4.86E+06 | 37.83% | 73.44% | 39.97% |
| | | Vial 6 | 4.68E+07 | 4.86E+05 | 5.58E+06 | 35.60% | 87.21% | 44.43% |
| W-46 Thaw Bags | 9 Jun. 2020 | Bag 1 | 5.67E+07 | 7.20E+05 | 6.48E+06 | 51.69% | 70.87% | 66.61% |
| | | Bag 2 | 5.04E+07 | 7.29E+05 | 6.21E+06 | 51.03% | 80.24% | 57.68% |
| | | Bag 3 | 3.96E+07 | 5.59E+05 | 5.22E+06 | 55.30% | 79.34% | 62.43% |

Colony Forming Unit Assay

| Sample | Concentration | Average BFU-E/10^5 | Average CFU-GM/10^5 | Average CFU-GEMM/10^5 | Average Total/10^5 | Comments |
|---|---|---|---|---|---|---|
| W-46 Fresh | Low | 130 | 150 | 20 | 100 | N/A |
| | High | — | — | — | — | Over-plated |

TABLE 18-continued

Donor W437520000046 Thaw Data

| | | | | | | |
|---|---|---|---|---|---|---|
| W-46 Thaw | Low | 0 | 50 | 0 | 50 | N/A |
| Vial 1 | High | 50 | 40 | 0 | 90 | N/A |
| W-46 Thaw | Low | 400 | 50 | 0 | 450 | N/A |
| Vial 2 | High | 60 | 35 | 5 | 100 | N/A |
| W-46 Thaw | Low | 50 | 150 | 50 | 250 | N/A |
| Vial 3 | High | 45 | 25 | 10 | 80 | N/A |
| W-46 Thaw | Low | 0 | 200 | 0 | 200 | N/A |
| Vial 4 | High | 40 | 35 | 0 | 75 | N/A |
| W-46 Thaw | Low | 0 | 50 | 0 | 50 | N/A |
| Vial 5 | High | 45 | 20 | 5 | 70 | N/A |
| W-46 Thaw | Low | 150 | 0 | 0 | 150 | N/A |
| Vial 6 | High | 15 | 35 | 0 | 50 | N/A |
| W-46 Thaw | Low | 0 | 0 | 0 | 0 | N/A |
| Bag 1 | High | 70 | 25 | 0 | 95 | N/A |
| W-46 Thaw | Low | 50 | 50 | 0 | 100 | N/A |
| Bag 2 | High | 25 | 35 | 5 | 65 | N/A |
| W-46 Thaw | Low | 0 | 150 | 0 | 150 | N/A |
| Bag 3 | High | 50 | 20 | 5 | 75 | N/A |

Example 8. CD34+ Cell Enrichment and Buffer Optimization

Miltenyi CD34 reagent system is most commonly used for clinical stem cell isolation, which utilizes a separation column placed in magnetic field to capture magnetic beads conjugated to antibody labeled cells. BM from deceased donors (fresh or thawed) is susceptible to generation of severe cell aggregates during processing using standard method as instructed by the CliniMACS user manual. The aggregates can clot the pre-system filter or the separation column and cause an instrument-related stop of the CliniMACS device. The aggregates can also lead to the loss of target cells.

The deceased donor marrow is unavoidably chilled prior to processing it. Cooling below 10° C. causes platelet activation and speeds up granulocyte half-life, causing a bolus of free DNA in the solution, causing cell aggregation. The MACS buffer is designed for CD34 selection from non-chilled stem cell mobilized and apheresed peripheral blood units. The MACS buffer contains EDTA to deal with higher concentrations of platelets than observed in deceased donor derived bone, to help prevent clotting (which also causes cell aggregation but through a different process). Addition of Benzonase to MACS buffer to clear the free DNA to MACS buffer doesn't work, because there is not enough Mg++ for the enzyme. Addition of Benzonase and Mg++(such as Gluconate) still can't overcome the EDTA. The in-house buffer (#4 on the list) is one way to stabilize the cells for isolation without causing cell aggregation. This has been done largely in preparation for CD34+ cells for organ tolerance studies. Adequate cell yields of 1M CD34+ cells per Kg patient body weight, with very low CD3+ numbers are targeted.

This required developing a buffer to prevent the formation of aggregates.
  Buffer 1: MACS buffer (PBS+0.5% HSA+2 mM EDTA)
  Buffer 2: MACS buffer+20 U/ml Benzonase;
  Buffer 3: MACS buffer+20 U/ml Benzonase+1.5 mMMg Gluconate
  Buffer 4: In-house Labelling stabilization buffer (Plasmalyte+0.5% HSA+10 U/ml Heparin+20 U/ml Benzonase)

Table 19 illustrates the viability, CD45 expression, and CD34 expression of the bone marrow cells processed from chilled or frozen/thawed sample with Buffer 1, 2, 3, or 4. Bone marrow cells isolated via Buffer 2, 3, or 4 have shown various improvements in viability or CD45 expression. 750 ul of bone marrow sample was used with each buffer.

TABLE 19

Comparison of Bone Marrow Cells Processed with Buffer 1, 2, 3, and 4

| | Buffer 1 | Buffer 2 | Buffer 3 | Buffer 4 |
|---|---|---|---|---|
| Purity % in CD45 | 52.3 | 57.5 | 18.44 | 44.2 |
| Viability % | 96.9 | 98.6 | 94.2 | 91 |
| CD3 % in CD45 | 7.3 | 6.5 | 16.2 | 3.4 |
| Absolute count of viable CD34 x$10^4$ | 2.1 | 1.5 | 6.3 | 8.3 |

Figure 17A:
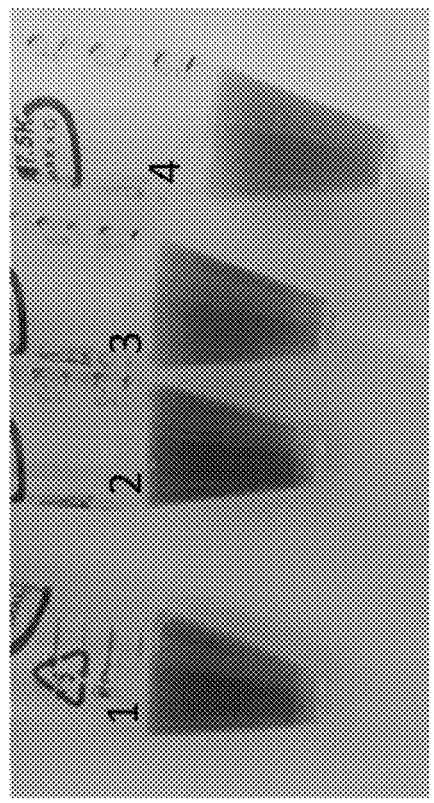
FIG. 17A-17E illustrate the prevention of formation of aggregates when the bone marrow cells were processed from chilled sample with the stabilization buffer.
Figure 17B:
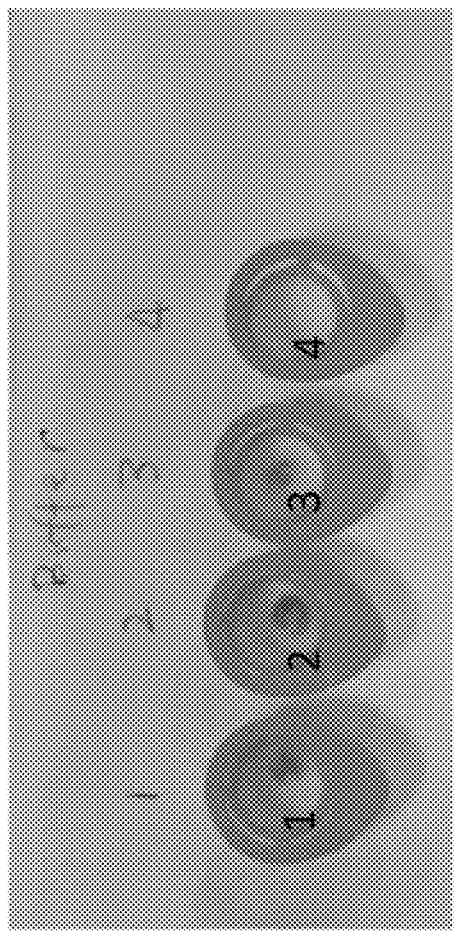
Figure 17C:
Figure 17D:
Figure 17E:
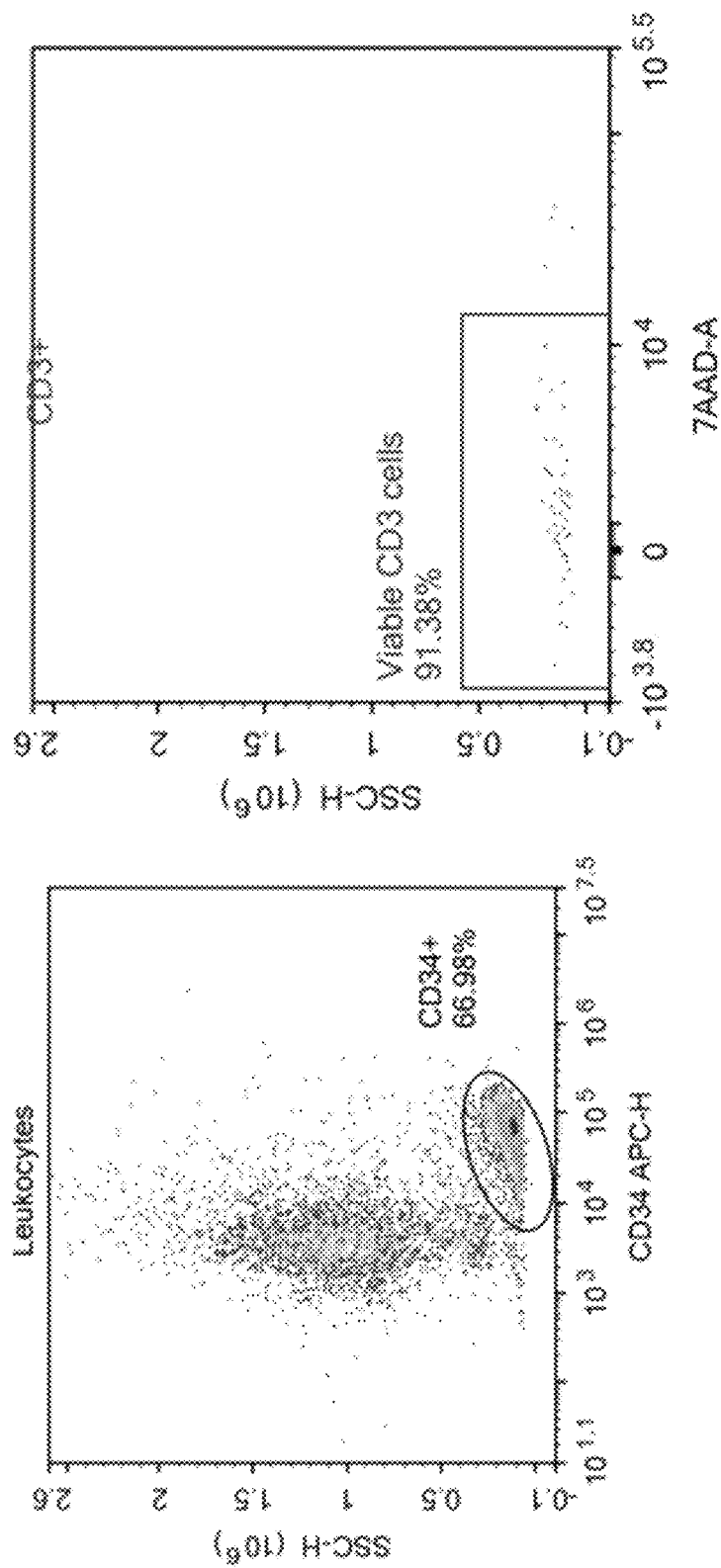
Figure 18:
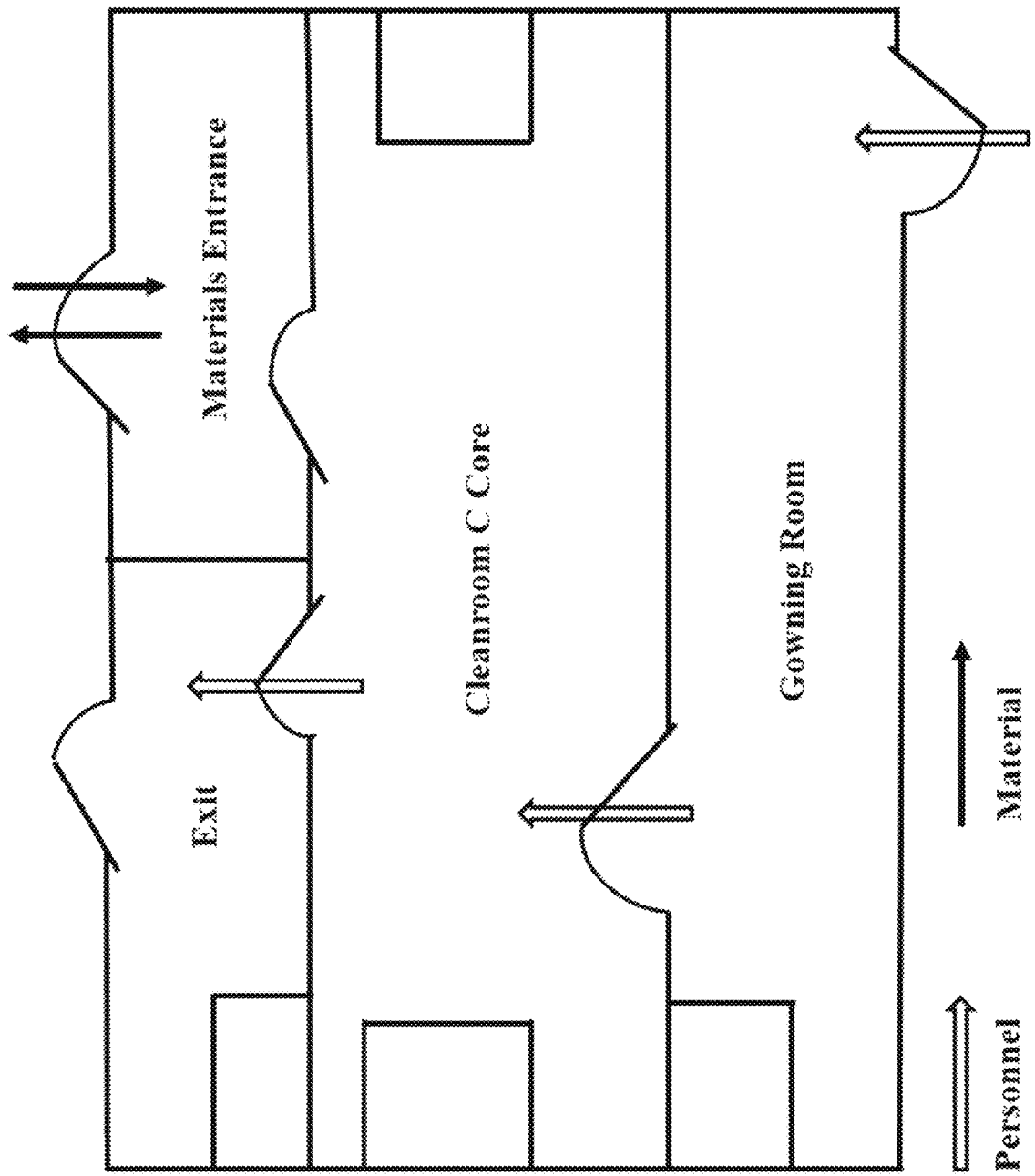
FIG. 18 illustrates an exemplary cleanroom diagram for the Cleanroom C in Example 9.

FIG. 18 illustrates the prevention of formation of aggregates when the bone marrow cells were processed from chilled sample with the stabilization buffer. FIG. 17A shows the bone marrow cells slurry after antibody labeling. The numerical numbering corresponds to the buffer used. Bone marrow cell sample processed with the stabilization buffer (4) exhibited absence of aggregates. FIG. 17B shows lack of aggregate being trapped after filtration in the bone marrow cell sample processed with the stabilization buffer. FIG. 17C and FIG. 17D illustrates the formation of aggregates of bone marrow cells processed with CliniMACS buffer (FIG. 17C) or absence of aggregates of bone marrow cells processed with the stabilization buffer (FIG. 17D). FIG. 17E shows that the bone marrow cells processed with the stabilization buffer exhibited increased yield of viability and CD34 expression of bone marrow cells.

Example 9. Thawing of Cryopreserved Bone Marrow Samples

Described herein is an exemplary procedure for thawing cryopreserved bone marrow (BM). In some cases, the procedure can be for thawing cryopreserved BM bags and vials for testing. In some instances, when thawing bags or vials (e.g. clinical process validations, clinical development, etc.), it can be used to thawing of bone marrow product or thawing of bone marrow vials.
  A. Preparation
    1) Prepare Rinse Media per Example 1. Obtain at least 5 mL of Rinse Media per sample.
    2) Prepare a biosafety cabinet (BSC). Ensure all supplies are in the BSC prior to beginning the thaw. Label a 150 mL bottle or a 50 mL conical tube with ISBT donor #, bag #, and final dilution factor (DF=3).
3) Ensure a water bath has sufficient water (1 inch from top) and is prewarmed to 37±1° C. Place the water bath within a few feet of the storage location.

B. Thawing
1) Initiate and complete thawing of bone marrow product or bone marrow vials.
2) Locate the desired cryopreserved sample in the storage location and indicate which location samples will be removed from (−86° C. or vapor nitrogen). Minimize the number of vials and bags thawed at once to ensure timely and accurate completion of the procedure.
3) Remove samples from inventory.
4) For bags, remove the sample from the cassette and immediately submerge in water bath.
5) For bags: Touch bag gently while submerged. Avoid forcibly cracking ice in bag. Continue just until a few small pieces of ice remain. Remove from the water bath. Record time removed from water bath and immediately take the temperature using an IR thermometer.
6) For vials: Swirl and mix sample while submerged to ensure even thawing. Continue until the last visible ice melts. Remove from the water bath. Never allow samples to sit in bath after thawing.

C. Dilution
1) Spray the sample container with ethanol and place in BSC. All of the remaining steps will be performed in a BSC.
2) For bags: Remove the cap from the bottle or conical tube. Spray and wipe scissors with 70% ethanol. Cut BM bag tubing and drain into bottle or tube. Remove a 1 mL sample using a micropipette and transfer to a 5 mL or 15 mL conical tube.
3) For vials: Transfer entire 1 mL sample volume using a micropipette and transfer to a 5 mL or 15 mL conical tube.
4) Start a timer. Using Rinse Media, add 10% of the 1 mL sample volume (100 μL) each minute for 10 minutes.
5) Add another 1 mL of Rinse Media all at once to the same sample above. The final dilute sample volume is 3 mL (DF=3).

D. Sampling
1) Flow Cytometry Sample
  1. In a microcentrifuge tube, add 200 μl, of thawed dilute cells (DF=3) and 400 μl, of Rinse Media. Label with donor ID, sample ID, flow, non-sterile (NS), and DF=9.
  2. Count NS sample per TNC Quantitation of Thawed Bone Marrow Using the Sysmex XP-300 Hematology Analyzer to obtain counts on the Sysmex XP-300.
  3. Record Sysmex result of thawing of bone marrow product or thawing of bone marrow vials.
  4. Use the remaining NS sample for flow cytometry analysis for Bone Marrow Staining for CD45, CD34, and CD3 markers using flow cytometry.
2) CFU Sample
  1. In 15 mL conical tube, add 100 μL of cells and 9.9 mL of Rinse Media. Label with donor ID, sample ID, CFU, sterile, and DF=300.
  2. Remove a 500 μL aliquot and label with donor ID, sample ID, CFU, NS, and DF-300.
  3. Count NS sample. Record count and calculate volumes.
  4. Perform the CFU assay per Colony Forming Unit Assay for Cryopreserved Bone Marrow.

Example 10. Process Design for Cadaveric Donor HPC, Marrow Production

Described herein is an exemplary design of process improvements to the production of HPC, Marrow from deceased donor vertebral bodies.

Colorado Custom Fab (CCF) Bone Grinder: The validated process for HPC, Marrow utilized a cancellous bone grinder manufactured by Biorep. This grinder had a large motor that would take up half of the workspace in the BSC. A custom BSC was designed so that the motor was on a cart outside the BSC and only the front side with the cutting attachments was pushed through an opening in the side of the BSC. The Biorep grinder is purpose-built prototype device that is not adequate for sustained, industrial scale use and requires more preventative maintenance. During routine use, the Biorep attachments are easily damaged. The CCF grinder, while also purpose-built, is based on a platform utilized throughout the world for bone processing in industrial cGMP settings. The CCF was evaluated and compared to the Biorep grinder to verify that a comparable number of cells are recovered from each piece of equipment for VBs from the same donor (see attached report). This is a positive change because the CCF grinders will be less expensive and can withstand repeated use with minimal maintenance. They are smaller and weigh less than the Biorep grinders, facilitating human factors engineering by making them easier to move in and out of the BSC. CCF grinders can be inside the BSC during use and can be removed easily after use to free up workspace for the remainder of the process. The CCF grinder also grinds VBs more efficiently, decreasing the process time of bone marrow extraction.

Freezing Method: Currently in the validated process for HPC, Marrow, 65±5 mL bags of HPC, Marrow are placed in freezing cassettes and then placed in Smartcool boxes for a 2-step cryopreservation process involving passive cooling to −86° C. freezer followed by plunging into LN2 vapor phase for long term storage. The vials of HPC, Marrow are placed in a CoolCell LX passive cooling container in a pre-cooled Instapak box, and then placed in the −86° C. freezer. It has been noted that the QC vials often outperform bags post thaw with respect to viability testing, likely due to the volume and container differences that impact the cooling rate. To increase the post-thaw viability of the HPC, Marrow product and the consistency in viability between bags and vials, experiments were conducted where the bags were placed in cassettes only then put directly on the shelf of the −86° C. freezer without a SmartCool box. Several trial runs were executed to show that the increased cooling rate resulted in increased cell viability post-thaw and more consistency between bags and vials (see attached report). This is a positive change because it will increase cell viability post-thaw, result in more consistent viability between bags and vials so that vials may be used as a surrogate for the bags, and eliminate the need to use and maintain the SmartCool boxes.

Orbital Shaker: In the validated HPC, Marrow process, all the bone grindings were poured into the collection container of the Bone Marrow Collection Kit after grinding was complete. The collection container of the bone marrow collection kit was massaged to agitate the grindings with each rinse; however, this method is inherently variable and does not ensure maximum yield. To maximize cell yield at this step, an orbital shaker will be used to agitate the grindings for a specific time and speed for each rinse. This is a positive change because it will maximize yield and increase the average number of bags produced per donor (see attached report).

Figure 19:
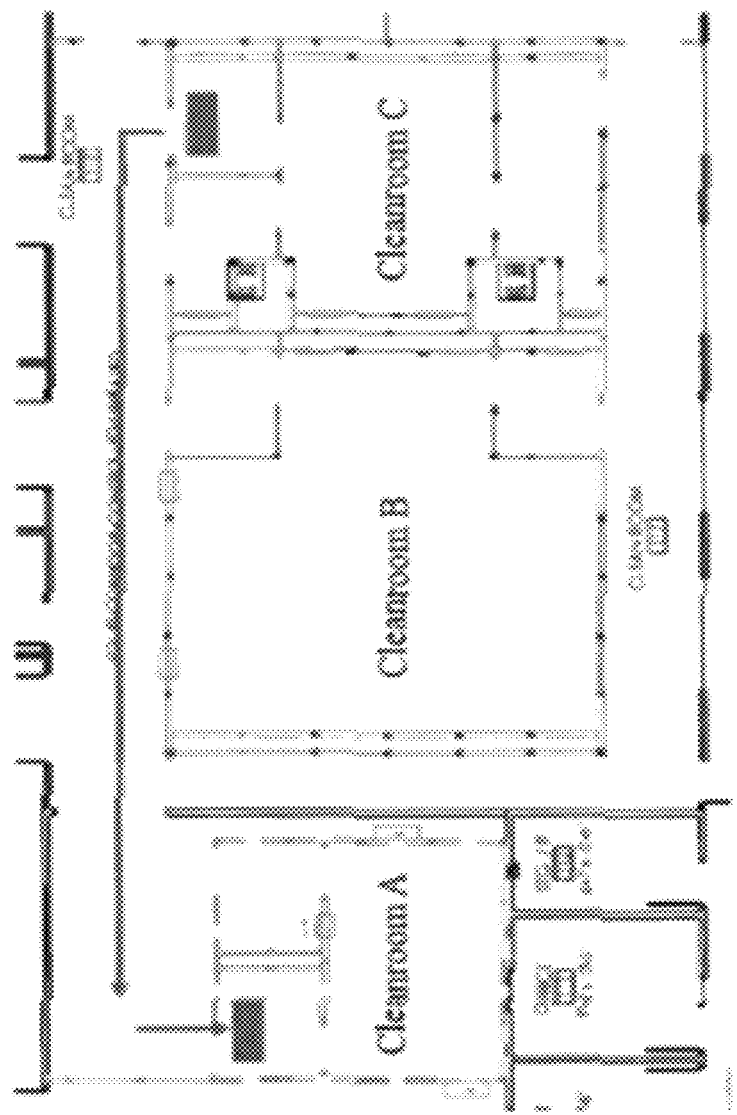
FIG. 19 illustrates an exemplary cleanroom workflow for decontamination of VBs as described in Example 9.

Workflow change for Tissue Debriding and Surface Decontamination: Currently, the entire validated process for HPC, Marrow is done in a single cleanroom (Cleanroom A). The results have been tracked and trended since the initial validation was completed. In some cases, the same organisms are present on the OPO swab and in the final product, but not on the swabs after surface decontamination. These cases suggest that the bone grindings or bone marrow extract is being re-contaminated after the VBs are soaked in bleach. To mitigate this risk, vertebral bodies will be debrided in one cleanroom (Cleanroom C, see FIG. 18 and Table 20), placed in two layers of sterile bags with 10% bleach solution, then transferred to a different cleanroom (Cleanroom A) for the rinsing with hydrogen peroxide and the remaining process. The inner and outer bag of VBs will be cleaned with Peridox before leaving the first cleanroom, then cleaned with 70% IPA before placement in the BSC in the second cleanroom. FIG. 19 shows the path that the support tech will take to bring the bag of VBs from Cleanroom C materials entrance to Cleanroom A materials entrance. This is a positive change because it will allow the pre-surface decontamination part of the process to be done in a separate room by separate staff and reduce the potential for recontamination of the product with contaminated equipment or gowning.

TABLE 20

Cleanroom C Sampling Sites

| Sampling Type | Room | Location | Site Code |
|---|---|---|---|
| Viable Air | Core | East side of room | A24 |
| Viable Air | Core | North side of room | A25 |
| Viable Air | Core | South side of room | A26 |
| Viable Air | Gowning Room | Center of gowning room | A27 |
| Viable Air | Materials Entrance | Center of gown out room | A28 |
| Viable Air | Exit Room | Center of materials | A29 |

TABLE 20-continued

| Viable Air | Support Area | Outside materials entrance | A30 |
|---|---|---|---|
| Particle Count | Core | BSC- Process Start | P19 |
| Particle Count | Core | BSC- Middle of Process | P20 |
| Particle Count | Core | BSC- End of Process | P21 |
| Particle Count | Core | East side of room | P22 |
| Particle Count | Core | North side of room | P23 |
| Particle Count | Core | South side of room | P24 |
| Particle Count | Gowning Room | Center of gowning room | P25 |
| Particle Count | Materials Entrance | Center of gown out room | P26 |
| Particle Count | Exit Room | Center of materials entrance | P27 |
| Surface | Core | Center of BSC tray | S24 |
| Surface | Core | Table | S25 |
| Surface | Gowning Room | Gowning Bench | S26 |
| Surface | Core | South wall near BSC | S27 |
| Surface | Core | North wall near BSC | S28 |
| Surface | Core | Door to gowning room | S29 |
| Surface | Core | Door to materials entrance | S30 |
| Surface | Core | Floor in center of room | S31 |
| Surface | Gowning room | Floor in center of room | S32 |
| Surface | Materials entrance | Floor in center of room | S33 |
| Surface | Exit | Floor in center of room | S34 |

Increased Centrifuge Speed and Duration: To further optimize cell yield, the centrifuge will be set to a higher speed (600×g instead of 500×g) and the time of centrifugation increased to 30 minutes per run instead of 15 minutes. Donors processed in the pilot runs with the new centrifuge parameters resulted in an increase in the average TNC per gram of bone compared to the groups with only the shaker improvement (Table 21). Since TNC and CD34+ absolute count and viability is inherently variable between donors, these results were tracked and trended following the process change to confirm that there is no negative impact to cell viability with a larger data set.

TABLE 21

Pilot Run Data of Increased Centrifuge Speed and Duration

| Process | Donor ID | Mass (g) | QC2 Sysmex TNC/g bone | QC2 Sysmex TNC Average | QC3 Sysmex TNC/g bone | QC3 Sysmex TNC Average |
|---|---|---|---|---|---|---|
| Before process improvements | Multiple* | Avg: 300 | N/A | 1.30E08 | N/A | 1.38E08 |
| Shaker Only | W437520000122 | 290 | 1.38E+08 | 1.50E+08 | 1.32E+08 | 1.44E+08 |
| Shaker Only | W437520000131 | 218 | 1.39E+08 | | 1.56E+08 | |
| Shaker Only | W437520000133 | 258 | 1.72E+08 | | 1.45E+08 | |
| Shaker + Centrifuge | W437520000137 | 244 | 1.72E+08 | 1.56E+08 | 1.6E+08 | 1.55E+08 |
| Shaker + Centrifuge | W437520000139 | 164 | 1.62E+08 | | 1.45E+08 | |
| Shaker + Centrifuge | W437520000149 | 308 | 1.33E+08 | | 1.60E+08 | |

*43 donors processed without the process improvements

Establishing a Strategy for Process Control:
1) The process knowledge established in Example 1 formed the basis for the overall process control strategy. Strategies for process control were designed in the previous process design and validation to reduce variation in the starting material (deceased donor vertebral bodies) and variation during processing (design of custom equipment, in-process calculations to account for variable cell yield between donors, etc.) to reduce the variability of the final product. These process improvements further reduce variation during processing:
   1. Variation in cell yield is reduced between staff members due to how many times and how firmly they massage the grindings. The orbital shaker will ensure that the grindings are sufficiently agitated during each rinse to maximize cell yield.
   2. Variation in cell viability between bags and vials is reduced by freezing the cassettes without the Smart-cool boxes.
2) Production staff performed 3 pilot runs with all changes except the centrifuge parameters, then 3 additional runs were performed with all changes described in this report. These pilot runs provided adequate training for staff members on the process changes. In addition to the pilot runs, staff was separately trained on the operation, cleaning, and maintenance of the CCF grinder and orbital shaker.

Example 11. Irradiated NSG Mouse Xenotransplantation with HPC, Marrow CD34+ Cells Described herein is an exemplary experiment to evaluate engraftment of HPC, Marrow CD34-selected hematopoietic stem and progenitor cells in the immunocompromised NOD.Cg-Prkdc$^{scid}$ IL2r$\gamma^{tm1Wjl/Sz}$ (NSG) mouse model. The experiment and its data determined whether HPC, Marrow possesses hematopoietic cells capable of engrafting long-term and producing mature blood cells.

Acronyms

NSG mice: NOD.Cg-Prkdc$^{scid}$ IL2r$\gamma^{tm1Wjl/Sz}$. A mouse strain genetically engineered to lack a functional IL2 receptor, resulting in the inability to produce mature lymphocytes. The strain was developed and is distributed by Jackson Laboratories.

CD34: a cell surface epitope found on human hematopoietic stem and progenitor cells HSPC: an acronym for hematopoietic stem and progenitor cells.

EasySep system: immunomagnetic microbeads coated with an antibody specific for the CD34 protein. Manufactured by Stem Cell Technologies.

CliniMACs: a semiautomated closed system for immunomagnetic selection of CD34+ cells.

Ficoll-Paque PLUS: a sterile medium containing Ficoll PM400, sodium diatrizoate and disodium calcium EDTA with a density of 1.077 g/mL. Ficoll was manufactured by GE Healthcare companies.

HSA: human serum albumin.

Plasma-Lyte A: Plasma-Lyte A Injection pH 7.4 (Multiple Electrolytes Injection, Type 1, USP) is a sterile, nonpyrogenic isotonic solution.

DMSO: A solution of 10% DMSO, 2.5% HSA in Plasma-Lyte A.

Cryopreservation medium: Grinding and elution with 1 volume of Grind Media.

Umbilical cord blood CD34+ cells: a positive control for functional human CD34+ HSPC commonly used in NSG xenotransplantation studies.

Bone marrow engraftment studies were performed in the immunocompromised NOD.Cg-Prkdc$^{scid}$ IL2r$\gamma^{tm1wjl}$/Sz (NSG) mouse model. The NSG mouse is a widely used model to study the in vivo function of human cells. HPC, Marrow was recovered from VBs of two donors and processed to enrich for CD34+ cells by immunomagnetic bead separation. Donor AGGU049 BM was processed fresh using the EasySep system (Stem Cell Technologies). Donor AGEJ150 BM was thawed from cryopreservation and processed using the CliniMACS system. Control CD34+ cells were selected from umbilical cord blood (UCB) from donor C141019000564 (obtained from GenCure) using the EasySep system. Selected cells were characterized by flow cytometry to ensure that both CD34+ cell purity and viability were >90%. Selected CD34+ cells were resuspended in cryopreservation medium, controlled rate cooled to −86° C. and cryopreserved in vapor phase liquid nitrogen. Thus, CD34-selected cells from donor AGGU049 were cryopreserved once, whereas CD34-selected cells from donor AGEJ150 were cryopreserved twice prior to testing.

A total of 25 Female NSG mice (6-10 weeks old) were irradiated with a sublethal dose (300 cGy). Mice were assigned to receive CD34-selected cells from either BM (2 groups of 10 mice each) or umbilical cord blood (1 group of 5 mice). A third non-irradiated group (3 mice) was untreated to serve as an antibody staining control. CD34+ cells were thawed and administered by intravenous injection at approximately 4 hours after irradiating. Doses of CD34+ cells were $5 \times 10^5$ (BM) and $1.5 \times 10^5$ (UCB). Peripheral blood was withdrawn at 8 weeks for an interim analysis of human cell engraftment using a human-specific CD45 antibody. The endpoint for the study would be 16 weeks, when all animals would be bled and sacrificed to collect bone marrow, spleen and thymus for analysis of human cell engraftment and function.

Figure 20:
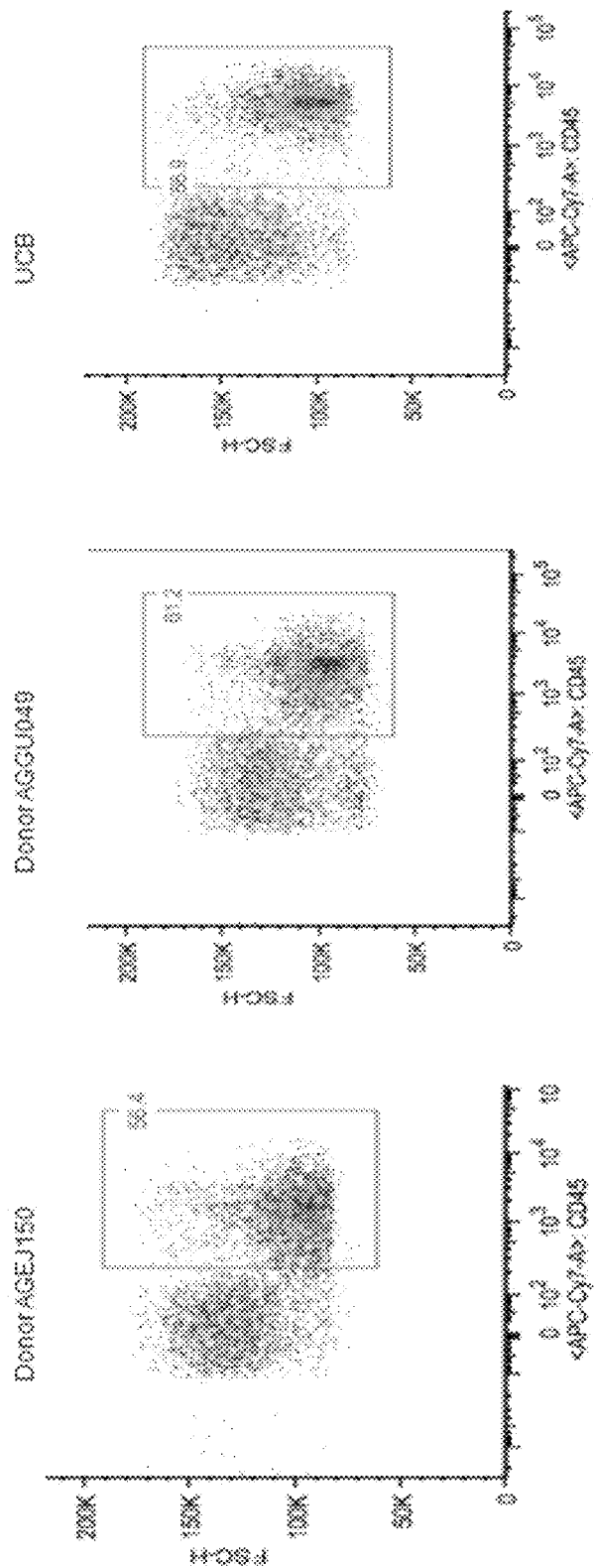
FIG. 20 illustrates an exemplary flow cytometry plots of human CD34+ in blood at 8 weeks.

Results of the 8 week interim analysis demonstrated robust engraftment of human CD34+ cells in the NSG mice as determined by levels of circulating leukocytes staining positive for the human-specific CD45 antibody (Table 22). The results demonstrated that an average of 47.5% and 61.4% circulating leukocytes cells in mice treated with BM CD34+ cells were human origin, compared to 43% for the human UCB CD34+ cells (positive control). A low level (10%) of non-specific binding of the human CD45 antibody was observed in the non-irradiated, untreated controls. Representative flow cytometry plots of human CD45+ percentage in the blood of animals treated with each CD34+ cell preparation are shown in FIG. 20.

TABLE 22

| Levels of chimerism in mouse blood at 8 weeks after CD34+ cell treatment | |
|---|---|
| CD34 cell source | Positivity for Human CD45+ (% leukocytes; mean ± sd) |
| UCB | 42.9 ± 20.1 |
| Human BM AGEJ150 | 61.4 ± 18.3 |
| Human BM AGGU049 | 47.5 ± 10.0 |
| Non-irradiated, untreated controls | 10.2 ± 6.3 |

Example 12. HPC, Marrow Compared to Living Donor Aspirated Bone Marrow

Described herein is an exemplary experiment to compare the numbers and activity of hematopoietic stem and progenitor cells in fresh whole bone marrow from living and deceased donors selected for. The experiment and its data can be used to determine whether HPC, marrow possesses functional hematopoietic cells as compared to living donor BM.

Acronyms

7-Aminoactinomycin D (7-AAD): a membrane impermeable dye that is excluded from viable cells but crosses the membrane of necrotic and apoptotic cells. Once the dye is intracellular, it intercalates within the DNA and is easily identified by flow cytometry using an argon (488 nm) laser and a red wavelength detector (~647 nm).
BM: bone marrow.
CD3: a cell surface epitope found on T lymphocytes.
CD34: a cell surface epitope found on human hematopoietic stem and progenitor cells.
CD45: an antigen is present on all human leukocytes, including lymphocytes, monocytes, granulocytes, eosinophils, and basophils. It has a role in signal transduction and is weakly expressed on hematopoietic progenitor cells.
HSPC: An acronym for hematopoietic stem and progenitor cells.
CFU: colony forming unit.
CFU-GM: CFU-granulocyte/macrophage.
CFU-total: total CFUs comprising, CFU-GM, CFU-granulocyte/erythroid/macrophage/megakaryocyte (GEMM), and burst-forming units-erythroid (BFU-E).

Experimental Method/Results

HPC, Marrow was recovered from VBs of six deceased donors. Whole bone marrow was aspirated from three living donor iliac crests and was purchased from Lonza (Walkersville, Md., USA). Donor information is shown in Table 23.

TABLE 23

| Donor used for studies of HPC, Marrow Compared to Living Donor Aspirated Bone Marrow | | | | | |
|---|---|---|---|---|---|
| Ossium | | | Lonza | | |
| Donor | Age | Sex | Donor | Age | Sex |
| AGEJ150 | 19 | M | LBM1 | 20 | F |
| AGCA414 | 30 | M | LBM2 | 23 | F |
| AGDQ072 | 24 | M | LBM3 | 28 | M |
| AGB2425 | 25 | M | | | |
| AGDZ004 | 26 | M | | | |
| AGBE058 | 25 | M | | | |

Figure 21:
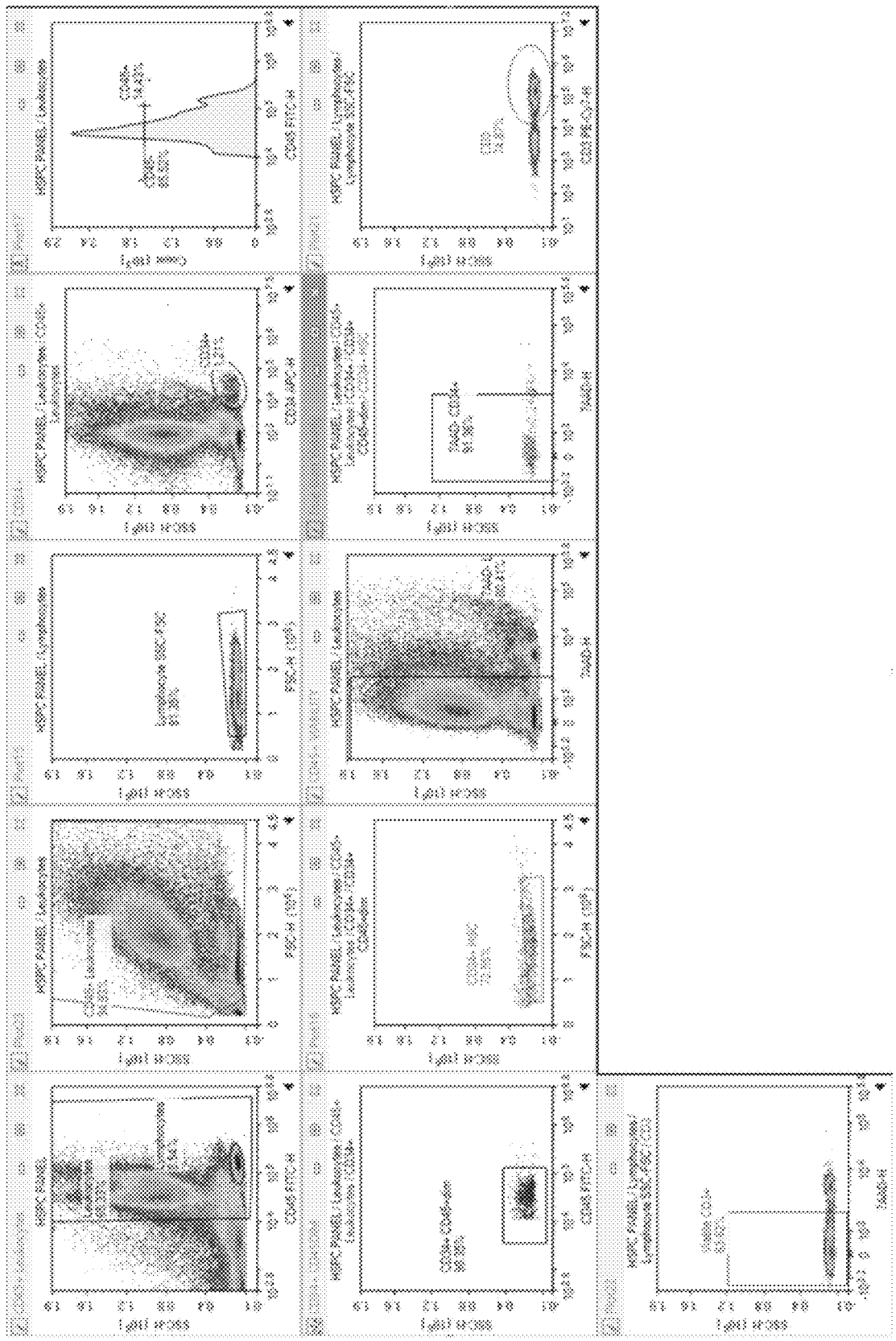
FIG. 21 illustrates gating strategy used to determine phenotypes of BM cells isolated from deceased and living donors.
Figure 22:
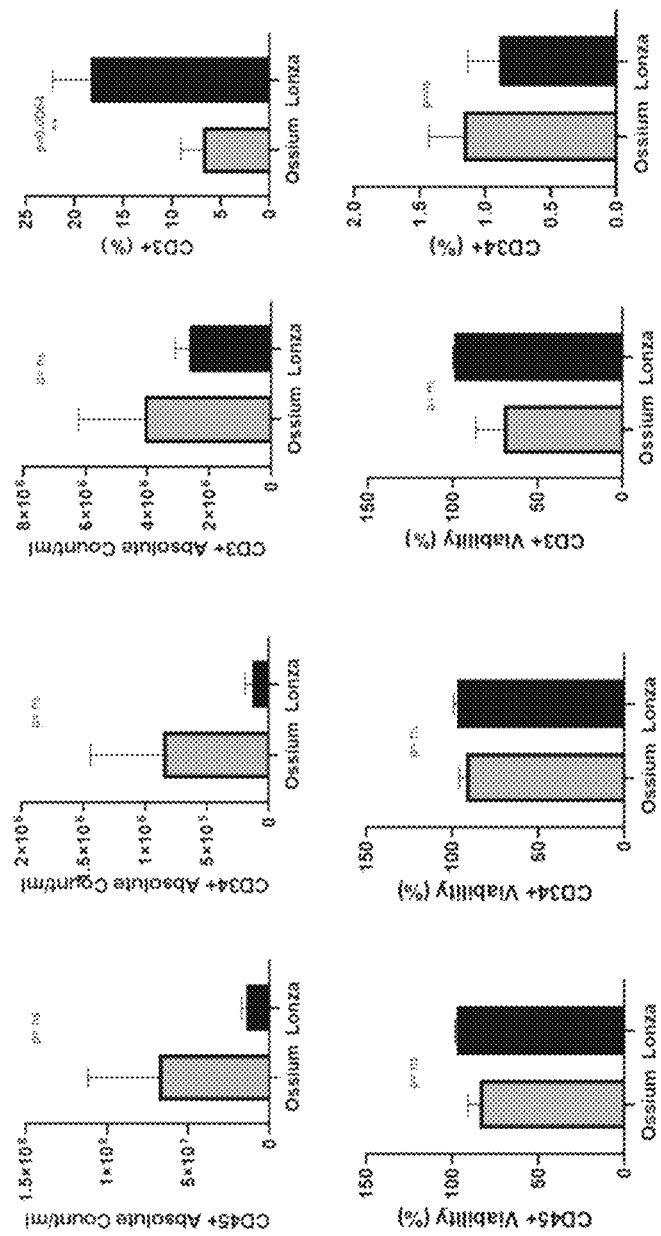
FIG. 22 illustrates relative and absolute values for CD45+ leukocytes, CD34+ HSPC and CD3+ T cells in living versus deceased donor BM. Bars represent averages +/−standard deviations.

Cells were stained with fluorescent dye-conjugated antibodies to CD45, CD34 and CD34 and analyzed by flow cytometry. Gating strategies are shown in FIG. 21. Average numbers and percentages of cell types are shown in FIG. 22 and Table 24. The absolute as well as relative numbers of CD45+ leukocytes and CD34+ HSPC in BM from the 3 living donors was not significantly different than the 3 deceased donor BM specimens (donors AGEJ150, AGCA414 and AGDQ072). The only significant difference observed was the higher relative percentage of CD3+ T cells in living versus deceased donor BM (FIG. 22).

TABLE 24

| Flow cytometric comparison of HPC, Marrow and living donor bone marrow (average and standard deviations (SD) are shown) | | | | | | | | | | |
|---|---|---|---|---|---|---|---|---|---|---|
| Source | Ossium | | | | | Lonza | | | | |
| Donor | AGEJ150 | AGCA414 | AGDQ072 | Average | SD | LBM1 | LBM2 | LBM3 | Average | SD |
| Total CD3+ | 7.21E+08 | 4.11E+09 | 5.91E+08 | 1.81E+09 | 2.00E+09 | 2.97E+07 | 2.85E+07 | 2.10E+07 | 2.64E+07 | 4.69E+06 |
| Total CD34+ | 1.53E+08 | 3.78E+08 | 1.56E+08 | 2.29E+08 | 1.29E+08 | 1.91E+06 | 7.76E+05 | 1.31E+06 | 1.33E+06 | 5.68E+05 |
| Total CD45+ | 1.23E+10 | 4.37E+10 | 1.12E+10 | 2.24E+10 | 1.84E+10 | 1.77E+08 | 1.25E+08 | 1.35E+08 | 1.45E+08 | 2.78E+07 |
| CD3+ (%) | 5.81% | 9.45% | 5.27% | 6.85% | 2.27% | 16.78% | 22.80% | 15.56% | 18.38% | 3.88% |
| CD34+ (%) | 1.23% | 0.87% | 1.39% | 1.16% | 0.27% | 1.08% | 0.62% | 0.97% | 0.89% | 0.24% |
| CD3+ Viability (%) | 88.48% | 63.62% | 57.00% | 69.70% | 16.60% | 99.61% | 99.36% | 98.98% | 99.32% | 0.32% |
| CD34+ Viability (%) | 95.95% | 91.36% | 88.00% | 91.77% | 3.99% | 98.70% | 97.55% | 94.69% | 96.98% | 2.06% |
| CD45+ Viability (%) | 91.67% | 80.41% | 80.00% | 84.03% | 6.62% | 97.80% | 98.01% | 96.86% | 97.56% | 0.61% |
| CD3+ Absolute Count/ml | 6.28E+06 | 2.06E+06 | 3.94E+06 | 4.09E+06 | 2.12E+06 | 2.97E+06 | 2.85E+06 | 2.10E+06 | 2.64E+06 | 4.69E+05 |

TABLE 24-continued

Flow cytometric comparison of HPC, Marrow and living donor bone marrow
(average and standard deviations (SD) are shown)

| Source | Ossium | | | | | Lonza | | | | |
|---|---|---|---|---|---|---|---|---|---|---|
| Donor | AGEJ150 | AGCA414 | AGDQ072 | Average | SD | LBM1 | LBM2 | LBM3 | Average | SD |
| CD34+ Absolute Count/ml | 1.33E+06 | 1.89E+05 | 1.04E+06 | 8.54E+05 | 5.94E+05 | 1.91E+05 | 7.76E+04 | 1.31E+05 | 1.33E+05 | 5.68E+04 |
| CD45+ Leukocyte Absolute Count/ml | 1.08E+08 | 2.18E+07 | 7.47E+07 | 6.80E+07 | 4.32E+07 | 1.77E+07 | 1.25E+07 | 1.35E+07 | 1.45E+07 | 2.78E+06 |
| Total Volume (ml) | 114.73 | 2000 | 150 | — | — | 10 | 10 | 10 | — | — |

Figure 23:
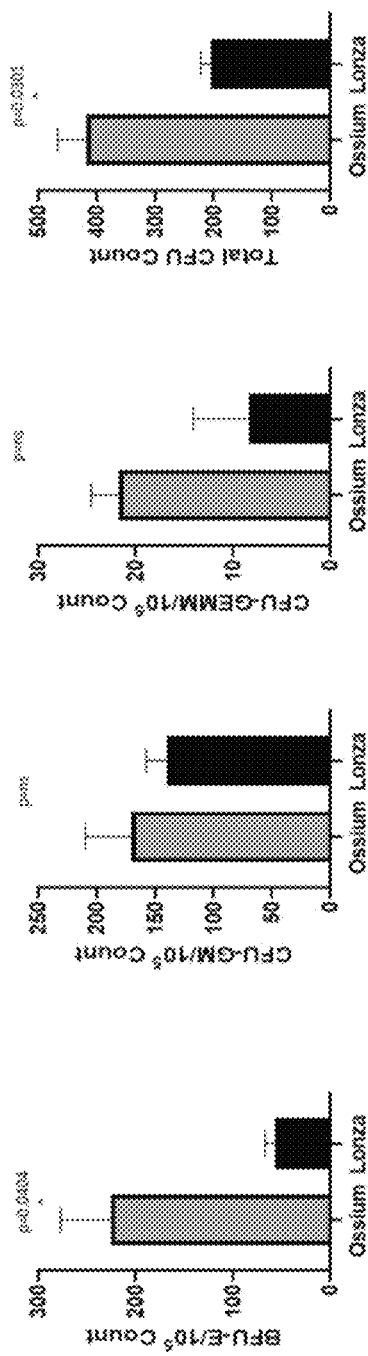
FIG. 23 illustrates CFU potential comparison between HPC, Marrow and living donor BM.

An additional 3 HPC, Marrow donors (AGB2425, AGDZ004, AGBE058) were compared to BM from living donors (Table 23). The total number of CFU as well as BFU-E were significantly higher in HPC, Marrow compared to living donor BM (FIG. 23 and Table 25).

TABLE 25

Average colony forming potential of HPC, marrow and living donor BM (percentage of progenitors for each donor shown as "back calculated progenitor %")

| | Donor | BFU-E/ $10^5$ | CFU-GM/ $10^5$ | CFU-GEMM/ $10^5$ | Total CFU/ $10^5$ | Back Calculated Progenitor % |
|---|---|---|---|---|---|---|
| Ossium | AGDZ004 | 250 | 200 | 20 | 470 | 0.47% |
| | AGB2425 | 260 | 125 | 25 | 410 | 0.41% |
| | AGBE058 | 165 | 185 | 20 | 370 | 0.37% |
| | Average | 225.0 | 170.0 | 21.7 | 416.7 | 0.42% |
| | SD | 52.2 | 39.7 | 2.9 | 50.3 | 0.05% |
| Lonza | LBM1 | 60 | 120 | 15 | 195 | 0.20% |
| | LBM2 | 45 | 145 | 5 | 195 | 0.20% |
| | LBM3 | 65 | 155 | 5 | 225 | 0.23% |
| | Average | 57.6 | 140.0 | 8.3 | 205.0 | 0.21% |
| | Standard Deviation | 10.4 | 18.0 | 5.8 | 17.3 | 0.02% |

Figure 24:
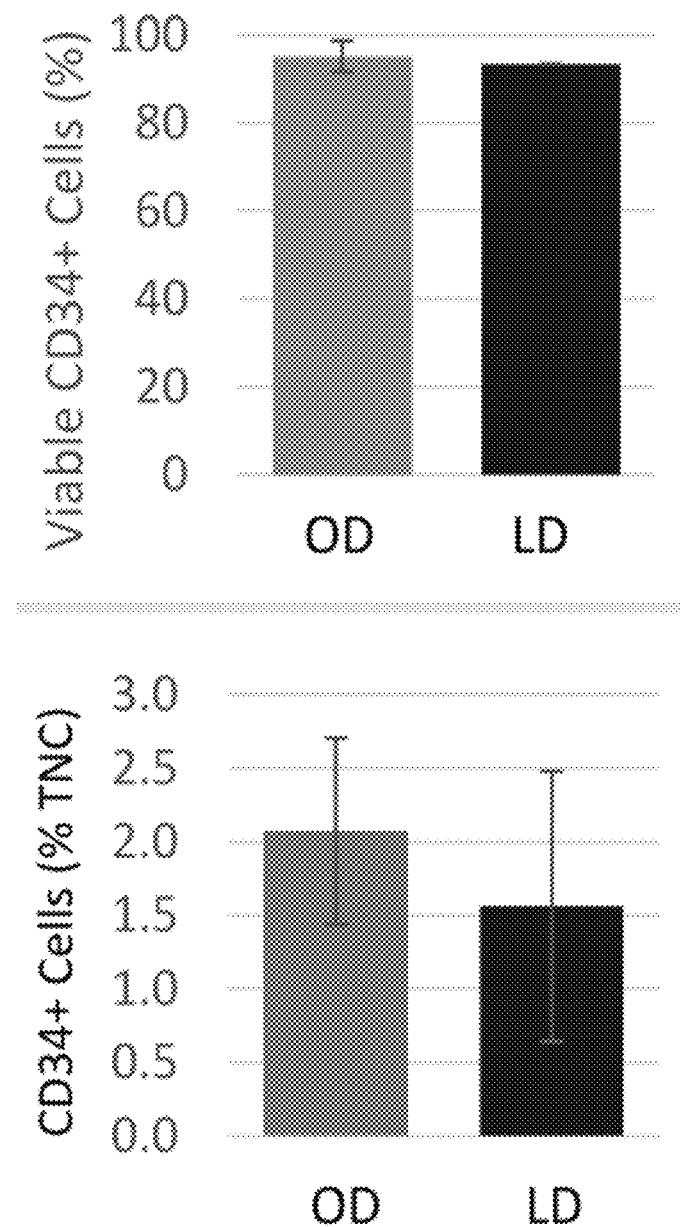
FIG. 24 illustrates similar viability and number of CD34+ HSC isolated from organ donor (OD) and living donor (LD) BM. Means from five studies.

Example 13. Development of Bank of Organ and Tissue Donor Derived while BM and BM-Derived Hematopoietic Stem/Progenitor Cells (HSPCs), Mesenchymal Stem/Stromal Cells (MSCs), and Mature Cells for Medical Purpose Recovery of functional BM from deceased donors is conceptually similar to the procurement of organs and tissues. Published studies have confirmed that stem and progenitor cells within deceased organ donor BM are highly viable and comparable to living donor cells (FIG. 24). The instant disclosure illustrates an development of optimized recovery systems including specialized kits and shippers for uniform recovery by multiple OPO partners and characterization of warm and cold ischemia times for optimum cellular yield. The processing methodology described herein yields highly functionally viable cells from deceased donor BM, with colony forming unit-granulocyte/macrophage (CFU-GM) averaging 170±40 and total CFU averaging 417±50 per $10^5$ total nucleated cells plated as compared to live donor controls that yielded 140±18 and 205±17, respectively (mean±SEM; n=4 experimental and 2 control; live donor BM purchased from Lonza) as well as stable engraftment in a humanized immunocompromised mouse model.

For end user ease, the instant disclosure illustrates packaging HPC, Marrow at 70 mL volumes in 250 mL cryostorage bags. Multiple such units can be prepared from each donor, ranging from 3 to 12 based on the donor size and recovery outcomes. For the bank to service the greatest number of patients, cryopreservation is essential. Bone marrow or mobilized stem cells have been cryopreserved and transplanted for decades, with varying protocols mostly consisting of slow cooling (1-2° C./min) in a cryopreservative of 10% DMSO and storage in vapor phase or liquid nitrogen until prepared for use by rapidly warming, typically in a 37° C. water bath. Controlled rate cooling and passive cryopreservation approaches have both been used with success. To develop the protocol for use as described in the instant disclosure, initially 2 controlled rate cooling methods and a passive approach were considered. The VIA Freeze Quad (Cytiva, Marlborough, Mass., USA) and the CryoMed (ThermoFisher Scientific, Waltham, Mass., USA) were evaluated as controlled rate cooling options, and a passive approach was evaluated utilizing a "box in box" method. The VIA Freeze was adapted to cryopreserve 6 bags at a time to meet the requirements described herein. This initial study indicated no difference among methods, with each yielding high post thaw survival with mean post thaw CD34 viability and CFU-GM equivalent among methods.

Given the scale of production with multiple donors per day each yielding from 3 to 12 cryostorage bags, and the relative simplicity of the process, a version of the passive cooling approach was further investigated and subsequently validated for routine use. For this, an ultracold mechanical freezer (CryoCube F740, Eppendorf, Enfield, N.C., USA) was temperature mapped using a Part-11 compliant data capture system (Ellab Denver, Colo., USA). Preliminary experiments indicated a chamber setting of −86° C. to be optimum for uniform temperatures across each of the 3 freezer shelves. Surrogate bags containing cryoprotectant only (10% DMSO in saline with 2.5% human serum albumin) were prepared, placed into aluminum cassettes, and used in further preliminary experiments which indicated that cooling rates would be faster if cassettes were placed directly against the walls of the freezer but were consistent across the bulk of the shelves (data not shown). An experiment was designed in which surrogate bags were prepared including T-type thermocouples placed in the cryoprotectant solution with an Omega OM-USB-TC data capture system (Omega, Norwalk, Conn., USA) utilized to record freeze curves. The bags were placed in cassettes which were then placed on each shelf of the freezer maintaining a minimum of 11 cm distance from the walls and held for a minimum of 6 hours. The resulting freezing curves were very consistent. Mean cooling rates (MCR) for each bag across a range from −10 to 40° C. were determined to be −1.39±0.13° C. (top shelf), −1.38±0.16° C., (middle shelf) and −1.30±0.14° C. (bottom shelf) (mean±SD), respectively.

Next, experiments were performed with 3 organ donor bone marrow products. For these experiments, the same protocol and temperature monitoring system was used, however thermocouples were taped to the outside of the bags to avoid contaminating the products, and after 6-24 hours at −86° C. the cassettes were transferred to vapor LN2 storage. Taping thermocouples to the bags allowed for an approximation of the actual freeze curve but was less accurate than the immersion method and prone to failure due to detaching. Again, freezing curves were very consistent, with MCRs of −1.50±0.17° C. (n=3 bags), −1.52±0.14° C. (n=3 bags), and 1.56° C. (only one bag measured due to thermocouple failures) (mean±SD), respectively.

After storage for >1 week, bags were thawed and evaluated for CD34+ cell viability and CFU-GM potential. All donors exhibited high viability and robust colony growth (Table 26).

thermal resistance so that the chamber temperature can be easily adjusted to result in ideal cooling rates. This robust method is relatively insensitive to user error and equipment failure as well. For clinical production, all units banked are tested for post-thaw viability for 100% verification to allow use of this method for ongoing clinical production.

Example 14: Post Thaw Functional Characteristics of Cryopreserved Selected CD34 Cells Cell Isolation Isolation of cellular subsets from whole bone marrow may require partially purifying the cells of interest. The most common separation method used was Ficoll density gradient centrifugation. By varying the density of Ficoll, it was determined that percentages less than 100% Ficoll were optimal for deceased donor HPC, Marrow due to changes that occurred in bone marrow during variable periods of warm and cold ischemia.

CD34 Selection

Standard commercial methods utilizing paramagnetic beads coupled to a monoclonal CD34 antibody were used. Initial methods used the Miltenyi MACS system for research purposes. Due to speed and convenience subsequent research isolations were performed with the Stem Cell Technologies EasySep system (catalog #17856)—the stabilization buffers described in previous Example 8 were used. In one instance, the CliniMACS+ system was used for selection. Cryopreserved cells from this preparation were used in a NSG mouse xenotransplant model. In each case the manufacturer's protocols were followed. Fresh selected CD34+ cells were characterized by flow cytometry (viability) and colony forming unit assay (function).

TABLE 26

Post thaw viability assessed via flow cytometry (USP<127>) and colony forming assay

| CD34 viability (%) | Bag 1 | Bag 2 | Bag 3 | Mean (±SD) |
| --- | --- | --- | --- | --- |
| Donor 1 | 96.71 | 97.51 | 97.69 | 97.3 ± 0.52 |
| Donor 2 | 70.87 | 80.24 | 79.34 | 76.8 ± 5.16 |
| Donor 3 | 90.04 | 88.05 | 82.06 | 86.7 ± 4.15 |
| CFU-GM (per $10^5$ cells) | Bag 1 | Bag 2 | Bag 3 | Mean (±SD) |
| Donor 1 | 40 | 30 | 35 | 35.0 ± 5.0 |
| Donor 2 | 25 | 35 | 20 | 26.7 ± 7.6 |
| Donor 3 | 45 | 95 | 60 | 66.7 ± 25.7 |

This experiment was repeated without the temperature monitoring with 3 additional donors and results were confirmed with a post thaw CD34+ viability of 86.81±8.35% and mean CFU-GM of 51±29 colonies per $10^5$ cells plated (mean±SD).

With smaller volume products (e.g. umbilical cord blood cryopreserved in 25 mL volumes), directly placing cassettes in a static −86° C. chamber could result in a cooling rate faster than desirable. The larger volume units carry sufficient Cryopreservation Processing All selected cells were cryopreserved in CS-10 (Biolife Solutions), using a validated controlled-rate freezing device (Cool Cell) placed at −86° C. before transferring cryotubes to the vapor phase of liquid nitrogen.

Cell were kept in liquid nitrogen for 6-64 days before thawing and analyzing (Table 27). In some cases, the cells were used for mouse engraftment studies which required a thawing at a later time point as indicated.

TABLE 27

Selection and thawing dates as well as selection method

| | Selection date | Thaw date- in vitro study | Thaw date- animal study | Selection Method |
|---|---|---|---|---|
| AGEJ150 | 06JUN2019 | 09AUG2019 | 29AUG2019 | CliniMACS |
| AGGU049 | 25JUL2019 | 30JUL2019 | 29AUG2019 | EasySep |
| 190000061 | 12DEC2019 | 09JAN2020 | NA | EasySep |
| 190000062 | 13DEC2019 | 10JAN2020 | NA | EasySep |
| 20000001 | 03JAN2020 | 18JAN2020 | A | EasySep |
| AHAB005 | 07JAN2020 | 13JAN2020 | 19JAN2020 | EasySep |

Thawing and Analysis

Tubes were removed from liquid nitrogen storage and thawed quickly in a 37° C. waterbath with swirling. Aliquots were removed from flow cytometry and colony forming unit (CFU) assays.

TABLE 28

Viability (% of total cells)

| Donor | Fresh | Thawed | Cryopreservation time (days) |
|---|---|---|---|
| AGEJ150 | 98.7 | 99.3 | 64 |
| AGGU049 | 97.8 | 97.9 | 34 |
| 190000061 | 99 | 98.8 | 5 |
| 190000062 | 95 | 96.3 | 28 |
| 20000001 | 98.3 | 97.8 | 15 |
| AHAB005 | 98.9 | 99 | 6 |
| average | 98.0 | 98.2 | |
| SD | 1.5 | 1.1 | |

Viability as determined by flow cytometry indicated that selected CD34+ cells remained highly viable during cryopreservation (Table 28). The cryopreserved cells also retained the ability to differentiate into functional cell types (Table 29).

TABLE 29

CFU

| | Fresh | Thawed |
|---|---|---|
| AGEJ150 | 47 | 43.5 |
| AGGU049 | 47 | 42 |
| 19000061 | 42.5 | 56 |
| 19000062 | 31 | 35.5 |
| 20000001 | 70 | 18 |
| AHAB005 | 59.5 | 57 |
| Average | 49.5 | 42.0 |
| SD | 13.6 | 14.4 |

These data indicate that CD34+ cells selected by either method maintain high post-thaw viability and function when cryopreserved for up to 64 days.

Mouse Engraftment with Selected CD34+

Engraftment of the selected human CD34+ cells was evaluated in an irradiated (300 cGy) immunocompromised NOD.Cg-Prkdc$^{scid}$ IL2rg$^{tm1Wjl}$/Sz (NSG) mouse model. The cells were thawed on the day of injection (N=10 mice/group. Selection of CD34+ cells was performed with fresh (AGGU049 and AHAB005-1) or frozen then thawed (AGEJ150 and AHAB005-2) HPC, Marrow. The latter was intended to determine impact of multiple freeze-thaw cycles on viability and function. Control CD34+ cells selected from umbilical cord blood were injected into a separate group of mice (N=5).

Mice were subjected to 300 cGy total body irradiation and injected IV 4 hours later with HPC, Marrow CD34+ cells ($5\times10^5$; 10 mice/donor) or cord blood (CB) CD34+ cells ($1\times10^5$; 5 mice/donor). An additional 3 non-irradiated NSG were used as sham controls for background antibody staining.

The level of engraftment in bone marrow, peripheral blood and spleen was evaluated at 16 weeks. The level of bone marrow chimerism was determined using antibodies specific to human hematopoietic cells (CD45). The bone marrow was collected from mice receiving primary transplants with AGEJ150 and AGGU049 and used to evaluate secondary transplant potential in new groups (N=10) of irradiated NSG mice. Secondary transplant NSG mice were treated as above, except that $1\times10^7$ whole bone marrow cells were injected. This secondary transplant procedure is commonly used to demonstrate the presence of long-term repopulating hematopoietic stem cells in the original graft.

Figure 25:
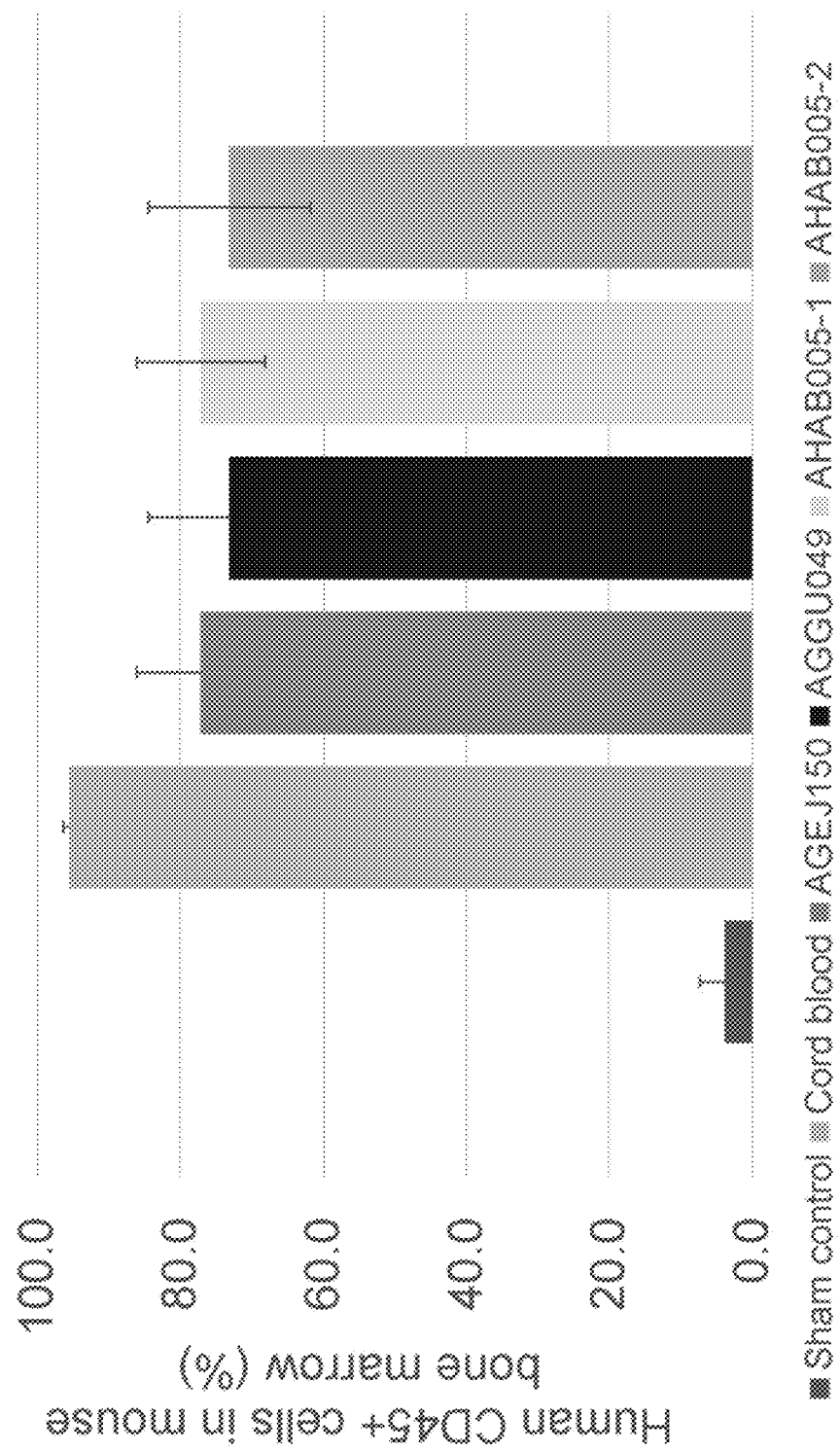
FIG. 25 illustrates levels of human CD45+ cells in bone marrow of irradiated NSG mice 16 weeks after injection of CD34+ cells. Sham control is bone marrow from non-irradiated, untreated mice. Cell surface CD45 expression was determined by flow cytometry. Thick bars represent means of N=5 (cord blood) or 10 (HPC, Marrow) mice. Standard deviations shown by think vertical lines.
Figure 26:
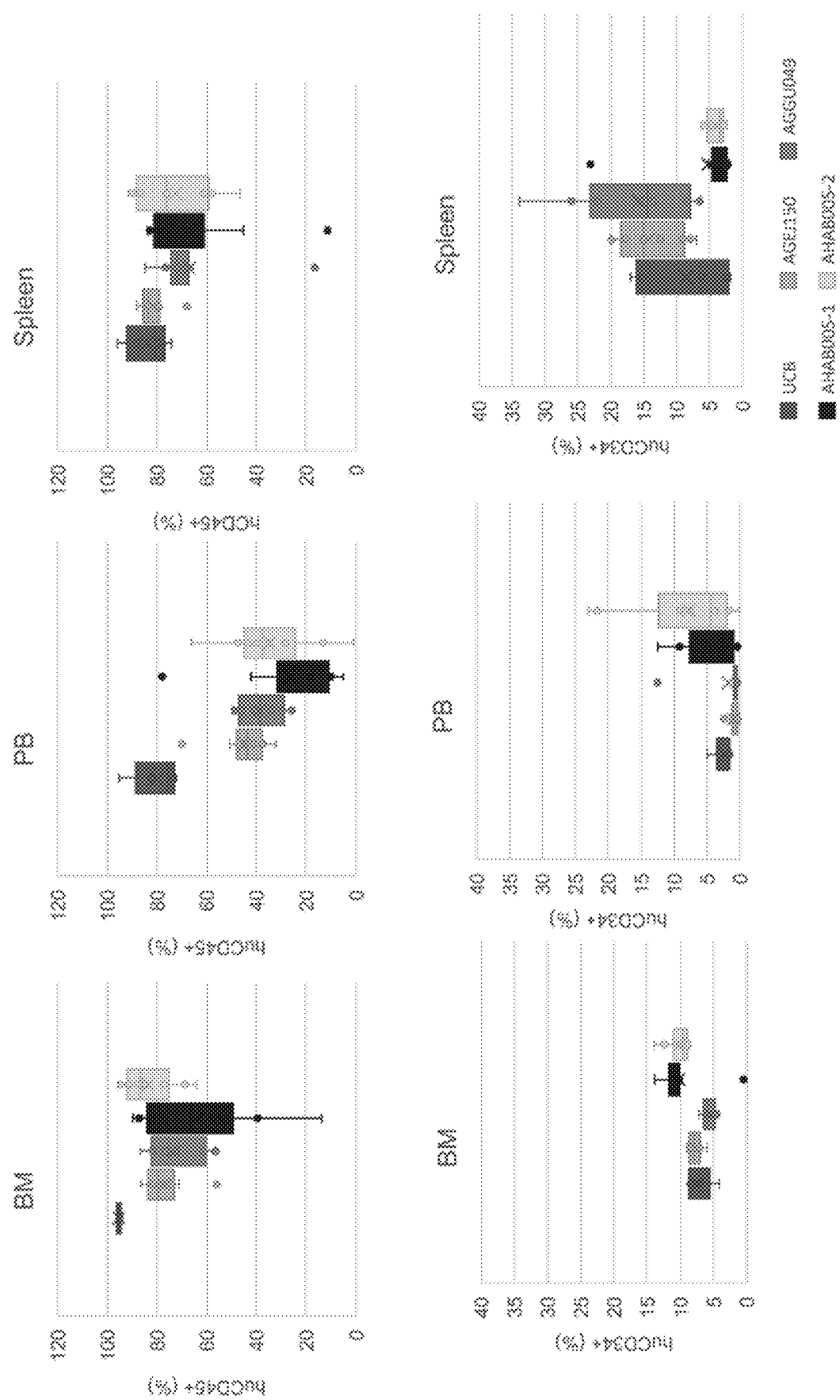
FIG. 26 illustrates the percentage of human CD45+ and CD34+ cells in bone marrow (BM), peripheral blood (PB) and spleens 16 weeks after irradiation and transplantation of NSG mice with CD34+ cells.

Long-term bone marrow engraftment of human CD45+ cells was observed with HPC, Marrow CD34+ cells from each of the donors (FIG. 25). These cells, as well as CD34+ subsets, were also detected at high frequency in Peripheral Blood (PB) and spleens at 6 weeks (FIG. 26).

Figure 27:
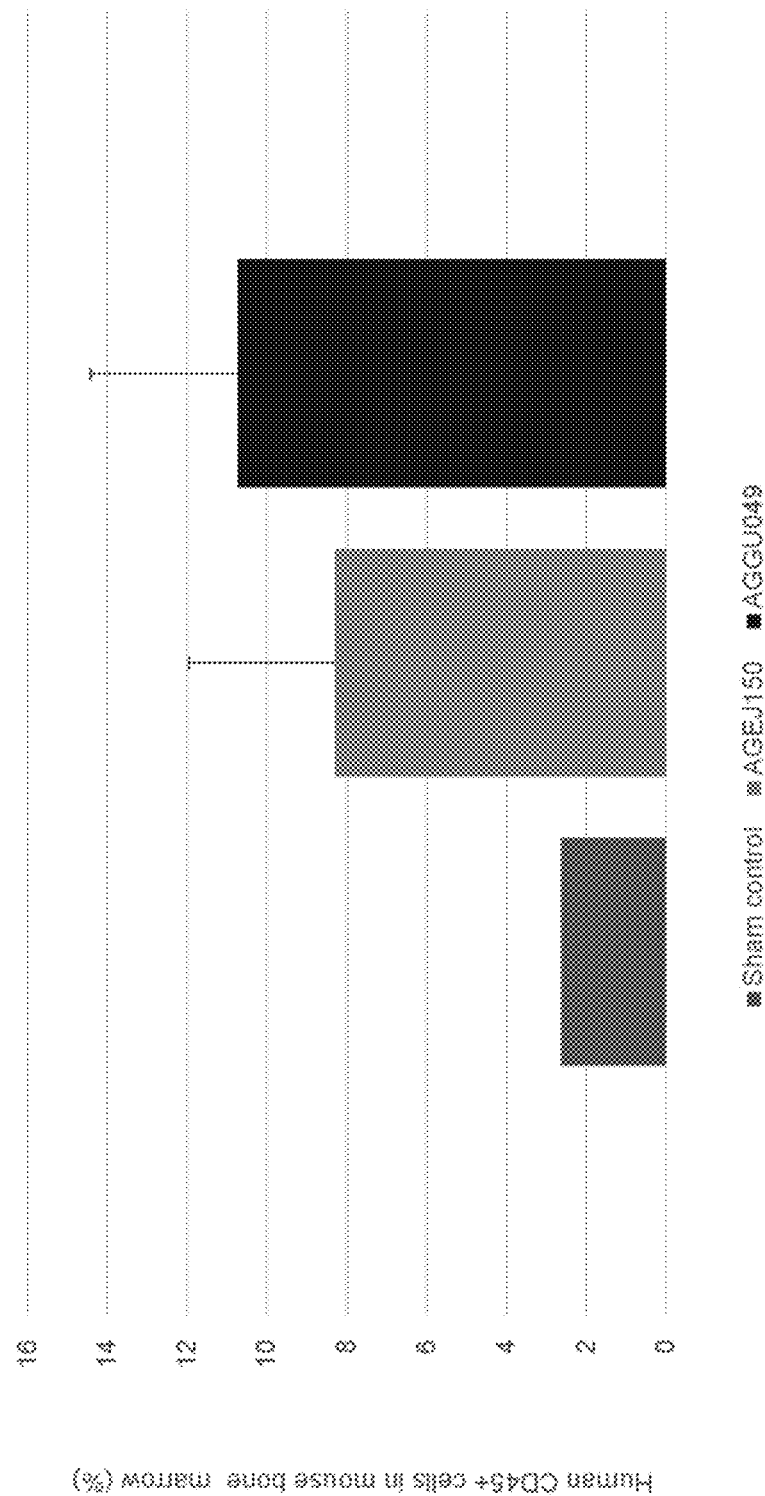
FIG. 27 depicts secondary transplants. Levels of human CD45+ cells in bone marrow of irradiated NSG mice 16 weeks after injection of total bone marrow from mice engrafted with CD34+ cells from the indicated donors. Sham control is bone marrow from non-irradiated, untreated mice. Cell surface CD45 expression was determined by flow cytometry. Thick bars represent means of N=10 mice. Standard deviations shown by think vertical lines.
Figure 28:
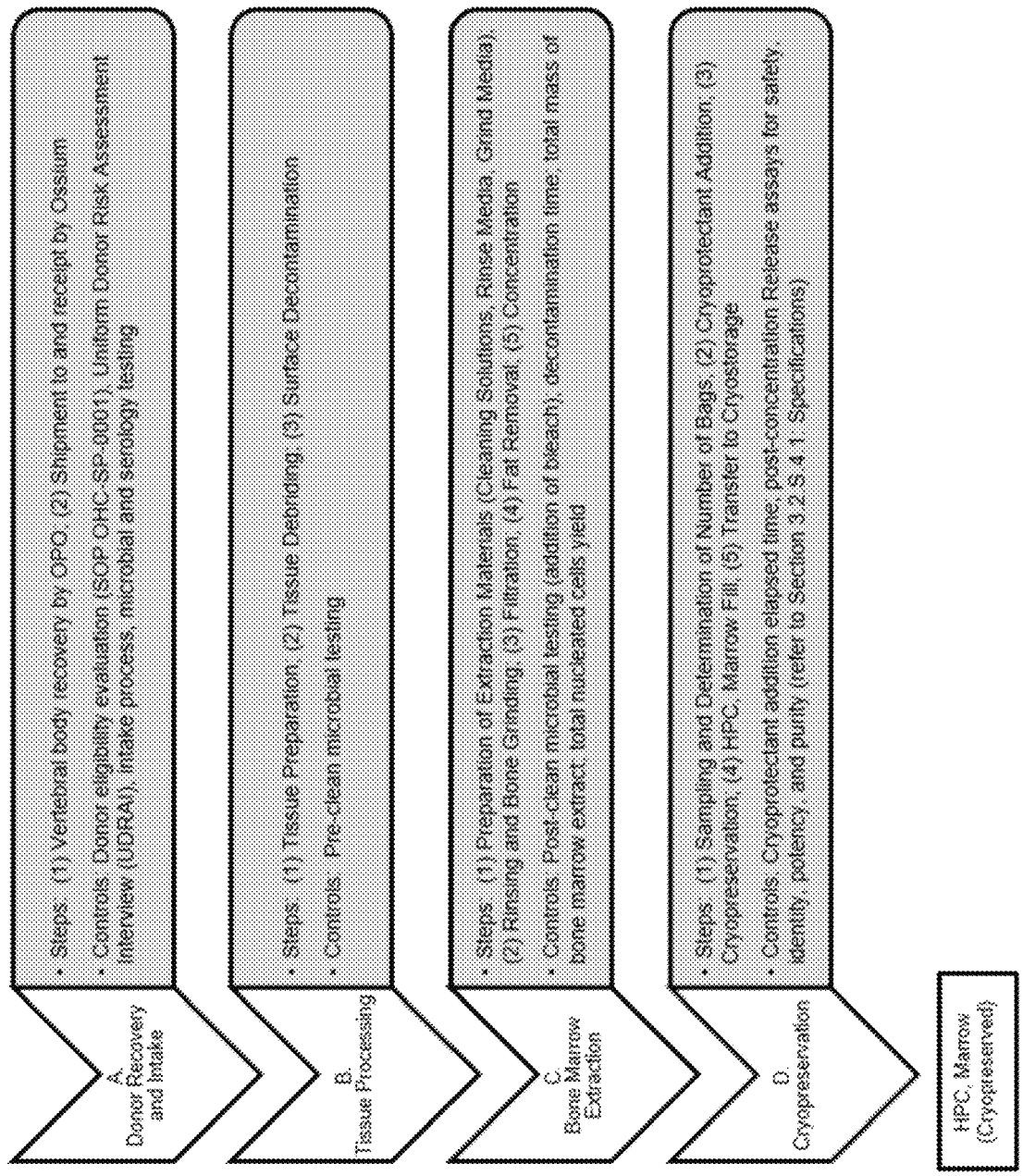
FIG. 28 is an overall continuous manufacturing and process control flowchart that produces cryopreserved bone marrow ("HPC, Marrow") and as described in Example 16.

Secondary engraftment of human CD34+ cells from donors AGEJ150 and AGGU049 was performed as a definitive test for long-term potential hematopoietic stem cells. Average engraftment was >8%, indicating that the original bone marrow contained primordial stem cells (FIG. 27).

Mean values and standard deviations for each human hematologic cell type analyzed in bone marrow (BM), peripheral blood and spleen samples are presented in Table 30 (as a percentage of total cell count).

TABLE 30

Values and standard deviations of engraftment in hematological cell types

| | | | Cell Sources | | | | |
|---|---|---|---|---|---|---|---|
| | | | UCB | AGEJ150 | AGGU049 | AHAB005-1 | AHAB005-2 |
| BM | huCD45+ | mean | 95.5 | 77.1 | 73.1 | 63.5 | 83.9 |
| | | SD | 0.9 | 9.0 | 11.3 | 24.6 | 10.6 |

TABLE 30-continued

Values and standard deviations of engraftment in hematological cell types

|     |        |      | Cell Sources |         |         |           |           |
|-----|--------|------|------|---------|---------|-----------|-----------|
|     |        |      | UCB  | AGEJ150 | AGGU049 | AHAB005-1 | AHAB005-2 |
|     | huCD19+ | mean | 91.3 | 73.0 | 71.2 | 27.7 | 34.1 |
|     |         | SD   | 1.4  | 14.7 | 10.5 | 12.9 | 5.6  |
|     | huCD33+ | mean | 10.1 | 7.1  | 8.4  | 39.2 | 33.0 |
|     |         | SD   | 3.8  | 0.9  | 2.1  | 21.3 | 5.1  |
|     | huCD34+ | mean | 7.4  | 7.8  | 5.7  | 10.2 | 10.3 |
|     |         | SD   | 2.0  | 1.0  | 1.0  | 3.6  | 1.7  |
|     | huCD38+ | mean | 2.2  | 9.5  | 8.5  | 31.7 | 33.0 |
|     |         | SD   | 0.7  | 15.1 | 1.6  | 11.4 | 5.1  |
| PB  | huCD45+ | mean | 79.8 | 44.9 | 38.2 | 26.6 | 34.8 |
|     |         | SD   | 9.4  | 10.3 | 9.4  | 21.1 | 18.2 |
|     | huCD19+ | mean | 61.2 | 33.7 | 26.8 | 11.3 | 14.2 |
|     |         | SD   | 2.4  | 9.5  | 9.1  | 8.3  | 7.7  |
|     | huCD33+ | mean | 0.8  | 0.9  | 0.8  | 5.8  | 10.4 |
|     |         | SD   | 0.9  | 1.5  | 0.7  | 4.8  | 6.2  |
|     | huCD34+ | mean | 2.4  | 0.8  | 1.9  | 4.2  | 7.8  |
|     |         | SD   | 1.5  | 0.7  | 3.7  | 4.1  | 8.1  |
|     | huCD38+ | mean | 7.3  | 1.9  | 0.9  | 12.7 | 19.2 |
|     |         | SD   | 7.6  | 2.3  | 0.6  | 6.7  | 10.2 |
| Spleen | huCD45+ | mean | 83.7 | 81.5 | 67.1 | 66.6 | 72.2 |
|     |         | SD   | 8.5  | 5.7  | 18.6 | 22.6 | 16.0 |
|     | huCD19+ | mean | 72.9 | 70.9 | 62.8 | 51.1 | 54.4 |
|     |         | SD   | 7.5  | 18.7 | 17.8 | 19.0 | 13.6 |
|     | huCD33+ | mean | 5.4  | 17.9 | 28.2 | 18.0 | 17.7 |
|     |         | SD   | 1.3  | 5.3  | 13.2 | 10.3 | 5.1  |
|     | huCD34+ | mean | 8.6  | 14.3 | 15.8 | 5.3  | 4.1  |
|     |         | SD   | 7.1  | 4.9  | 9.1  | 6.3  | 1.4  |
|     | huCD38+ | mean | 26.1 | 13.3 | 15.5 | 28.4 | 30.1 |
|     |         | SD   | 17.1 | 8.1  | 11.1 | 9.7  | 7.6  |

It is concluded from this study that HPC, Marrow possesses highly viable and functional CD34+ HSPC which stably engraft irradiated mouse bone marrow and differentiate into various hematologic lineage cells. It was further determined that these characteristics are stable through multiple cryopreservation and thaws.

Example 15: Cadaveric Donor HPC, Bone Marrow Production

Donor Intake: Each donor was screened and deemed acceptable for cleanroom processing according to the data in Table 31.

TABLE 31

Donor Intake Data

| Donor ID | UNOS ID | Date Processed | Warm Ischemia (hh:mm) | Cold Ischemia at Process Start* (hh:mm) | Total Process Time (hh:mm) |
|---|---|---|---|---|---|
| W437520000180 | AHIY121 | 30SEP2020 | 07:41 | 36:07 | 06:52 |
| W437520000188 | AHJD073 | 06OCT2020 | 01:55 | 28:59 | 07:00 |
| W437520000183 | AHJC354 | 09OCT2020 | 04:45 | 27:44 | 08:06 |

*Process start time is time when vertebral bodies are removed from the refrigerator.

Donor processing was performed as previously described. The steps included on these three batch records were performed consecutively, not exceeding a total process time of 12 hours. Donor acceptance criteria is described in Table 32.

TABLE 32

| In-Process Acceptance Criteria | |
|---|---|
| Donor ID | Meets Acceptance Criteria |
| W437520000180 | Yes |
| W437520000183 | Yes |
| W437520000188 | Yes |

Pre-freeze samples were tested per the Colony Forming Unit Assay for Fresh, Never Frozen Bone Marrow, ISHAGE Gating for CD45, CD34, and CD3 Enumeration, Bone Marrow Staining for CD45, CD34, and CD3 Enumeration Using Flow Cytometry, and TNC Quantitation of Concentrated Bone Marrow Using the Sysmex XP-300 Hematology Analyzer. Supernatant was prepared and tested per the Benzonase Detection in Bone Marrow Supernatant Using the Benzonase ELISA Kit II. Results were reported on forms specified in the test procedure and stored in the test file for the donor.

Bags and vials were thawed after ≥6 hours of passive cooling (<−70° C.) and final storage in vapor nitrogen (<−130° C.) per Thawing of Cryopreserved Bone Marrow Samples (described previously herein). The thawing procedure was recorded as it was performed and all applicable times were recorded on bags and vials. Following dilution, samples were taken per TNC Quantitation of Thawed Bone Marrow Using the Sysmex XP-300 Hematology Analyzer for Sysmex counts, Flow Cytometry, and the CFU assay. Samples were tested per the Colony Forming Unit Assay for Cryopreserved Bone Marrow.

All results are retained with the donor testing record. The results reported in the following tables for CFU-GM/$10^5$ cells plated are results of the high plate.

W437520000180 data is summarized in Table 33.

TABLE 33

W437520000180 Results

| Sample ATTRIBUTE | Method | Acceptance Criterion | Result | Pass/Fail |
|---|---|---|---|---|
| Final product (pre-cryopreservation, without DMSO) POTENCY | Colony Forming Unit (CFU) Assay | ≥1 CFU-GM/$10^5$ cells plated (Positive for CFU-GM) | 200 | Pass |
| Final product (pre-cryopreservation, DMSO loaded) POTENCY | CD34+ HSC absolute cell count (flow cytometry) | ≥2.0 × $10^7$/unit HPC, Marrow | 7.55 × $10^7$ | Pass |
| | CD34+ HSC viability (flow cytometry) | ≥70% viable | 91.90% | Pass |
| Final product (pre-cryopreservation, DMSO loaded) PURITY | Residual Benzonase (QC-4) | ≤1 ng/mL (≤70 ng/unit) | ≤1 ng/mL | Pass |
| Final product (post-thaw vial and product bag) | CD34+ HSC viability (flow cytometry) | ≥50% viable | Vial: 89.92% Bag: 90.64% | Pass |
| POTENCY | CFU Assay | ≥1 CFU-GM/$10^5$ cells plated (Positive for CFU-GM) | Vial: 45 Bag: 70 | Pass |

W437520000183 data is summarized in Table 34.

TABLE 34

W437520000183 Results

| Sample ATTRIBUTE | Method | Acceptance Criterion | Result | Pass/Fail |
|---|---|---|---|---|
| Final product (pre-cryopreservation, without DMSO) POTENCY | Colony Forming Unit (CFU) Assay | ≥1 CFU-GM/$10^5$ cells plated (Positive for CFU-GM) | 335 | Pass |
| Final product (pre-cryopreservation, DMSO loaded) | CD34+ HSC absolute cell count (flow cytometry) | ≥2.0 × $10^7$/unit HPC, Marrow | 1.70 × $10^8$ | Pass |
| POTENCY | CD34+ HSC viability (flow cytometry) | ≥70% viable | 97.62% | Pass |
| Final product (pre-cryopreservation, DMSO loaded) PURITY | Residual Benzonase (QC-4) | ≤1 ng/mL (≤70 ng/unit) | ≤1 ng/mL | Pass |
| Final product (post-thaw vial and product bag) | CD34+ HSC viability (flow cytometry) | ≥50% viable | Vial: 94.52% Bag: 94.31% | Pass |
| POTENCY | CFU Assay | ≥1 CFU-GM/$10^5$ cells plated (Positive for CFU-GM) | Vial: 95 Bag: 135 | Pass |

W437520000188 data is summarized in Table 35.

TABLE 35

W437520000188 Results

| Sample ATTRIBUTE | Method | Acceptance Criterion | Result | Pass/Fail |
|---|---|---|---|---|
| Final product (pre-cryopreservation, without DMSO) POTENCY | Colony Forming Unit (CFU) Assay | ≥1 CFU-GM/$10^5$ cells plated (Positive for CFU-GM) | 240 | Pass |
| Final product (pre-cryopreservation, DMSO loaded) | CD34+ HSC absolute cell count (flow cytometry) | ≥2.0 × $10^7$/unit HPC, Marrow | 6.87 × $10^7$ | Pass |
| POTENCY | CD34+ HSC viability (flow cytometry) | ≥70% viable | 93.67% | Pass |
| Final product (pre-cryopreservation, DMSO loaded) PURITY | Residual Benzonase (QC-4) | ≤1 ng/mL (≤70 ng/unit) | ≤1 ng/mL | Pass |
| Final product (post-thaw vial and product bag) | CD34+ HSC viability (flow cytometry) | ≥50% viable | Vial: 93.51% Bag: 95.57% | Pass |
| POTENCY | CFU Assay | ≥1 CFU-GM/$10^5$ cells plated (Positive for CFU-GM) | Vial: 70 Bag: 30 | Pass |

All samples met the acceptance criteria.

Example 16: Manufacturing Method for HPC, Marrow

Vertebral Body Recovery and Shipping

OPO's recover VBs via aseptic technique and in accordance with standard surgical protocol, including recovery sequence and zone and instrumentation segregation. Vertebral segments must be carefully recovered, preferably from the thoracic and lumbar vertebrae. The segments are incised and removed using an osteotome and mallet. As much of the spinal cord as possible is removed. A licensed surgeon may have oversight of these steps to assure effective recovery of VBs and prevention of disease transmission and translocation of bacteria.

Once recovered, the vertebral segments are swabbed for microbial culture testing and placed in a sterile, labeled bag with saline-soaked sterile pads. These are then positioned between wet ice packs in a cooler for shipment. Recovery of VBs occurs with a minimal warm ischemia time (≤8 hours). Shipment and initiation of processing must be completed within a minimal cold ischemia time (≤40 hours). The package is finally shipped to Ossium's central processing facility in Indianapolis, Ind. for Donor Intake.

VB logs are wrapped and double bagged. Bags are placed in an insulated shipper with bagged wet ice surrounding them. Shippers are sealed and sent a processing site via medical courier. Upon arrival, packaging is checked for compliance with protocols and vertebral body temperature is measured to ensure compliance with shipping requirements.

Tissue Debriding

Following preparation of the cleanroom, the donor specimen is carefully unpacked for processing, noting the condition of the packing materials and the spine. Debriding involves removal of unnecessary components of the vertebral segments, including soft tissue on and surrounding the VB surface. If pedicles are present, they are sawed off and discarded along with accompanying posterior elements of the vertebra, while simultaneously ensuring that the cancellous tissue—the meshwork of spongy tissue in the anterior body—is not exposed. This body is retained for further processing.

The number of VBs recovered, total mass of bone, and VB temperature are recorded. Debrided VBs are then swabbed for microbial culture testing prior to surface decontamination.

Clean Up

After tissue debriding, cleanroom, BSC and equipment undergo thorough cleaning to assure decontamination using 70% isopropyl alcohol and a broad-spectrum, EPA-registered disinfectant and cleaner.

Media Preparation

Bleach Solution

This is a preparation of 10% bleach solution (0.5% sodium hypochlorite in sterile water) to be used as part of surface decontamination of the vertebral bodies for processing.

Hydrogen Peroxide Solution

This is a preparation of hydrogen peroxide solution (3% hydrogen peroxide in Plasma-Lyte A) to be used as part of surface decontamination.

Rinse Media

The rinsing solution used throughout the manufacturing process is composed of Plasma-Lyte A and Human Serum Albumin (HSA). Plasma-Lyte A Injection pH 7.4 (Multiple Electrolytes Solution, Type 1, USP) is a sterile, nonpyrogenic isotonic solution that is a base source of water and electrolyte-balanced crystalloids for the cells. HSA (25%, USP) is a stabilizing reagent and storage agent, and is diluted to 2.5% HSA for the Rinse Media.

Grind Media

The grind solution used to wash bone grindings consists of Heparin and Benzonase. Heparin (Heparin Sodium Injection, USP) is a cGMP grade, highly pure anticoagulant used to reduce viscosity. The grind media contains 10 U/mL heparin. This component was used in the manufacturing process for the initial stored lots of cryopreserved HPC, Marrow. However, complete removal of Heparin in the manufacturing process is currently being validated for future production lots as part of process improvement. Benzonase® is a cGMP grade, highly pure endonuclease used in nano-quantity to reduce clotting of the initial preparation. The grind media contains 3 U/mL Benzonase in Rinse Media.

Rinsing and Grinding

Surface decontamination involves soaking the debrided VBs in 10% bleach solution (sodium hypochlorite) in a sterile bag for 15-25 minutes, then transferring them into another sterile bag and rinsing them with 3% hydrogen peroxide solution. After that, the VBs are transferred into another sterile bag and rinsed with Plasma-Lyte A. VBs are rinsed a second time with Plasma-Lyte in another sterile bag. They are then swabbed for post-decontamination microbial culture testing.

The surface decontaminated VBs are chopped into smaller pieces using a VB chopper or a hand cutting tool. They are immediately submerged into a pitcher filled with approximately 300 mL of the grinding media that was previously prepared in the last step. The cut pieces are then inserted into the inlet of a bone grinder to be ground and alternately washed with another 300 mL of fresh grinding media until all bones have been processed. Bone grindings are caught by a second pitcher of 300 mL grinding media, ensuring that all pieces are always submerged. The remaining 100 mL of grinding media is used as final rinse to wash the bone grinder and plunger. The second pitcher with bone fragments should at the end of this process contain a total of 1 L of Grind Media.

Filtration

The ground bone fragments containing bone marrow from the last step undergoes immediate filtration using an assembled, disposable Bone Marrow Collection Kit with flexible prefilter and in-line serial filters (FIG. 1).

First, the bone marrow and bone grindings from the last step is shaken for 10 minutes at 150 RPM. In the meantime, a 600-mL Bone Marrow Collection Kit is assembled (see SOP OHC-SOP-0079: Bone Marrow Collection and Filtration). After the initial shake, bone marrow extract are then transferred to a collection bag and eluted by gravity through a series of 500-micron filters into a large transfer pack bag provided with the kit. During the elution process, Rinse Media is used to wash the remaining bone grindings for bone marrow extract. (Note: The washed bone grindings can be aseptically set aside in sterile bags for further processing or for research use.)

The bone marrow extract inside the large transfer pack bag is connected to a second BM collection kit and filtered by gravity through a series of 200-micron filters into several small transfer pack bags. The total processing volume used should be 2 L divided equally between Grind Media and Rinse Media.

Each 600-mL transfer pack (6 in total) is weighed, and the total mass of all bags is calculated. The total mass of the bone marrow extract is thus calculated:

$$\text{Total Mass of Bone Marrow Extract (g)} = \text{Total Mass of All Filled Transfer Packs(g)} - (\text{Mass of Empty Transfer Pack(g)} \times 6)$$

The total mass of the bone marrow extract must be greater than or equal to 1800 g. Out of specification result would trigger a QA alert.

From the first transfer pack filled, 1.3 mL of filtered bone marrow is removed for QC testing on a hematology analyzer. The concentration of cells is counted and documented. The Total Nucleated Count (TNC) is thus calculated:

$$\text{TNC}(\times 10^3 \text{ cells/}\mu L) = \text{Cell Count}(\times 10^3 \text{ cells/}\mu L) \times \text{Total Mass of Bone Marrow Extract (g)} \times 1000)$$

The bone marrow extract in each transfer pack is visually inspected to verify that no tissue, bone grindings, or excessive clumping is noticeable. The bags are then centrifuged for 30 minutes.

Fat Removal

Fat is removed by mostly draining the centrifuged transfer packs, placing a clip just below the fat layer while allowing the rest of the pellet out into post-fat intermediate collection bags.

Concentration

The post-fat intermediate bags are then centrifuged 600×g (~2315 rpm) for 30 minutes. The supernatant is removed from the bone marrow pellets using a plasma extractor and into a waste bag. Waste is discarded using standard biohazard protocol. The pellets are then combined into a pre-weighed bulk bag and resuspended using Rinse Media.

Sampling and Accountability 0.5 mL of bone marrow extract from the pellets is removed and submitted for QC testing. Samples are tested for microbial testing, CFU, viability and potency (CD34+, CD45+ and CD3+) and residual Benzonase. Cell concentration is also tested using the hematology analyzer. The following measurements are calculated:

$$\text{Mass of BM Extract (g)} = \text{Mass of Bulk Bag of BM Extract (g)} - \text{Mass of Preweighed Bulk Bag}$$

$$\text{Concentration}(\times 10^3 \text{ cells}/\mu L) = \text{Cell Count}(\times 10^3 \text{ cells}/\mu L) \times \text{Dilution Factor} \times 1000)$$

$$\text{TNC}(\times 10^3 \text{ cells}/\mu) = \text{Cell Count}(\times 10^3 \text{ cells}/\mu L) \times \text{Total Mass of BM Extract (g)} \times 1000)$$

$$\text{Percent (\%) Yield} = (\text{Filtration TNC Count}(\times 10^3 \text{ cells}/\mu L)/\text{Concentration TNC Count}(\times 10^3 \text{ cells}/\mu L)) \times 100$$

Determination of Number of Bags

The number of bags and vials prepared for cryopreservation correspond to the Total Nucleated Cell (TNC) count and yield based on the resulting concentrated HPC, Marrow intermediate material in the last step. The resulting Total Volume Needed is calculated using the following formula:

$$\text{Total Volume Needed (mL)} = \text{Filtration TNC Count}(\times 10^3 \text{ cells})/(140 \times 10^3)$$

The result dictates the number of cryopreservation product bags and number of QC samples per batch of cryopreserved HPC, Marrow as shown in Table 36.

TABLE 16

Correlation of Total Volume Needed to Determination of Number of Product Bags and Vials Per Batch

| Total Volume Needed | Number of Product | Number of OC |
|---|---|---|
| 87.8-161.0 | 1 | 2 |
| 161.1-234.3 | 2 | 3 |
| 234.4-307.7 | 3 | 4 |
| 307.8-381.0 | 4 | 5 |
| 381.1-454.3 | 5 | 6 |
| 454.4-527.7 | 6 | 7 |
| 527.8-601.0 | 7 | 8 |
| 601.1-674.4 | 8 | 9 |
| 674.5-747.7 | 9 | 10 |
| 747.8-821.0 | 10 | 11 |

Addition of Cryoprotectant

One batch of cryopreserved HPC, Marrow is composed of cryopreservation bags and surrogate vials containing concentrated bone marrow in Freeze Media. Freeze Media consists of 100% dimethyl sulfoxide (DMSO) and the components of the Rinse Media (Plasma-Lyte A and HSA). The Freeze Media is prepared using the volumes calculated in the previous bag-determination step.

The total volume of Freeze Media (approximately equating mass and volume, i.e., g≈mL), volume of DMSO, volume of Rinse Media, and volume of sterility sample are calculated per the following formulas:

$$\text{Total Volume of Freeze Media (mL)} = \text{Total Volume Needed} - \text{Mass of BM Extract (g)}$$

$$\text{Volume of DMSO (mL)} = \text{Total Volume Needed} \times 0.1$$

$$\text{Volume of Rinse Media (mL)} = \text{Total Volume of Freeze Media} - \text{Volume of DMSO}$$

$$\text{Volume of Sterility Sample (mL)} = \text{Filtration TNC Count}(\times 10^3 \text{ cells})/(140 \times 10^3)$$

The volume of Rinse Media calculated is pipetted aseptically to a sterile bottle labeled "Freeze Media." The volume of DMSO is added into the Rinse Media and gently mixed. The Freeze Media must be ≤25° C. before adding it to the bone marrow bulk bag at a predetermined rate (10% of the Freeze Media volume per minute) based on the following formula:

$$\text{Volume of Freeze Media to add per minute} = \text{Total Volume of Freeze Media (mL)} \times 0.1$$

The elapsed time for adding the cryoprotectant to the bone marrow bulk bag must not exceed 9-11 minutes. Note that product and samples must be frozen as fast as possible after the addition of DMSO.

HPC, Marrow Fill

All containers are filled aseptically with the bone marrow+ cryoprotectant from the bulk bag. Cryopreservation bags are prepared based on the number of bags calculated per Table 3 with additional cryopreservation bag(s) prepared for sterility sampling. QC testing microcentrifuge tubes and Reserve cryovials for retains are also prepared.

QC testing and retain samples are pulled. Four segments of the tubing for cryopreservation bags intended for clinical use are sealed. The actual number of bags filled, not including the sterility bag, is recorded. Extra bone marrow left in the bag can be prepared in vials and used for research use if authorized.

Cryostorage

Each cryopreservation bag and representative surrogate cryovials are placed in −86° C. quarantine freezer. The bags are placed in in cassettes and/or directly onto shelves (see FIG. 14 and FIG. 15) while the cryovials are placed separately in a CoolCell® freezing storage system and then in front of the box of cassettes into the freezer. Ossium uses Freezerworks® to manage inventory.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for processing a biological sample comprising cells, the method comprising:
   (a) generating a transplantable unit of the biological sample comprising cells, wherein the transplantable unit comprises a first volume of the cells at a first concentration;
   (b) generating a surrogate unit of the biological sample comprising cells, wherein the surrogate unit comprises a second volume of the cells at a second concentration, wherein the second volume is less than the first volume and the second concentration is no more than 30% different from the first concentration;
   (c) cooling the cells of the transplantable unit and the cells of the surrogate unit at a common optimized rate which balances damage from intracellular ice formation with damage from extracellular ice formation; and
   (d) storing the transplantable unit and the surrogate unit in the same long-term storage container which exposes the cells of the transplantable unit and the cells of the surrogate unit to similar conditions over a long-term storage duration
   thereby providing an equivalent survival and viability for cells from the transplantable unit and for cells from the surrogate unit including a post-thaw cell proliferation rate of the cells of the surrogate unit which is no more than 30% different from a post-thaw cell proliferation rate of the cells of the transplantable unit such that the surrogate unit accurately represents the transplant unit.

2. The method of claim 1, wherein the transplantable unit and the surrogate unit are located in the same freezer during a period of the first cooling rate and during a period of the second cooling rate.

3. The method of claim 1, wherein the second volume is less than 50% of the first volume, less than 40% of the first volume, less than 37.5% of the first volume, less than 35% of the first volume, less than 30% of the first volume, less than 20% of the first volume, less than 15% of the first volume, less than 10% of the first volume, less than 5% of the first volume, or less than 1% of the first volume.

4. The method of claim 1, wherein a post-thaw viability rate of the cells in of the transplantable unit is no more than 30% different, no more than 25% different, no more than 20% different, no more than 15% different, no more than 13.6% different, no more than 10% different, or no more than 5% different than a post-thaw viability rate of the cells of the surrogate unit.

5. The method of claim 1, wherein a post-thaw cell proliferation rate of the cells of the transplantable unit is no more than 25% different, no more than 20% different, no more than 15% different, no more than 13.6% different, no more than 10% different, or no more than 5% different than a post-thaw cell proliferation rate of the cells of the surrogate unit.

6. The method of claim 1, wherein a post-thaw viability rate of the cells of the transplantable unit and the cells of the surrogate unit are at least 50%, at least 60%, at least 70%, at least 80%, or at least 90%.

7. The method of claim 1, wherein the post-thaw cell proliferation rate of the cells of the transplantable unit and/or the cells of the surrogate unit is at least 1 CFU-GM/$10^5$ cells.

8. The method of claim 1, wherein the first cooling rate and the second cooling rate comprise a supra-freeze rate from about −0.1° C./min to about −5° C./min and until at least ice has nucleated in a freezing medium.

9. The method of claim 8, wherein the first cooling rate and the second cooling rate comprise a supra-freeze rate from about −2.5° C./min to about −4° C./min, from about −2.5° C./min to about −3.5° C./min, or from about −1° C./min to about −2° C./min and until at least when ice has nucleated in a freezing medium.

10. The method of claim 9, wherein the first cooling rate and the second cooling rate comprise a supra-freeze rate of about −1° C./min.

11. The method of claim 2, wherein step (c) occurs in one static freezer or one controlled-rate freezer, wherein the freezer is set to from about −70° C. to about −90° C.

12. The method of claim 11, wherein the transplantable unit and the surrogate unit are disposed on the same shelf of the freezer.

13. The method of claim 11, wherein the freezer is set at −86° C.

14. The method of claim 1, wherein the surrogate unit second volume is placed directly in an insulating container.

15. The method of claim 1, wherein the method further comprises arranging the transplantable unit and/or the surrogate unit inside the static freezer such that the transplantable unit and/or the surrogate unit does not contact a wall of the freezer.

16. The method of claim 1, wherein the biological sample comprising cells of the transplantable unit and the biological sample comprising cells of the surrogate unit experience the same cooling rate.

17. The method of claim 16, wherein the cells are stem cells or immune cells.

18. The method of claim 17, wherein the stem cells comprise hematopoietic stem cells (HSC), mesenchymal stem cells (MSC), or both.

19. The method of claim 1, wherein the biological sample comprises one or more organs, blood, or both.

20. The method of claim 1, further comprising a step of transferring the transplantable unit and the surrogate unit to a long-term storage container which is colder than −86° C. such that the surrogate unit experiences the same temperature fluctuations as the transplantable unit.

* * * * *